(12) United States Patent
Morrisroe

(10) Patent No.: US 7,737,397 B2
(45) Date of Patent: Jun. 15, 2010

(54) DEVICES AND SYSTEMS INCLUDING A BOOST DEVICE

(75) Inventor: Peter Morrisroe, New Milford, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 11/969,759

(22) Filed: Jan. 4, 2008

(65) Prior Publication Data

US 2008/0173810 A1    Jul. 24, 2008

Related U.S. Application Data

(63) Continuation of application No. 11/156,274, filed on Jun. 17, 2005.

(51) Int. Cl.
*H01J 49/00* (2006.01)

(52) U.S. Cl. .................. 250/288; 250/281

(58) Field of Classification Search .......... None
See application file for complete search history.

(56) References Cited

U.S. PATENT DOCUMENTS

| | | | |
|---|---|---|---|
| 4,118,618 A | 10/1978 | Gauthier et al. | |
| 4,419,575 A | 12/1983 | Lakatos et al. | |
| 4,540,885 A | 9/1985 | Stafford et al. | |
| 4,578,589 A * | 3/1986 | Aitken | 250/492.2 |
| 4,629,940 A | 12/1986 | Gagne et al. | |
| 4,766,287 A | 8/1988 | Morrisroe et al. | |
| 4,798,464 A | 1/1989 | Boostrom | |
| 4,818,916 A | 4/1989 | Morrisroe | |
| 4,906,900 A * | 3/1990 | Asmussen | 315/111.81 |
| 4,955,717 A | 9/1990 | Henderson | |
| 5,024,725 A | 6/1991 | Chen et al. | |
| 5,438,194 A * | 8/1995 | Koudijs et al. | 250/288 |
| 5,526,110 A | 6/1996 | Braymen | |
| 5,534,998 A | 7/1996 | Eastgate et al. | |
| 5,648,701 A | 7/1997 | Hooke et al. | |
| 5,818,581 A | 10/1998 | Kurosawa et al. | |
| 6,329,757 B1 | 12/2001 | Morrisroe et al. | |
| 6,614,021 B1 * | 9/2003 | Kalinitchenko | 250/294 |
| 6,627,877 B1 * | 9/2003 | Davis et al. | 250/287 |
| 6,639,227 B1 * | 10/2003 | Glavish et al. | 250/492.2 |
| 6,809,312 B1 * | 10/2004 | Park et al. | 250/281 |
| 7,106,438 B2 | 9/2006 | Morrisroe | |

(Continued)

FOREIGN PATENT DOCUMENTS

EP    0671386 A1    9/1995

OTHER PUBLICATIONS

EP Communication for EP 06784915.8.

(Continued)

*Primary Examiner*—Bernard E Souw
*Assistant Examiner*—Andrew Smyth
(74) *Attorney, Agent, or Firm*—Woods Rogers PLC

(57) ABSTRACT

A device for mass spectroscopy comprising a chamber configured to provide an atomization source, a boost device configured to provide radio frequency energy to the chamber, and a mass analyzer in fluid communication with the chamber and configured to separate species based on mass-to-charge ratios is disclosed. In certain examples, a boost device may be used with a flame or plasma to provide additional energy to a flame or plasma to enhance desolvation, atomization, and/or ionization.

25 Claims, 69 Drawing Sheets

U.S. PATENT DOCUMENTS

| | | | | |
|---|---|---|---|---|
| 7,119,330 | B2* | 10/2006 | Kalinitchenko | 250/288 |
| 2004/0001295 | A1 | 1/2004 | Kumar | |
| 2004/0169855 | A1 | 9/2004 | Morrisroe et al. | |
| 2005/0082471 | A1* | 4/2005 | Kalinitchenko | 250/286 |
| 2006/0136158 | A1* | 6/2006 | Goldberg et al. | 702/76 |

OTHER PUBLICATIONS

First Official Action for CN 200680021600.X.
Second Official Action for CN 200680021600.X.
Boswell et al, Helicons—The Early Years, IEEE Transactions on Plasma Science, 25: Dec. 4, 1997.

Eden et al., "Microplasma devices fabricated in silicon, ceramic, and metal/polymer structures: arrays, emitters and photodetectors," J. Phys. D: Appl. Phys. 36: 2869-2877, Dec. 2003.

Kikuchi et al., "Rf microplasma jet at atmospheric pressure: characterization and application to thin film processing," J. Phys. D: Apply Phys. 37: 1537-1543, Jun. 7, 2004.

International Report on Patentability and Search Report for corresponding International Application PCT/US2006/023277.

Citations 1-4 in this section are not provided either because was previously cited by or submitted to the office in a prior application, U.S. Appl. No. 11/156,274, filed Jun. 17, 2005.

* cited by examiner

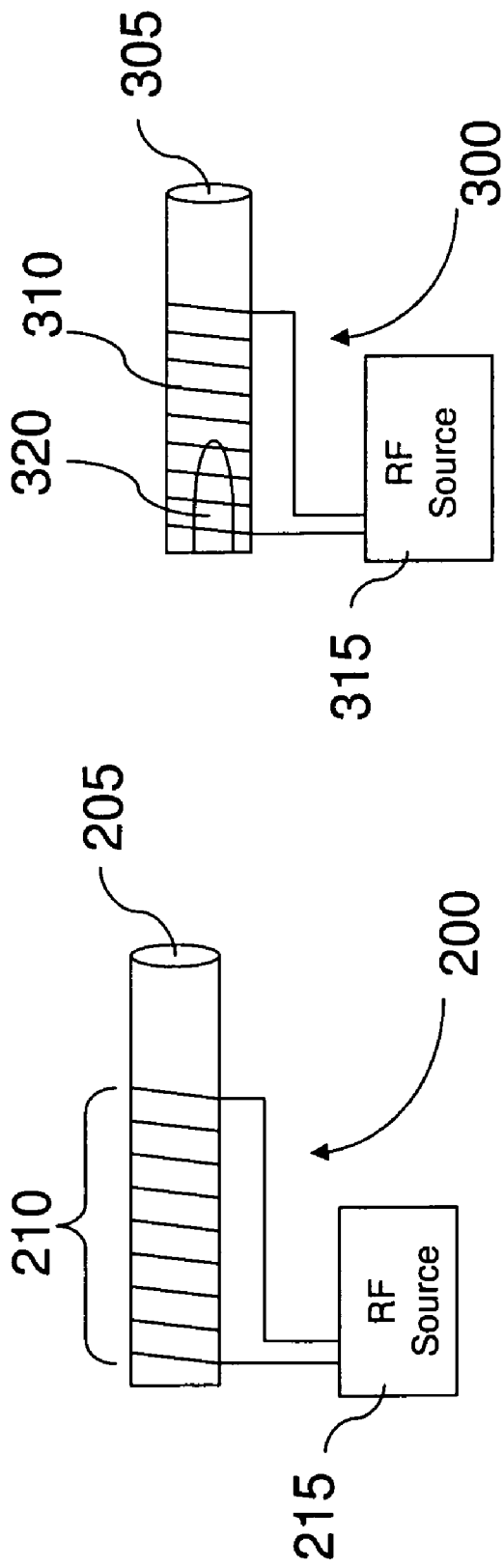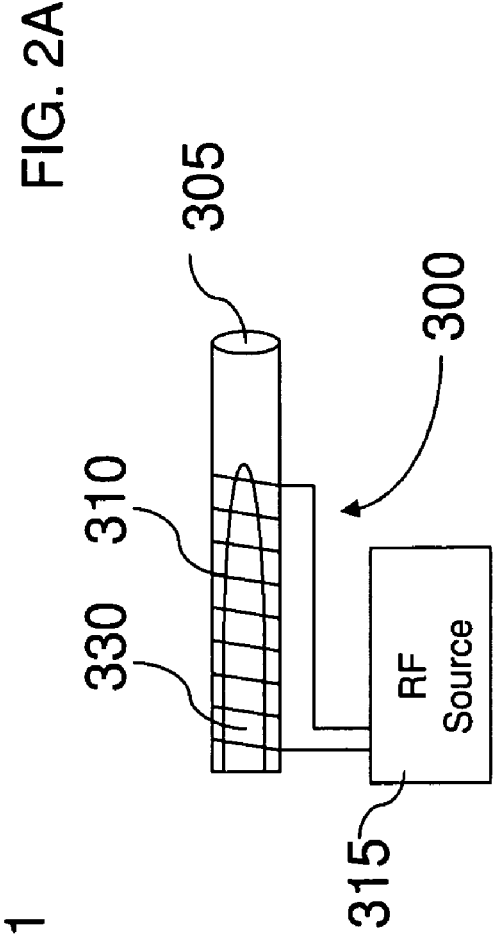

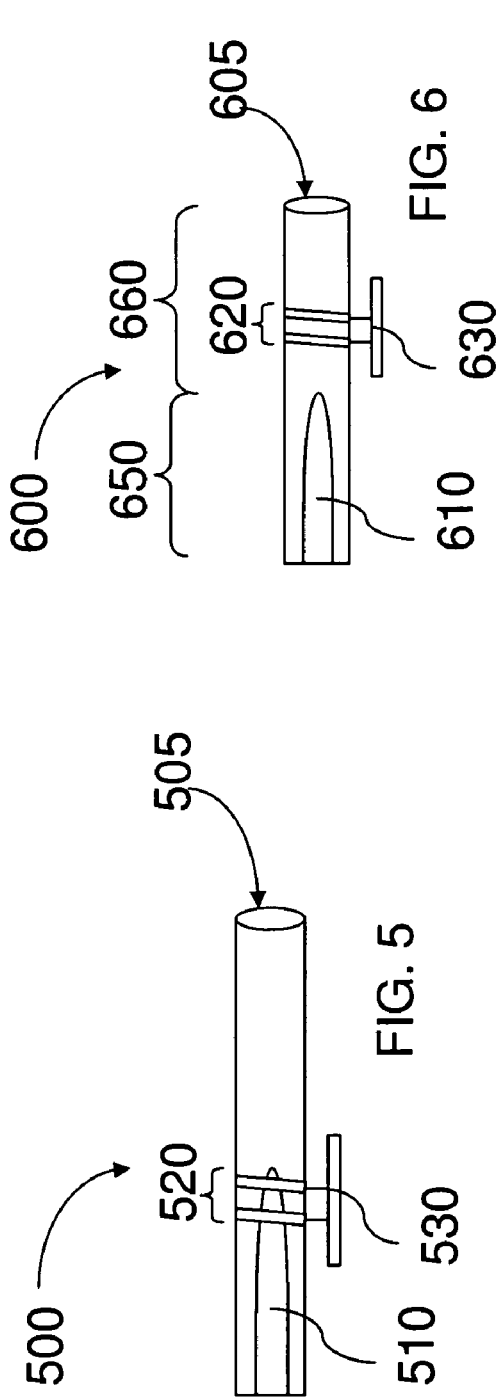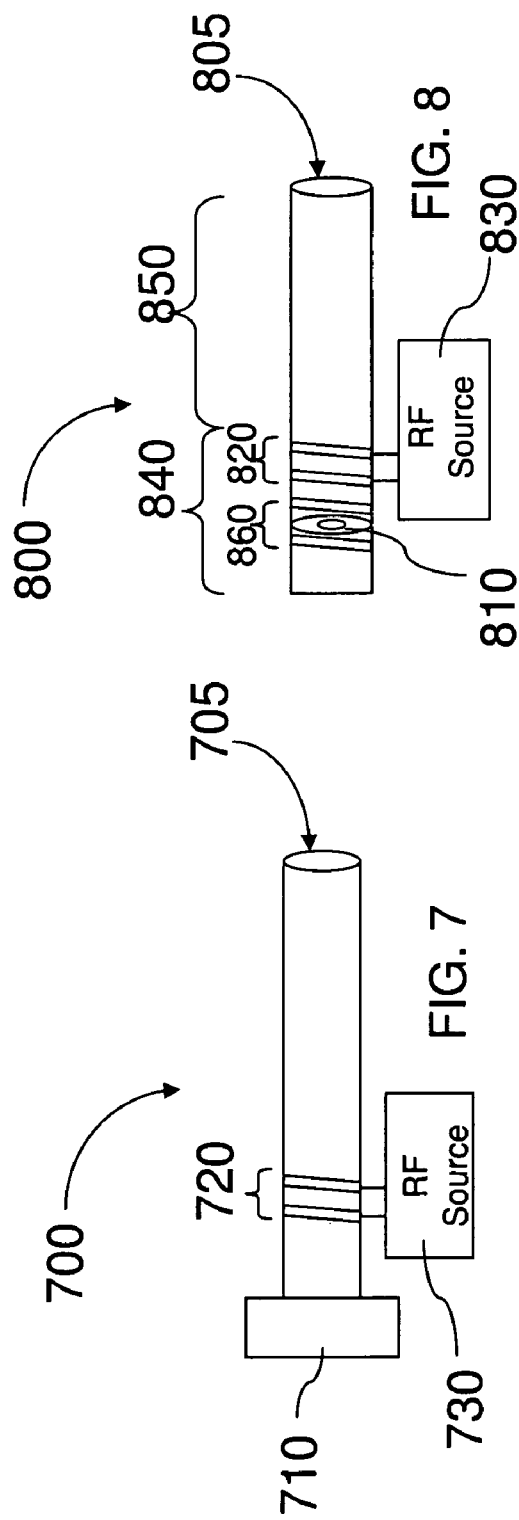

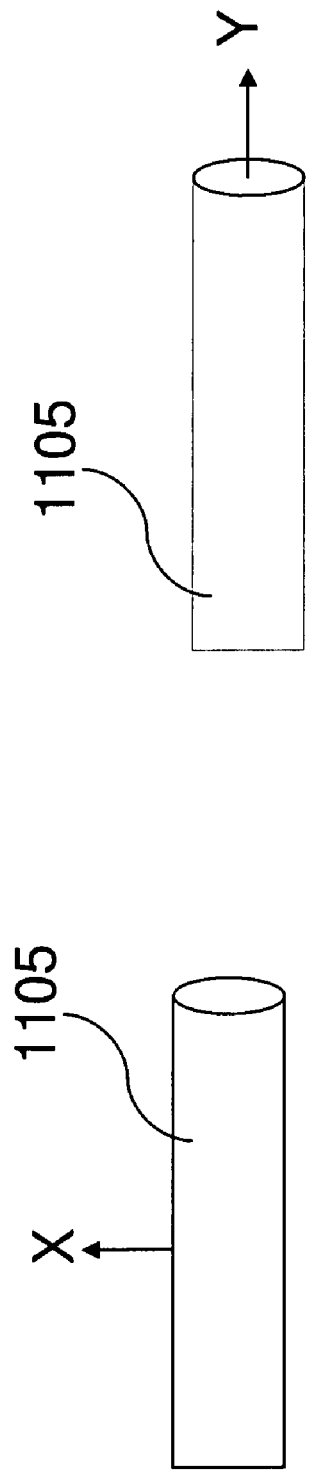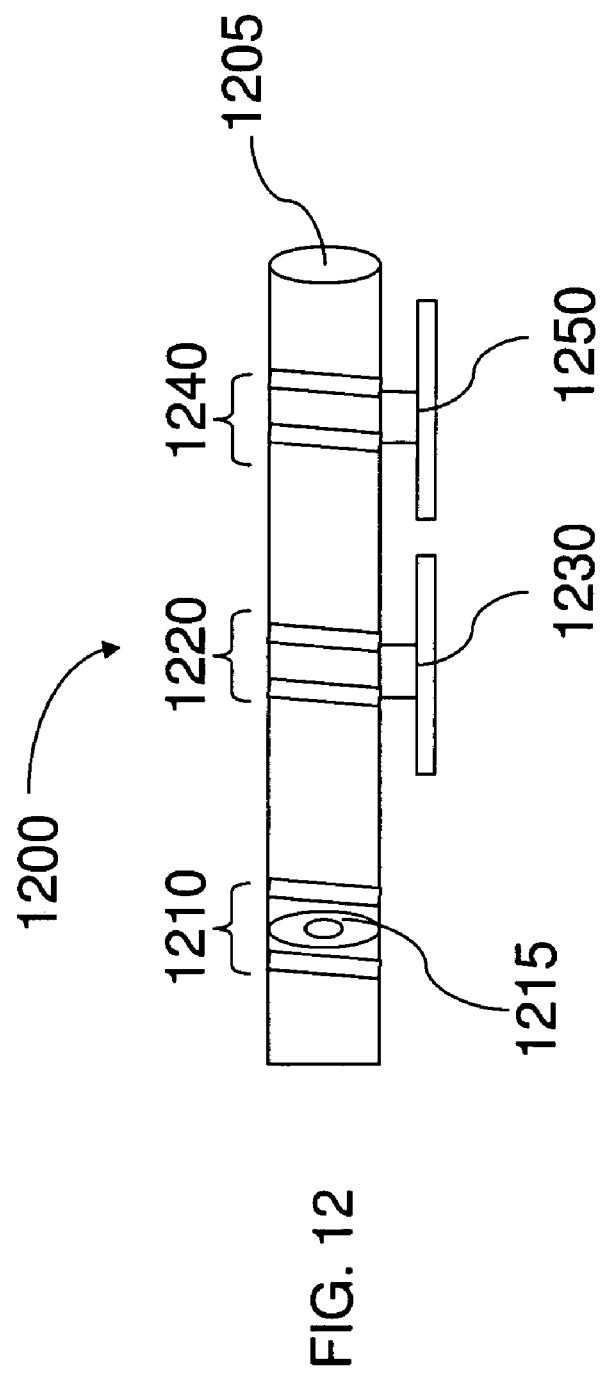

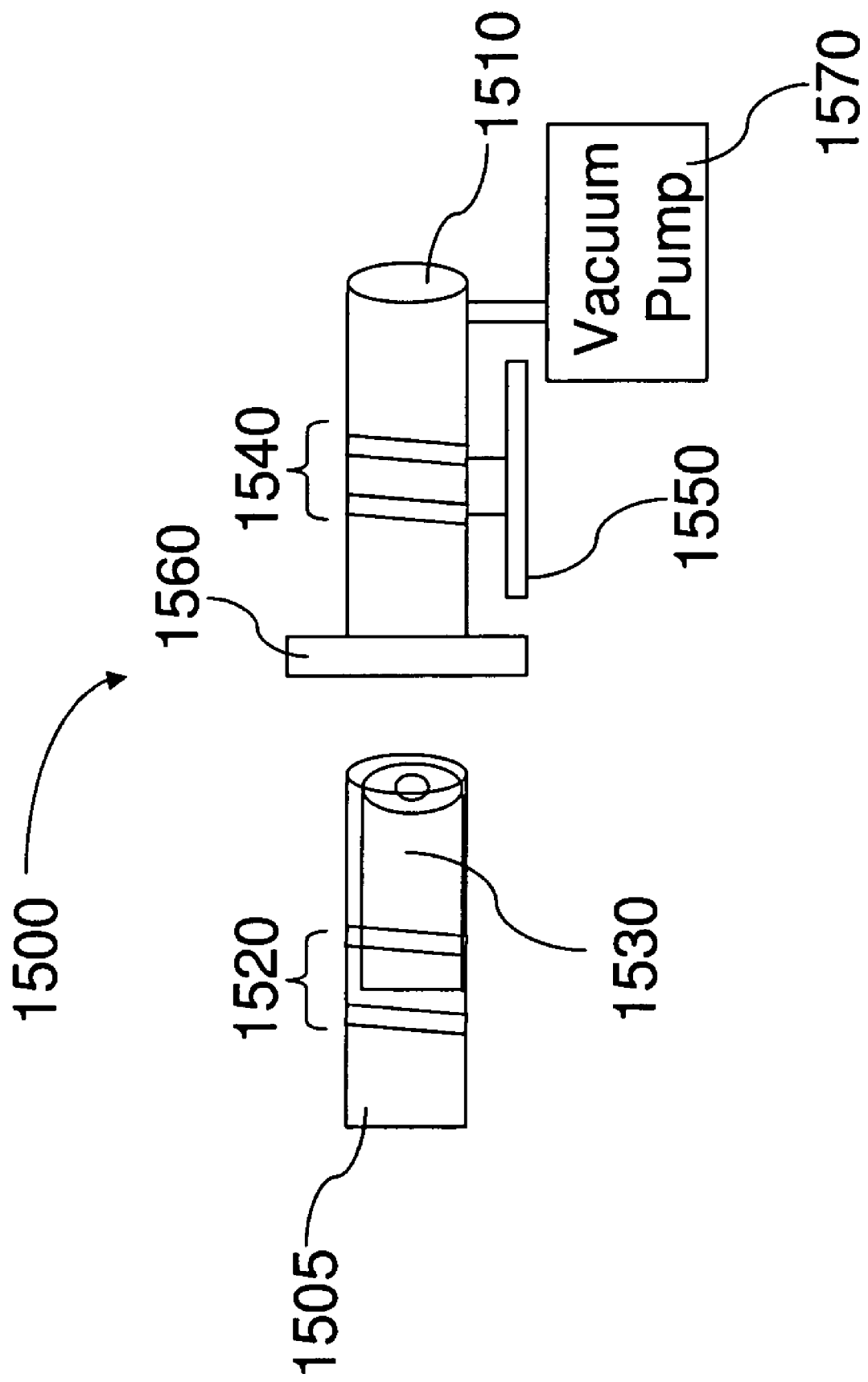

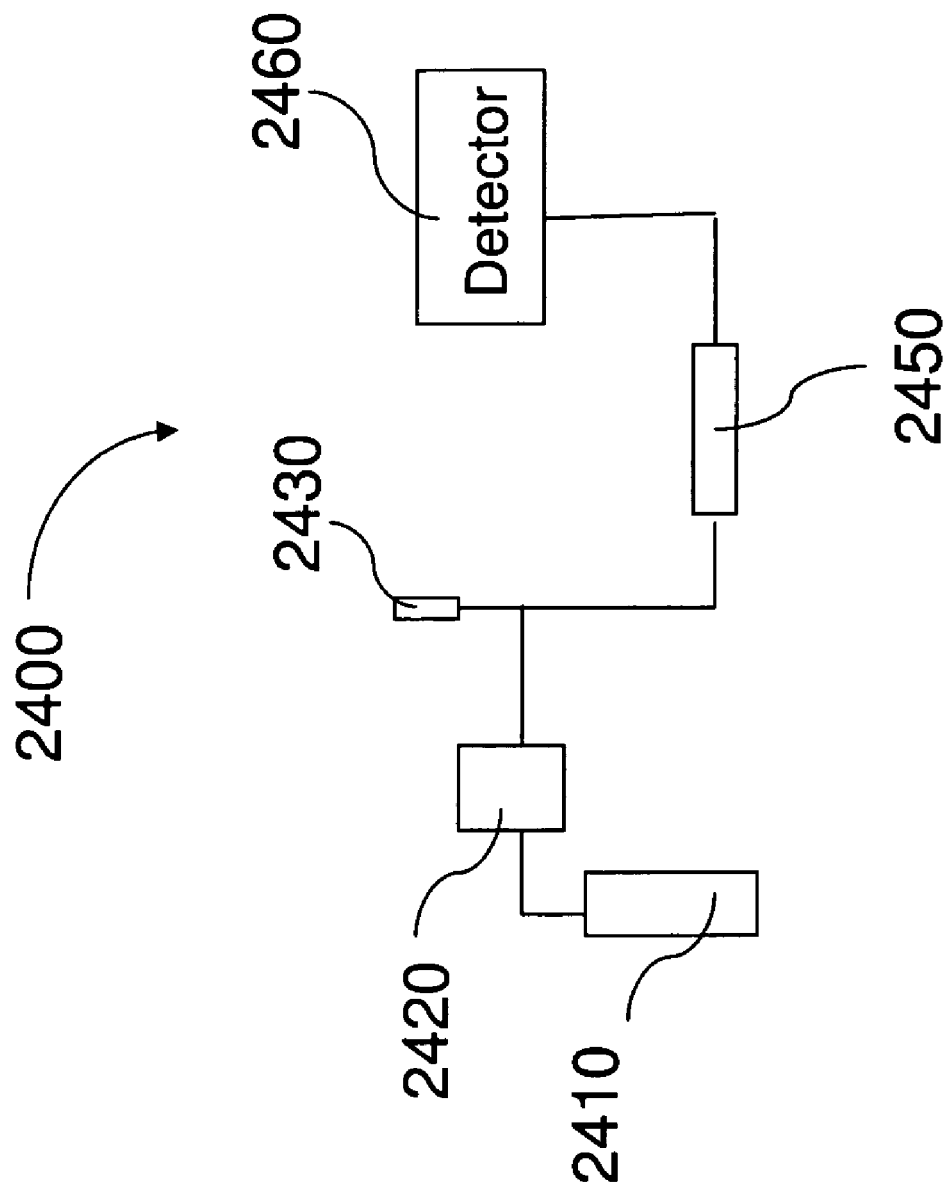

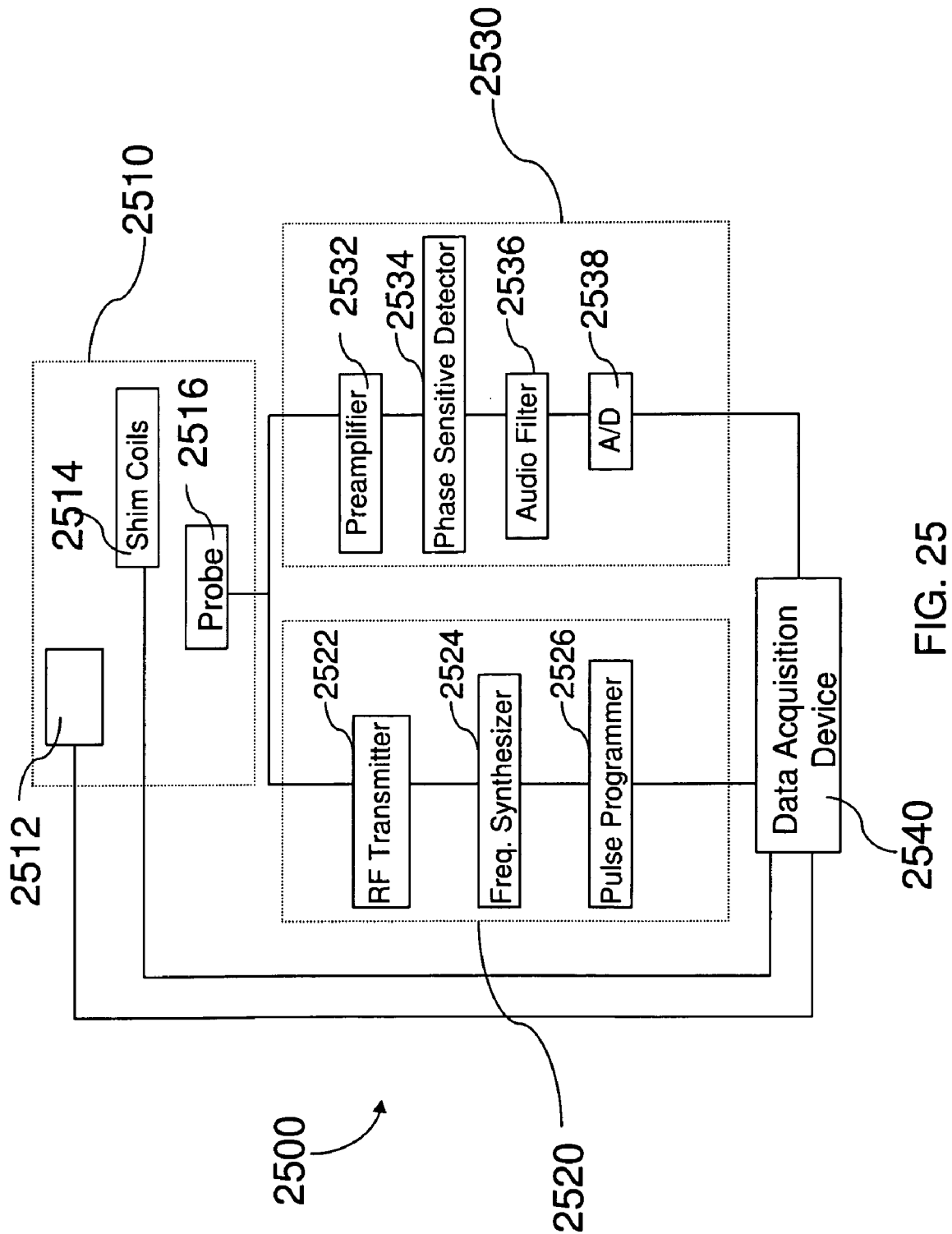

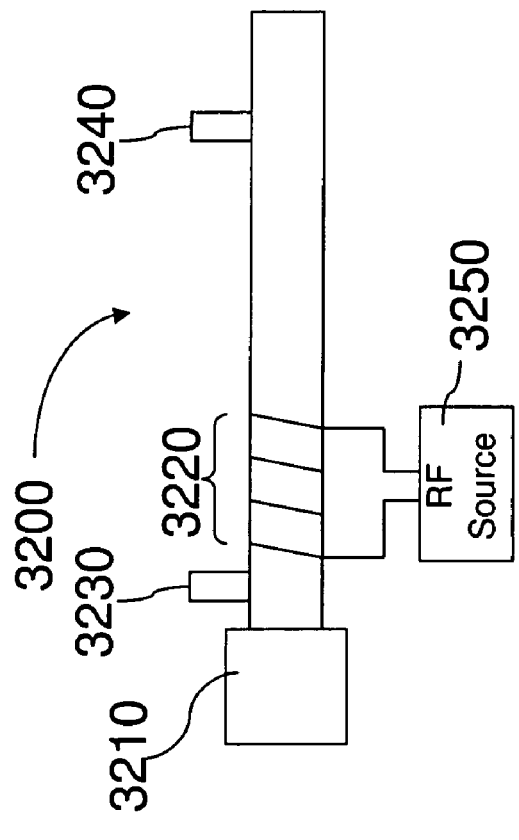
FIG. 32
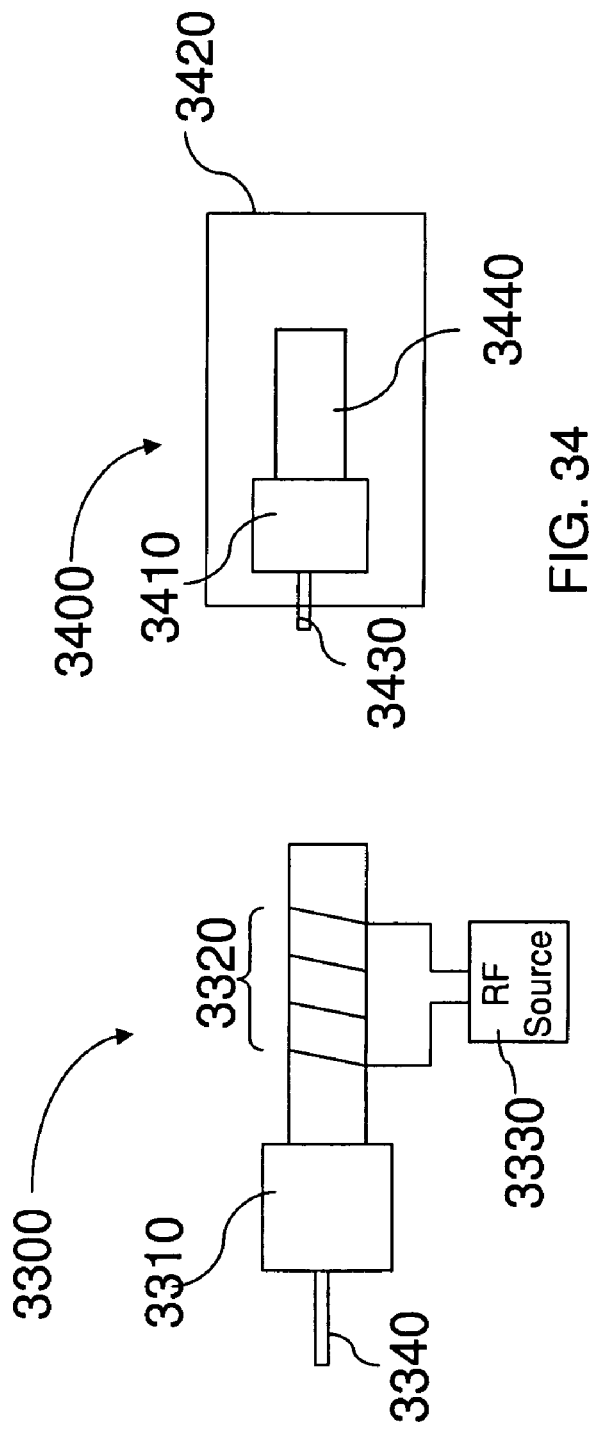
FIG. 34
FIG. 33

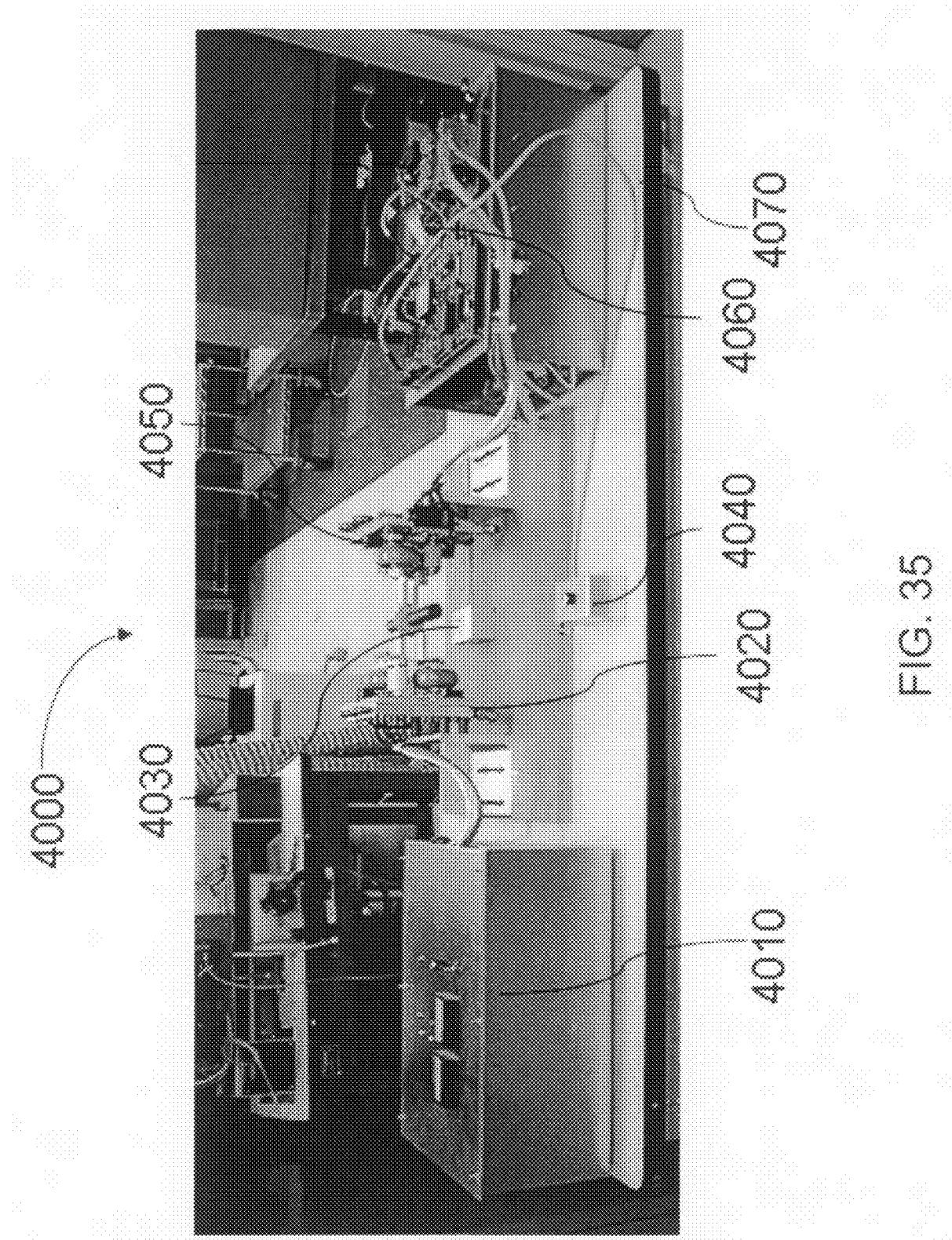

4310

4320

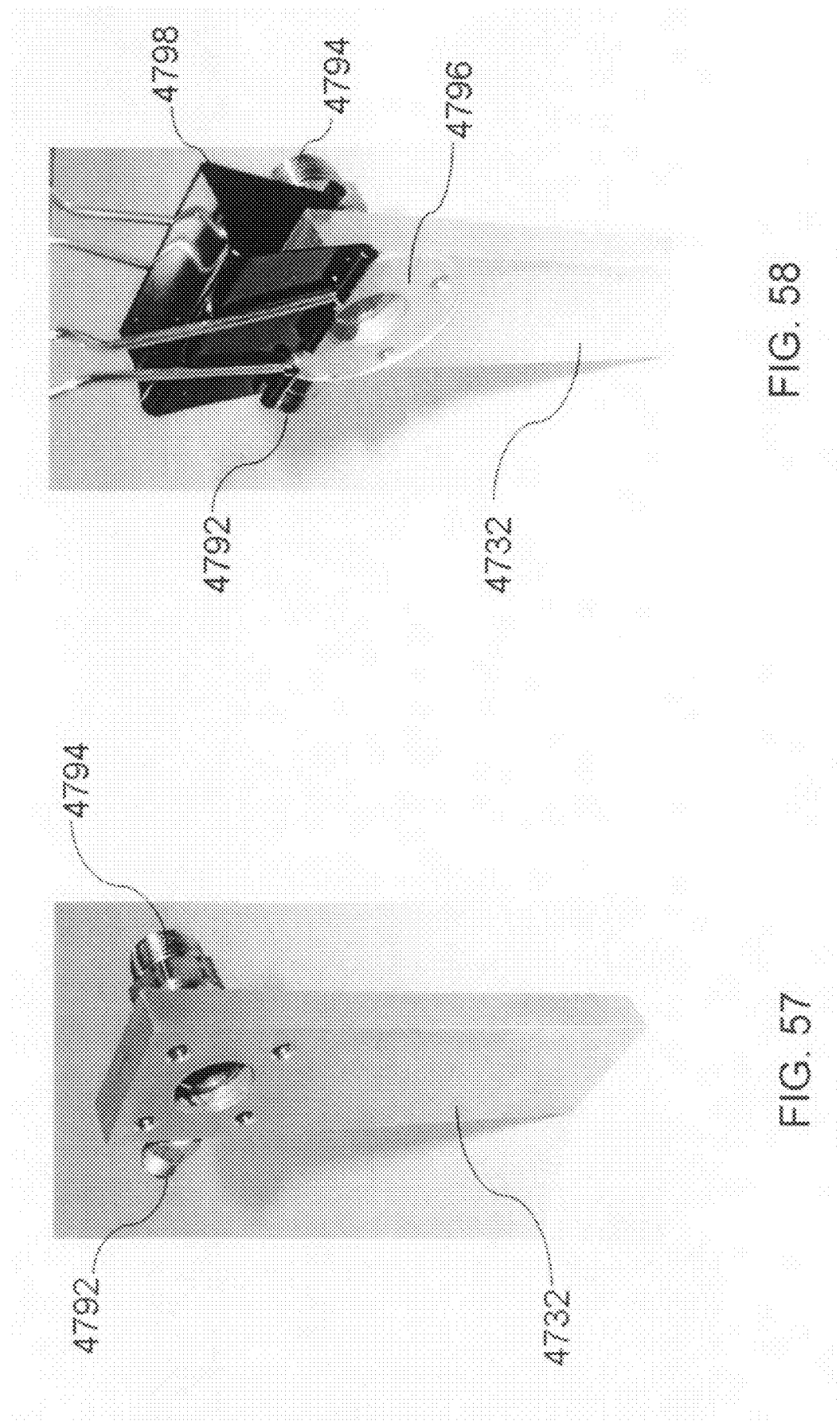

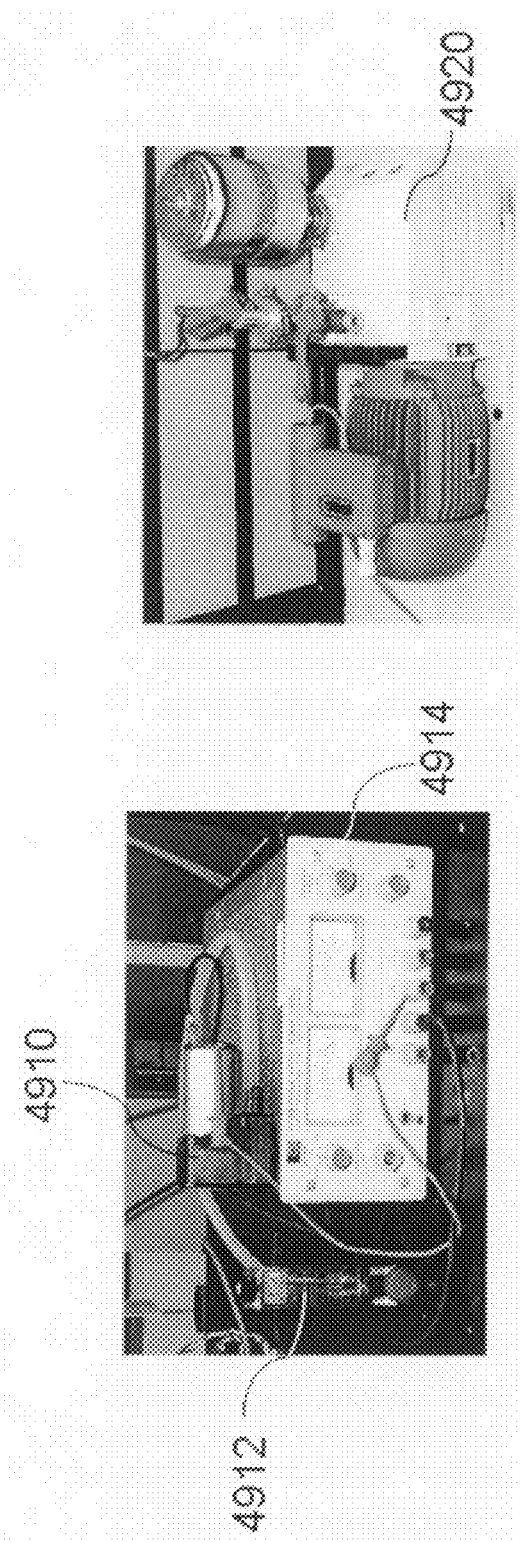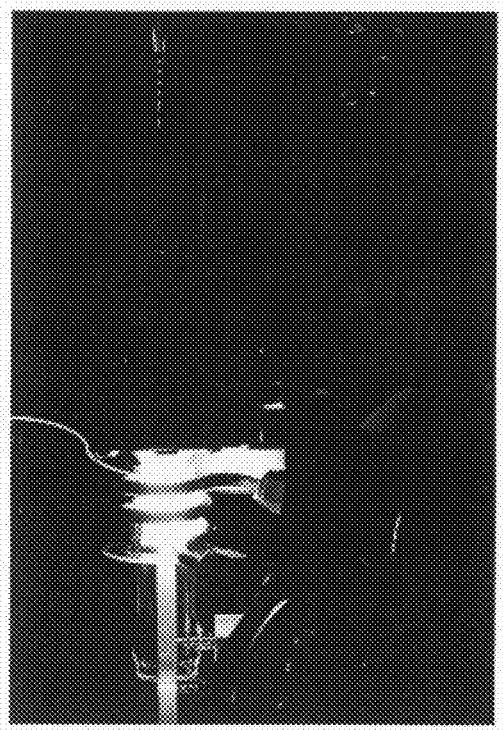
FIG. 59
FIG. 60
FIG. 61

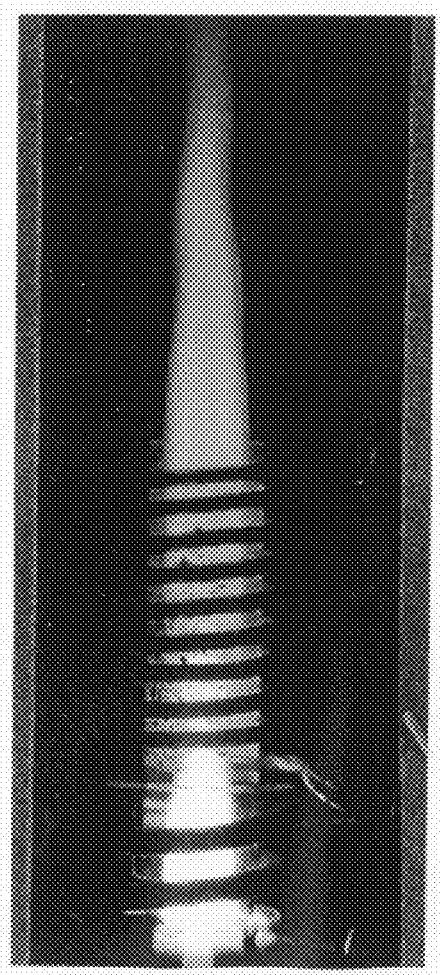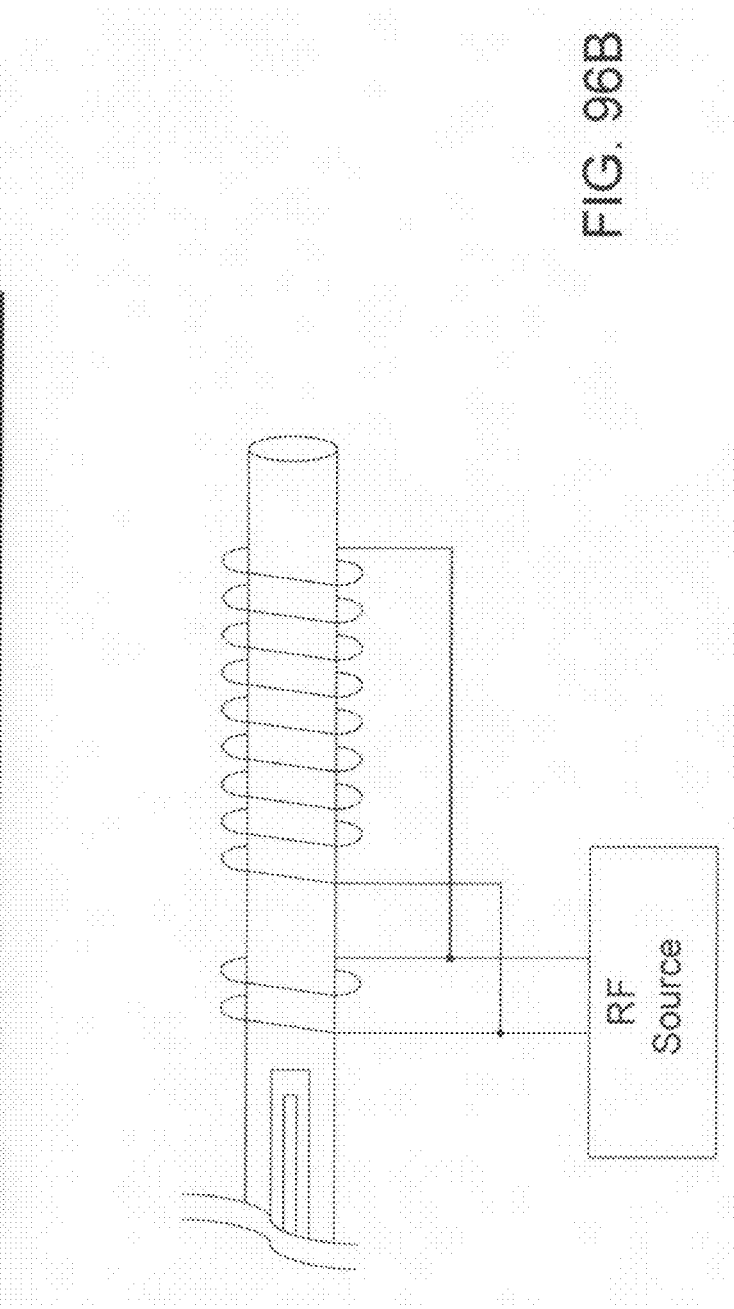
FIG. 96B

DEVICES AND SYSTEMS INCLUDING A BOOST DEVICE

PRIORITY APPLICATION

This application claims the benefit of, and is a continuation application of, U.S. Ser. No. 11/156,274 filed on Jun. 17, 2005.

FIELD OF THE TECHNOLOGY

Certain examples disclosed herein relate generally to boost devices, for example, boost devices configured to provide radio frequencies. More particularly, certain examples relate to boost devices that may be used to provide additional energy to an atomization source, such as a flame or a plasma.

BACKGROUND

Atomization sources, such as flames, may be used for a variety of applications, such as welding, chemical analysis and the like. In some instances, flames used in chemical analyses are not hot enough to vaporize the entire liquid sample that is injected into the flame. In addition, introduction of a liquid sample may result in zonal temperatures that may provide mixed results.

Another approach to atomization is to use a plasma source. Plasmas have been used in many technological areas including chemical analysis. Plasmas are electrically conducting gaseous mixtures containing large concentrations of cations and electrons. The temperature of a plasma may be as high as around 6,000-10,000 Kelvin, depending on the region of the plasma, whereas the temperature of a flame is often about 1400-1900 Kelvin, depending on the region of the flame. Due to the higher temperatures of the plasma, more rapid vaporization, atomization and/or ionization of chemical species may be achieved.

Use of plasmas may have several drawbacks in certain applications. Viewing optical emissions from chemical species in the plasma may be hindered by a high background signal from the plasma. Also, in some circumstances, plasma generation may require high total flow rates of argon (e.g., about 11-17 L/min) to create the plasma, including a flow rate of about 5-15 L/min of argon to isolate the plasma thermally. In addition, injection of aqueous samples into a plasma may result in a decrease in plasma temperature due to evaporation of solvent, i.e., a decrease in temperature due to desolvation. This temperature reduction may reduce the efficiency of atomization and ionization of chemical species in some contexts.

Higher powers have been used in plasmas to attempt to lower the detection limits for certain species, such as hard-to-ionize species like arsenic, cadmium, selenium and lead, but increasing the power also results in an increase in the background signal from the plasma.

Certain aspects and examples of the present technology alleviate some of the above concerns with previous atomization sources. For example, a boost device is shown here as a way to assist other atomization sources, such as flames, plasmas, arcs and sparks. Certain of these embodiments may enhance atomization efficiency, ionization efficiency, decrease background noise and/or increase emission signals from atomized and ionized species.

SUMMARY

In accordance with a first aspect, a boost device is disclosed. As used throughout this disclosure, the term "boost device" refers to a device that is configured to provide additional energy to another device, or region of that device, such as, for example, an atomization chamber, desolvation chamber, excitation chamber, etc. In certain examples, a radio frequency (RF) boost device may be configured to provide additional energy, e.g., in the form of radio frequency energy, to an atomization source, such as a flame, plasma, arc, spark or combinations thereof. Such additional energy may be used to assist in desolvation, atomization and/or ionization of species introduced into the atomization source, may be used to excite atoms or ions, may be used to extend optical path length, may be used to improve detection limits, may be used to increase sample size loading or may be used for many additional uses where it may be desirable or advantageous to provide additional energy to an atomization source. Other uses of the boost devices disclosed herein will be recognized by the person of ordinary skill in the art, given the benefit of this disclosure, and exemplary additional uses of the boost devices in chemical analysis, welding, sputtering, vapor deposition, chemical synthesis and treatment of radioactive waste are provided below to illustrate some of the features and uses of certain illustrative boost devices disclosed herein.

In accordance with other aspects, an atomization device is provided. In certain examples, the atomization device may include a chamber configured with an atomization source and at least one boost device configured to provide radio frequency energy to the chamber. The atomization source may be a device that may atomize and/or ionize species including but not limited to flames, plasmas, arcs, sparks, etc. The boost device may be configured to provide additional energy to a suitable region or regions of the chamber such that species present in the chamber may be atomized, ionized and/or excited. Suitable devices and components for designing or assembling the atomization source and the boost device will be readily selected by the person of ordinary skill in the art, given the benefit of this disclosure, and exemplary devices and components are discussed below.

In accordance with yet other aspects, another example of an atomization device is disclosed. In certain examples, the atomization devices include a first chamber and a second chamber. The first chamber includes an atomization source. The atomization source may be a device that may atomize and/or ionize species including but not limited to flames, plasmas, arcs, sparks, etc. The second chamber may include at least one boost device configured to provide radio frequency energy to the second chamber to provide additional energy to excite any atoms or ions that enter into the second chamber. In this embodiment, the first and second chambers may be in fluid communication such that species that are atomized or ionized in the first chamber may enter into the second chamber. Suitable examples of configurations for providing fluid communication between the first chamber and the second chamber are discussed below, and additional configurations may be selected by the person of ordinary skill in the art, given the benefit of this disclosure.

In accordance with other aspects, a device for optical emission spectroscopy ("OES") is disclosed. In certain examples, the OES device may include a chamber that includes an atomization source and at least one boost device configured to provide radio frequency energy to the chamber. In other examples, the OES device may include a first chamber that includes an atomization source and a second chamber that may include a boost device configured to provide radio frequencies to the second chamber. The atomization source may be a flame, plasma, arc, spark or other suitable devices that may atomize and/or ionize chemical species introduced into the first chamber. The OES device may further include a light detector configured to detect the amount of light and/or the wavelength of light emitted by species that are atomized and/or ionized using the OES device. Depending on the configuration of the OES device, the OES device may be used to detect atomic emission, fluorescence, phosphorescence and other light emissions. The OES device may further include suitable circuitry, algorithms and software. It will be within the ability of the person of ordinary skill in the art, given the benefit of this disclosure, to design suitable OES devices for an intended use. In certain examples, the OES device may include two or more plasma sources for atomization, ionization and/or detection of species.

In accordance with still other aspects, a device for absorption spectroscopy ("AS") is disclosed. In certain examples, the AS device may include a chamber that includes an atomization source and at least one boost device configured to provide radio frequency energy to the chamber. In other examples, the AS device may include at least a first chamber that includes an atomization source and a second chamber in fluid communication with the first chamber. The second chamber may include at least one boost device configured to provide radio frequency energy to the second chamber. The atomization source may be a flame, plasma, arc, spark or other suitable sources that may atomize and/or ionize chemical species. The AS device may further include a light source configured to provide one or more wavelengths of light and a light detector configured to detect the amount of light absorbed by the species present in one or more of the chambers. The AS device may further include suitable circuitry, algorithms and software of the type known in the art for such devices.

In accordance with yet other aspects, a device for mass spectroscopy ("MS") is disclosed. In certain examples, the MS device may include an atomization device coupled or hyphenated to a mass analyzer, a mass detector or a mass spectrometer. In some examples, the MS device includes an atomization device with a chamber that includes an atomization source and at least one boost device configured to provide radio frequency energy to the chamber. In other examples, the MS device includes a first chamber that includes an atomization source and a second chamber in fluid communication with the first chamber. The second chamber may include at least one boost device configured to provide radio frequency energy to the second chamber. The atomization source may be a flame, plasma, arc, spark or other suitable sources that may atomize and/or ionize chemical species. In some examples, the MS device may be configured such that the chamber, or first and second chambers, may be coupled or hyphenated to a mass analyzer, a mass detector or mass spectrometer such that species that exit the chamber, or first and second chambers, may enter into the mass analyzer, mass detector or mass spectrometer for detection. In other examples, the MS device may be configured such that species first enter into the mass analyzer, mass detector or mass spectrometer and then enter into the chamber, or first and second chambers, for detection using optical emission, absorption, fluorescence or other spectroscopic or analytical techniques. It will be within the ability of the person of ordinary skill in the art, given the benefit of this disclosure, to select suitable devices and methods to couple mass analyzers, mass detectors or mass spectrometers with the atomization devices disclosed herein to perform mass spectroscopy.

In accordance with yet other aspects, a device for infrared spectroscopy ("IRS") is disclosed. In certain examples, the IRS device may include an atomization device coupled or hyphenated to an infrared detector or infrared spectrometer. In some examples, the IRS device may include an atomization device with a chamber that includes an atomization source and at least one boost device configured to provide radio frequency energy to the chamber. In other examples, the IRS device may include a first chamber that includes an atomization source and a second chamber in fluid communication with the first chamber. The second chamber may also include at least one boost device configured to provide radio frequency energy to the second chamber. The atomization source may be a flame, plasma, arc, spark or other suitable sources that may atomize and/or ionize chemical species. In some examples, the IRS device may be configured such that the chamber, or first and second chambers, may be coupled or hyphenated to an infrared detector or infrared spectrometer such that species that exit the chamber, or the first and second chambers, may enter into the infrared detector for detection. In other examples, the IRS device may be configured such that species first enter into the infrared detector or infrared spectrometer and then enter into the chamber, or first and second chambers, for detection using optical emission, absorption, fluorescence or other suitable spectroscopic or analytical techniques.

In accordance with additional aspects, a device for fluorescence spectroscopy ("FLS") is disclosed. In certain examples, the FLS device may include an atomization device coupled or hyphenated to a fluorescence detector or fluorimeter. In some examples, the FLS device may include an atomization device with a chamber that includes an atomization source and at least one boost device configured to provide radio frequency energy to the chamber. In other examples, the FLS device may include a first chamber that includes an atomization source and a second chamber in fluid communication with the first chamber. The second chamber may include at least one boost device configured to supply radio frequency energy to the second chamber. The atomization source may be a flame, plasma, arc, spark or other suitable sources that may atomize and/or ionize chemical species. In some examples, the FLS device may be configured such that the chamber, or first and second chambers, of the atomization device may be coupled or hyphenated to a fluorescence detector or fluorimeter such that species that exit the chamber, or first and second chambers, may enter into the fluorescence detector for detection. In other examples, the FLS device may be configured such that species first enter into the fluorescence detector or fluorimeter and then enter into the chamber, or first and second chambers, of the atomization device for detection using optical emission, absorption, fluorescence or other suitable spectroscopic or analytical techniques.

In accordance with further aspects, a device for phosphorescence spectroscopy ("PHS") is disclosed. In certain examples, the PHS device may include an atomization device coupled or hyphenated to a phosphorescence detector or phosphorimeter. In some examples, the PHS device may include an atomization device with a chamber that includes an atomization source and at least one boost device configured to provide radio frequency energy to the chamber. In other examples, the PHS device may include a chamber that includes an atomization source and a second chamber in fluid communication with the first chamber. The second chamber may include at least one boost device configured to provide radio frequency energy to the chamber. The atomization source may be a flame, plasma, arc, spark or other suitable sources that may atomize and/or ionize chemical species. In some examples, the PHS device may be configured such that the chamber, or first and second chambers, of the atomization device may be coupled or hyphenated to a phosphorescence detector or phosphorimeter such that species that exit the chamber, or first and second chambers, may enter into the phosphorescence detector for detection. In other examples, the PHS device may be configured such that species first enter into the phosphorescence detector or phosphorimeter and then enter into the chamber, or first and second chambers, of the atomization device for detection using optical emission, absorption, fluorescence or other suitable spectroscopic or analytical techniques.

In accordance with other embodiments, a device for Raman spectroscopy ("RAS") is disclosed. In certain examples, the RAS device may include an atomization device coupled or hyphenated to a Raman detector or Raman spectrometer. In some examples, the RAS device may include an atomization device with a chamber that includes an atomization source and at least one boost device configured to provide radio frequency energy to the chamber. In other examples, the RAS device may include a first chamber that includes an atomization source and a second chamber in fluid communication with the first chamber. The second chamber may include a boost device configured to supply radio frequency energy to the second chamber. The atomization source may be a flame, plasma, arc, spark or other suitable sources that may atomize and/or ionize chemical species. In some examples, the RAS device may be configured such that the chamber, or first and second chambers, of the atomization device may be coupled or hyphenated to a Raman detector or Raman spectrometer such that species that exit the chamber, or first and second chambers, may enter into the Raman detector or spectrometer for detection. In other examples, the RAS device may be configured such that species first enter into the Raman detector or Raman spectrometer and then enter into the chamber, or first and second chambers, of the atomization device for detection using optical emission, absorption, fluorescence or other suitable spectroscopic or analytical techniques.

In accordance with other aspects, a device for X-ray spectroscopy ("XRS") is disclosed. In certain examples, the XRS device may include an atomization device coupled or hyphenated to an X-ray detector or an X-ray spectrometer. In some examples, the XRS device may include an atomization device with a chamber that includes an atomization source and at least one boost device configured to provide radio frequency energy to the chamber. In other examples, the XRS device may include a first chamber that includes an atomization source and a second chamber in fluid communication with the first chamber. The second chamber may include a boost device configured to supply radio frequency energy to the second chamber. The atomization source may be a flame, plasma, arc, spark or other suitable sources that may atomize and/or ionize chemical species. In some examples, the XRS device may be configured such that the chamber, or first and second chambers, of the atomization device may be coupled or hyphenated to an X-ray detector or an X-ray spectrometer such that species that exit the chamber, or first and second chamber, may enter into the X-ray detector or spectrometer for detection. In other examples, the XRS device may be configured such that species first enter into the X-ray detector or an X-ray spectrometer and then enter into the chamber, or first and second chambers, of the atomization device for detection using optical emission, absorption, fluorescence or other suitable spectroscopic or analytical techniques.

In accordance with additional aspects, a device for gas chromatography ("GC") is disclosed. In certain examples, the GC device may include an atomization device coupled or hyphenated to a gas chromatograph. In some examples, the GC device may include an atomization device with a chamber that includes an atomization source and at least one boost device configured to provide radio frequency energy to the chamber. In other examples, the GC device may include a first chamber that includes an atomization source and a second chamber in fluid communication with the first chamber. The second chamber may include at least one boost device configured to provide radio frequency energy to the second chamber. The atomization source may be a flame, plasma, arc, spark or other suitable sources that may atomize and/or ionize chemical species. In some examples, the GC device may be configured such that the chamber, or first and second chambers, of the atomization device may be coupled or hyphenated to a gas chromatograph such that species that exit the chamber, or first and second chambers, may enter into the gas chromatograph for separation and/or detection. In other examples, the GC device may be configured such that species first enter into the gas chromatograph and then enter into the chamber, or first and second chambers, of the atomization device for detection using optical emission, absorption, fluorescence or other suitable spectroscopic or analytical techniques.

In accordance with other aspects, a device for liquid chromatography ("LC") is disclosed. In certain examples, the LC device may include an atomization device coupled or hyphenated to a liquid chromatograph. In some examples, the LC device may include an atomization device with a chamber that includes an atomization source and at least one boost device configured to provide radio frequency energy to the chamber. In other examples, the LC device may include a first chamber that includes an atomization source and a second chamber in fluid communication with the first chamber. The second chamber may include at least one boost device configured to provide radio frequency energy to the second chamber. The atomization source may be a flame, plasma, arc, spark or other suitable sources that may atomize and/or ionize chemical species. In some examples, the LC device may be configured such that the chamber, or first and second chambers, of the atomization device may be coupled or hyphenated to a liquid chromatograph such that species that exit the chamber, or first and second chambers, may enter into the liquid chromatograph for separation and/or detection. In other examples, the LC device may be configured such that species first enter into the liquid chromatograph and then enter into the chamber, or first and second chambers, of the atomization device for detection using optical emission, absorption, fluorescence or other suitable spectroscopic or analytical techniques.

In accordance with still other aspects, a device for nuclear magnetic resonance ("NMR") is disclosed. In certain examples, the NMR device may include an atomization device coupled or hyphenated to a nuclear magnetic resonance detector or a nuclear magnetic resonance spectrometer. In some examples, the NMR device includes an atomization device with a chamber that includes an atomization source and at least one boost device configured to provide radio frequency energy to the chamber. In other examples, the NMR device may include a first chamber that includes an atomization source and a second chamber in fluid communication with the first chamber. The second chamber may include at least one boost device configured to provide radio frequency energy to the second chamber. The atomization source may be a flame, plasma, arc, spark or other suitable sources that may atomize and/or ionize chemical species. In some examples, the NMR device may be configured such that the chamber, or first and second chambers, of the atomization device may be coupled or hyphenated to a nuclear magnetic resonance detector or a nuclear magnetic resonance spectrometer such that species that exit the chamber, or first and second chambers, may enter into the nuclear magnetic resonance detector or nuclear magnetic resonance spectrometer for detection. In other examples, the nuclear magnetic resonance detector or nuclear magnetic resonance spectrometer may be configured such that species first enter into the nuclear magnetic resonance detector or nuclear magnetic resonance spectrometer and then enter into the chamber, or first and second chambers, of the atomization device for detection using optical emission, absorption, fluorescence or other spectroscopic or analytical techniques. It will be within the ability of the person of ordinary skill in the art, given the benefit of this disclosure, to select suitable devices and methods to couple nuclear magnetic resonance detectors or nuclear magnetic resonance spectrometers with the atomization devices disclosed here to perform nuclear magnetic resonance spectroscopy.

In accordance with additional aspects, a device for electron spin resonance ("ESR") is provided. In certain examples, the ESR device may include an atomization device coupled or hyphenated to an electron spin resonance detector or an electron spin resonance spectrometer. In some examples, the ESR device may include an atomization device with a chamber that includes an atomization source and at least one boost device configured to provide radio frequency energy to the chamber. In other examples, the ESR device may include a first chamber that includes an atomization source and a second chamber in fluid communication with the first chamber. The second chamber may include at least one boost device configured to provide radio frequency energy to the second chamber. The atomization source may be a flame, plasma, arc, spark or other suitable sources that may atomize and/or ionize chemical species. In some examples, the ESR device may be configured such that the chamber, or first and second chambers, of the atomization device may be coupled or hyphenated to an electron spin resonance detector or an electron spin resonance spectrometer such that species that exit the chamber, or first chamber and second chambers, may enter into the electron spin resonance detector or the electron spin resonance spectrometer for detection. In other examples, the electron spin resonance detector or the electron spin resonance spectrometer may be configured such that species first enter into the electron spin resonance detector or the electron spin resonance spectrometer and then enter into the chamber, or first and second chambers, of the atomization device for detection using optical emission, absorption, fluorescence or other spectroscopic or analytical techniques.

In accordance with other aspects, a welding device is disclosed. The welding device may include an electrode, a nozzle tip and at least one boost device surrounding at least some portion of the electrode and/or the nozzle tip and configured to provide radio frequencies. Welding devices which include a boost device may be used in suitable welding applications, for example, in tungsten inert gas (TIG) welding, plasma arc welding (PAW), submerged arc welding (SAW), laser welding, and high frequency welding. Exemplary configurations implementing the boost devices disclosed here in combination with torches for welding are discussed below and other suitable configurations will be readily selected by the person of ordinary skill in the art, given the benefit of this disclosure.

In accordance with additional aspects, a plasma cutter is provided. In certain examples, the plasma cutter may include a chamber or channel that includes an electrode. The chamber or channel in this example may be configured such that a cutting gas may flow through the chamber and may be in fluid communication with the electrode and such that a shielding gas may flow around the cutting gas and the electrode to minimize interferences such as oxidation of the cutting surface. The plasma cutter of this example may further include at least one boost device configured to increase ionization of the cutting gas and/or increase the temperature of the cutting gas. Suitable cutting gases may be readily selected by the person of ordinary skill in the art, given the benefit of this disclosure, and exemplary cutting gases include, for example, argon, hydrogen, nitrogen, oxygen and mixtures thereof.

In accordance with yet additional aspects, a vapor deposition device is disclosed. In certain examples, the vapor deposition device may include a material source, a reaction chamber, an energy source with at least one boost device, a vacuum system and an exhaust system. The vapor deposition device may be configured to deposit material onto a sample or substrate.

In accordance with yet other aspects, a sputtering device is disclosed. In certain examples, the sputtering device may include a target and a heat source including at least one boost device. The heat source may be configured to cause ejection of atoms and ions from the target. The ejected atoms and ions may be deposited, for example, on a sample or substrate.

In accordance with other aspects, a device for molecular beam epitaxy is disclosed. In certain examples, the device may include a growth chamber configured to receive a sample, at least one material source configured to provide atoms and ions to the growth chamber, and at least one boost device configured to provide radio frequency energy to the at least one material source. The molecular beam epitaxy device may be used, for example, to deposit materials onto a sample or substrate.

In accordance with further aspects, a chemical reaction chamber is disclosed. In certain examples, the chemical reaction chamber includes a reaction chamber with an atomization source and at least one boost device configured to provide radio frequency energy to the chemical reaction chamber. The reaction chamber may further include an inlet for introducing reactants and/or catalysts into the reaction chamber. The reaction chamber may be used, for example, to control or promote reactions between products or to favor one or more products produced from the reactants.

In accordance with yet other aspects, a device for treatment of radioactive waste is disclosed. In certain examples, the device includes a chamber configured to receive radioactive waste, an atomization source configured to atomize and/or oxidize radioactive waste and an inlet for introducing additional reactants or species that may react with, or interact with, the radioactive materials to provide stabilized forms. The stabilized forms may be disposed of, for example, using suitable disposal techniques, e.g., burial, etc.

In accordance with additional aspects, a light source is disclosed. In certain examples, the light source may include an atomization source and at least one boost device. The atomization source may be configured to atomize a sample, and the boost device may be configured to excite the atomized sample, which may emit photons to provide a source of light, by providing radio frequency energy to the atomized sample.

In accordance with yet other aspects, an atomization device that includes an atomization source and a microwave source (e.g., a microwave oven among other things) is disclosed. In certain examples, the microwave source may be configured to provide microwaves to the atomization source to create a plasma plume or extend a plasma plume. Atomization devices including microwave sources may be used for numerous applications including, for example, chemical analysis, welding, cutting and the like.

In accordance with other aspects, a miniaturized atomization device is disclosed. In certain examples, the miniaturized atomization device may be configured to provide devices that may be taken for in-field analyses. In certain other examples, microplasmas including at least one boost device are disclosed.

In accordance with additional aspects, a limited use atomization device is disclosed. In certain examples, the limited use atomization device may be configured with at least one boost device and may be further configured to provide sufficient power and/or fuel for one, two or three measurements. The limited use device may include a detector for measurement of species, such as, for example, arsenic, chromium, selenium, lead, etc.

In accordance with yet other aspects, an optical emission spectrometer configured to detect arsenic at a level of about 0.6 µg/L or lower is disclosed. In certain examples, the spectrometer may include a device that may excite atomized arsenic species for detection at levels of about 0.3 µg/L or lower.

In accordance with other aspects, an optical emission spectrometer configured to detect cadmium at a level of about 0.014 µg/L or lower is disclosed. In certain examples, the spectrometer may include a device that may excite atomized cadmium species for detection at levels of about 0.007 µg/L or lower.

In accordance with additional aspects, an optical emission spectrometer configured to detect lead at a level of about 0.28 µg/L or lower is disclosed. In certain examples, the spectrometer may include an atomization device and a boost device that may excite atomized lead species for detection at levels of about 0.14 µg/L or lower.

In accordance with yet additional aspects, an optical emission spectrometer configured to detect selenium at a level of about 0.6 µg/L or lower is disclosed. In certain examples, the spectrometer may include a device that may excite atomized selenium species for detection at levels of about 0.3 µg/L or lower.

In accordance with further aspects, a spectrometer including an inductively coupled plasma and at least one boost device is disclosed. In certain examples, the spectrometer may be configured to increase a sample emission signal without significantly increasing background signal. In some examples, the spectrometer may be configured to increase the sample emission signal at least about five-times or more, when compared with the emission signal of a device not including a boost device or a device operating with a boost device turned off. In other examples, the emission signal may be increased, e.g., about five times or more, without a substantial increase in background signal using a boost device.

In accordance with more aspects, a device for OES that includes an inductively coupled plasma and at least one boost device is disclosed. In certain examples the OES device may be configured to dilute the sample with a carrier gas by less than about 15:1. In certain other examples, the OES device may be configured to dilute the sample with a carrier gas by less than about 10:1. In yet other examples, the OES device may be configured to dilute the sample with a carrier gas by less than about 5:1.

In accordance with additional aspects, a spectrometer comprising an inductively coupled plasma and at least one boost device is provided. In certain examples, the spectrometer may be configured to at least partially block the signal from the primary plasma discharge.

In accordance with other aspects, a spectrometer including at least one boost device and configured for low UV measurements is provided. As used herein, "low UV" refers to measurements made by detecting light emitted or absorbed in the 90 nm to 200 nm wavelength range. In certain examples, the chamber comprising the boost device may be fluidically coupled to a vacuum pump to draw sample into the chamber. In other examples, the chamber comprising the boost device may also be optically coupled to a window or an aperture on a spectrometer such that substantially no air or oxygen may be in the optical path.

In accordance with yet other aspects, a method of enhancing atomization of species using a boost device is provided. Certain examples of this method include introducing a sample into an atomization device, and providing radio frequency energy from at least one boost device during atomization of the sample to enhance atomization. The atomization device may include any of the atomization sources with boost devices disclosed herein or other suitable atomization sources that will be selected by the person of ordinary skill in the art, given the benefit of this disclosure.

In accordance with additional aspects, a method of enhancing excitation of atomized species using a boost device is disclosed. Certain embodiments of this method include introducing a sample into an atomization device, atomizing and/or exciting the sample using the atomization device, and enhancing excitation of the atomized sample by providing radio frequency energy from at least one boost device. The atomization device may include any of the atomization sources with boost devices disclosed herein and other suitable atomization sources that will be selected by the person of ordinary skill in the art, given the benefit of this disclosure.

In accordance with further aspects, a method of enhancing detection of chemical species is provided. Certain embodiments of this method include introducing a sample into an atomization device configured to desolvate and atomize the sample, and providing radio frequency energy from at least one boost device to increase a detection signal from the atomized sample.

In accordance with yet additional aspects, a method of detecting arsenic at levels below about 0.6 µg/L is provided. Certain embodiments of this method include introducing a sample comprising arsenic into an atomization device configured to desolvate and atomize the sample, and providing radio frequency energy from at least one boost device to provide a detectable signal from an introduced sample comprising arsenic at levels less than about 0.6 µg/L. In certain examples, the sample signal to background signal ratio may be at least three or greater.

In accordance with yet other aspects, a method of detecting cadmium at levels below about 0.014 µg/L is disclosed. Certain embodiments of this method include introducing a sample comprising cadmium into an atomization device configured to desolvate and atomize the sample, and providing radio frequency energy from at least one boost device to provide a detectable signal from an introduced sample comprising cadmium at levels less than about 0.014 µg/L. In certain examples, the sample signal to background signal ratio may be at least three or greater.

In accordance with additional aspects, a method of detecting lead at levels below about 0.28 µg/L is disclosed. Certain embodiments of this method include introducing a sample comprising selenium into an atomization device configured to desolvate and atomize the sample, and providing radio frequency energy from at least one boost device to provide a detectable signal from an introduced sample comprising lead at levels less than about 0.28 µg/L. In certain examples, the sample signal to background signal ratio may be at least three or greater.

In accordance with other aspects, a method of detecting selenium at levels below about 0.6 µg/L is disclosed. Certain embodiments of this method include introducing a sample comprising selenium into an atomization device configured to desolvate and atomize the sample, and providing radio frequency energy from at least one boost device to provide a detectable signal from an introduced sample comprising selenium at levels less than about 0.6 μg/L. In certain examples, the sample signal to background signal ratio may be at least three or greater.

In accordance with yet other aspects, a method of separating and analyzing a sample comprising two or more species is provided. Certain embodiments of this method include introducing a sample into a separation device, eluting individual species from the separation device into an atomization device comprising at least one boost device, and detecting the eluted species. In some examples, the atomization device may be configured to desolvate and atomize the eluted species. In certain examples, the separation device may be a gas chromatograph, a liquid chromatograph (or both) or other suitable separation devices that will be readily selected by the person of ordinary skill in the art, given the benefit of this disclosure.

It will be recognized by the person of ordinary skill in the art, given the benefit of this disclosure, that the methods and devices disclosed herein provide a breakthrough in the ability to atomize, ionize and/or excite materials for various purposes such as materials analysis, welding, hazardous waste disposal, etc. For example, some embodiments disclosed herein permit devices to be constructed using a boost device as disclosed herein to provide chemical analyses, devices and instrumentation that may achieve detection limits that are substantially lower than those obtainable with existing analyses, devices and instrumentation, or such analyses, devices, and instrumentation may provide comparable detection limits at a lower cost (in equipment, time and/or energy). In addition, the devices disclosed herein may be used, or adapted for use, in numerous applications, including but not limited to chemical reactions, welding, cutting, assembly of portable and/or disposable devices for chemical analysis, disposal or treatment of radioactive waste, deposition of titanium on turbine engines, etc. These and other uses of the novel devices and methods disclosed herein will be recognized by the person of ordinary skill in the art, given the benefit of this disclosure, and exemplary uses and configurations using the devices are described below to illustrate some of the uses and various aspects of certain embodiments of the technology described.

BRIEF DESCRIPTION OF THE DRAWINGS

Certain examples are described below with reference to the accompanying drawings in which:

FIG. 1 is a first example of a boost device, in accordance with certain examples;

FIGS. 2A and 2B are examples of a boost device configured for use with a flame or primary plasma source, in accordance with certain examples;

FIGS. 2C and 2D are examples of a boost device comprising a microwave cavity, in accordance with certain examples;

FIGS. 3A and 3B are examples of pulsed and continuous mode application of a boost device, in accordance with certain examples;

FIGS. 4A and 4B are examples of a boost device, in accordance with certain examples;

FIG. 5 is an example of an atomization device including a boost device, in accordance with certain examples;

FIG. 6 is another example of an atomization device including a boost device, in accordance with certain examples;

FIG. 7 is an example of an atomization device with an electrothermal atomization source and a boost device, in accordance with certain examples;

FIG. 8 is an example of an atomization device with a plasma source and a boost device, in accordance with certain examples;

FIG. 9A is an example of a inductively coupled plasma, in accordance with certain examples;

FIG. 9B is an example of a helical resonator, in accordance with certain examples;

FIG. 10 is another example of an atomization device including a plasma source and a boost device, in accordance with certain examples;

FIG. 11A is an example of radial monitoring and FIG. 11B is an example of axial monitoring, in accordance with certain examples;

FIG. 12 is an example of an atomization device including a plasma source, a first boost device and a second boost device, in accordance with certain examples;

FIGS. 13A and 13B are examples of a second chamber including a manifold or interface, in accordance with certain examples;

FIG. 14A is an example of an atomization device with a first chamber with a flame or primary plasma source and a second chamber including a boost device, in accordance with certain examples;

FIG. 14B is an example of another boost device configuration suitable for providing energy to a chamber, such as, for example, the second chamber in FIG. 14A, in accordance with certain examples;

FIG. 15 is an example of a first chamber with a plasma source and a second chamber including a boost device, in accordance with certain examples;

FIG. 16 is an example of a first chamber with a plasma source and a second chamber including a first boost device and a second boost device, in accordance with certain examples;

FIG. 17 is an example of device for optical emission spectroscopy that includes a boost device, in accordance with certain examples;

FIG. 18 is an example of a single beam device for absorption spectroscopy that includes a boost device, in accordance with certain examples;

FIG. 19 is an example of a dual beam device for absorption spectroscopy that includes a boost device, in accordance with certain examples;

FIG. 20 is an example of a device for mass spectroscopy that includes a boost device, in accordance with certain examples;

FIG. 21 is an example of a device for infrared spectroscopy that includes a boost device, in accordance with certain examples;

FIG. 22 is an example of a device with a boost device suitable for use in fluorescence spectroscopy, phosphorescence spectroscopy or Raman scattering, in accordance with certain examples;

FIG. 23 is an example of a gas chromatograph that may be hyphenated to devices including a boost device, in accordance with certain examples;

FIG. 24 is an example of a liquid chromatograph that may be hyphenated to devices including a boost device, in accordance with certain examples;

FIG. 25 is an example of a nuclear magnetic resonance spectrometer suitable for use with devices including a boost device, in accordance with certain examples;

FIG. 26A is an example of a welding torch including a boost device, in accordance with certain examples;

FIG. 26B is an example of a DC or AC arc welder comprising a boost device, in accordance with certain examples;

FIG. 26C is another example of a DC or AC arc welder comprising a boost device, in accordance with certain examples;

FIG. 32 is an example of a device suitable for treating radioactive waste that includes a boost device, in accordance with certain examples;

FIG. 33 is an example of a device for providing a light source that includes a boost device, in accordance with certain examples;

FIG. 34 is an example of a device including an atomization source and a microwave source, in accordance with certain examples;

FIG. 35 is an example of the computer controlled hardware setup, in accordance with certain examples;

FIG. 41 is a schematic of the circuitry used with the supply and control box shown in FIGS. 37-39, in accordance with certain examples;

FIG. 57 shows the rear mounting block of the second chamber used in the hardware setup shown in FIG. 52, in accordance with certain examples;

FIG. 58 shows the rear mounting block of the second chamber with a quartz viewing window mounted, in accordance with certain examples;

FIG. 59 is a picture of a vacuum pump and power supply suitable for use in a computer controlled hardware setup, in accordance with certain examples;

FIG. 60 is a picture of a vacuum pump that was used in performing Example 4 described below, in accordance with certain examples;

FIG. 61 is a picture of a device including a first chamber with a plasma and a second chamber with a boost device turned off, in accordance with certain examples;

FIG. 96B shows the optical emission of an yttrium sample using the device of FIG. 96A, in accordance with certain examples;

Figure 98B:
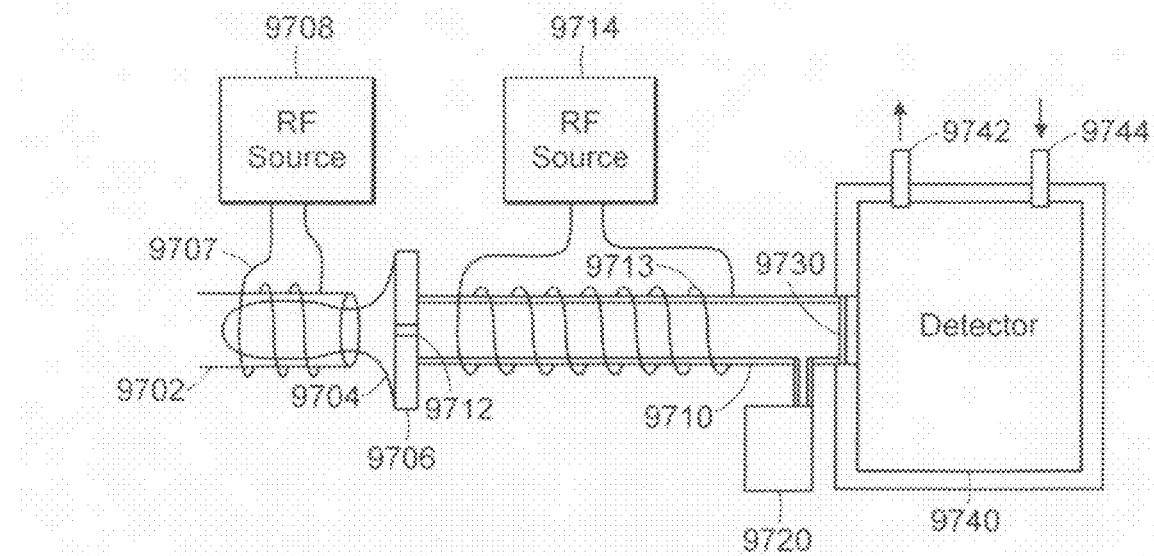
Figure 98A:
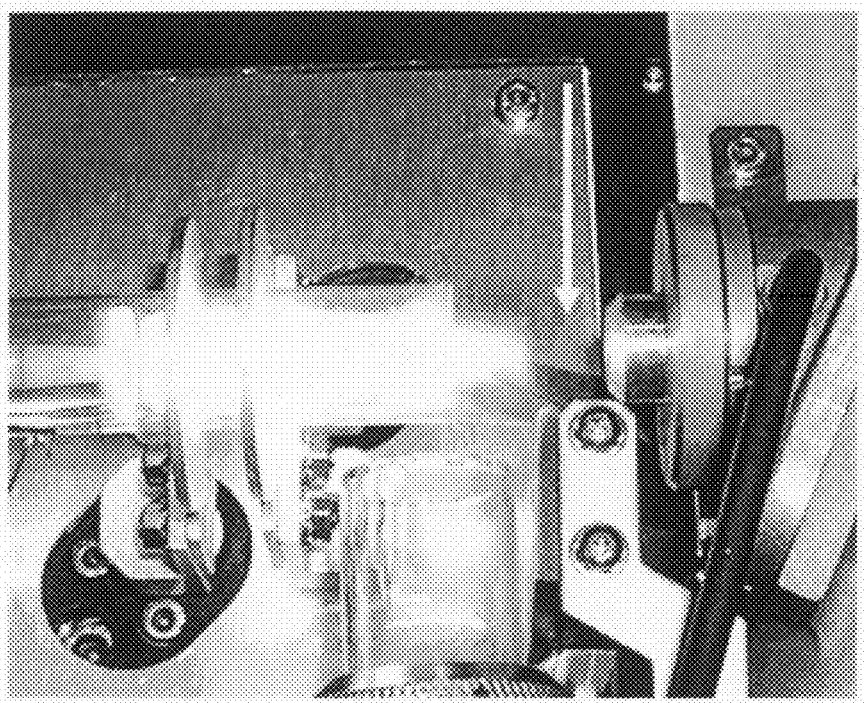
Figure 98C:
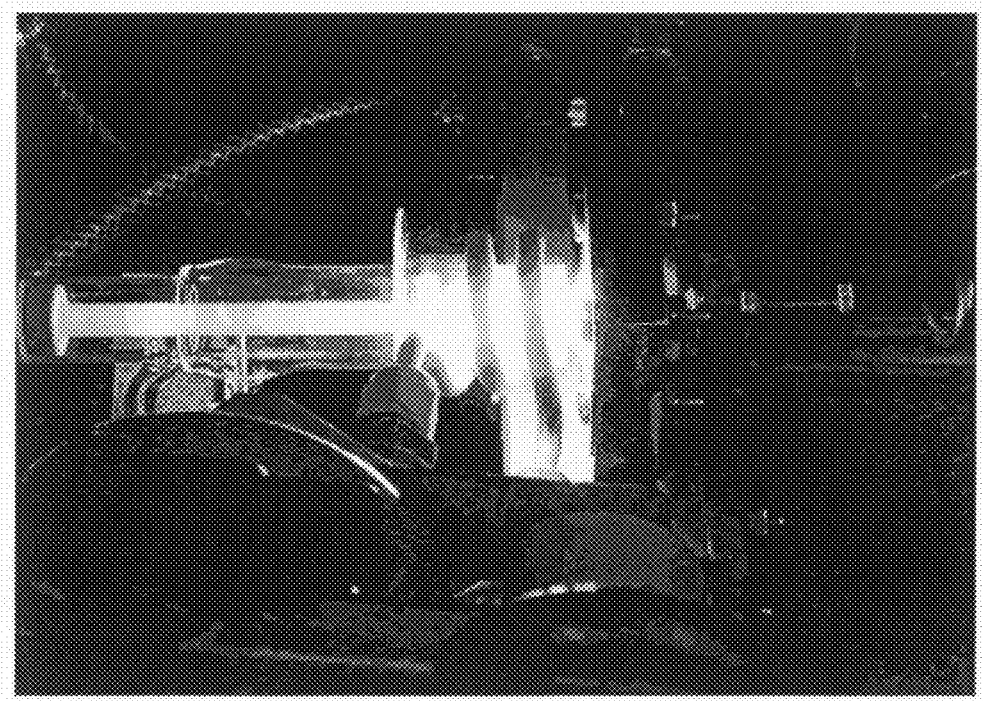
Figure 99:
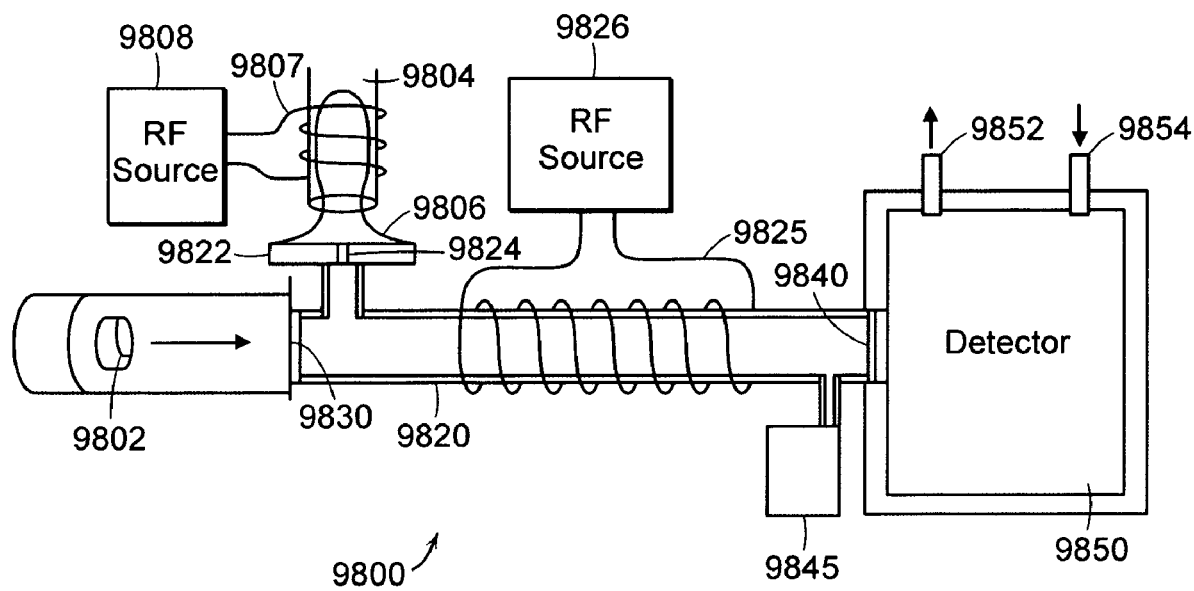

FIG. 98A is a photograph of an existing ICP-OES configuration, FIG. 98B is a schematic of an optical emission spectrometer configured for use in low UV measurements and FIG. 98C is a photograph of the configuration of FIG. 98B in operation, in accordance with certain examples; and FIG. 99 is a schematic of a spectrometer configured for use in low UV measurements, in accordance with certain examples.

It will be apparent to the person of ordinary skill in the art, given the benefit of this disclosure, that the exemplary electronic features, components, tubes, injectors, RF induction coils, boost coils, flames, plasmas, etc. shown in the figures are not necessarily to scale. For example, certain dimensions, such as the dimensions of the boost devices, may have been enlarged relative to other dimensions, such as the length and width of the chamber, for clarity of illustration and to provide a more user-friendly description of the illustrative examples discussed below. In addition, various shadings, dashes and the like may have been used to provide a more clear disclosure, and the use of such shadings, dashes and the like is not intended to refer to any particular material or orientation unless otherwise clear from the context.

DETAILED DESCRIPTION

The boost devices disclosed here represent a technological advance. Methods and/or devices including at least one boost device have numerous and widespread uses including, but not limited to, chemical analysis, chemical reaction chambers, welders, destruction of radioactive waste, plasma coating processes, vapor deposition processes, molecular beam epitaxy, assembly of pure light sources, low UV measurements, etc. Additional uses will be readily recognized by the person of ordinary skill in the art, given the benefit of this disclosure.

In accordance with certain examples ("certain examples" being intended to refer to some examples, but not all examples, of the present technology), atomization devices, spectrometers, welders and other devices disclosed below that include one or more boost devices may be configured with suitable shielding to prevent unwanted interference with other components included in the devices. For example, boost devices may be contained within lead chambers to shield other electrical components from the radio frequencies generated by the boost devices. In some examples, one or more ferrites may be used to minimize or reduce RF signals that might interfere with electronic circuitry. Other suitable shielding materials may be implemented including, but not limited to, aluminum, steel, and copper enclosures, honeycomb air filters, filtered connectors, RF gaskets and other RF shielding materials that will be readily selected by the person of ordinary skill in the art, given the benefit of this disclosure.

In accordance with certain examples, boost devices disclosed here may take numerous forms, such as, for example, a coil of wire electrically coupled to a radio frequency generator and/or radio frequency transmitter. In other examples, boost devices may include one or more circular plates or coils in electrical communication with a RF generator. In some examples, the boost device may be constructed by placing a coil of wire in electrical communication with a radio frequency generator. The coil of wire may be wrapped around a chamber to supply radio frequencies to the chamber.

Suitable RF generators and transmitters will be readily selected by the person of ordinary skill in the art, given the benefit of this disclosure, and exemplary RF generators and transmitters include, but are not limited to, those commercially available from ENI, Trazar, Hunttinger and the like. In some examples, the boost devices may be in electrical communication with a primary RF generator, such as an RF source used to power a primary induction coil. That is, in certain examples, the devices disclosed herein may include a single RF generator that is used to power both a primary energy source, e.g., an atomization source such as a plasma, as well as one or more boost devices. Accordingly, in some embodiments, a boost device can be understood to be one or more secondary RF energy sources, that, for example, may be coupled to a RF generator that may also be coupled to one or more primary RF energy sources.

In accordance with certain examples, devices disclosed herein may include one or more stages. For example, a device may include a desolvation stage that removes liquid solvent from a sample, an ionization stage that may convert atoms to ions and/or one or more excitation stages that may provide energy to excite atoms. The boost devices disclosed herein may be used in any one or more of these stages to provide additional energy.

In accordance with certain examples, an example of a boost device is shown in FIG. 1. In this example, a boost device 200 is shown coiled around a chamber 205. The boost device 200 includes radio frequency coils 210 electrically coupled to an RF generator 215. The boost device 210 is configured to provide radio frequency signals into the chamber 205. The exact frequency and power may vary depending on numerous factors including, but not limited to, the desired effect, the configuration of the chamber, etc. In certain examples, the boost device provides signals at a frequency of about 25 MHz to about 50 MHz, more particularly about 35 MHz to about 45 MHz, e.g., about 40.6 MHz. In other examples, the boost device provides signals at a frequency of about 5 MHz to about 25 MHz, more particularly about 7.5 to about 15 MHz, e.g., about 10.4 MHz. In yet other examples, the frequency ranges from about 1 kHz to about 100 GHz. For example, at lower frequencies the energy may be inductively coupled with the use of load coils or induction coils, such as those described in commonly owned U.S. application Ser. No. 10/730,779, the entire disclosure of which is hereby incorporated herein by reference for all purposes. At most frequencies, the energy may be capacitively coupled using plates or conductive coatings. At high frequencies, helical resonators or cavities may be used. Other suitable frequencies will be readily selected by the person of ordinary skill in the art, given the benefit of this disclosure, for various applications. In certain examples, the boost device may provide radio frequencies at a power of about 1 Watt to about 10,000 Watts, more particularly about 10 Watts to about 5,000 Watts. In other examples, the boost device provides radio frequencies at a power of about 100 Watts to about 2,000 Watts. In examples where a plasma is formed in a small capillary, such as a GC capillary tube using a dry gas, then a power of 1 watt or less may be used. If a large secondary chamber, e.g., having dimensions similar to a large fluorescent light tube, and high solvent loads are used, then powers as large as 10,000 watts or higher may be desirable to provide the desired results. Other suitable powers will be readily selected by the person of ordinary skill in the art, given the benefit of this disclosure. Suitable devices for providing radio frequency signals include, but are not limited to, radio frequency transmitters commercially available from numerous sources such as ENI, Trazar, Hunttinger and Nautel, and radio frequency circuits such as Impedance Matching Networks from ENI, or Trazar. Suitable circuitry for generating radio frequencies will be readily selected and/or designed by the person of ordinary skill in the art, given the benefit of this disclosure. In some examples, two or more radio frequency coils are used with each radio frequency coil being tuned to the same frequency or a different frequency and/or providing radio frequencies at the same power or a different power. Other configurations will be selected by the person of ordinary skill in the art, given the benefit of this disclosure.

In accordance with certain examples, the boost devices disclosed here may be configured to provide additional energy to "boost" or increase the energy already present in a chamber, such as the chamber of an atomization device that includes an atomization source. As used here, "atomization device" is used in the broad sense and is intended to include other processes that may take place in the chamber, such as desolvation, vaporization, ionization, excitation, etc. Atomization source refers to a heat source that is operative to atomize, desolvate, ionize, excite, etc. species introduced into the atomization source. Suitable atomization sources for various applications will be readily selected by the person of ordinary skill in the art, given the benefit of this disclosure, and exemplary atomization sources include, but are not limited to, flames, plasmas, arcs, sparks, etc.

Without wishing to be bound by any particular scientific theory or by this example, understanding of certain aspects may be had with reference to the introduction of a liquid sample. As liquid sample is introduced into an atomization device, an atomization source within the chamber may rapidly cool, due to desolvation. That is, a material amount of energy may be used to convert the liquid solvent into a gas, which may result in a decrease in temperature (or other loss of energy) of the atomization source. A result of this cooling is that less energy may be available to atomize, ionize and/or excite any species that were dissolved in the solvent. Using certain embodiments of boost devices disclosed here, additional energy may be provided to enhance atomization and/or ionization of any species present in the introduced sample and, in certain examples, the additional energy may be used to excite atoms and/or ions present in a sample. For example, referring to FIG. 2A and without wishing to be bound by any particular scientific theory or application or this one embodiment, atomization device 300 includes a chamber 305 that is surrounded by an induction coil 310 in communication with a radio frequency generator 315. Atomization source is shown in a first state 320 and is contained within chamber 305. In the example shown in FIG. 2A, the radio frequency generator 315 is turned off such that no radio frequencies are provided to radio frequency coils 310. Referring now to FIG. 2B, when radio frequency generator 315 is turned on, radio frequencies are provided to chamber 305, which results in conversion of the atomization source from the first state 320 to a second state 330. A result of application of radio frequencies to chamber 305 is the extension of the atomization source along the axial and/or radial lengths of the chamber to provide an increased effective area of energy for atomizing, ionizing and exciting a sample.

In accordance with certain examples, an additional example of adding energy to enhance atomization and/or ionization of chemical species is shown in FIGS. 2C and 2D. Referring to FIG. 2C, a high frequency source 250, which may be, for example, a 2.54 gigahertz magnetron, may be configured to be electrically coupled with a power supply 252 and a waveguide adapter 254. An electrical lead 256 provides electrical communication between a waveguide adapter 254 and a circulator 258, which itself may be electrically coupled to a coaxial resistor load 260, e.g., a 50 ohm load. The circulator 258 is in electrical communication with a microwave cavity 262, which is operative to provide radio frequencies into a chamber 264, which passes through the microwave cavity 262. In FIG. 2C, the high frequency source 250 is turned off so that no radio frequencies are transmitted to the microwave cavity 262 or the chamber 264 and the atomization source remains in a first state 266. Referring now to FIG. 2D, when the high frequency source 250 is turned on, radio frequencies are provided to the chamber 264, which results in conversion of atomization source from a first state 266 to a second state 268. A result of application of radio frequencies to the chamber 264 is the extension of the atomization source along the axial and/or radial lengths of the chamber to provide an increased effective area of energy for atomizing, ionizing and exciting a sample. Suitable commercially available devices for implementing the configurations shown in FIGS. 2A-2D will be readily selected by the person of ordinary skill in the art, given the benefit of this disclosure, and illustrative microwave generators and power supplies are commercially available from Aalter Reggio Emlia (Italy), illustrative coaxial resistors are commercially available from Bird Electronic Corp. (Solon, Ohio), and illustrative circulators are commercially available from National Electronics (Geneva, Ill.). Illustrative waveguide adapters may be fabricated, for example, using cross-bar mode transducers, which are commercially available from numerous sources, and by reference to numerous publications, such as, for example, the "ITT Reference Data for Radio Engineers (Sixth Edition)" section under "Waveguides and Resonators." Microwave cavities may be commercially obtained from numerous sources or will be readily fabricated by the person of ordinary skill in the art, given the benefit of this disclosure, and optionally with the guidance of C. J. M. Beenakker, *Spectrochimica Acta*, Vol. 31B, pp. 483 to 486 Pergamon Press 1976.

In accordance with certain examples, the person of ordinary skill in the art, given the benefit of this disclosure, may be able to extend the length of an atomization source by a selected or suitable amount. In certain examples, the length of the atomization source may be extended by using the boost devices. As one example, the atomization source may be extended by at least about three times its normal length along a longitudinal axis of a chamber using a boost device as disclosed herein. In other embodiments, the atomization source may be extended by at least about five times its normal length along the longitudinal axis of the chamber or at least about ten times it normal length along the longitudinal axis of the chamber using a boost device as disclosed herein.

In accordance with certain examples, the boost devices may be operated in a pulsed or continuous mode. As used here pulsed mode refers to providing radio frequencies in a non-continuous manner by providing radio frequencies followed by a delay before any subsequent radio frequencies are provided to the chamber. For example, referring to FIGS. 3A and 3B, channel A represents radio frequencies provided to a chamber, such as chamber 205 shown in FIG. 1. Channel B represents the time intervals in which any resulting signal is measured from the chamber, using, for example, a detector such as those discussed herein. The example shown in FIG. 3A is based on sampling of a detectable signal when radio frequencies are not provided. Without wishing to be bound by any particular scientific theory or this example, by sampling any detectable signal during periods where no radio frequencies are provided, higher signal-to-noise values may be achieved. It is possible, however, to sample a detectable signal from a species during periods where radio frequencies are provided. For example and referring to FIG. 3B, in a continuous mode, the radio frequencies are provided continuously and any resulting signal may be monitored continuously or intermittently. It will be within the ability of the person of ordinary skill in the art, given the benefit of this disclosure, to collect suitable signals during and/or between applications of radio frequencies using the boost devices disclosed herein.

In accordance with certain other examples, an additional example of a boost device is shown in FIGS. 4A and 4B. In the configuration shown in FIGS. 4A and 4B, a boost device 400 includes a support or plate 405, a first electrode 410 and a second electrode 420 each mounted to support 405. Each of the first electrode 410 and the second electrode 420 may be configured to receive a chamber within the interior of the electrodes. The support or plate 405 may be electrically coupled to a radio frequency transmitter or generator to provide radio frequencies to the first electrode 410 and the second electrode 420. In this example, the first electrode 410 and the second electrode 420 may be operated at the same frequency or may be individually tuned to provide different frequencies.

In certain examples, the first electrode 410 may be operated with a radio frequency of about 10 MHz to about 2.54 GHz, and in other examples the second electrode 420 may be operated with a radio frequency of about 100 kHz to about 2.54 GHz. In other examples, the first electrode 410 may be operated with radio frequencies from about 10 MHz to about 200 MHz, and second electrode 420 may be operated with radio frequencies from about 100 kHz to about 200 MHz. The first electrode 410 and the second electrode 420 may take the form of the induction coil shown below in FIG. 9 or the induction coils discussed in commonly assigned patent applications U.S. Ser. No. 10/730,779, filed on Dec. 9, 2003, and entitled "ICP-OES and ICP-MS Induction Current," the entire disclosure of which is hereby incorporated herein by reference for all purposes. For the first electrode 410 and for the second electrode 420, radio frequencies from about 20 MHz to about 500 MHz may be provided using, for example, helical resonators, an example of which is shown in FIG. 9B and is discussed in more detail below. In some examples, the first electrode 410 and the second electrode 420 may be operated using radio frequencies from about 500 MHz to about 5 GHz using a microwave cavity or resonant cavity, an example of which is shown in FIG. 2C. In certain examples, capacitive coupling of energy may also be used in place of second electrode 420; an example of this configuration is shown in FIG. 14B and is described in more detail below. Other suitable radio frequencies and powers will be readily selected by the person of ordinary skill in the art, given the benefit of this disclosure.

In accordance with certain examples, an example of an atomization device is shown in FIG. 5. Atomization device 500 includes a chamber 505, a flame source 510, and a boost device 520. The boost device 520 is electrically coupled to support 530, which itself may be electrically coupled to radio frequency transmitter or generator or both (not shown). The chamber 505 may be constructed of suitable materials, such as quartz, and may include a cooling tube or jacket (not shown) to surround the chamber to reduce the temperatures experienced by the boost device. In this example, the flame source 510 may be any suitable flame, such as a methane/air flame, a methane/oxygen flame, hydrogen/air flame, a hydrogen/oxygen flame, an acetylene/air flame, an acetylene/oxygen flame, an acetylene/nitrous oxide flame, a propane/air flame, a propane/oxygen flame, a propane/nitrous flame, a naphtha/air flame, a naphtha/oxygen flame, a natural gas/nitrous flame, a natural gas/air flame, a natural gas/oxygen flame and other flames that may be generated using a suitable fuel source and a suitable oxidant gas. Such flames may generally be created by introducing fuel and oxygen in selected ratios and igniting the mixture with a spark, arc, flame or the like. The exact temperature of the flames may vary depending on the fuel and oxidant gas source and depending on the distance from the burner tip. For example, the highest flame temperatures are typically found slightly above the primary combustion zone with lower temperatures in the interconal region and in the outer cone. In at least certain examples, the temperature of at least some portion of the flame may be at least about 1700° C. For example, a natural gas/air flame may have a temperature of about 1700-1900° C., whereas a natural gas/oxygen flame may have a temperature of about 2700-2900° C. and a hydrogen/oxygen flame may have a temperature of about 2550-2700° C. Without wishing to be limited thereby, flame sources may be efficient at desolvation in some applications, but inefficient at atomization and ionization due to relatively low temperatures. Using the boost devices disclosed here, however, the efficiency of ionization and/or atomization may be increased using flame sources, such as hydrogen/oxygen flames, in combination with a boost device. For example, using one or more boost devices disclosed here in combination with a hydrogen/oxygen flame, it may be possible to achieve the benefits of having a high heat capacity of a flame for desolvation and (e.g., followed by) extreme plasma temperatures for greater excitation. This result is advantageous for several reasons including, but not limited to, reduced operating costs, simpler design, less RF noise, better signal-to-noise ratios, etc., although not every embodiment will meet or address one or more of these advantages.

In addition, a flame may tolerate increased sample loading while leaving the RF power from the boost device available for sample ionization. To minimize the spectral background of the flame while maintaining high gas purity, a "water welder" may be used to decompose any produced water to its elements of hydrogen and oxygen. Suitable water welders are commercially available, for example, from SRA (Stan Rubinstein Assoc.) or KingMech Co., LTD. The flame (in certain embodiments) also preferably should not present significant additional background signal than the background observed with the desolvation of aqueous samples. The person of ordinary skill in the art, given the benefit of this disclosure, will be able to design suitable atomization devices including flame sources and boost devices.

In accordance with certain examples, when using the device shown in FIG. 5, a fluid sample may be introduced into the flame to desolvate the sample. Desolvation may (in certain embodiments) be accomplished by spraying the species into the chamber in the form of a fine mist. Suitable devices for creating mists of species include nebulizers such as those commercially available from J. E. Meinhard Assoc. Inc or CPI International. A fluid sample may be introduced into a nebulizer and may be mixed with an aerosol carrier gas, such as argon, neon, etc. The carrier gas nebulizes the liquid sample droplets to provide finely divided droplets that may be carried into the atomization device. Other suitable devices for delivering samples to the atomization device will be readily selected by the person of ordinary skill in the art, given the benefit of this disclosure, and illustrative devices include, but are not limited to, a concentric nebulizer, a cross-flow nebulizer, an ultrasonic nebulizer and the like.

In accordance with certain examples, as sample is introduced through a nebulizer into the atomization device shown in FIG. 5, fluid may be vaporized from the sample by a flame or a primary plasma. Chemical species in the sample may be atomized and/or ionized using the energy produced by the flame or the primary plasma. To increase the efficiency of atomization and/or ionization, the boost device may be used to provide radio frequencies to chamber 505. Boost device may be configured to provide additional energy such that energy lost due to desolvation is restored by the boost, and, in certain examples, the total energy in the chamber exceeds the amount of energy present when only a flame or primary plasma is used. Such additional energy increases the amount of species that are atomized and/or ionized, which increases the number of species available for detection. In certain examples, atomization devices including the boost devices disclosed here may allow for the use of reduced amounts of sample due to the higher efficiency of atomization and ionization.

Another example of an atomization device is disclosed in FIG. 6. Atomization device 600 includes a chamber 605, a flame or primary plasma 610, and a boost device 620. The boost device 620 includes a support 630, which may be electrically coupled to a radio frequency transmitter or generator (not shown). In the configuration shown in FIG. 6, the boost device 620 has been positioned downstream from the flame or primary plasma 610 in the "ionization region" of chamber 605. As used here, for illustrative purposes only, the ionization region refers to the region of a chamber where signal is measured or detected. For example and again for illustrative purposes only, region 650 in FIG. 6 is referred to in some instances herein as the desolvation region and region 660 is referred to in some instances herein as the ionization region. It will be understood by the person of ordinary skill in the art, given the benefit of this disclosure, however, the desolvation may occur at least to some extent in the ionization region and detection of chemical species may occur at least to some extent in the desolvation region depending on the exact configuration of the device, and it will also be understood by the person of ordinary skill in the art, given the benefit of this disclosure, that there need not be fixed or discrete boundaries that separate the desolvation and ionization regions. As sample is introduced into the flame or primary plasma 605, the flame or primary plasma 605 desolvates, atomizes, ionizes and/or excites the sample. The atomized and/or ionized sample may be carried downstream toward boost device 620 using for example an assist or carrier gas such as nitrogen gas, argon gas, etc. The atoms and ions may not be excited when exiting the desolvation region and in certain embodiments provide little or no detectable signal. Using boost device 620, atomized and/or ionized sample that enters the ionization region may be excited to provide a detectable signal. For example, atoms and ions may be excited by the radio frequencies introduced by boost device 620 such that optical emission occurs, which may be detected using suitable detectors as discussed in more detail below. It will be within the ability of the person of ordinary skill in the art, given the benefit of this disclosure, to position boost devices at suitable positions along a chamber to provide a desired result such as, for example, atomization, ionization or excitation.

In accordance with certain examples, an example of an atomization device using an electrothermal atomization source is shown in FIG. 7. An atomization device 700 includes a chamber 705, an electrothermal atomizer 710, a boost device 720 and a radio frequency generator 730. Electrothermal atomizers, such as graphite tubes or cups, atomize sample by first evaporating liquid from the sample at a relatively low temperature (e.g., about 1200° C.) and then ashing the sample at a higher temperature (e.g., about 2000-3000° C.), which results in atomization of the sample. The atomized sample may be carried down chamber 705 using a carrier gas, such as argon, nitrogen, etc., and may be excited for detection using the boost device 720. The person of ordinary skill in the art, given the benefit of this disclosure, will be able to design atomization devices with electrothermal atomizers and boost devices.

In accordance with certain examples, an example of an atomization device using a plasma is shown in FIG. 8. An atomization device 800 includes a chamber 805, a plasma 810, and a boost device 820. The boost device 820 includes a support which may be in electrical communication with a radio frequency generator 830. Without wishing to be bound by any particular scientific theory, plasmas suffer less than flames from interferences, such as oxide formation, because of the higher temperatures of the plasmas. In addition, spectra may be obtained from a plurality of sample species under a single set of conditions, which allows for measurement of many species simultaneously. The higher temperatures in the plasmas may also provide improved detection limits and be useful for detection of non-metal species. A plasma may be created when a gas, such as argon, is excited and/or ionized to form ions and electrons, and in certain instances cations. The ions may be maintained at high temperatures by using an external power source, such as a DC electrical source. For example, two or more electrodes may be positioned around high temperature argon ions and electrons to provide current between the electrodes to maintain the plasma temperature. Other suitable power sources for sustaining plasmas include, but are not limited to, radio frequency induction coils, such as those used in inductively coupled plasmas, and microwaves, such as those used in microwave induced plasmas. For convenience purposes only, an inductively coupled plasma device is described below, but the boost devices disclosed herein may be readily used with other plasma devices.

Figure 2C:
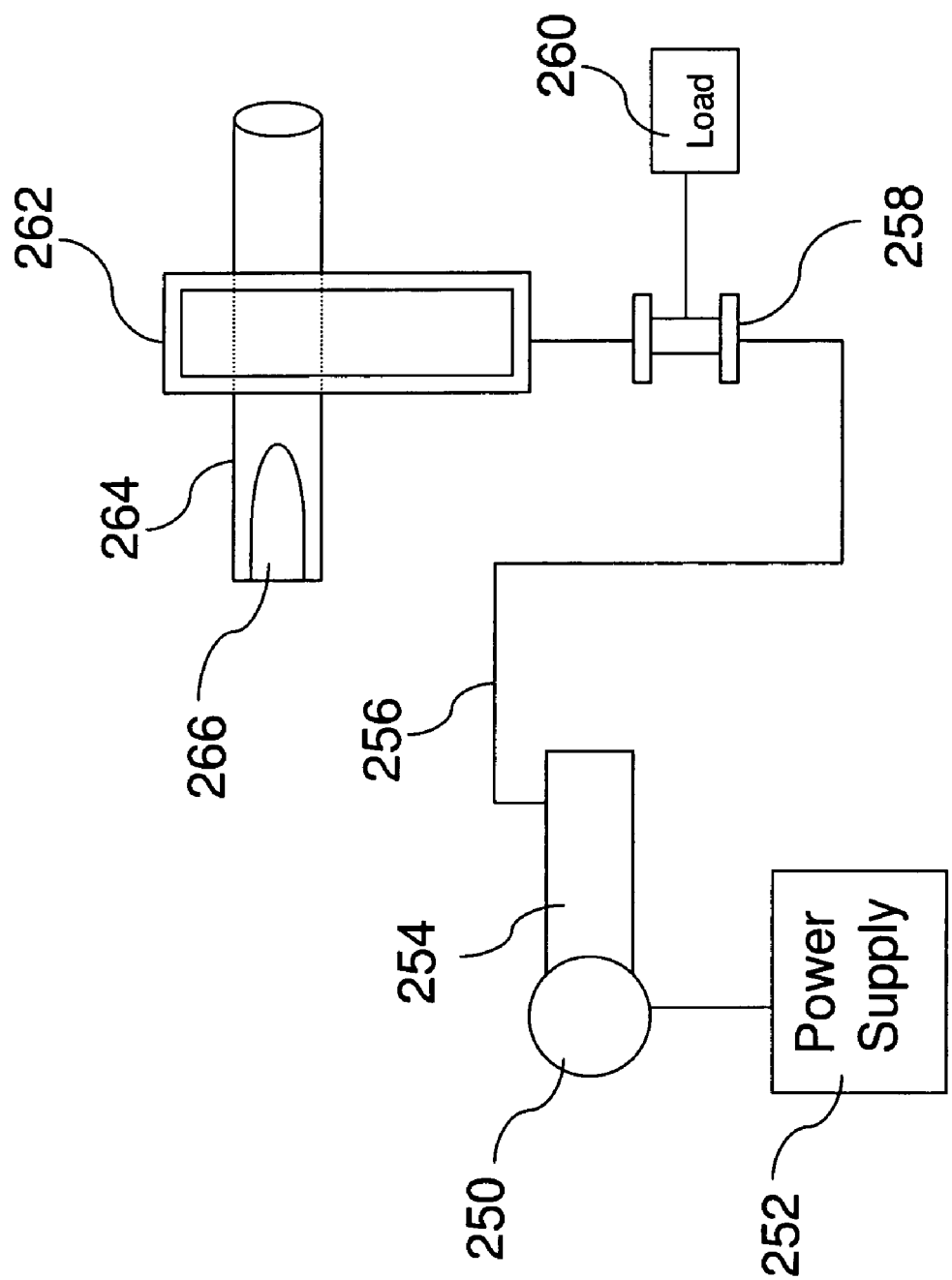
Figure 2D:
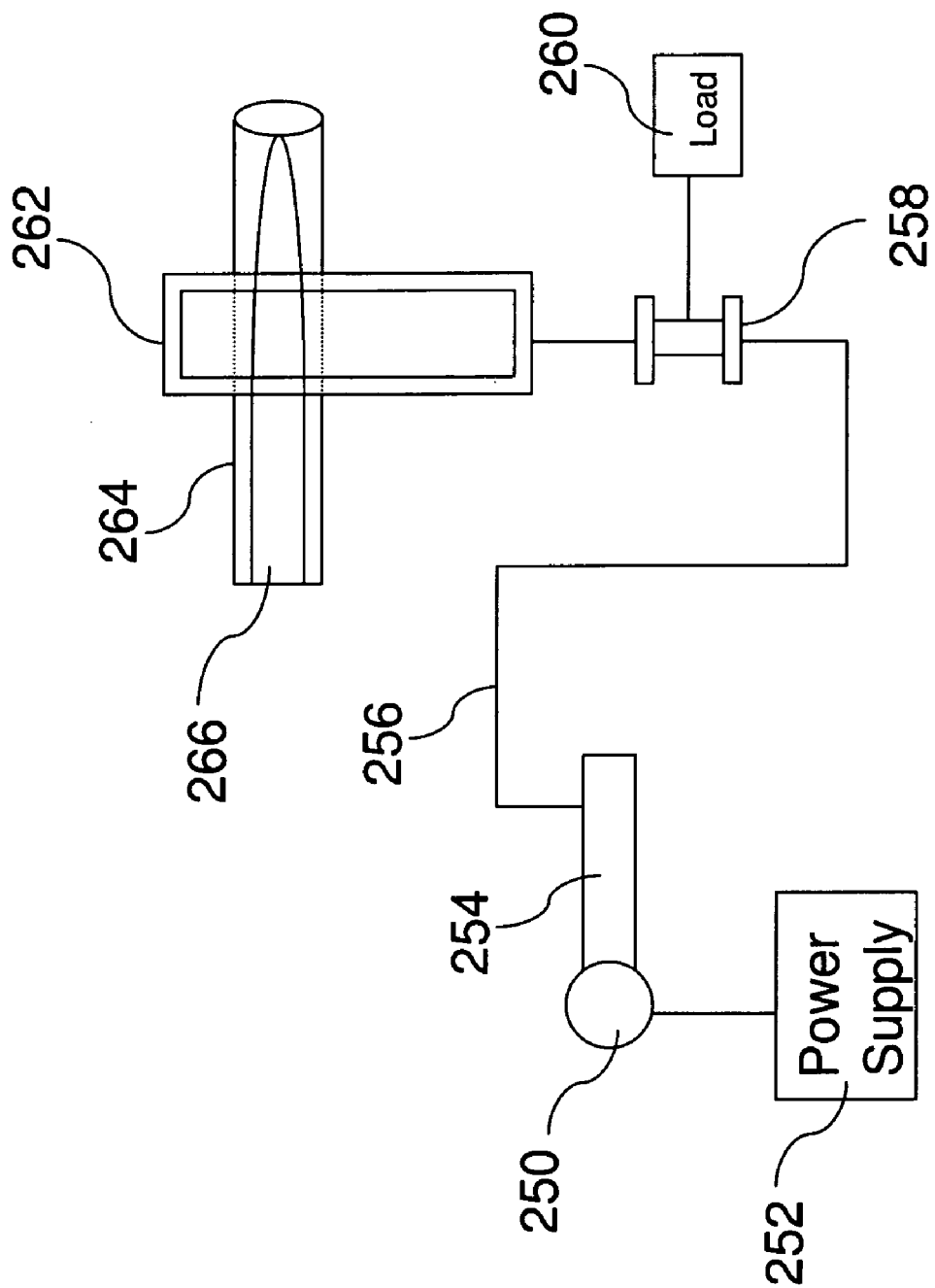
Figure 3A:
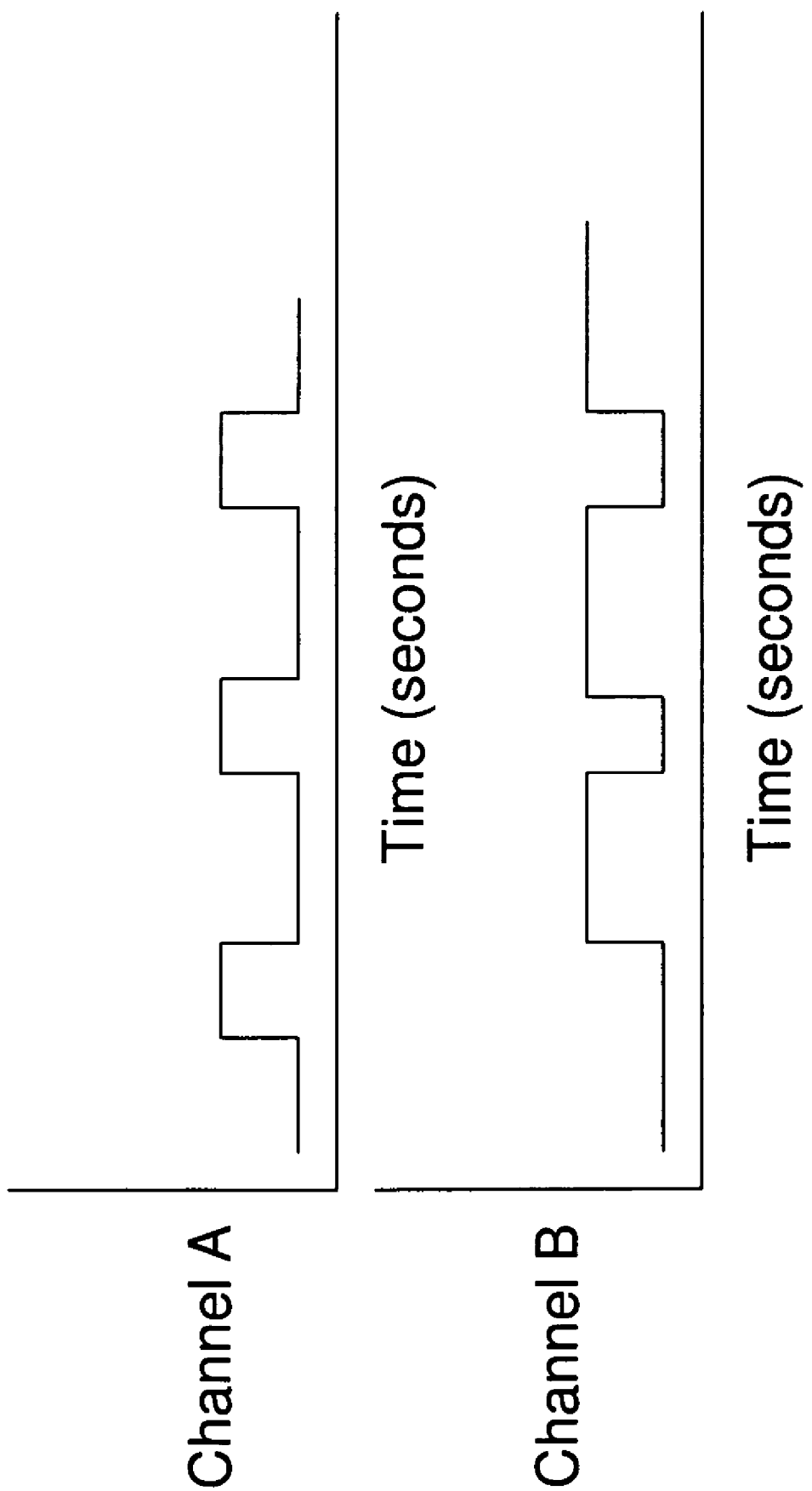
Figure 3B:
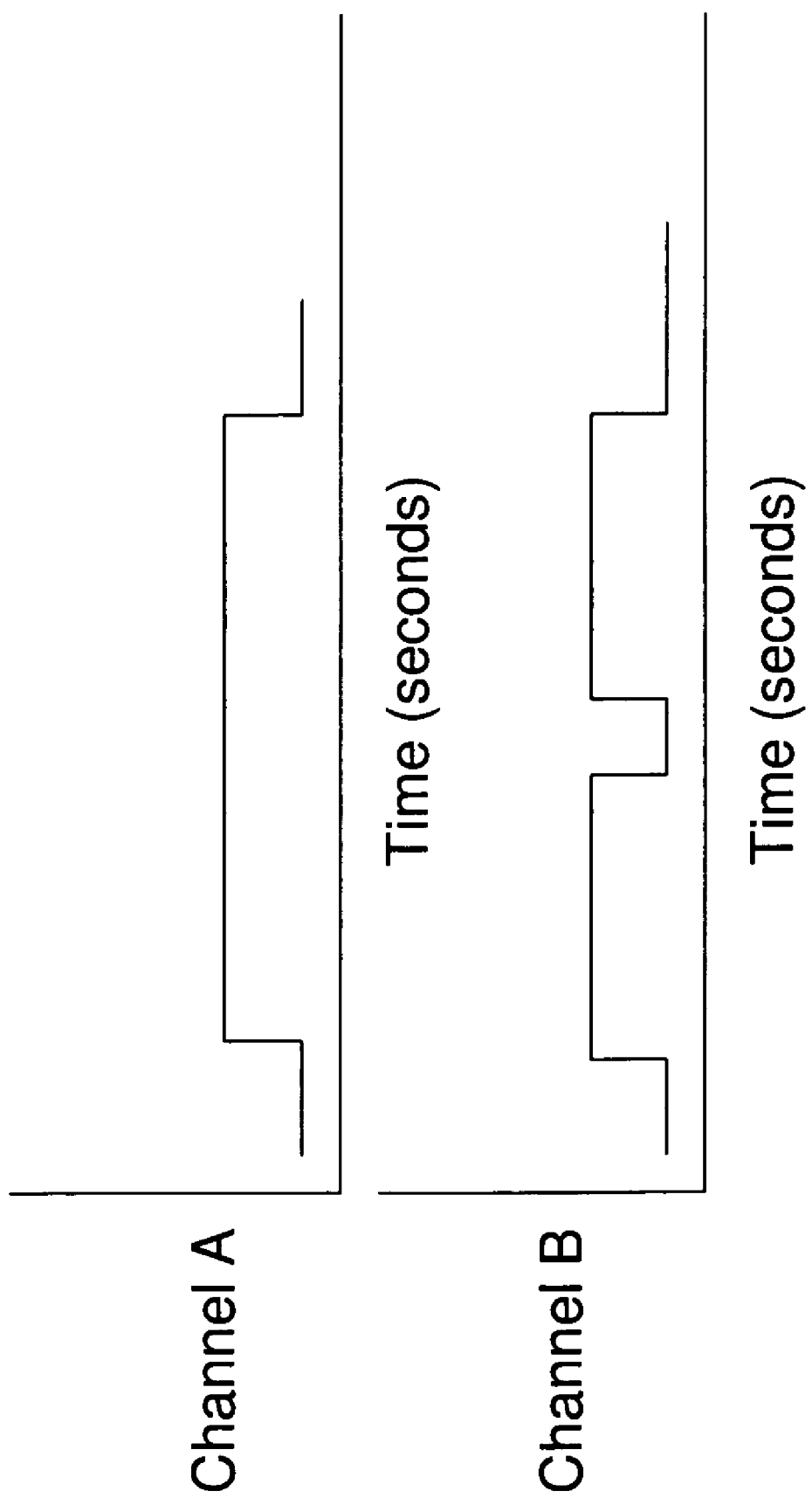
Figure 4B:
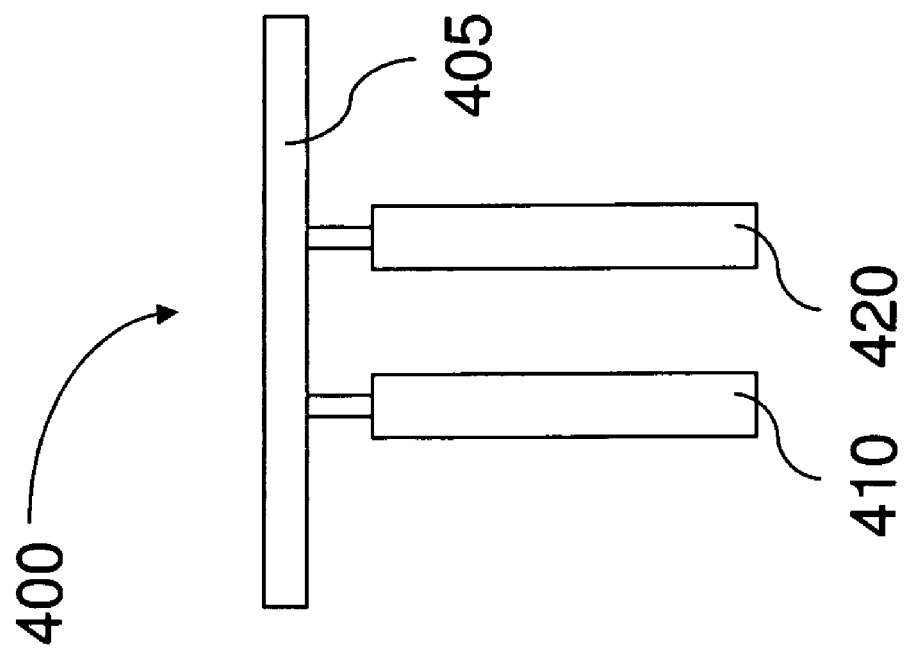
Figure 4A:
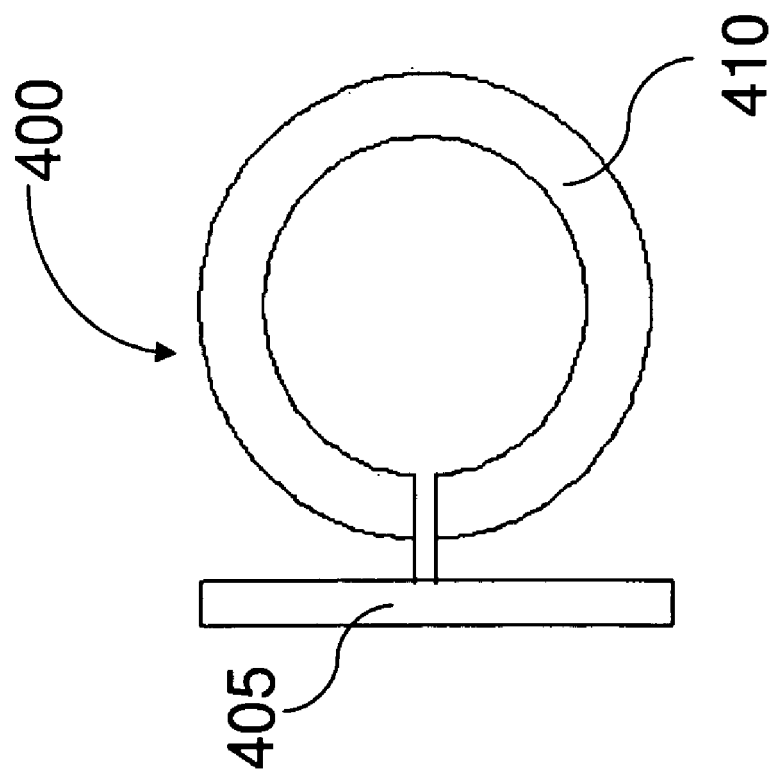
Figure 9A:
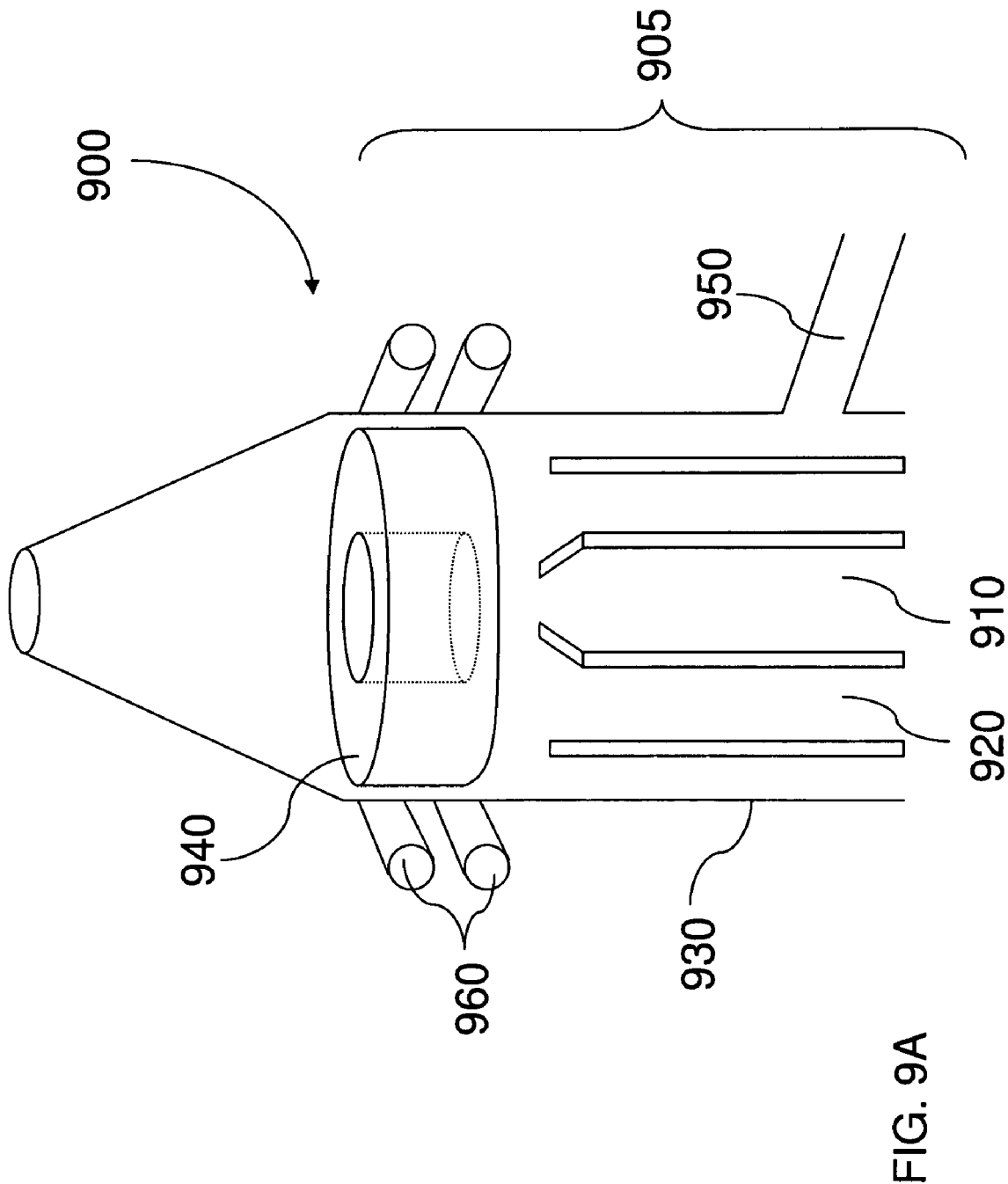
Figure 9B:
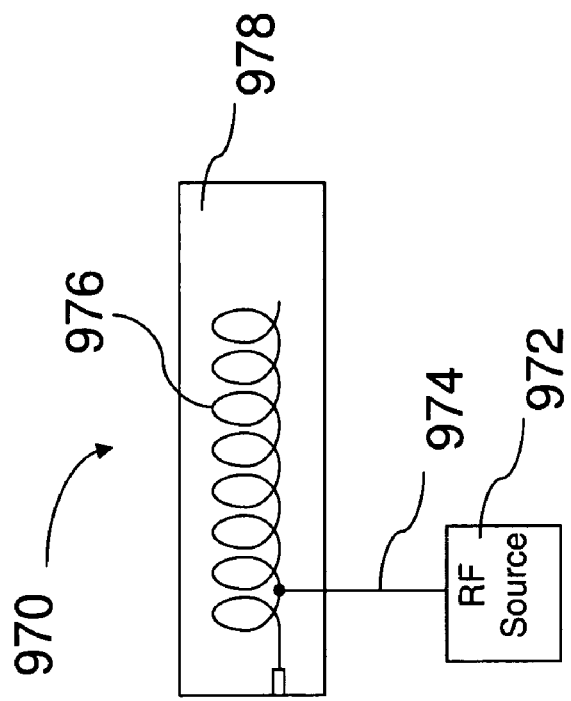

Referring to FIG. 9A, inductively coupled plasma device 900 includes chamber 905 comprising three or more tubes, such as tubes 910, 920 and 930. The tube 910 is in fluid communication with a gas source, such as argon, and a sample introduction device. The argon gas aerosolizes the sample and carries it into the desolvation and ionization regions of a plasma 940. The tube 920 may be configured to provide tangential gas flow throughout the tube 930 to isolate plasma 940 from the tube 930. Without wishing to be bound by any particular scientific theory, gas is introduced through inlet 950, and the tangential flow acts to cool the inside walls of center tube 910 and centers plasma 940 radially. Radio frequency inductions coils 960 may be in electrical communication with a radio frequency generator (not shown) and are configured to create plasma 940 after the gas is ionized using an arc, spark, etc. The person of ordinary skill in the art, given the benefit of this disclosure, will be able to select or design suitable plasmas including, but not limited to inductively coupled plasmas, direct current plasmas, microwave induced plasmas, etc., and suitable devices for generating plasmas are commercially available from numerous manufacturers including, but not limited to, PerkinElmer, Inc., Varian Instruments, Inc. (Palo Alto, Calif.), Teledyne Leeman Labs, (Hudson, N.H.), and Spectro Analytical Instruments (Kleve, Germany). An exemplary device for providing radio frequencies is shown in FIG. 9B. A helical resonator 970 comprises an RF source 972, an electrical lead 974, which typically is a coaxial cable, configured to provide electrical communication with a coil 976 in a resonant cavity 978. The resonant cavity 974 with the coil 978 may be configured to receive a chamber. In certain examples, radio frequencies from about 20 MHz to about 500 MHz may be provided using, for example, helical resonators. Exemplary dimensional information for construction of helical resonators may be found, for example, in the International Telephone and Telegraph, *Reference Data for Radio Engineers*. Fifth Edition. Referring again to FIG. 8, after creation of plasma 810 using, for example atomized and ionized argon and radio frequency induction coils 860, sample may be introduced into the plasma 810. Without wishing to be bound by any particular scientific theory or this example, desolvation of the sample may reduce the temperature of the plasma and may result in lesser amounts of energy available for atomization and ionization. The boost device 820 may be used to provide radio frequencies to boost the energy in the plasma to increase the efficiency of atomization and ionization. For example, the boost device 820 may be positioned such that the energy in the desolvation region 840 is increased to promote more efficient desolvation which may provide more atoms and ions to generate a detectable signal in the ionization region 850. It will be within the ability of the person of ordinary skill in the art, given the benefit of this disclosure, to design atomization devices including plasmas and boost devices to enhance desolvation, atomization, ionization and excitation.

Figure 10:
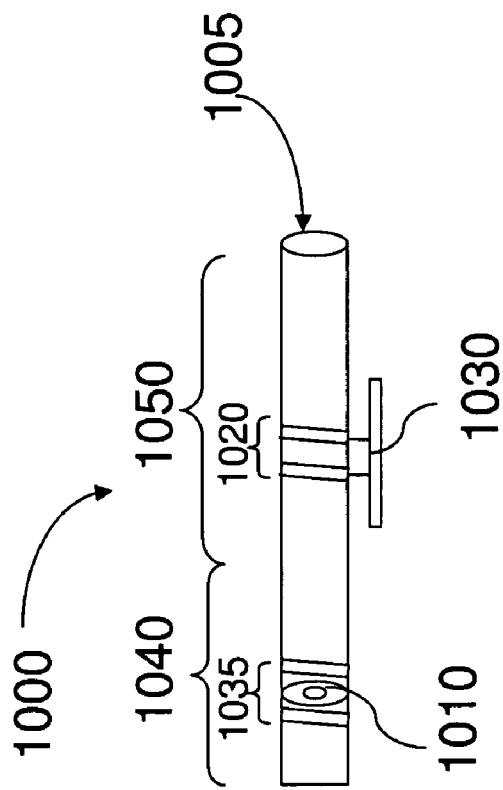

In accordance with certain examples, another example of an atomization device including a plasma is shown in FIG. 10. An atomization device 1000 includes a chamber 1005, a plasma 1010, and a boost device 1020. The boost device 1020 includes a support 1030, which may be in electrical communication with a radio frequency transmitter or generator (not shown). The atomization device 1000 also includes radio frequency induction coils 1035 which are constructed and arranged to maintain plasma 1010, which is shown as a torus. In this example the boost device 1020 is positioned downstream from a desolvation region 1040 in an ionization region 1050. Introduction of a sample into plasma 1010 may result in a decrease in plasma temperature as energy in the plasma is used to desolvate the sample. This temperature decrease may reduce the efficiency of ionization and atomization and may reduce the number of ions and atoms that are excited. Using the boost device 1020, ions and atoms that travel down the chamber 1005 to the ionization region 1050 may be excited. For example, radio frequencies at about 11 MHz and at a power of about 1.2 kilowatts may be provided to an analytical region 1050 to excite atoms and ions present in the ionization region. The excited atoms may be detected using suitable methods such as optical emission spectroscopy. The ionization region may be extended almost indefinitely by placing one or more boost devices along the ionization region of chamber 1005. As discussed further below, the boost devices may be configured in stages and may be individually tuned to different frequencies and/or powers. The person of ordinary skill in the art, given the benefit of this disclosure, will be able to detect excited ions and atoms using the atomization devices disclosed here along with suitable optics, detectors and the like.

In accordance with certain examples, the signal originating from excited atoms and/or ions may be viewed or detected at least two ways. An example of the ionization region of a chamber, such as those used in the atomization devices disclosed here, is shown in FIGS. 11A and 11B. Any signal from a chamber 1105 may be viewed in at least one of two directions—axially or radially. Referring to FIG. 11A, when monitored or detected radially, signal from the chamber 1105 may be monitored in one or more planes parallel to the radius of the chamber 1105. For example, in an instrument configured to measure optical emissions radially, a detector may be positioned to detect signals that are emitted in the direction of arrow X in FIG. 11A. Referring to FIG. 11B, when detected or monitored axially, signal from the chamber 1105 may be monitored or detected in one or more planes parallel to the axis of the chamber. For example, in an instrument configured to measure optical emissions axially, a detector may be positioned to detect signals that are emitted in the direction of arrow Y in FIG. 11B. It will be recognized by the person of ordinary skill in the art, given the benefit of this disclosure, that axial and radial detection are not limited to optical emissions but may be used to detect signals from numerous other analytical techniques including absorption, fluorescence, phosphorescence, scattering, etc.

In accordance with certain examples, an atomization device that includes at least two boost devices is shown in FIG. 12. An atomization device 1200 may include a chamber 1205 and a radio frequency induction coil 1210 configured to generate a plasma 1215. The atomization device 1200 may also include a first boost device 1220 in electrical communication with a support 1230 and a second boost device 1240 in electrical communication with a support 1250. In the example shown in FIG. 12, a first boost device 1230 and a second boost device 1250 are positioned in the ionization region of the chamber 1205 to provide additional energy to excite atoms and ions present in the ionization region. The boost devices 1230 and 1250 may be configured to provide the same or different frequency of radio frequencies. For example, each of boost devices may be configured to provide radio frequencies of about 15 MHz and at a power of about 1000 Watts. The boost devices 1230 and 1250 may independently provide radio frequencies in either pulsed or continuous modes. For example, the boost device 1230 may provide radio frequencies in a pulsed mode while the boost device 1250 may provide radio frequencies continuously. In the alternative, the boost device 1230 may provide radio frequencies continuously while the boost device 1250 may provide radio frequencies in a pulsed mode. In other examples, both of boost devices 1230 and 1250 may provide radio frequencies continuously, or both of boost devices 1230 and 1250 may provide radio frequencies in a pulsed mode. It will be within the ability of the person of ordinary skill in the art, given the benefit of this disclosure, to provide radio frequencies in a selected manner or mode using multiple boost devices. While the configuration shown in FIG. 12 includes two boost devices positioned in the ionization region of chamber 1205, in certain examples one of the boost devices may be positioned in the desolvation region with the second boost device positioned in the ionization region. In yet other examples, both of the boost devices may be positioned in the desolvation region. Additional configurations for arranging two or more boost devices along a chamber will be readily selected by the person of ordinary skill in the art, given the benefit of this disclosure.

Figure 13A:
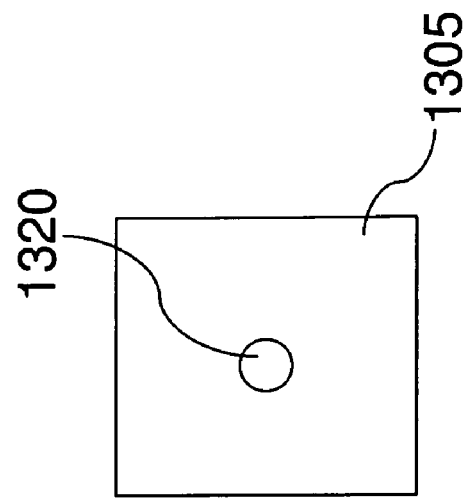
Figure 13B:
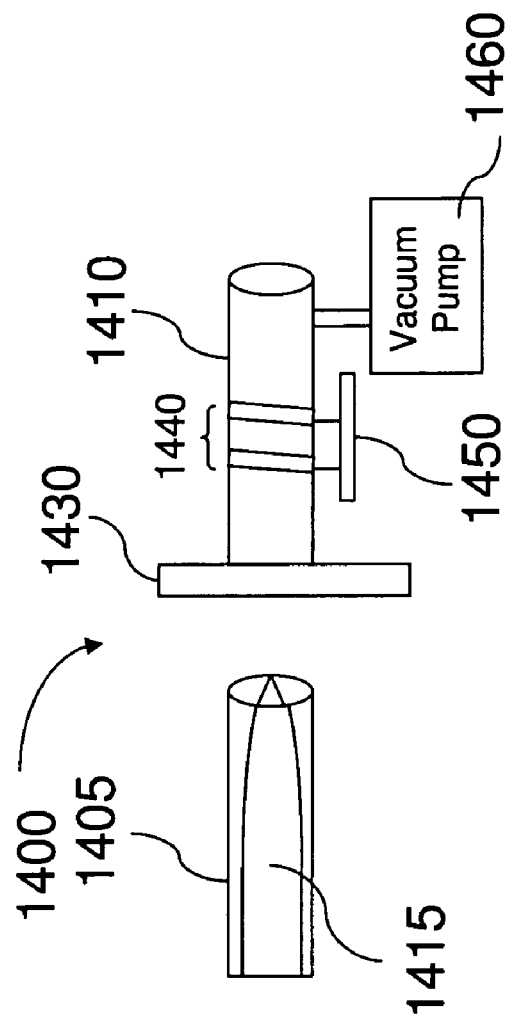

In accordance with certain examples, a chamber comprising a manifold or interface is disclosed. Referring to FIG. 13A, a chamber 1300 comprises a manifold or interface 1305 in contact with a chamber cavity 1310. As shown in FIG. 13B, the interface 1305 includes a small opening or a port 1320 configured to receive sample. The port 1320 may take numerous sizes and forms. In certain examples, the port may be circular and have a diameter of about 0.25 mm to about 25 mm, more particularly about 4 mm. In other examples, the port may be rectangular with length and width measurements each about 0.25 mm to about 4 mm. Other port shapes, such as rhomboidal, trapezoidal, triangular, octahedral, etc., and port sizes will be readily selected by the person of ordinary skill in the art, given the benefit of this disclosure. In certain examples, the port may be positioned centrally, such as the position of port 1320 shown in FIG. 13B, whereas in other examples, the port may be positioned at any selected region or area of the interface. In examples where the port is positioned at the center of the interface, the discharge from the atomization source may be blocked, or partially blocked, by the interface. Without wishing to be bound by any particular scientific theory or this example, blockage of the discharge may lower the detection limit due to removal, or reduction, of background signal from the discharge, which may increase the signal-to-noise ratio. This result may be achieved with both axial and radial detection of signals from the chamber 1300. Also, the working pressure of the boosted discharge may have some effect on the spectral emission quality, and may be optimized for the specific operating conditions based on sample, hardware, detection schemes, etc. An example of one way to control the working pressure of the secondary chamber is by controlling the exit gas flow rate and selecting the interface port size. Another example is to select the port diameter and directly control the exit gas pressure. Another example may be to have a higher exhaust flow and provide an additional bleed gas into the chamber. The exact pressure and power may vary depending on numerous factors including, but not limited to, the desired effect, the configuration of the chamber, etc.

In accordance with certain examples, the chamber 1300 may include a vacuum pump (not shown) that may be operative to draw sample through the port 1320 into the secondary chamber for detection. In certain examples, the interface may be configured with a side port or outlet that is in fluid communication with the second chamber. A vacuum pump may be coupled to the side port to draw sample into the chamber 1300. In other examples, sample diffuses or flows into the secondary chamber, because the pressure in the secondary chamber may be less than the pressure in the atomization source chamber. For example, pressures in chambers including flames are higher than atmospheric pressure due to the high flow rates of gases introduced into the chamber. Pressures in plasmas may be higher than atmospheric pressure due to the high flow rates of gases through the chamber. In certain examples, the pressure of the chamber with the interface is approximately atmospheric pressure such that atoms and ions may flow down a pressure gradient from the high pressure chamber where atomization and/or ionization has occurred to a lower pressure chamber, e.g., where excitation may occur through the use of a boost device as disclosed herein. The person of ordinary skill in the art, given the benefit of this disclosure, will be able to construct suitable chambers with interfaces for receiving and/or detecting atoms and ions generated using one or more atomization sources.

Figure 14A:
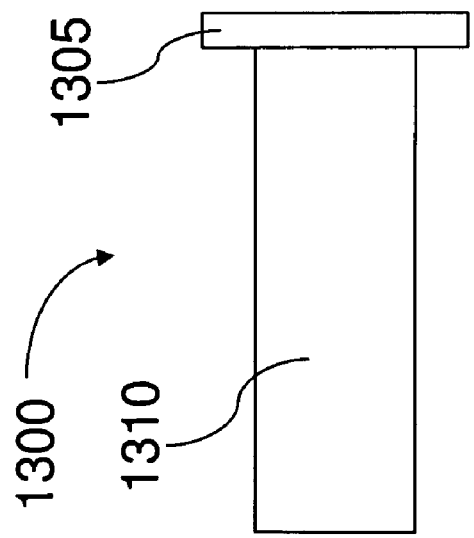

In accordance with certain examples, an atomization device comprising two or more chambers and a flame or primary plasma source is disclosed. Referring to FIG. 14A, an atomization device 1400 may include a first chamber 1405 and a second chamber 1410. A flame or primary plasma source 1415 may be positioned within the first chamber 1405. The second chamber 1410 may include an interface or manifold 1430 and a boost device 1440, which may be in electrical communication with a support 1450. In certain examples, the second chamber 1410 may also include a vacuum pump 1460 which may be configured to draw atomized or ionized species from the first chamber 1405 into the second chamber 1410, whereas in other examples species flow or diffuse into the second chamber 1410 from the first chamber 1405. A vacuum pump 1460 may be in direct fluid communication with the second chamber 1410 or, in certain other examples, an additional interface may be positioned at the end of the second chamber 1410 and may be configured to provide fluid communication between the second chamber 1410 and the vacuum pump 1460. In the example shown in FIG. 14A, as atoms and/or ions enter into second chamber 1410, boost device 1440 may provide radio frequencies to excite the atoms and ions. As discussed herein, such radio frequencies may be provided in a continuous mode or a pulsed mode. Also as discussed herein, radio frequency pulses from the boost device 1440 may be varied during detection of any atoms or species within the second chamber 1410. In other examples, as discussed in more detail below, the second chamber 1410 may also include one or more additional boost devices, or, in certain examples, the first and second chamber are each configured with at least one boost device. In some examples, the atomization device may include additional chambers any one or more of which may include a boost device. The person of ordinary skill in the art, given the benefit of this disclosure, will be able to design suitable atomization devices that include flame or primary plasma sources and multiple chambers some of which may include a boost device.

Figure 14B:
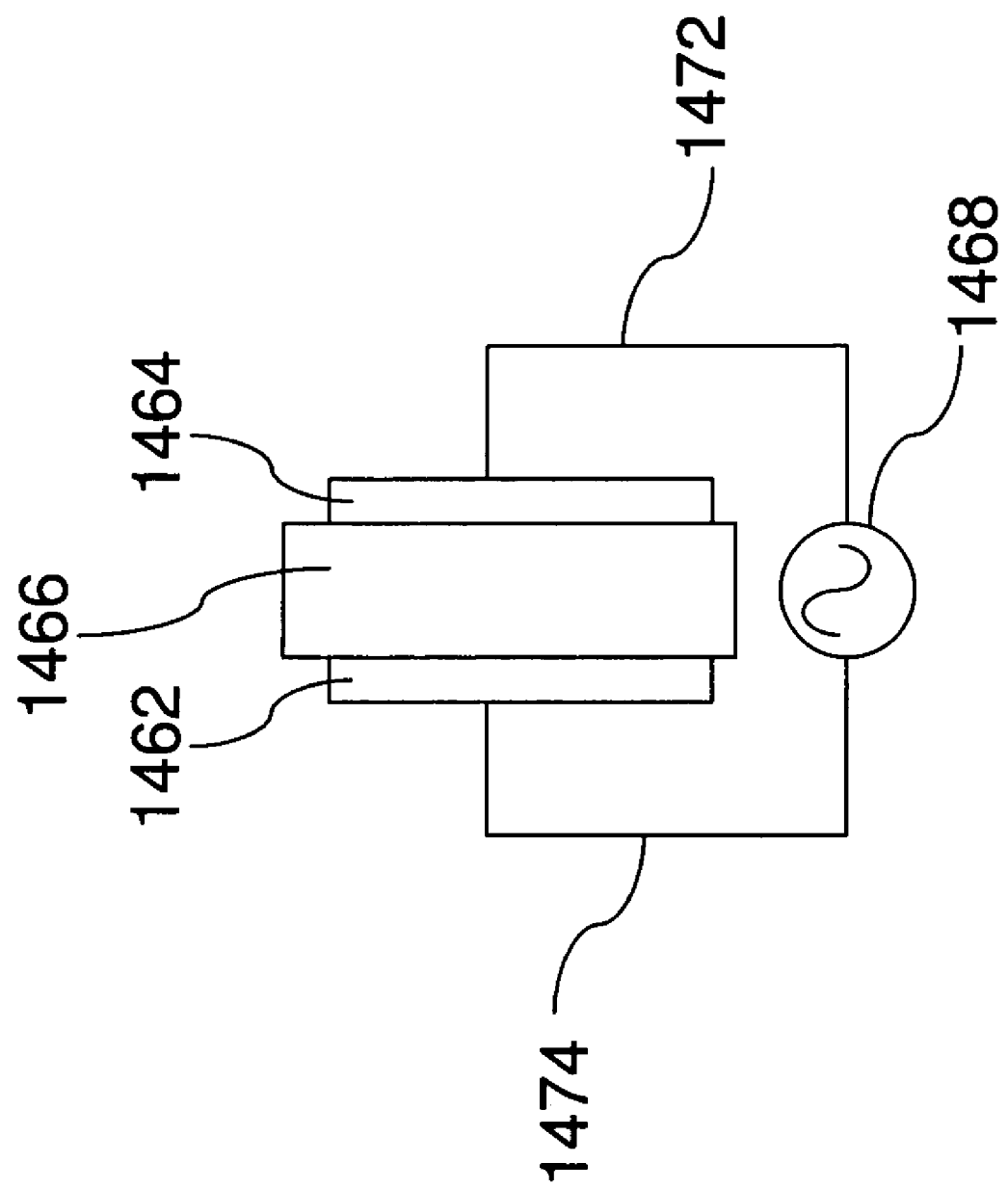

In accordance with certain examples, capacitive coupling may be used to provide additional energy in place of the boost devices. Referring to FIG. 14B an axial view of a configuration for capacitive coupling is shown. Conductive plates 1462 and 1464 may be positioned around a chamber, such as a second chamber 1466, e.g., a quartz tube or other non-conductive material, and may be in electrical communication with a high voltage RF source 1468 through electrical leads 1472 and 1474. Capacitive coupling may provide sufficient energy to the chamber to excite and/or ionize atoms in the chamber within the conductive plates 1462 and 1464. Additional configurations using conductive plates and high energy RF sources will be readily selected by the person of ordinary skill in the art, given the benefit of this disclosure.

In accordance with other examples, an atomization device comprising two or more chambers and a plasma source is provided. Referring to FIG. 15, an atomization device 1500 may include a first chamber 1505 and a second chamber 1510. The first chamber 1505 may be surrounded by a radio frequency induction coil 1520 which may be configured to generate a plasma 1530. The second chamber 1510 also may be configured with a boost device 1540 which may be in electrical communication with a support 1550. The second chamber 1510 may also include an interface 1560 that may be configured to receive a portion of atoms or ions from the first chamber 1505. In certain examples, the second chamber 1510 may also include a vacuum pump (not shown) which may be configured to draw atomized or ionized species from the first chamber 1505 into the second chamber 1510, whereas in other examples species may flow or diffuse into the second chamber 1510 from the first chamber 1505. In yet other examples, the second chamber 1510 may include a second interface positioned opposite the interface 1560. The second interface may be configured to provide fluid communication between the second chamber 1510 and a vacuum pump 1570. In the example shown in FIG. 15, as atoms and/or ions enter into the second chamber 1510, the boost device 1540 may provide radio frequencies to excite the atoms and ions. As discussed herein, such radio frequencies may be provided in a continuous mode or a pulsed mode. Also as discussed herein, the radio frequency power may be varied during detection of any atoms or species within the second chamber 1510. In other examples, as discussed in more detail below, the second chamber may also include one or more additional boost devices, or, in certain examples, the first and second chamber are each configured with at least one boost device. In some examples, the atomization device may include additional chambers any one or more of which may include a boost device. The person of ordinary skill in the art, given the benefit of this disclosure, will be able to design suitable atomization devices that include plasma sources and multiple chambers some of which may include a boost device.

Figure 16:
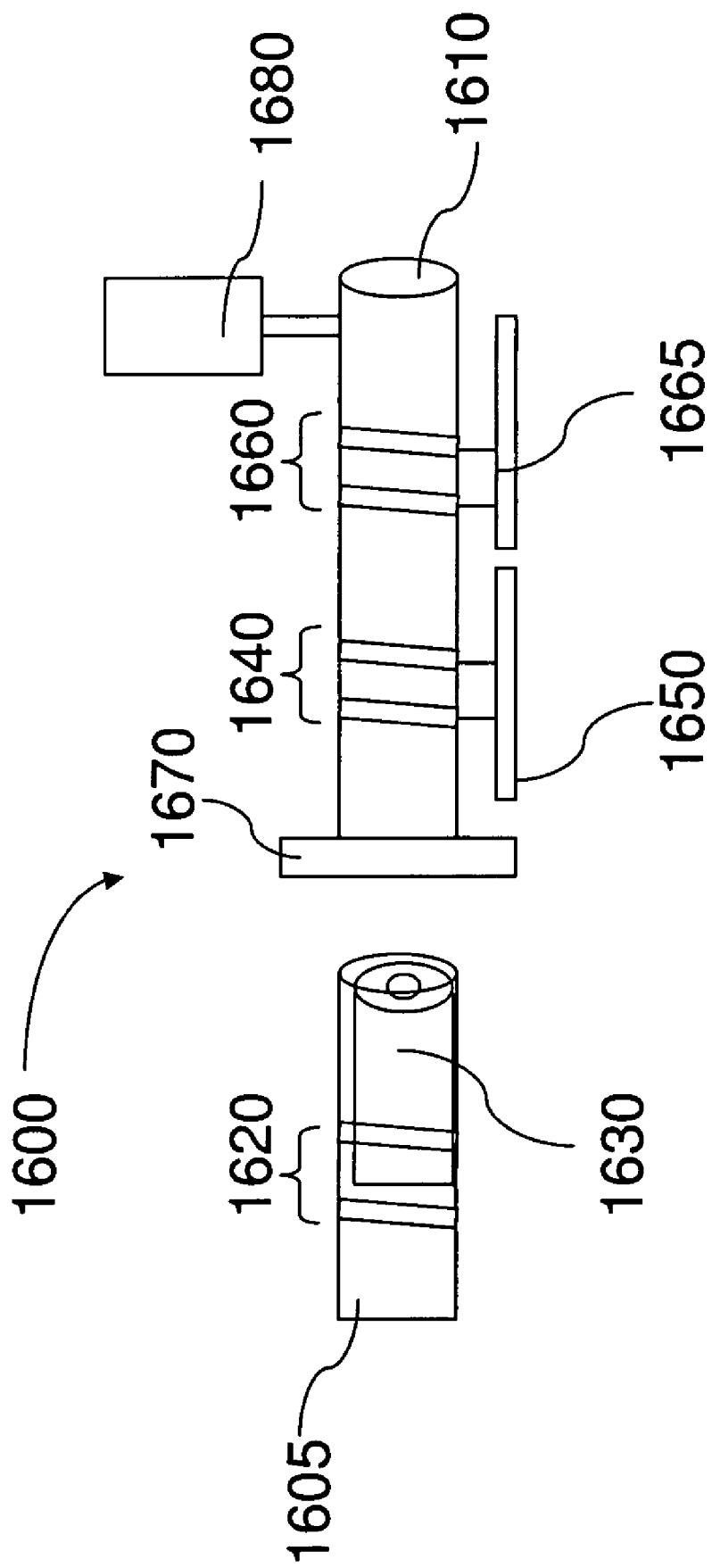

In accordance with certain examples, an atomization device including a first chamber and a second chamber with multiple boost devices is shown in FIG. 16. An atomization device 1600 may include a first chamber 1605 and a second chamber 1610. The first chamber 1605 may be surrounded by a radio frequency induction coil 1620 which may be configured to generate a plasma 1630. The second chamber 1610 may be configured with a first boost device 1640, which may be in electrical communication with a support 1650, and a second boost device 1660, which may be in electrical communication with a support 1665. The second chamber 1610 may also include an interface or manifold 1670 that may be configured to receive a portion of atoms or ions from the first chamber 1605. In certain examples, the second chamber 1610 may also include a vacuum pump 1680 which may be configured to draw atomized or ionized species from the first chamber 1605 into the second chamber 1610, whereas in other examples species may flow or diffuse into the second chamber 1610 from the first chamber 1605. In yet other examples, the second chamber 1610 may include a second interface positioned opposite the interface 1670. The second interface may be configured to provide fluid communication between the second chamber 1610 and the vacuum pump 1680. In the example shown in FIG. 16, as atoms and/or ions enter into the second chamber 1610, the first boost device 1640 may provide radio frequencies to excite the atoms and ions. The second boost device 1660 may also provide radio frequencies to excite atoms and ions in the second chamber 1610. The radio frequencies supplied by first boost device 1640 and second boost device 1660 may be the same or different. The radio frequencies from each of the boost devices may be provided in a continuous mode or a pulsed mode. Also, the radio frequency power from each boost device may be varied during detection of any atoms or species within the second chamber 1610. In other examples, the first chamber may also include one or more boost devices. In some examples, the atomization device may include additional chambers any one or more of which may include one or more boost devices. The person of ordinary skill in the art, given the benefit of this disclosure, will be able to design suitable atomization devices that include multiple chambers including one or more boost devices.

In accordance with certain examples, an atomization device including a single RF generator in electrical communication with a radio frequency induction coil and a boost device is disclosed. Examples using a single radio frequency generator, e.g. a single RF source, may allow for operation of the radio frequency induction coil and boost device at different inductances to tailor or to tune the radio frequency induction coil or boost device or both for a particular region or area of the device. A specific example of this configuration is described in more detail below with reference to FIG. 96B. Even though a single radio frequency generator may be used, the induction coil and the boost device may be designed for different plasma impedances in each region with respect to its location. For example, the inductance value of the induction coil and the boost device may be different to provide devices having different properties and performance characteristics. In other examples, the properties of the induction coil and the boost device may be varied by varying the diameter, coupling or shape of each of the induction coil and the boost device. For example, the primary RF supply and each of the induction coil and the boost device may be configured to provide radio frequencies of about 40 MHz and at a power of about 1100 Watts in the primary discharge and a power of about 400 watts in the boost device region. In some examples, two or more coils from a single RF Source may be used, for example, where the primary discharge is separated from the secondary boost region by an interface (as shown in FIG. 96C). It will be within the ability of the person of ordinary skill in the art, given the benefit of this disclosure, to design atomization devices including a single radio frequency generator in electrical communication with a radio frequency induction coil and one or more boost devices.

Spectroscopic Devices

Figure 17:
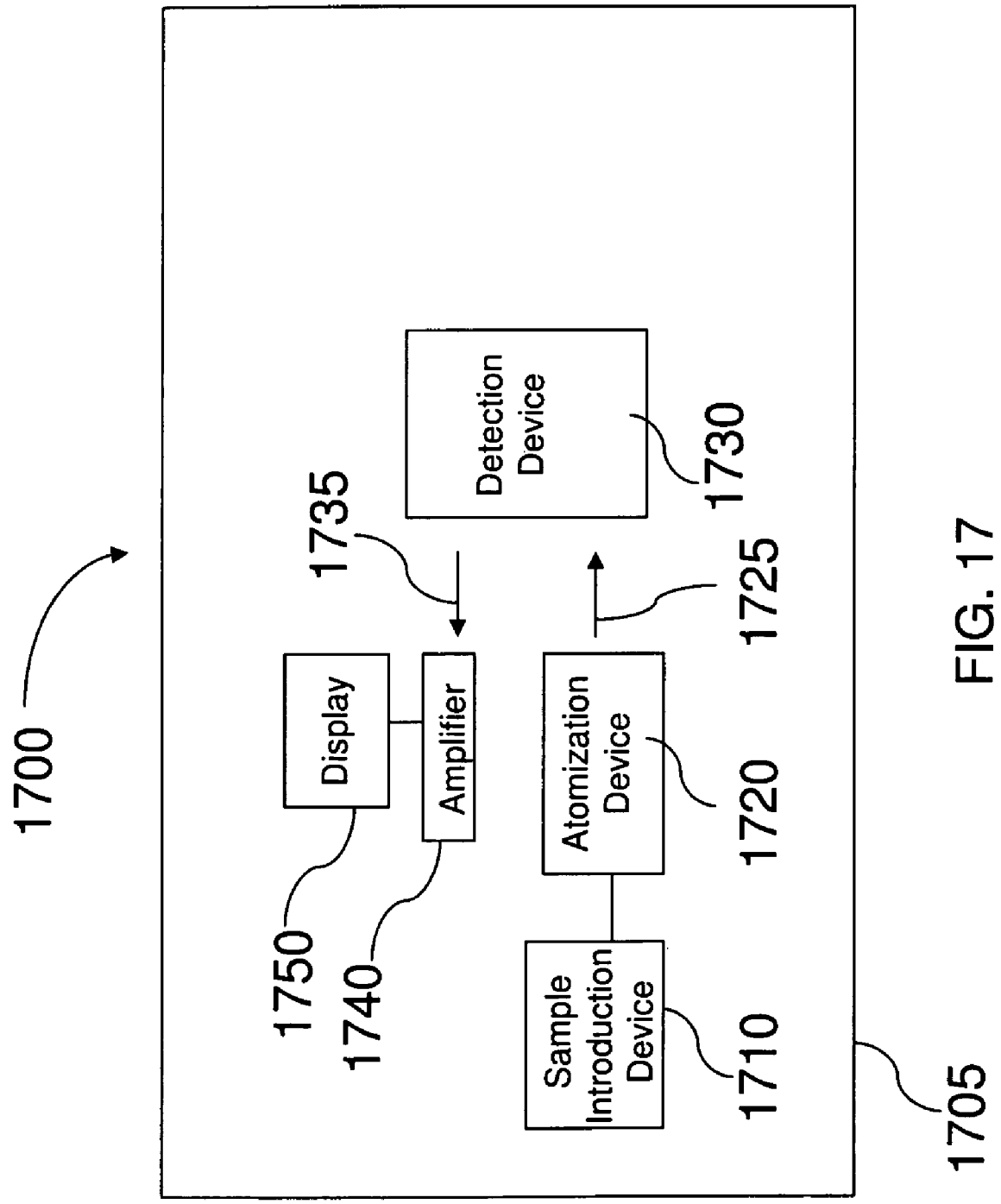

In accordance with certain examples, a device for optical emission spectroscopy (OES) is shown in FIG. 17. Without wishing to be bound by any particular scientific theory, as chemical species are atomized and/or ionized, the outermost electrons may undergo transitions which may emit light (potentially including non-visible light). For example, when an electron of an atom is in an excited state, the electron may emit energy in the form of light as it decays to a lower energy state. Suitable wavelengths for monitoring optical emission from excited atoms and ions will be readily selected by the person of ordinary skill in the art, given the benefit of this disclosure. Exemplary optical emission wavelengths include, but are not limited to, 396.152 nm for aluminum, 193.696 nm for arsenic, 249.772 nm for boron, 313.107 nm for beryllium, 214.440 nm for cadmium, 238.892 nm for cobalt, 267.716 nm for chromium, 224.700 nm for copper, 259.939 nm for iron, 257.610 nm for manganese, 202.031 nm for molybdenum, 231.604 nm for nickel, 220.353 nm for lead, 206.836 nm for antimony, 196.206 nm for selenium, 190.801 nm for tantalum, 309.310 nm for vanadium and 206.200 nm for zinc. The exact wavelength of optical emission may be red-shifted or blue-shifted depending on the state of the species, e.g. atom, ion, etc., and depending on the difference in energy levels of the decaying electron transition, as known in the art.

In accordance with certain examples and referring to FIG. 17, OES device 1700 includes a housing 1705, a sample introduction device 1710, an atomization device 1720, and a detection device 1730. The sample introduction device 1710 may vary depending on the nature of the sample. In certain examples, the sample introduction device 1710 may be a nebulizer that is configured to aerosolize liquid sample for introduction into the atomization device 1720. In other examples, the sample introduction device 1710 may be an injector configured to receive sample that may be directly injected or introduced into the atomization device. Other suitable devices and methods for introducing samples will be readily selected by the person of ordinary skill in the art, given the benefit of this disclosure. The atomization device 1720 may be any one or more of the atomization devices discussed herein or other atomization devices that include a boost device that the person of ordinary skill in the art, given the benefit of this disclosure, may readily design or select. The detection device 1730 may take numerous forms and may be any suitable device that may detect optical emissions, such as optical emission 1725. For example, the detection device 1730 may include suitable optics, such as lenses, mirrors, prisms, windows, band-pass filters, etc. The detection device 1730 may also include gratings, such as echelle gratings, to provide a multi-channel OES device. Gratings such as echelle gratings may allow for simultaneous detection of multiple emission wavelengths. The gratings may be positioned within a monochromator or other suitable device for selection of one or more particular wavelengths to monitor. In certain examples, the detection device 1730 may include a charge coupled device (CCD). In other examples, the OES device may be configured to implement Fourier transforms to provide simultaneous detection of multiple emission wavelengths. The detection device may be configured to monitor emission wavelengths over a large wavelength range including, but not limited to, ultraviolet, visible, near and far infrared, etc. The OES device 1700 may further include suitable electronics such as a microprocessor and/or computer and suitable circuitry to provide a desired signal and/or for data acquisition. Suitable additional devices and circuitry are known in the art and may be found, for example, on commercially available OES devices such as Optima 2100DV series and Optima 5000 DV series OES devices commercially available from PerkinElmer, Inc. The optional amplifier 1740 may be operative to increase a signal 1735, e.g., amplify the signal from detected photons, and provides the signal to display 1750, which may be a readout, computer, etc. In examples where the signal 1735 is sufficiently large for display or detection, the amplifier 1740 may be omitted. In certain examples, the amplifier 1740 is a photomultiplier tube configured to receive signals from the detection device 1730. Other suitable devices for amplifying signals, however, will be selected by the person of ordinary skill in the art, given the benefit of this disclosure. It will also be within the ability of the person of ordinary skill in the art, given the benefit of this disclosure, to retrofit existing OES devices with the atomization devices disclosed here and to design new OES devices using the atomization devices disclosed here. The OES devices may further include autosamplers, such as AS90 and AS93 autosamplers commercially available from PerkinElmer, Inc. or similar devices available from other suppliers.

Figure 18:
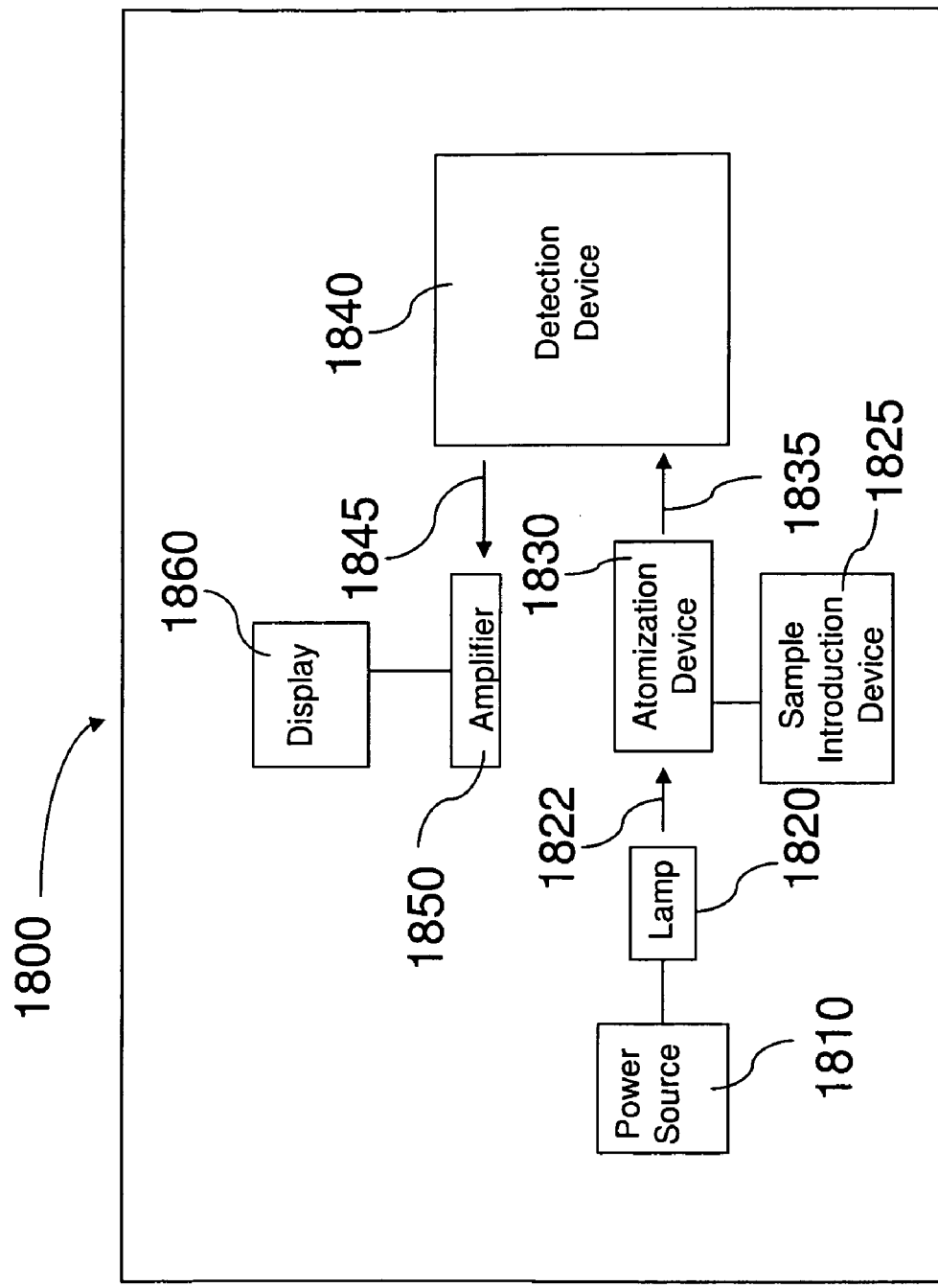

In accordance with certain examples, a single beam device for absorption spectroscopy (AS) is shown in FIG. 18. Without wishing to be bound by any particular scientific theory, atoms and ions may absorb certain wavelengths of light to provide energy for a transition from a lower energy level to a higher energy level. An atom or ion may contain multiple resonance lines resulting from transition from a ground state to a higher energy level. The energy needed to promote such transitions may be supplied using numerous sources, e.g., heat, flames, plasmas, arc, sparks, cathode ray lamps, lasers, etc, as discussed further below. Suitable sources for providing such energy and suitable wavelengths of light for providing such energy will be readily selected by the person of ordinary skill in the art, given the benefit of this disclosure.

In accordance with certain examples and referring to FIG. 18, a single beam AS device 1800 includes a housing 1805, a power source 1810, a lamp 1820, a sample introduction device 1825, an atomization device 1830, a detection device 1840, an optional amplifier 1850 and a display 1860. The power source 1810 may be configured to supply power to the lamp 1820, which provides one or more wavelengths of light 1822 for absorption by atoms and ions. Suitable lamps include, but are not limited to mercury lamps, cathode ray lamps, lasers, etc. The lamp may be pulsed using suitable choppers or pulsed power supplies, or in examples where a laser is implemented, the laser may be pulsed with a selected frequency, e.g. 5, 10, or 20 times/second. The exact configuration of the lamp 1820 may vary. For example, the lamp 1820 may provide light axially along the atomization device 1830 or may provide light radially along the atomization device 1830. The example shown in FIG. 18 is configured for axial supply of light from the lamp 1820. As discussed above, there may be signal-to-noise advantages using axial viewing of signals. The atomization device 1830 may be any of the atomization devices discussed herein or other suitable atomization devices including a boost device that may be readily selected or designed by the person of ordinary skill in the art, given the benefit of this disclosure. As sample is atomized and/or ionized in the atomization device 1830, the incident light 1822 from the lamp 1820 may excite atoms. That is, some percentage of the light 1822 that is supplied by the lamp 1820 may be absorbed by the atoms and ions in the atomization device 1830. The remaining percentage of the light 1835 may be transmitted to the detection device 1840. The detection device 1840 may provide one or more suitable wavelengths using, for example, prisms, lenses, gratings and other suitable devices such as those discussed above in reference to the OES devices, for example. The signal may be provided to the optional amplifier 1850 for increasing the signal provided to the display 1860. To account for the amount of absorption by sample in the atomization device 1830, a blank, such as water, may be introduced prior to sample introduction to provide a 100% transmittance reference value. The amount of light transmitted once sample is introduced into atomization chamber may be measured, and the amount of light transmitted with sample may be divided by the reference value to obtain the transmittance. The negative $\log_{10}$ of the transmittance is equal to the absorbance. AS device 1800 may further include suitable electronics such as a microprocessor and/or computer and suitable circuitry to provide a desired signal and/or for data acquisition. Suitable additional devices and circuitry may be found, for example, on commercially available AS devices such as AAnalyst series spectrometers commercially available from PerkinElmer, Inc. It will also be within the ability of the person of ordinary skill in the art, given the benefit of this disclosure, to retrofit existing AS devices with the atomization devices disclosed here and to design new AS devices using the atomization devices disclosed here. The AS devices may further include autosamplers known in the art, such as AS-90A, AS-90plus and AS-93plus autosamplers commercially available from PerkinElmer, Inc.

Figure 19:
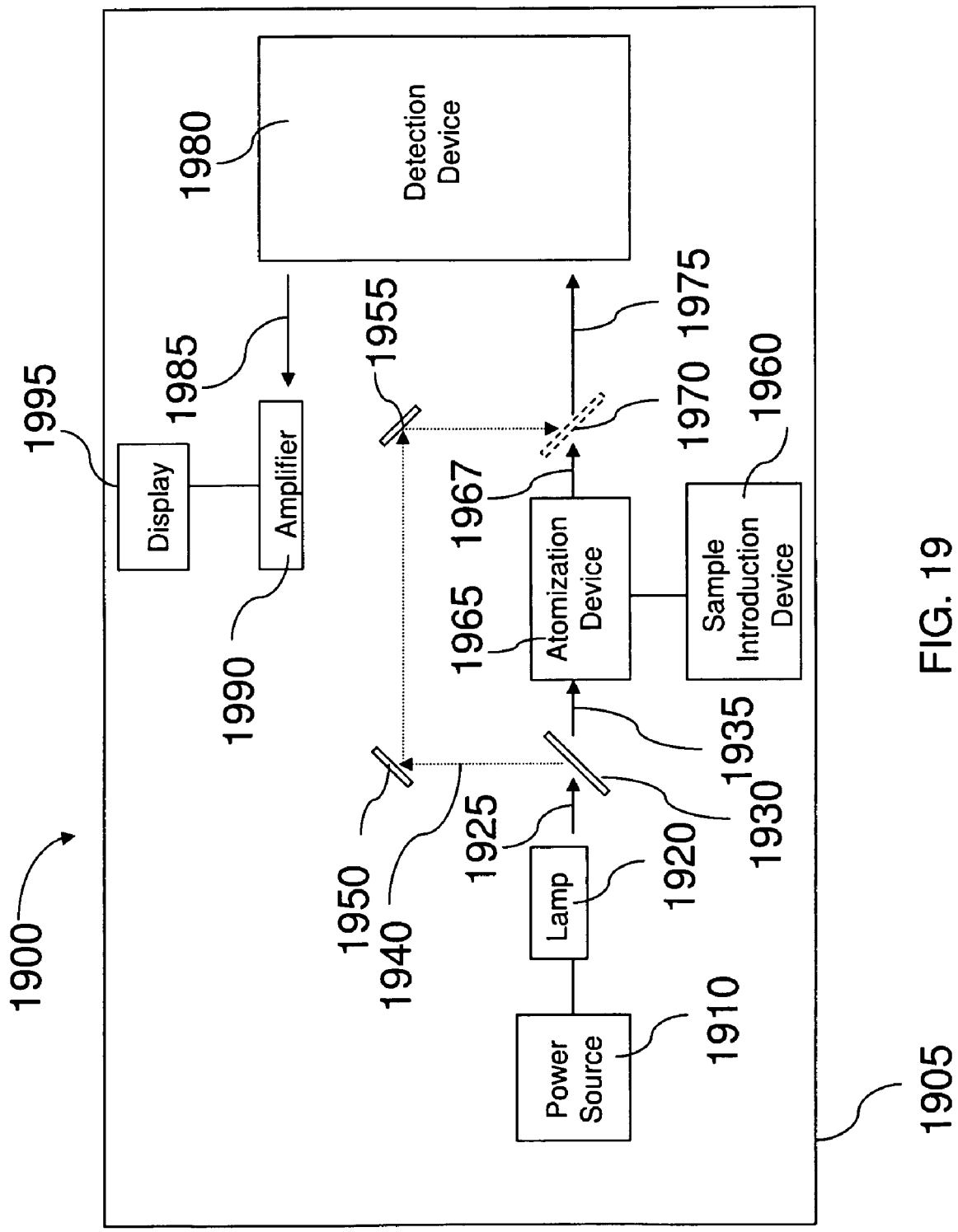

In accordance with certain examples and referring to FIG. 19, a dual beam AS device 1900 includes a housing 1905, a power source 1910, a lamp 1920, an atomization device 1965, a detection device 1980, an optional amplifier 1990 and a display 1995. The power source 1910 may be configured to supply power to the lamp 1920, which provides one or more wavelengths of light 1925 for absorption by atoms and ions. Suitable lamps include, but are not limited to, mercury lamps, cathode ray lamps, lasers, etc. The lamp may be pulsed using suitable choppers or pulsed power supplies, or in examples where a laser is implemented, the laser may be pulsed with a selected frequency, e.g. 5, 10 or 20 times/second. The configuration of the lamp 1920 may vary. For example, the lamp 1920 may provide light axially along the atomization device 1965 or may provide light radially along the atomization device 1965. The example shown in FIG. 19 is configured for axial supply of light from the lamp 1920. As discussed above, there may be signal-to-noise advantages using axial viewing of signals. The atomization device 1965 may be any of the atomization devices discussed herein or other suitable atomization devices including a boost device that may be readily selected or designed by the person of ordinary skill in the art, given the benefit of this disclosure. As sample is atomized and/or ionized in the atomization device 1965, the incident light 1925 from the lamp 1920 may excite atoms. That is, some percentage of the light 1925 that is supplied by the lamp 1920 may be absorbed by the atoms and ions in the atomization device 1965. The remaining percentage of the light 1967 is transmitted to the detection device 1980. In examples using dual beams, the incident light 1925 may be split using a beam splitter 1930 such that some percentage of light, e.g., about 10% to about 90%, may be transmitted as a light beam 1935 to atomization device 1965 and the remaining percentage of the light may be transmitted as a light beam 1940 to lenses 1950 and 1955. The light beams may be recombined using a combiner 1970, such as a half-silvered mirror, and a combined signal 1975 may be provided to the detection device 1980. The ratio between a reference value and the value for the sample may then be determined to calculate the absorbance of the sample. The detection device 1980 may provide one or more suitable wavelengths using, for example, prisms, lenses, gratings and other suitable devices known in the art, such as those discussed above in reference to the OES devices, for example. Signal 1985 may be provided to the optional amplifier 1990 for increasing the signal for provide to the display 1995. AS device 1900 may further include suitable electronics known in the art, such as a microprocessor and/or computer and suitable circuitry to provide a desired signal and/or for data acquisition. Suitable additional devices and circuitry may be found, for example, on commercially available AS devices such as AAnalyst series spectrometers commercially available from PerkinElmer, Inc. It will be within the ability of the person of ordinary skill in the art, given the benefit of this disclosure, to retrofit existing dual beam AS devices with the atomization devices disclosed here and to design new dual beam AS devices using the atomization devices disclosed here. The AS devices may further include autosamplers known in the art, such as AS-90A, AS-90plus and AS-93plus autosamplers commercially available from PerkinElmer, Inc.

Figure 20:
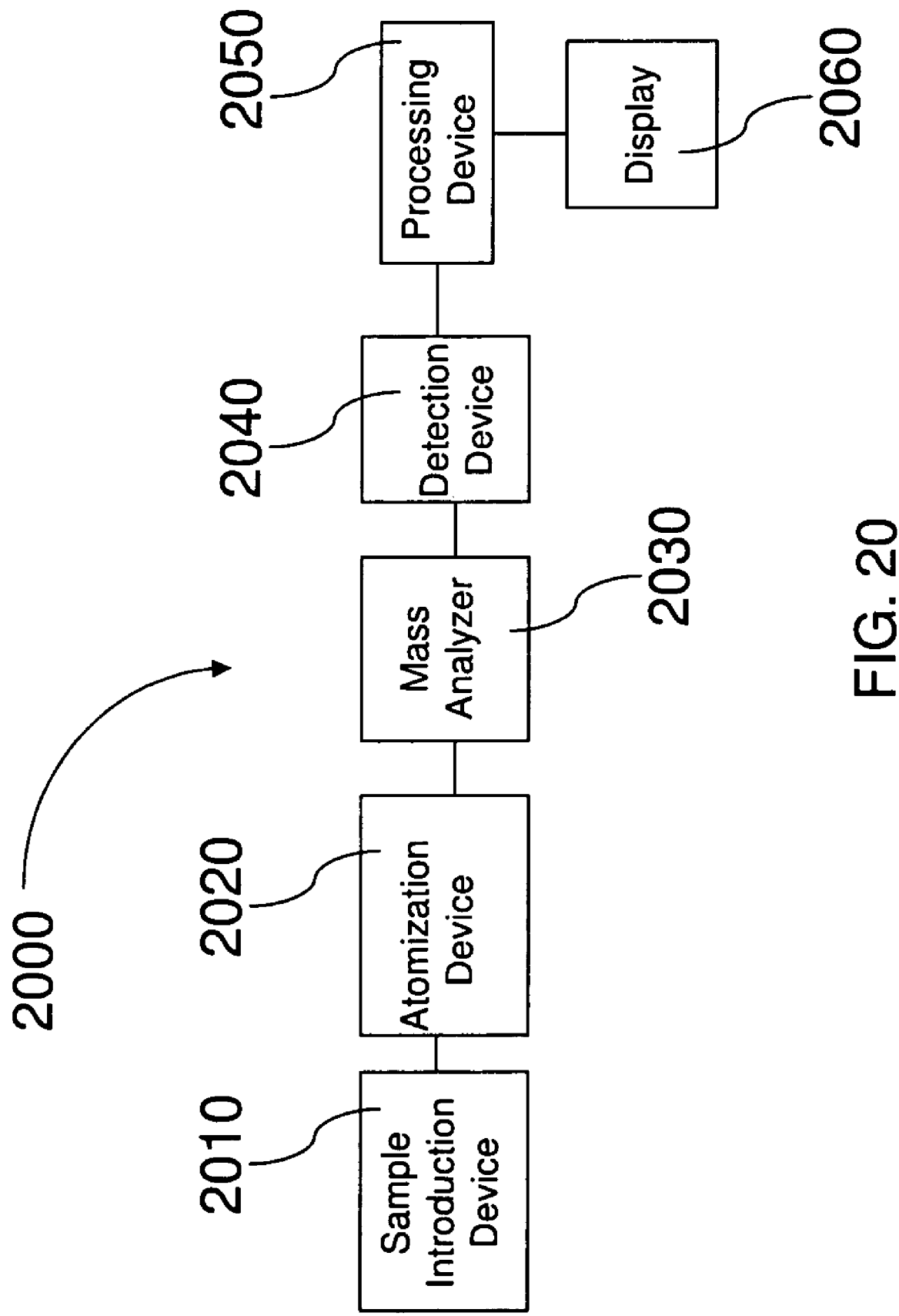

In accordance with certain examples, a device for mass spectroscopy (MS) is schematically shown in FIG. 20. MS device 2000 includes a sample introduction device 2010, an atomization device 2020, a mass analyzer 2030, a detection device 2040, a processing device 2050 and a display 2060. The sample introduction device 2010, the atomization device 2020, the mass analyzer 2030 and the detection device 2040 may be operated at reduced pressures using one or more vacuum pumps. In certain examples, however, only the mass analyzer 2030 and the detection device 2040 may be operated at reduced pressures. The sample introduction device 2010 may include an inlet system configured to provide sample to the atomization device 2020. The inlet system may include one or more batch inlets, direct probe inlets and/or chromatographic inlets. The sample introduction device 2010 may be an injector, a nebulizer or other suitable devices that may deliver solid, liquid or gaseous samples to the atomization device 2020. The atomization device 2020 may be any one or more of the atomization devices including a boost device discussed herein. As discussed herein, the atomization device 2020 may be a combination of two or more atomization devices at least one of which includes a boost device. The mass analyzer 2030 may take numerous forms depending generally on the sample nature, desired resolution, etc. and exemplary mass analyzers are discussed further below. The detection device 2040 may be any suitable detection device that may be used with existing mass spectrometers, e.g., electron multipliers, Faraday cups, coated photographic plates, scintillation detectors, etc., and other suitable devices that will be selected by the person of ordinary skill in the art, given the benefit of this disclosure. The processing device 2050 typically includes a microprocessor and/or computer and suitable software for analysis of samples introduced into MS device 2000. One or more databases may be accessed by the processing device 2050 for determination of the chemical identity of species introduced into MS device 2000. Other suitable additional devices known in the art may also be used with the MS device 2000 including, but not limited to, autosamplers, such as AS-90plus and AS-93plus autosamplers commercially available from PerkinElmer, Inc.

In accordance with certain examples, the mass analyzer of MS device 2000 may take numerous forms depending on the desired resolution and the nature of the introduced sample. In certain examples, the mass analyzer is a scanning mass analyzer, a magnetic sector analyzer (e.g., for use in single and double-focusing MS devices), a quadrupole mass analyzer, an ion trap analyzer (e.g., cyclotrons, quadrupole ions traps), time-of-flight analyzers (e.g., matrix-assisted laser desorbed ionization time of flight analyzers), and other suitable mass analyzers that may separate species with different mass-to-charge ratios. The atomization devices disclosed herein may be used with any one or more of the mass analyzers listed above and other suitable mass analyzers. In certain examples, the atomization device in an MS device is a single chamber inductively coupled plasma with a boost device. In other examples, the atomization device is a single chamber flame source with a boost device. In yet other examples, the atomization device may include two or more chambers in which at least one of the chambers comprises a boost device as disclosed herein.

In accordance with certain other examples, the boost devices disclosed here may be used with existing ionization methods used in mass spectroscopy. For example, electron impact sources with boost devices may be assembled to increase ionization efficiency prior to entry of ions into the mass analyzer. In other examples, chemical ionization sources with boost devices may be assembled to increase ionization efficiency prior to entry of ions into the mass analyzer. In yet other examples, field ionization sources with a boost device may be assembled to increase ionization efficiency prior to entry of ions into the mass analyzer. In still other examples, the boost devices may be used with desorption sources such as, for example, those sources configured for fast atom bombardment, field desorption, laser desorption, plasma desorption, thermal desorption, electrohydrodynamic ionization/desorption, etc. In yet other examples, the boost devices may be configured for use with thermospray ionization sources, electrospray ionization sources or other ionization sources and devices commonly used in mass spectroscopy. It will be within the ability of the person of ordinary skill in the art, given the benefit of this disclosure, to design suitable devices for ionization including boost devices for use in mass spectroscopy.

In accordance with certain other examples, the MS devices disclosed here may be hyphenated with one or more other analytical techniques. For example, MS devices may be hyphenated with devices for performing liquid chromatography, gas chromatography, capillary electrophoresis, and other suitable separation techniques. When coupling an MS device that includes a boost device with a gas chromatograph, it may be desirable to include a suitable interface, e.g., traps, jet separators, etc., to introduce sample into the MS device from the gas chromatograph. When coupling an MS device to a liquid chromatograph, it may also be desirable to include a suitable interface to account for the differences in volume used in liquid chromatography and mass spectroscopy. For example, split interfaces may be used so that only a small amount of sample exiting the liquid chromatograph may be introduced into the MS device. Sample exiting from the liquid chromatograph may also be deposited in suitable wires, cups or chambers for transport to the atomization devices of the MS device. In certain examples, the liquid chromatograph may include a thermospray configured to vaporize and aerosolize sample as it passes through a heated capillary tube. In some examples, the thermospray may include its own boost device to increase ionization of species using the thermospray. Other suitable devices for introducing liquid samples from a liquid chromatograph into a MS device will be readily selected by the person of ordinary skill in the art, given the benefit of this disclosure. In certain examples, MS devices, at least one of which includes a boost device, are hyphenated with each other for tandem mass spectroscopy analyses. For example, one MS device may include a first type of mass analyzer and the second MS device may include a different or similar mass analyzer as the first MS device. In other examples, the first MS device may be operative to isolate the molecular ions, and the second MS device may be operative to fragment/detect the isolated molecular ions. It will be within the ability of the person of ordinary skill in the art, given the benefit of this disclosure, to design hyphenated MS/MS devices at least one of which includes a boost device.

Figure 21:
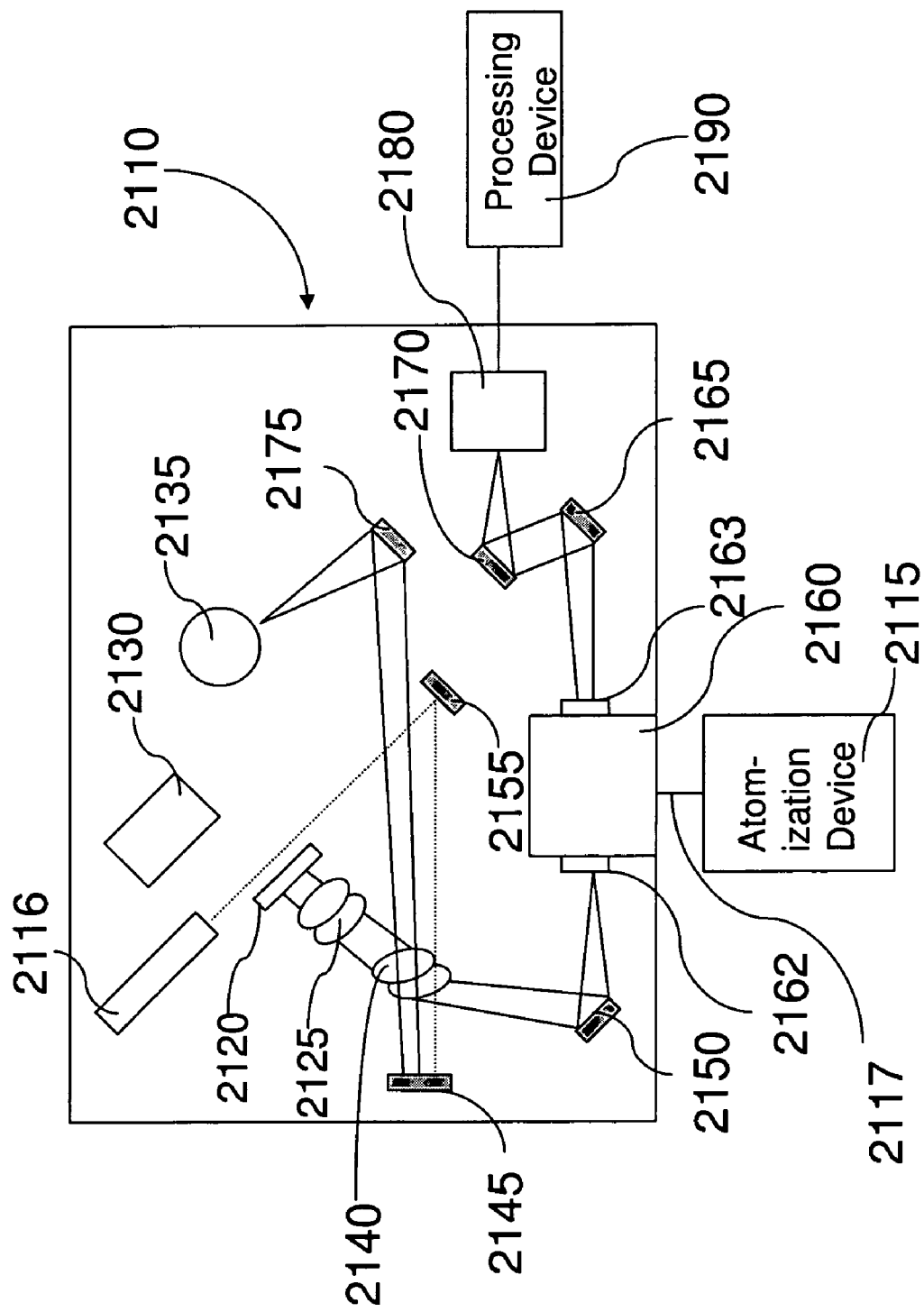

In accordance with certain examples, a device for infrared spectroscopy (IRS) is provided. An IRS device includes a sample introduction device and an atomization device coupled or hyphenated to the infrared spectrometer. The atomization device may be any of the atomization devices discussed herein or other suitable atomization devices including a boost device. The atomization device may be configured to provide atoms and/or ions to the infrared spectrometer for detection. The infrared spectrometer may be a single or double-beam spectrophotometer, an interferometer, such as those commonly used to perform Fourier transform infrared spectroscopy, etc. and exemplary infrared spectrometers and devices for use in infrared spectrometers are described in U.S. Pat. Nos. 4,419,575, 4,594,500, and 4,798,464, the entire disclosure of each of which is incorporated herein by reference for all purposes. For illustrative purposes only, an example of a single-beam FTIR spectrometer 2110 coupled to an atomization device 2115 is shown in FIG. 21. The spectrometer 2110 comprises a light source 2116, such as a HeNe laser, an interferometer flat mirror 2120, interferometer scan mirrors 2125, a dessicant box 2130, an infrared light source 2135, a beam splitter 2140, an interferometer flat mirror 2145, an adjustable toroidal window 2150, a fixed toroidal window 2175, a sample chamber 2160 with KBr windows 2162 and 2163, fixed toroidal windows 2165 and 2170 and an infrared detector 2180. The infrared spectrometer 2110 may employ a single interferometer for detection of species introduced into the sample chamber 2160. Sample may be atomized or ionized using the atomization device 2115 and introduced into the sample chamber 2160 through a tube 2117, which provides fluid communication between the atomization device 2115 and the sample chamber 2160. The tube 2117 may include cooling devices such that the temperature of any atoms or ions exiting the atomization device 2115 may be reduced prior to entry into the sample chamber 2160. After sample has entered into the sample chamber 2160, a valve or port (not shown) may be closed such that no additional sample exits or enters into the sample chamber. In certain examples, the sample chamber 2160 may include temperature control to maintain the sample at a selected temperature. After a suitable number of scans have been obtained, the valve or port may be opened such that sample may be permitted to exit the sample chamber 2160 and may go to waste (not shown). In other examples, the flow from the atomization device 2115 into the sample chamber 2160 may be continuous. Other configurations for introducing atomized and/or ionized samples from atomization devices into an infrared spectrometer will be readily selected by the person of ordinary skill in the art, given the benefit of this disclosure. In certain examples, the infrared spectrometer may be in electrical communication with a processing device 2190, such as a microprocessor or computer, which may be used to perform any necessary Fourier transforms and/or other desired data analyses, e.g., quantitative or qualitative analyses. Suitable devices for coupling the atomization devices with infrared spectrometers will be readily selected by the person of ordinary skill in the art, given the benefit of this disclosure, and illustrative devices include, but are not limited to, capillary tubes, quartz tubes and other tubes. For example capillary ionization, may use very low power filament boost discharges and may be sustained in sub-millimeter bore quartz tubes, whereas with large secondary chambers with high solvent loads, or less expensive, low frequency high power RF sources, it may be desirable to use a very large secondary chamber diameter that is about 100 mm in diameter or larger.

Figure 22:
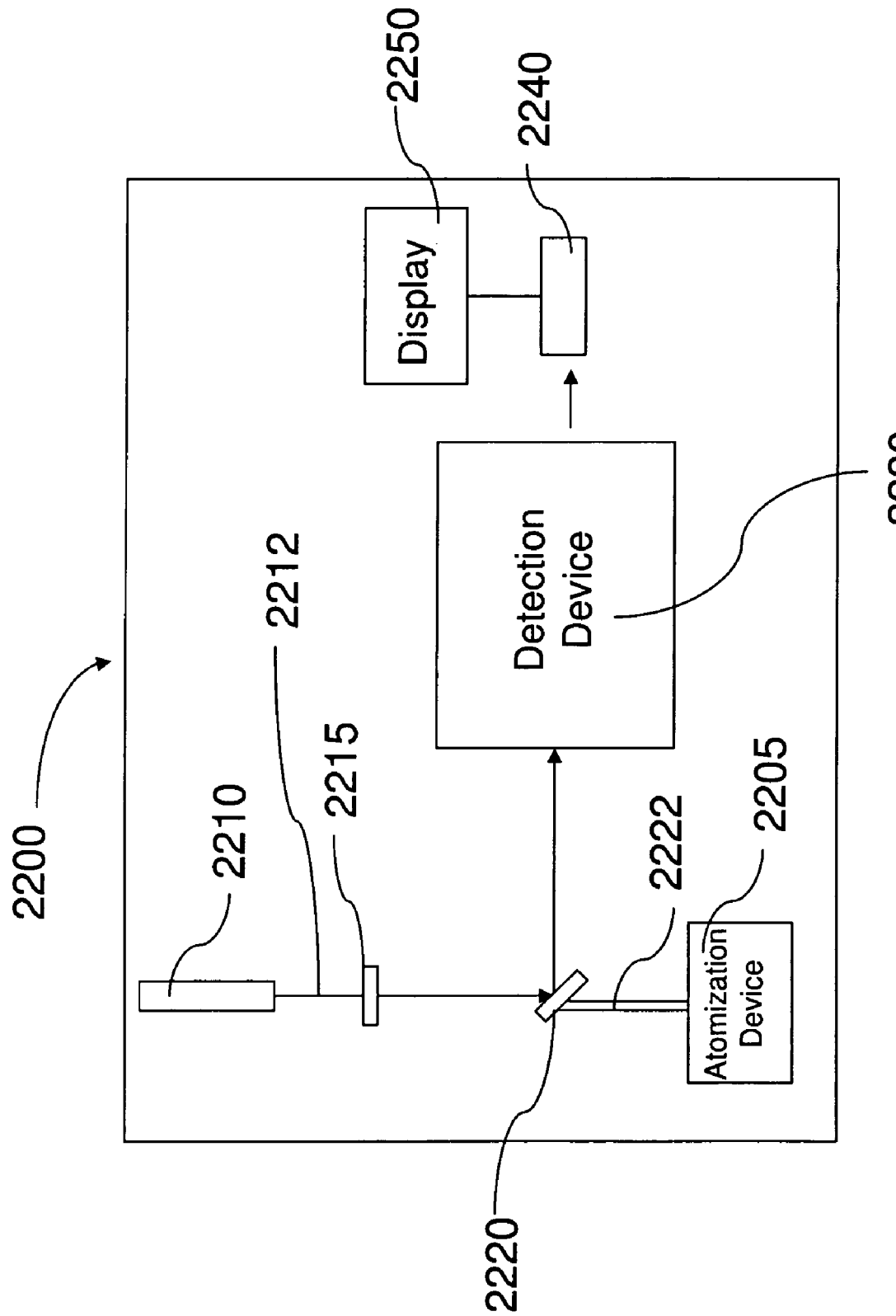

In accordance with certain examples, a device for fluorescence spectroscopy (FLS), phosphorescence spectroscopy (PHS) or Raman spectroscopy is shown in FIG. 22. Device 2200 includes an atomization device 2205, a light source 2210, a sample chamber 2220, a detection device 2230, an optional amplifier 2240 and a display 2250. The detection device 2230 may be positioned ninety degrees from incident light 2212 from the light source 2210 to minimize the amount of light from the light source 2210 that arrives at the detection device 2230. Fluorescence, phosphorescence and Raman emissions may occur in 360 degrees so the positioning of the detection device 2230 to collect light emissions is not critical. The atomization device 2205 may be any of the atomization devices discussed herein and other atomization devices configured with at least one boost device. The atomization device 2205 may be configured to provide atoms and ions to the sample chamber 2220 through the tube 2222 which may be in fluid communication with the sample chamber 2220. An optical chopper 2215 may be used where it is advantageous to pulse the light source 2210. Where the light source is a pulsed laser, the chopper 2215 may be omitted. As atomized and/or ionized sample enters into the sample chamber 2220, the light source 2210 excites one or more electrons into an excited state, e.g., into an excited singlet state, and the excited atom may emit photons as it decays back to a ground state Where the excited atom decays from an excited singlet state to the ground state with resultant emission of light, fluorescence emission is said to occur, and the maximum emission signal is typically red-shifted when compared to the wavelength of the excitation source. Where the excited atom decays from an excited triplet state to the ground state with resultant emission of light, phosphorescence emission is said to occur, and the maximum emission wavelength of phosphorescence is typically red-shifted when compared to the fluorescence maximum emission wavelength. For Raman spectroscopy, scattered radiation may be monitored and the Stokes or anti-Stokes lines may be monitored to provide detection of the sample. The emission signal may be collected using the detection device 2230, which may be, for example, a monochromator with suitable optics such as prisms, echelle gratings and the like. The detection device 2230 provides a signal to the optional amplifier 2240 for amplification of the signal, which may then be viewed using the display 2250. In examples, where the signal is sufficiently strong for detection, the optional amplifier 2240 may be omitted. In certain examples, the display 2250 is part of a computer or data acquisition system for analysis of the signals.

In accordance with certain examples, the sample chamber conditions may be varied depending on whether it is desirable to measure fluorescence, phosphorescence or Raman scattering. For many chemical species, the rate constant for internal conversion and/or fluorescence is typically much greater than the rate constant for phosphorescence and, as a result, either non-radiative emission or fluorescence emission dominates. By varying the sample conditions, it may be possible to favor phosphorescence, or scattering, over fluorescence. For example, the sample chamber 2220 may include a matrix or solid support, e.g., silica, cellulose, acrylamide, etc., that atoms and/or ions may be adsorbed to or trapped in. In other examples, the sample chamber 2220 may be operated at reduced temperatures, e.g., 77 Kelvin, such that atoms and ions entering into the sample chamber 2220 may be frozen in a matrix. For at least certain species, immobilization of the species in a matrix may result in increased intersystem crossing to populate triplet energy levels, which may favor phosphorescence emission over fluorescence emission. It will be within the ability of the person of ordinary skill in the art, given the benefit of this disclosure, to select suitable sampling conditions for monitoring fluorescence, phosphorescence and Raman scattering.

In accordance with certain examples, a device for performing X-ray spectroscopy that includes a boost device is disclosed. An atomization device including a boost device may be configured to provide atoms and ions to the sample chamber. Once in the sample chamber, the ions and atoms may be subjected to an X-ray source and X-ray absorption or emission may be monitored. Suitable instruments known in the art for performing X-ray spectroscopy include, for example, PHI 1800 XPS commercially available from Physical Electronics USA. It will be within the ability of the person of ordinary skill in the art, given the benefit of this disclosure, to adapt the boost devices disclosed here for use in X-ray spectroscopic techniques.

Figure 23:
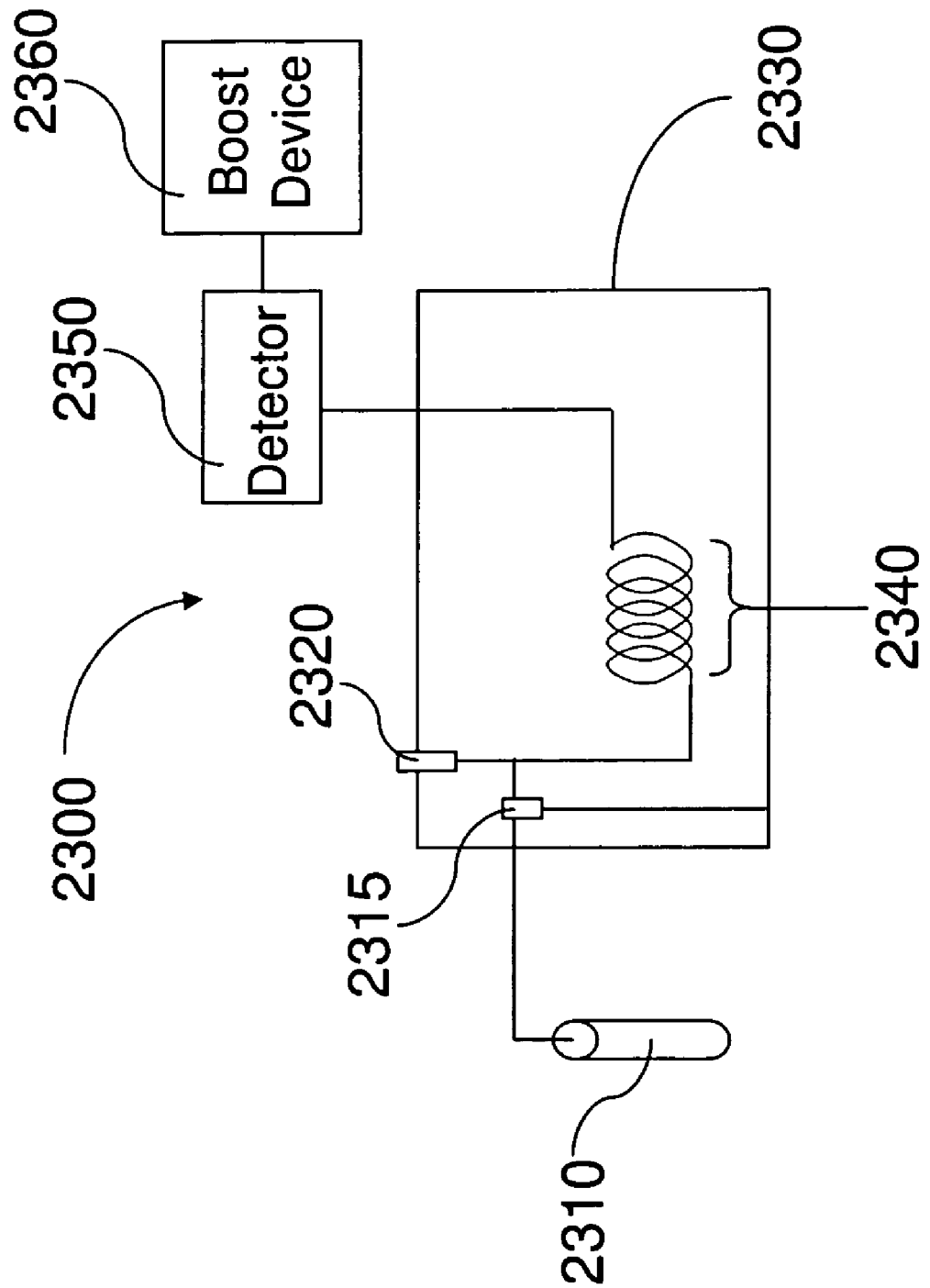

In accordance with certain examples, a gas chromatograph comprising a boost device is shown in FIG. 23. A gas chromatograph 2300 includes a carrier gas 2310 in fluid communication with an injector 2320. The flow rate of the carrier gas 2310 may be regulated using, for example, a pressure regulator, flow meter, etc. The flow of the carrier gas 2310 may be split using a flow splitter 2315 such that a portion of the carrier gas 2310 passes through a tube in fluid communication with the injector 2310 and the remaining carrier gas 2310 may pass to waste. The gas chromatograph 2300 may further include a heating device 2330, such as an oven. The heating device 2330 may be operative to vaporize liquid sample injected through the injector 2320. In certain examples, the heating device 2330 may include an internal boost device to assist with vaporization. Within the heating device 2330 is at least one column 2340 which may separate species within an introduced sample. The column 2340 includes one or more stationary phases such as, for example, polydimethyl siloxane, poly(phenylmethyldimethyl) siloxane, poly(phenylmethyl) siloxane, poly(trifluoropropyldimethyl)siloxane, polyethylene glycol, poly(dicanoallyldimethyl) siloxane and other stationary phases commercially available from numerous manufacturers such as, for example, Phenomenex (Torrance, Calif.). Separated species may elute from the column 2340 and may flow into detector 2350. The detector 2350 may be any one or more of detectors commonly used in gas chromatography including, but not limited to, flame ionization detectors, thermal conductivity detectors, thermionic detectors, electron-capture detectors, atomic emission detectors, photometric detectors, fluorescence detectors, photoionization detectors and the like. In the example shown in FIG. 23, the detector 2350 may include a boost device 2360, which may be used to promote ionization and/or excite ionized species in the detector 2350. It will be within the ability of the person of ordinary skill in the art, given the benefit of this disclosure, to configure gas chromatographs with suitable boost devices.

In accordance with certain other examples, a gas chromatograph may be hyphenated or coupled to an additional instrument. In some examples, the gas chromatograph may be coupled to an inductively coupled plasma that includes a boost device. For example, a gas chromatograph may be used to vaporize and separate species in a sample such that individual species elute from the gas chromatograph. The eluted species may be introduced into an inductively coupled plasma that is hyphenated to the gas chromatograph. The inductively coupled plasma may include one or more boost devices for providing radio frequencies to promote atomization and/or ionization efficiency or for providing radio frequencies to excite atomized and/or ionized species. In other examples, a gas chromatograph may be coupled to a mass spectrometer that includes a boost device. For example, a gas chromatograph may be used to vaporize and separate species in a sample, and the separated species may be introduced into a mass spectrometer for fragmentation and detection. In some examples, a gas chromatograph may be hyphenated to an inductively coupled plasma which itself is coupled to a mass spectrometer. Additional devices and instruments that include boost devices will be readily coupled to gas chromatographs by the person of ordinary skill in the art, given the benefit of this disclosure.

In accordance with certain examples, a device for liquid chromatography (LC), e.g., for performing LC, fast protein liquid chromatography (FPLC), high performance liquid chromatography (HPLC), etc., comprising a boost device is shown in FIG. 24. An LC device 2400 includes a carrier solvent reservoir 2410, a pump 2420, an injector 2430, a column 2450 and a detector 2460. In certain examples, additional pumps and solvents may be included so that solvent gradient techniques may be implemented during the separation. The carrier solvent generally depends on numerous factors including, but not limited to, the species in the sample to be separated and on the nature of the stationary phase in the column 2450. The solvent(s) is typically degassed, e.g., using fritted filtration, bubbling nitrogen through the solvent, etc., prior to any separations. Suitable solvents for performing a given separation and methods for degassing the solvents will be readily selected by the person of ordinary skill in the art, given the benefit of this disclosure. The injector 2430 may be any injector that is configured to provide reproducible injections and, in certain examples, the injector 2430 is a loop injector, such as those commercially available from PerkinElmer, Inc, Beckman Instruments and the like. As sample is injected into the injector 2430, solvent carries sample into the column 2450 where separation of the species in the sample may occur. The exact stationary phase in the column 2450 may vary depending the species to be separated, the solvent composition, etc., and in certain examples, the stationary phase may be selected from C18 based stationary phases, silica, strong anion exchange materials, strong cation exchange materials, size exclusion media, and other stationary phases commonly used in LC, FPLC, and HPLC. Suitable stationary phases and LC columns are commercially available from numerous manufacturers such as, for example, Phenomenex, Inc. (Torrance, Calif.). The separated species may elute from the column 2450 and enter into the detector 2460. The detector 2460 may take numerous forms including, but not limited to, UV/Visible absorbance detectors, fluorescence detectors, conductivity detectors, electrochemical detectors, refractive index detectors, evaporative light scattering detectors, mass analyzers, nuclear magnetic resonance detectors, electron spin resonance detectors, circular dichroism detectors, etc. In certain examples, such as where the liquid chromatograph 2400 may be configured with a mass analyzer, the liquid sample may be nebulized, vaporized and atomized prior to introduction into the mass analyzer. For example, a chromatographic peak may be eluted from the column 2450, and vaporized and atomized using, for example, an inductively coupled plasma prior to introduction into the mass analyzer. The inductively coupled plasma may include a boost device to promote ionization efficiency. It will be within the ability of the person of ordinary skill in the art, given the benefit of this disclosure to configure LC devices with the boost devices disclosed here.

In accordance with certain other examples, an LC device may be hyphenated or coupled to an additional instrument. In some examples, the liquid chromatograph may be coupled to an inductively coupled plasma that includes a boost device. For example, a liquid chromatograph may be used to separate species dissolved in a liquid sample, and the eluted species may be introduced into an inductively coupled plasma that may be hyphenated to the liquid chromatograph and where atomization and/or detection may occur. The inductively coupled plasma may include one or more boost devices for providing radio frequencies to promote atomization and/or ionization efficiency or for providing radio frequencies to excite atomized and/or ionized species. In other examples, the liquid chromatograph may be coupled to a mass spectrometer that includes a boost device. For example, the liquid chromatograph may be used to separate species in a sample, and the separated species may be introduced into a mass spectrometer for fragmentation and detection. It may be desirable to vaporize, using, for example, an inductively coupled plasma with a boost device, a thermospray with a boost device, etc., the liquid sample prior to introduction into the mass spectrometer. Additional devices and instruments that include boost devices will be readily coupled to liquid chromatographs by the person of ordinary skill in the art, given the benefit of this disclosure.

In accordance with certain examples, a device for nuclear magnetic resonance (NMR) including a boost device is disclosed. In certain examples, the NMR is hyphenated to one or more additional devices that include the boost device. For example, species may be analyzed using NMR and then subsequent to NMR analysis may be introduced into an atomization device with a boost device for detection. In other examples, the species may first be atomized using the atomization device with a boost device and then the atoms and/or ions may be analyzed using NMR. For example, gas phase NMR studies may be performed to identify impurities with a high vapor pressure. In certain examples, it may be necessary to pressurize the sample chamber, e.g., to about 10-50 atm, to obtain good spectra for gas phase species. For illustrative purposes only, a block diagram of an NMR device suitable for pulsed NMR experiments is shown in FIG. 25. An NMR device 2500 includes a magnet 2510, an RF generator 2520, a receiver 2530, and a data acquisition device 2540, such as a computer. The magnet 2510 includes a field-frequency lock 2512 and shim coils 2514 each of which may be in electrical communication with the data acquisition device 2540. The probe 2516 may be positioned within the magnet 2510. The probe 2516 may be electrically coupled to an RF transmitter 2522. The RF transmitter 2522 may be in electrical communication with a frequency synthesizer 2524. The frequency synthesizer 2524 may be in electrical communication with a pulse programmer 2526. The RF generator 2520 may be configured to provide RF pulses, e.g., ninety degree pulses, 180 degree pulses, etc., to the probe 2516 for detection of species present in a sample contained within the probe 2516. When a signal is transmitted from the probe 2516, the signal may be sent to the receiver 2530 for detection. The receiver 2530 may include a preamplifier 2532, a phase sensitive detector 2534, audio filters 2536 and an analog-to-digital converter 2538 for providing a signal to the data acquisition system 2540. The probe may be configured to detect one or more magnetically active nuclei, e.g. $^1H$, $^{13}C$, $^{15}N$, $^{31}P$, etc. In certain examples, the NMR device may be used for one, two, three, or four-dimensional NMR spectroscopic techniques, e.g., NOESY, COSY, TOCSY, etc. In certain examples, an NMR device may be hyphenated to an atomization device with a boost device that may detect atomized and/or ionized species. In other examples, the NMR device may be hyphenated to a mass analyzer, which itself may be coupled to an atomization device, for analysis based on mass-to-charge ratios. In certain examples, a tube or conduit may be provided between the probe of the NMR device and the additional device, e.g., an ICP or a mass analyzer, such that sample may be automatically transferred from the NMR device to the additional device. The person of ordinary skill in the art, given the benefit of this disclosure, will be able to select or design suitable NMR devices for hyphenating additional devices that include boost devices.

In accordance with additional example, a device for electron spin resonance (ESR) that is hyphenated to an additional device including a boost device is provided. Without wishing to be bound by any particular scientific theory, many metal species that may be detected by OES or AS may also be detected using ESR. For example, manganese with a spin number of 5/2 provides and ESR spectrum with 6 lines when free manganese is dissolved in water. The exact line shape and line widths of the ESR spectrum may provide some indication of the environment experienced by the manganese ions. The optical emission of atomic manganese may be detected at 257.610 nm. Using an ESR instrument hyphenated to an OES device, two measurements may be performed on the same sample. Suitable ESR instruments are commercially available from numerous manufacturers including, but not limited to, Bruker Instruments (Germany). The ESR may be coupled with an OES device using suitable tubing and connectors such that liquid sample from the ESR may be removed and delivered to the OES device without the need to manually inject sample into the OES device. It will be within the ability of the person of ordinary skill in the art, given the benefit of this disclosure, to couple ESR devices with additional devices and instruments including atomization devices with boost devices.

In accordance with certain examples, a spectrometer configured for measurement in the low UV and that includes a boost device is provided. As used herein "low UV" refers to measurements taken at or around 90-200 nm or less. At wavelengths of less than about 200-210 nm, oxygen in the optical path may absorb emitted light (in the case of an OES device) or may absorb light used to excite atoms and ions (in the case of an AS device). This absorption by the oxygen may prevent detection of emission lines of atoms, such as chlorine, that emit in the low UV range. By using a boost device with an OES device or with an AS device, low UV measurements may be obtained by eliminating any oxygen present in the optical path. This result may be accomplished, for example, by coupling a first chamber, or a second chamber, to the spectrometer. For example, a first chamber may be used to contain the atomization source, and an interface may be used to draw atomized sample into a second chamber. The second chamber may include a boost device. The second chamber may be in fluid communication with a window or aperture on the spectrometer such that the optical path of the spectrometer is sealed off from any outside air or oxygen. The optical path may be purged with a gas that does not absorb in the low UV, e.g., nitrogen, such that light emissions in the low UV, or light absorptions using low UV, are not interfered with by oxygen. In certain examples, the device includes a boost device optically coupled to a window on a spectrometer such that substantially no oxygen or air exists in the light path of the spectrometer. In certain examples, the device may be configured for optical emission such that light emissions in the low UV may be detected. In other examples, the device may be configured for atomic absorption such that species that absorb low UV light may be detected. In certain examples, the detector may be optically coupled to a chamber comprising a boost device such that light emissions or absorptions in the chamber may be detected. In some examples, the chamber may also be optically coupled to a light source, e.g., a UV light source such as a laser, arc lamp or the like, such that light may be provided to the chamber to detect the presence of species that absorb the low UV light. Illustrative configurations of low UV devices are described in more detail below in Examples 7 and 8 herein.

In other examples, an OES device with an inductively coupled plasma and a boost device and configured to detect metal species at levels at least about five-times less, more particularly at least ten times less, than detection levels obtainable using non-boosted ICP-OES devices is disclosed. Without wishing to be bound by any particular scientific theory, the boost devices disclosed here may increase the area of the emission region of OES devices by 5-fold, 10-fold or more. In certain examples using the RF boost devices disclosed herein, the emission region of OES devices increases by about 5-fold, 10-fold or more without a substantial increase in background emission. While in some examples the background signal may increase, the increase in background signal may be proportionately lower than the increase in emission signal intensity to provide lower detection levels. Such an increase in signal area may result in lowering of the OES detection limit of metals by at least about 5-fold, 10-fold or more. It will be within the ability of the person of ordinary skill in the art, given the benefit of this disclosure, to use OES devices that include boost devices to detect metal species at levels of at least about 5-times less than non boosted ICP-OES devices.

In accordance with yet other examples, an OES device with an inductively coupled plasma and a boost device and configured to detect aluminum at a level of about 0.18 µg/L or less is provided. As discussed herein, the boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of aluminum (about 0.9 µg/L) by at least 5-fold. In some examples, the OES device may be configured to detect aluminum at levels of about 0.11 µg/L or less, e.g. 0.09 µg/L, 0.045 µg/L or less. The OES device may include, for example, an atomization source and boost devices as disclosed herein, with such examples provided for illustration and not limitation.

In accordance with certain other examples, an OES device with an inductively coupled plasma and a boost device and configured to detect arsenic at a level of about 0.6 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of arsenic (about 3.0-3.6 µg/L) by at least 5-fold. In some examples, the OES device may be configured to detect arsenic at levels of about 0.4 µg/L or less, e.g. 0.3 µg/L, 0.15 µg/L or less. The OES device may include, for example, an atomization source and boost devices as disclosed herein, with such examples provided for illustration and not limitation.

In accordance with other examples, an OES device with an inductively coupled plasma and a boost device and configured to detect boron at a level of about 0.05 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of boron (about 0.25-1.0 µg/L) by at least 5-fold. In some examples, the OES device may be configured to detect boron levels of about 0.033 µg/L or less, e.g. 0.025 µg/L, 0.0125 µg/L or less. The OES device may include, for example, an atomization source and boost devices as disclosed herein, with such examples provided for illustration and not limitation.

In accordance with certain examples, an OES device with an inductively coupled plasma and a boost device and configured to detect beryllium at a level of about 0.003 µg/L or less is provided. As discussed herein, the boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of beryllium (about 0.017-1.0 µg/L) by at least 5-fold. In some examples, the OES device may be configured to detect beryllium levels of about 0.002 µg/L or less, e.g. 0.0017 µg/L, 0.00085 µg/L or less. The OES device may include, for example, an atomization source and boost devices as disclosed herein, with such examples provided for illustration and not limitation.

In accordance with certain examples, an OES device with an inductively coupled plasma and a boost device and configured to detect cadmium at a level of about 0.014 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of cadmium (about 0.07-0.1 µg/L) by at least 5-fold. In some examples, the OES device may be configured to detect cadmium levels of about 0.009 µg/L or less, e.g. 0.007 µg/L, 0.0035 µg/L or less. The OES device may include, for example, an atomization source and boost devices as disclosed herein, with such examples provided for illustration and not limitation.

In accordance with certain examples, an OES device with an inductively coupled plasma and a boost device and configured to detect cobalt at a level of about 0.05 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of cobalt (about 0.25 µg/L) by at least 5-fold. In some examples, the OES device may be configured to detect cobalt levels of about 0.033 µg/L or less, e.g., 0.025 µg/L, 0.01 µg/L or less. The OES device may include, for example, an atomization source and boost devices as disclosed herein, with such examples provided for illustration and not limitation.

In accordance with certain examples, an OES device with an inductively coupled plasma and a boost device and configured to detect chromium at a level of about 0.04 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of chromium (about 0.20-0.25 µg/L) by at least 5-fold. In some examples, the OES device may be configured to detect chromium levels of about 0.03 µg/L or less, e.g., 0.02 µg/L, 0.01 µg/L or less. The OES device may include, for example, an atomization source and boost devices as disclosed herein, with such examples provided for illustration and not limitation.

In accordance with certain examples, an OES device with an inductively coupled plasma and a boost device and configured to detect copper at a level of about 0.08 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of copper (about 0.4-0.9 µg/L) by at least 5-fold. In some examples, the OES device is configured to detect copper levels of about 0.053 µg/L or less, e.g., 0.04 µg/L, 0.02 µg/L or less. The OES device may include, for example, an atomization source and boost devices as disclosed herein, with such examples provided for illustration and not limitation.

In accordance with certain examples, an OES device with an inductively coupled plasma and a boost device and configured to detect iron at a level of about 0.04 µg/L or less is provided. As discussed herein, the boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of iron (about 0.2-0.4 µg/L) by at least 5-fold. In some examples, the OES device may be configured to detect iron levels of about 0.027 µg/L or less, e.g., 0.02 µg/L, 0.01 µg/L or less. The OES device may include, for example, an atomization source and boost devices as disclosed herein, with such examples provided for illustration and not limitation.

In accordance with certain examples, an OES device with an inductively coupled plasma and a boost device and configured to detect manganese at a level of about 0.006 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of manganese (about 0.03-0.10 µg/L) by at least 5-fold. In some examples, the OES device may be configured to detect manganese levels of about 0.004 µg/L or less, e.g., 0.003 µg/L, 0.0015 µg/L or less. The OES device may include, for example, an atomization source and boost devices as disclosed herein, with such examples provided for illustration and not limitation.

In accordance with certain examples, an OES device with an inductively coupled plasma and a boost device and configured to detect molybdenum at a level of about 0.08 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of molybdenum (about 0.40-2 µg/L) by at least 5-fold. In some examples, the OES device may be configured to detect molybdenum levels of about 0.053 µg/L or less, e.g., 0.04 µg/L, 0.02 µg/L or less. The OES device may include, for example, an atomization source and boost devices as disclosed herein, with such examples provided for illustration and not limitation.

In accordance with certain examples, an OES device with an inductively coupled plasma and a boost device and configured to detect nickel at a level of about 0.08 µg/L or less is provided. As discussed herein, the boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of nickel (about 0.4 µg/L) by at least 5-fold. In some examples, the OES device may be configured to detect nickel levels of about 0.053 µg/L or less, e.g., 0.04 µg/L, 0.02 µg/L or less. The OES device may include, for example, an atomization source and boost devices as disclosed herein, with such examples provided for illustration and not limitation.

In accordance with certain examples, an OES device with an inductively coupled plasma and a boost device and configured to detect lead at a level of about 0.28 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of lead (about 1.4 µg/L) by at least 5-fold. In some examples, the OES device may be configured to detect lead levels of about 0.19 µg/L or less, e.g., 0.14 µg/L, 0.007 µg/L or less. The OES device may include, for example, an atomization source and boost devices as disclosed herein, with such examples provided for illustration and not limitation.

In accordance with certain examples, an OES device with an inductively coupled plasma and a boost device and configured to detect antimony at a level of about 0.4 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of antimony (about 2-4 µg/L) by at least 5-fold. In some examples, the OES device may be configured to detect antimony levels of about 0.3 µg/L or less, e.g., 0.2 µg/L, 0.1 µg/L or less. The OES device may include, for example, an atomization source and boost devices as disclosed herein, with such examples provided for illustration and not limitation.

In accordance with certain examples, an OES device with an inductively coupled plasma and a boost device and configured to detect selenium at a level of about 0.6 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of selenium (about 3-4.5 µg/L) by at least 5-fold. In some examples, the OES device may be configured to detect selenium levels of about 0.4 µg/L or less, e.g., 0.3 µg/L, 0.15 µg/L or less. The OES device may include, for example, an atomization source and boost devices as disclosed herein, with such examples provided for illustration and not limitation.

In accordance with certain examples, an OES device with an inductively coupled plasma and a boost device and configured to detect tantalum at a level of about 0.4 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of tantalum (about 2-3.5 µg/L) by at least 5-fold. In some examples, the OES device may be configured to detect tantalum levels of about 0.27 µg/L or less, e.g., 0.2 µg/L, 0.1 µg/L or less. The OES device may include, for example, an atomization source and boost devices as disclosed herein, with such examples provided for illustration and not limitation.

In accordance with certain examples, an OES device with an inductively coupled plasma and a boost device and configured to detect vanadium at a level of about 0.03 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of vanadium (about 0.15-0.4 µg/L) by at least 5-fold. In some examples, the OES device may be configured to detect vanadium levels of about 0.02 µg/L or less, e.g., 0.015 µg/L, 0.0075 µg/L or less. The OES device may include, for example, an atomization source and boost devices as disclosed herein, with such examples provided for illustration and not limitation.

In accordance with certain examples, an OES device with an inductively coupled plasma and a boost device and configured to detect zinc at a level of about 0.04 µg/L or less is provided. The boost devices disclosed here may increase the emission region of OES devices by 5-fold or more. In certain other examples, the boost devices disclosed herein may increase the emission region of OES devices by 5-fold or more without a substantial increase in background emission. Such an increase may result in lowering of the OES detection limit of zinc (about 0.2 µg/L) by at least 5-fold. In some examples, the OES device may be configured to detect zinc levels of about 0.027 µg/L or less, e.g., 0.02 µg/L, 0.01 µg/L or less. The OES device may include, for example, an atomization source and boost devices as disclosed herein, with such examples provided for illustration and not limitation.

In accordance with certain examples, a spectrometer including an inductively coupled plasma and a boost device is provided. The spectrometer may be configured to increase the detection region, e.g., the region where optical emissions are monitored or the region where absorption takes place, by at least about 5-fold, more particularly at least about 10-fold. In certain other examples, the boost devices disclosed herein may increase the detection region of OES devices by 5-fold or more without a substantial increase in background emission. The spectrometer may be used for optical emissions and absorptions, fluorescence, phosphorescence, scattering, and other suitable techniques and may be hyphenated with one or more additional devices or instruments. It will be within the ability of the person of ordinary skill in the art, given the benefit of this disclosure, to assemble suitable spectrometers that are configured to increase the detection region by at least about 5-fold.

In accordance with additional examples, a device for optical emission spectroscopy (OES) that includes an inductively coupled plasma and a boost device is disclosed. In certain examples the OES device includes a first chamber comprising the inductively coupled plasma and a second chamber with at least one boost device for exciting atoms or species. Without wishing to be bound by any particular scientific theory, in a conventional OES device, the analyte may be diluted by at least about 20:1 with a carrier gas. This dilution results in lower sensitivity and/or requires the use of more concentrated samples to detect the species. The second chamber in certain OES devices may be configured to extract atomized and ionized species to avoid the dilution effect caused by the carrier gas. For example, the second chamber may include a suitable interface or manifold such that sample from the interior portion of the plasma plume in the first chamber may be drawn into the second chamber and the carrier gas and cooling gas circulating near the outer portions of the first chamber may be removed. This process may result in concentrating the sample in the second chamber. For example, the OES device may be configured such that sample introduced into the second chamber may be diluted by less than about 15:1 with carrier gas, more particularly by less than about 10:1 with carrier gas, e.g., the sample may be diluted by less than about 5:1 with carrier gas. Such concentrating of sample in the second chamber due to less dilution with carrier gas may provide increased emissions which may provide improved detection limits. For example, the sample may be at least about 2-4 times more concentrated in the second chamber than in the first chamber. In addition, the flame or primary plasma background signal may be removed from axial viewing by placing an optical stop or filter between the first and second chamber. This may result in further improvement of detection limits to at least about 5-fold lower than detection limits obtained using ICP-OES devices without second chambers including a boost device. The exact improvement in the detection limit will depend on numerous factors including the size of the orifice or port in the manifold or interface, the amount of sample drawn into the second chamber, the length of the second chamber, the number of boost devices used in the second chamber, etc. It will be within the ability of the person of ordinary skill in the art, given the benefit of this disclosure to select and design suitable ICP-OES devices including second chambers with boost devices.

In accordance with other examples, an OES device with an inductively coupled plasma in a first chamber and a second chamber that includes a boost device and configured to detect aluminum at a level of about 0.7 µg/L or less is provided. The second chamber with boost device may improve the detection limit by about 25-75% because the sample is diluted 25-75% less with carrier gas. This may result in lowering of the OES detection limit of aluminum (about 0.9 µg/L) by at least about 25-75% or more. In some examples, the OES device may be configured to detect aluminum at levels of about 0.45 µg/L or less, e.g. 0.225 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect arsenic at a level of about 2.25 µg/L or less is provided. Without wishing to be bound by any particular scientific theory, the second chamber with boost device may improve the detection limit by about 25-75% since the sample is diluted 25-75% less with carrier gas. Such an increase may result in lowering of the OES detection limit of arsenic (about 3.0-3.6 µg/L) by at least about 25-75% or more. In some examples, the OES device may be configured to detect arsenic at levels of about 1.5 µg/L or less, e.g. 0.75 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect boron at a level of about 0.18 µg/L or less is provided. The second chamber with boost device may improve the detection limit by about 25-75% because the sample is diluted 25-75% less with carrier gas. Such an increase may result in lowering of the OES detection limit of boron (about 0.25-1.0 µg/L) by at least about 25-75% or more. In some examples, the OES device may be configured to detect boron levels of about 0.125 µg/L or less, e.g., 0.06 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect beryllium at a level of about 0.013 µg/L or less is provided. The second chamber with boost device may improve the detection limit by about 25-75% because the sample is diluted 25-75% less with carrier gas. Such an increase may result in lowering of the OES detection limit of beryllium (about 0.017-1.0 µg/L) by at least about 25-75% or more. In some examples, the OES device may be configured to detect beryllium levels of about 0.085 µg/L or less, e.g. 0.045 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect cadmium at a level of about 0.0525 µg/L or less is provided. The second chamber with boost device may improve the detection limit by about 25-75% because the sample is diluted 25-75% less with carrier gas. Such an increase may result in lowering of the OES detection limit of cadmium (about 0.07-0.1 µg/L) by at least about 25-75% or more. In some examples, the OES device may be configured to detect cadmium levels of about 0.035 µg/L or less, e.g. 0.0175 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect cobalt at a level of about 0.19 µg/L or less is provided. The second chamber with boost device may improve the detection limit by about 25-75% since the sample is diluted 25-75% less with carrier gas. Such an increase may result in lowering of the OES detection limit of cobalt (about 0.25 µg/L) by at least about 25-75% or more. In some examples, the OES device may be configured to detect cobalt levels of about 0.125 µg/L or less, e.g., 0.0625 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect chromium at a level of about 0.15 µg/L or less is provided. The second chamber with boost device may improve the detection limit by about 25-75% since the sample is diluted 25-75% less with carrier gas. Such an increase may result in lowering of the OES detection limit of chromium (about 0.20-0.25 µg/L) by at least about 25-75% or more. In some examples, the OES device may be configured to detect chromium levels of about 0.10 µg/L or less, e.g., 0.05 µg/L or less. The second chamber may include a boost device, such as, for example, the boost devices disclosed herein.

In accordance with certain examples, an OES device with an inductively coupled plasma and a second chamber that includes a boost device and configured to detect copper at a level of about 0.30 µg/L or less is provided. The second chamber with boost device may improve the detection limit by about 25-75% because the sample is diluted 25-75% less with carrier gas. Such an increase may result in lowering of the OES detection limit of copper (about 0.4-0.9 µg/L) by at least about 25-75% or more. In some examples, the OES device may be configured to detect copper levels of about 0.20 µg/L or less, e.g., 0.1 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect iron at a level of about 0.15 µg/L or less is provided. The second chamber with boost device may improve the detection limit by about 25-75% because the sample is diluted 25-75% less with carrier gas. Such an increase may result in lowering of the OES detection limit of iron (about 0.2-0.4 µg/L) by at least about 25-75% or more. In some examples, the OES device may be configured to detect iron levels of about 0.10 µg/L or less, e.g., 0.05 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect manganese at a level of about 0.023 µg/L or less is provided. Without wishing to be bound by any particular scientific theory, the second chamber with boost device may improve the detection limit by about 25-75% since the sample is diluted 25-75% less with carrier gas. Such an increase may result in lowering of the OES detection limit of manganese (about 0.03-0.10 µg/L) by at least 25-75% or more. In some examples, the OES device is configured to detect manganese levels of about 0.015 µg/L or less, e.g., 0.008 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect molybdenum at a level of about 0.3 µg/L or less is provided. The second chamber with boost device may improve the detection limit by about 25-75% because the sample is diluted 25-75% less with carrier gas. Such an increase may result in lowering of the OES detection limit of molybdenum (about 0.40-2 µg/L) by at least about 25-75% or more. In some examples, the OES device may be configured to detect molybdenum levels of about 0.2 µg/L or less, e.g., 0.1 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect nickel at a level of about 0.3 µg/L or less is provided. The second chamber with boost device may improve the detection limit by about 25-75% because the sample is diluted 25-75% less with carrier gas. Such an increase may result in lowering of the OES detection limit of nickel (about 0.4 µg/L) by at least about 25-75% or more. In some examples, the OES device may be configured to detect nickel levels of about 0.20 µg/L or less, e.g., 0.10 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect lead at a level of about 1.0 µg/L or less is provided. The second chamber with boost device may improve the detection limit by about 25-75% because the sample is diluted 25-75% less with carrier gas. Such an increase may result in lowering of the OES detection limit of lead (about 1.4 µg/L) by at least about 25-75% or more. In some examples, the OES device may be configured to detect lead levels of about 0.014 µg/L or less, e.g., 0.7 µg/L, 0.35 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect antimony at a level of about 1.5 µg/L or less is provided. The second chamber with boost device may improve the detection limit by about 25-75% because the sample is diluted 25-75% less with carrier gas. Such an increase may result in lowering of the OES detection limit of antimony (about 2-4 µg/L) by at least about 25-75% or more. In some examples, the OES device may be configured to detect antimony levels of about 1 µg/L or less, e.g., 0.5 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect selenium at a level of about 2.25 µg/L or less is provided. The second chamber with boost device may improve the detection limit by about 25-75% because the sample is diluted 25-75% less with carrier gas. Such an increase may result in lowering of the OES detection limit of selenium (about 3-4.5 µg/L) by at least about 25-75% or more. In some examples, the OES device may be configured to detect selenium levels of about 1.5 µg/L or less, e.g., 0.75 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect tantalum at a level of about 1.5 µg/L or less is provided. The second chamber with boost device may improve the detection limit by about 25-75% since the sample is diluted 25-75% less with carrier gas. Such an increase may result in lowering of the OES detection limit of tantalum (about 2-3.5 µg/L) by at least about 25-75% or more. In some examples, the OES device may be configured to detect tantalum levels of about 1.0 µg/L or less, e.g., 0.5 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect vanadium at a level of about 0.11 µg/L or less is provided. The second chamber with boost device may improve the detection limit by about 25-75% since the sample is diluted 25-75% less with carrier gas. Such an increase may result in lowering of the OES detection limit of vanadium (about 0.15-0.4 µg/L) by at least about 25-75% or more. In some examples, the OES device may be configured to detect vanadium levels of about 0.075 µg/L or less, e.g., 0.038 µg/L or less. The second chamber may include a boost device, such as, for example, the boost devices disclosed herein.

In accordance with yet other examples, an OES device with an inductively coupled plasma in a first chamber and a second chamber that includes a boost device and configured to detect zinc at a level of about 0.15 µg/L or less is provided. The second chamber with boost device may improve the detection limit by about 25-75% since the sample is diluted 25-75% less with carrier gas. Such an increase may result in lowering of the OES detection limit of zinc (about 0.2 µg/L) by at least about 25-75% or more. In some examples, the OES device may be configured to detect zinc levels of about 0.10 µg/L or less, e.g., 0.05 µg/L or less. The second chamber may include a boost device, such as, for example, the boost devices disclosed herein.

In accordance with certain examples, a spectrometer comprising an inductively coupled plasma and a boost device is provided. In certain examples, the spectrometer may be configured to substantially block the signal from the primary discharge so that the detection limit of the instrument may be improved, e.g., lowered, by at least about 3-fold or greater. In certain examples, the detection limit may be lowered by at least about 5-fold, 10-fold or more using the boost devices provided herein.

Other Applications of Boost Devices

Figure 26A:
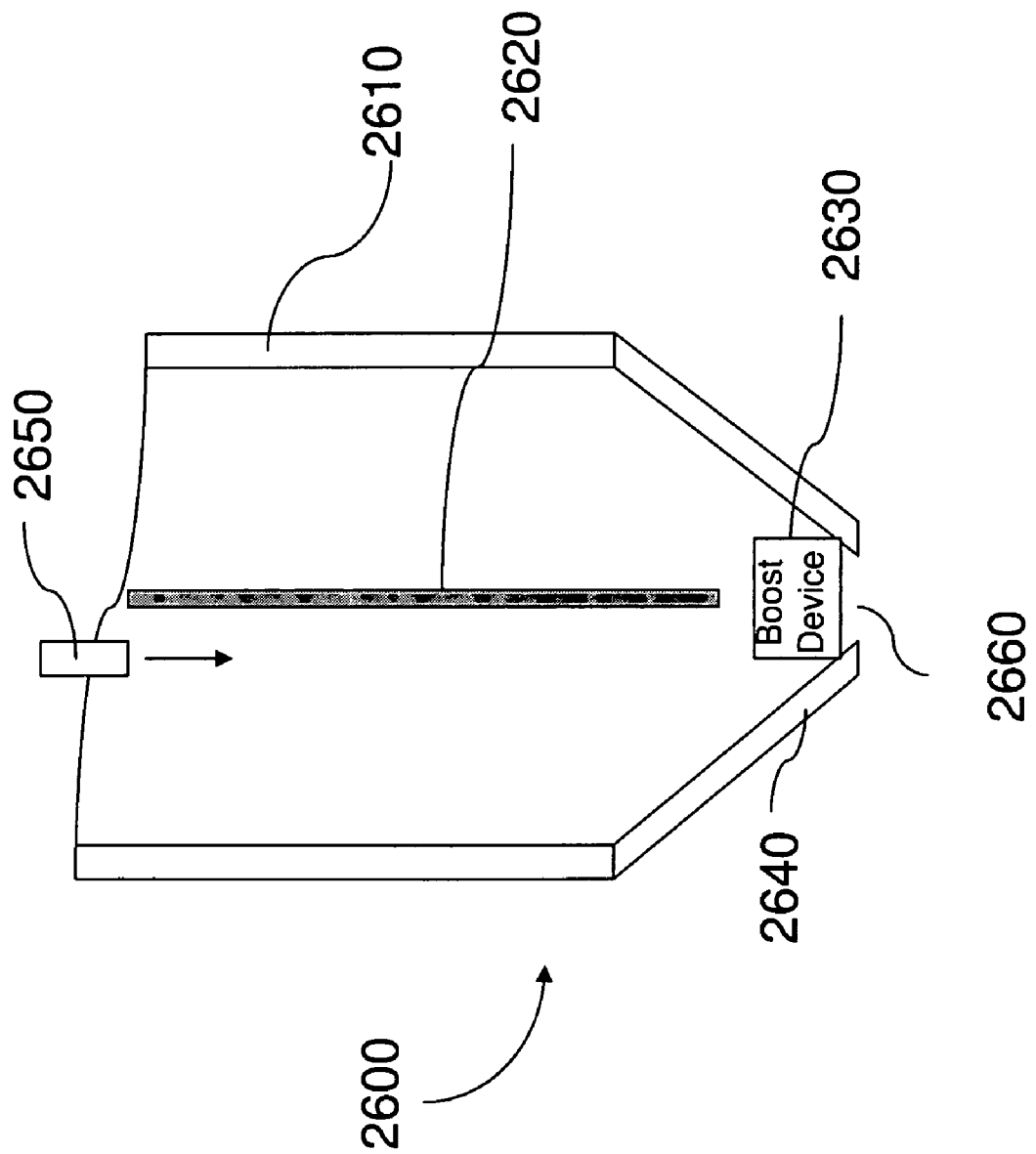
FIG. 26D is an example of a device configured for use in soldering or brazing that comprises a boost device, in accordance with certain examples.

In accordance with certain examples, a welding device with a boost device is provided. The welding device typically includes a torch and a boost device surrounding at least some portion of the torch plume. The boost devices may be used in combination with torches for tungsten inert gas (TIG) welding, plasma arc welding (PAW), submerged arc welding (SAW), laser welding, high frequency welding and other types of welding that will be selected by the person of ordinary skill in the art, given the benefit of this disclosure. For illustrative purposes only and without limitation, an exemplary plasma arc welder with boost device is shown in FIG. 26A. A plasma arc welder 2600 includes a chamber 2610 with an electrode 2620. The electrode 2620 may be any suitable material that may conduct a current, e.g., tungsten, copper, platinum, etc. A boost device 2630 may be positioned toward the terminus of the electrode 2620 and near a nozzle tip 2640 of the plasma arc welder 2600. The nozzle tip 2640 may be constructed from suitable materials known in the art, such as copper, for example. A gas, such as argon, neon, etc., may be introduced into chamber 2610, e.g., through an inlet 2650, and as current is passed through the electrode 2620, an arc is generated between the electrode 2620 and the nozzle tip 2640. A plasma may be created as the gas passes through the arc, and the boost device 2630, which may be in electrical communication with an RF transmitter or RF generator (not shown), may increase atomization and/or ionization of the gas to provide increased numbers of atoms and ions for welding. The arc and/or plasma may be forced through a restricted opening 2660 in the nozzle tip 2640 to provide a very concentrated high temperature area that may be used for welding. The plasma arc welder 2600 may further include a power supply, a water circulator for cooling, air supply regulators and additional devices to provide plasma arc welders including desired features. It will be within the ability of the person of ordinary skill in the art, given the benefit of this disclosure, to design suitable welding devices that include boost devices such as those disclosed herein.

Figure 26B:
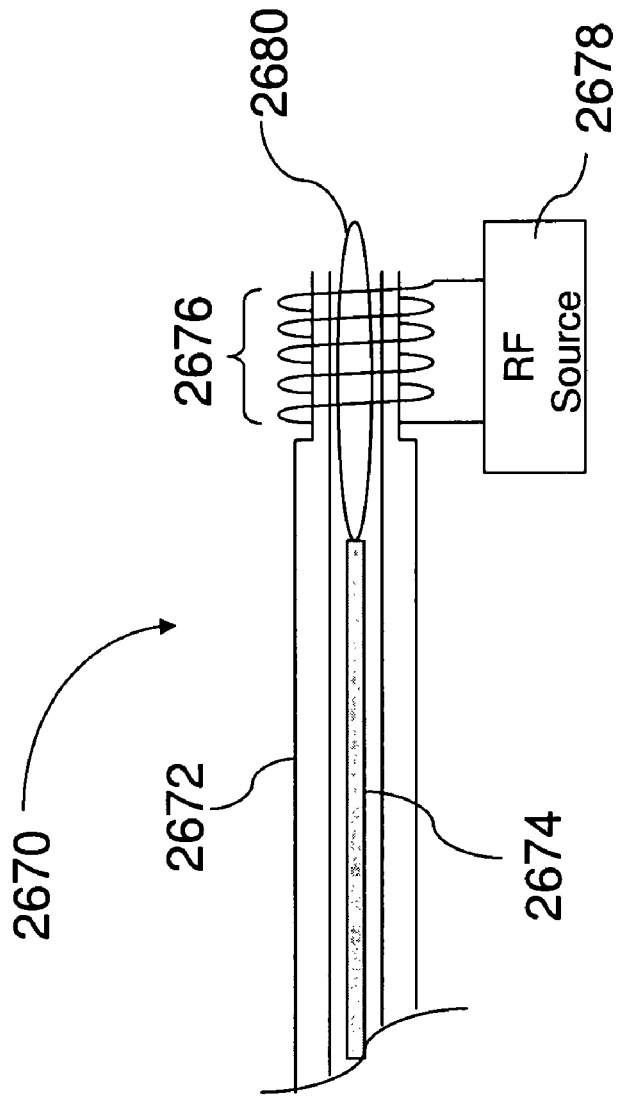

In accordance with certain examples, an additional configuration of a DC or AC arc welder is shown in FIG. 26B. An arc welder 2670 includes a torch body 2672, an electrode 2674, a boost source 2676, and an RF source 2678 in electrical communication with the boost device 2676. In operation, the boost device 2676 may be configured to increase the temperature of a discharge 2680 by providing radio frequencies to the terminus of a torch body 2672. Suitable DC or AC arc welders that include boost devices configured to increase the temperature of the discharge will be readily designed by the person of ordinary skill in the art, given the benefit of this disclosure.

Figure 26C:
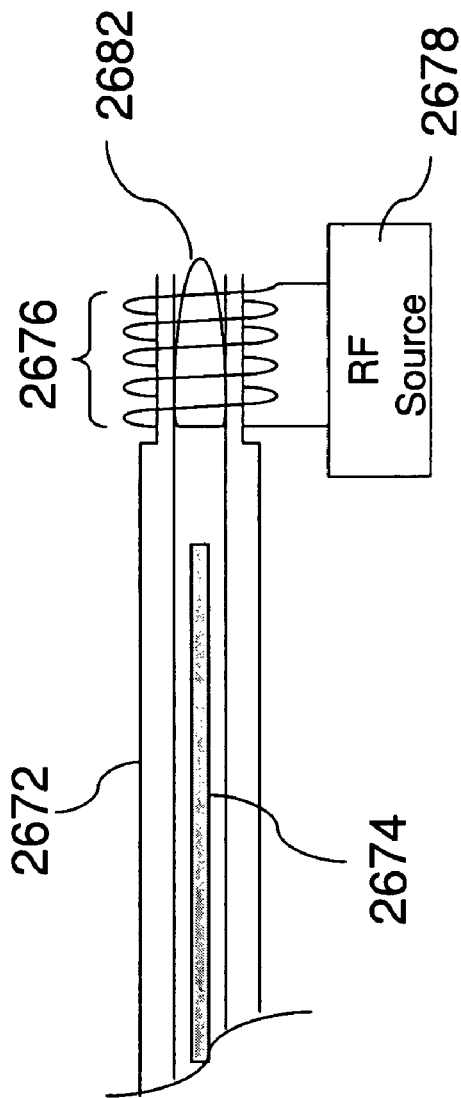

In accordance with certain examples, yet another configuration of a DC or AC arc welder is shown in FIG. 26C, where a primary shield gas is used such as, for example, argon, argon/oxygen, argon/carbon dioxide, or argon/helium. The shield gas itself may be used to support an inductively coupled plasma discharge allowing the power to the primary arc generated by the electrode to be turned off or greatly reduced to provide discharge 2682. The person of ordinary skill in the art, given the benefit of this disclosure, will be able to design suitable DC or AC arc welders, which include boost devices, that allow the power to the primary arc to be turned off or greatly reduced.

Figure 26D:
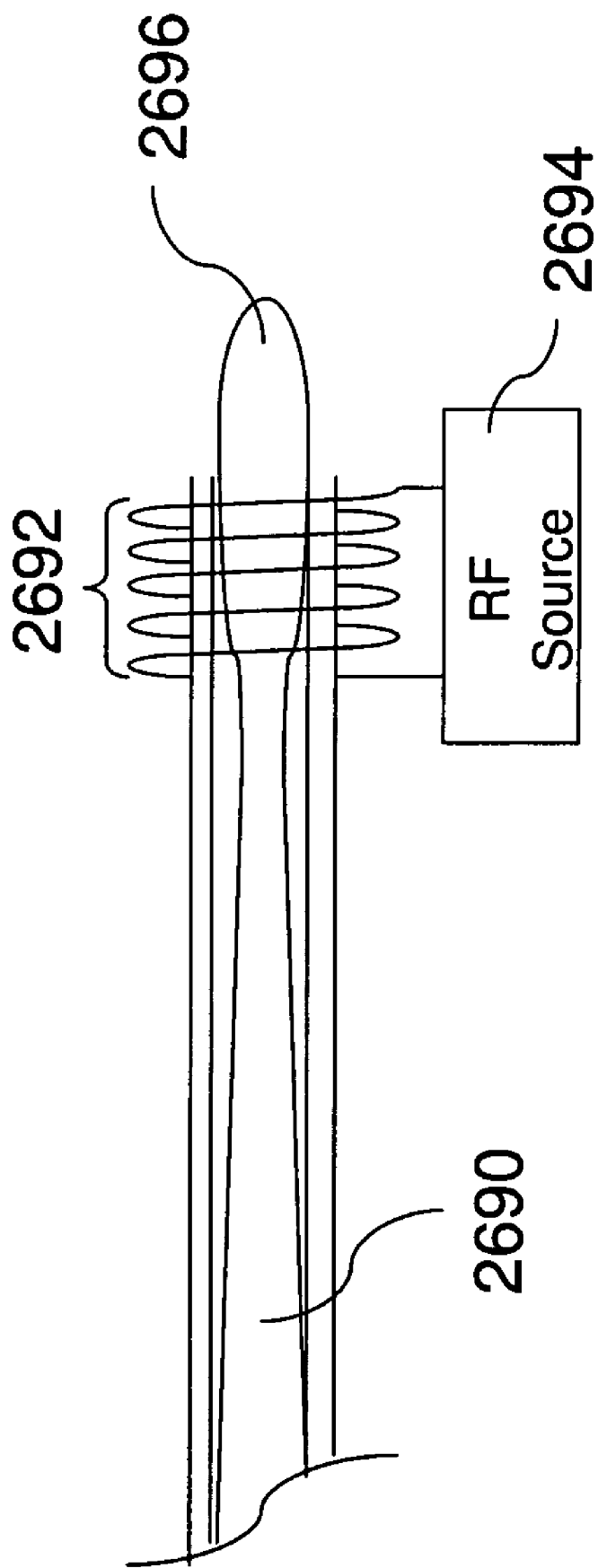

In accordance with certain examples, an example of a device configured for use in soldering or brazing is shown in FIG. 26D. A flame 2690, such as a flame used for flame brazing or soldering, may be boosted in temperature with a boost device 2692, which may be in electrical communication with an RF source 2694, to provide a discharge 2696, which has a temperature that may be higher than the temperature of the flame 2690. The flame 2690 may be any of the illustrative flames disclosed herein or other suitable flames that will be readily selected by the person of ordinary skill in the art, given the benefit of this disclosure. It will also be within the ability of the person of ordinary skill in the art, given the benefit of this disclosure, to design flame brazing and soldering devices suitable for an intended use.

Figure 27:
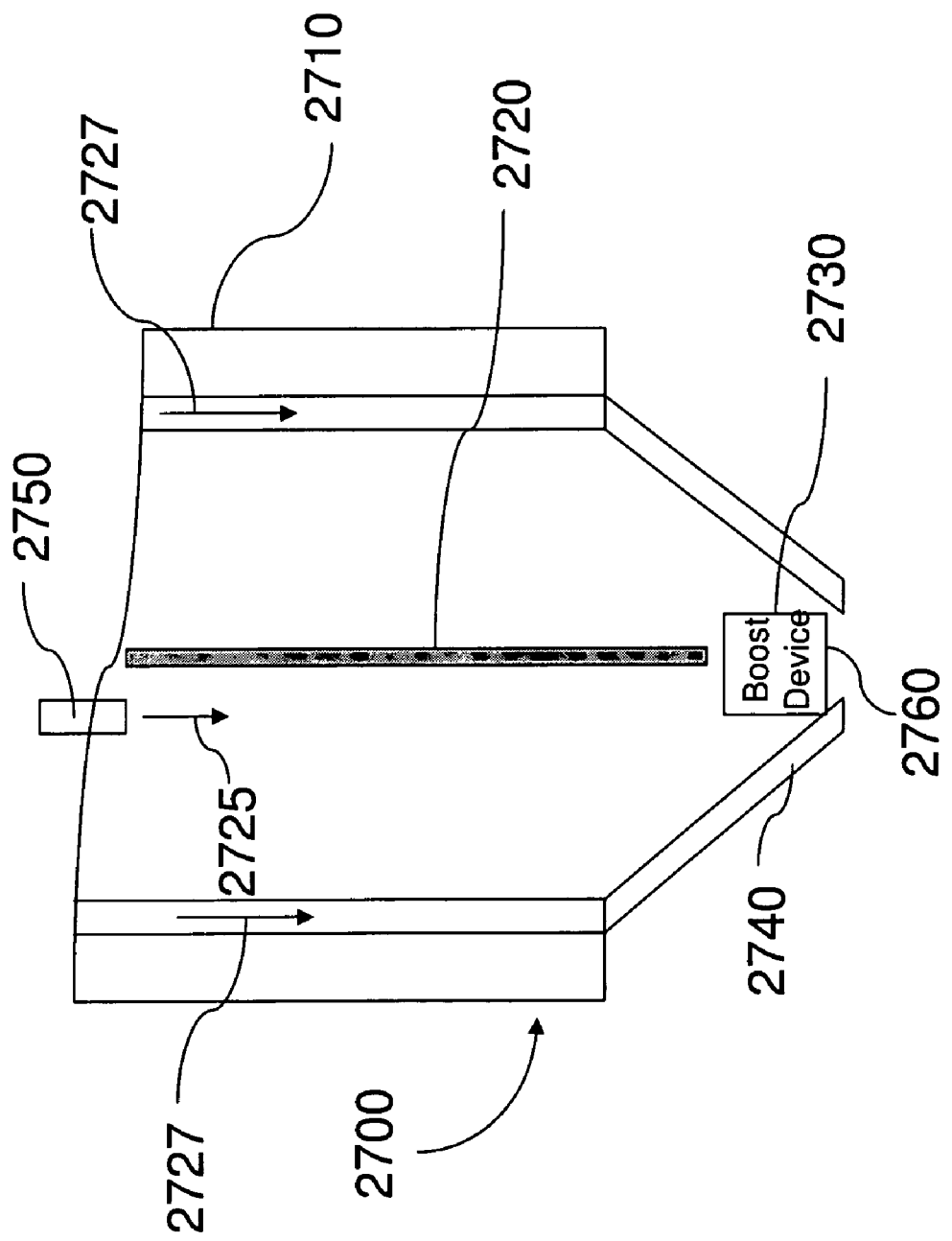
FIG. 27 is an example of plasma cutter that includes a boost device, in accordance with certain examples.

In accordance with certain examples, a plasma cutter including a boost device is disclosed. For illustrative purposes only and without limitation, an exemplary plasma cutter with boost device is shown in FIG. 27. A plasma cutter 2700 includes a chamber or channel 2710 that includes an electrode 2720. The chamber 2710 may be configured such that a cutting gas 2725 may flow through the chamber 2710 and may be in fluid communication with the electrode 2720. The chamber 2710 may also be configured such that a shielding gas 2727 may flow around a cutting gas 2725 and an electrode 2720 to minimize interferences such as oxidation of the cutting surface. A plasma cutter 2700 may further include a boost device 2730 configured to increase ionization of the cutting gas and/or increase the temperature of the cutting gas. Suitable cutting gases will be readily selected by the person of ordinary skill in the art, given the benefit of this disclosure, and exemplary cutting gases include, but are not limited to, argon, hydrogen, nitrogen, oxygen and mixtures thereof. As current is passed through electrode 2720, an arc may be created between the electrode 2720 and a nozzle tip 2740. The cutting gas 2725 may be introduced through an inlet 2750 and may be atomized and/or ionized as it passes through the arc to create a plasma. The arc and plasma may be forced through a restricted opening 2760 to provide a concentrated high temperature region that may be used for cutting, e.g., for cutting metals, steels, ceramics and the like. Additional devices may be used with the plasma cutter 2700 such as mechanical arms, robots, computers etc. In certain examples, the plasma cutter may be a component of a larger system that is configured to cut shapes or designs from a larger piece of metal. The cutting process may be automated using robotic or mechanical arms and suitable computers and software. The person of ordinary skill in the art, given the benefit of this disclosure, will be able to design suitable plasma cutters and systems implementing plasma cutters for cutting metals, ceramics and other materials.

Figure 28:
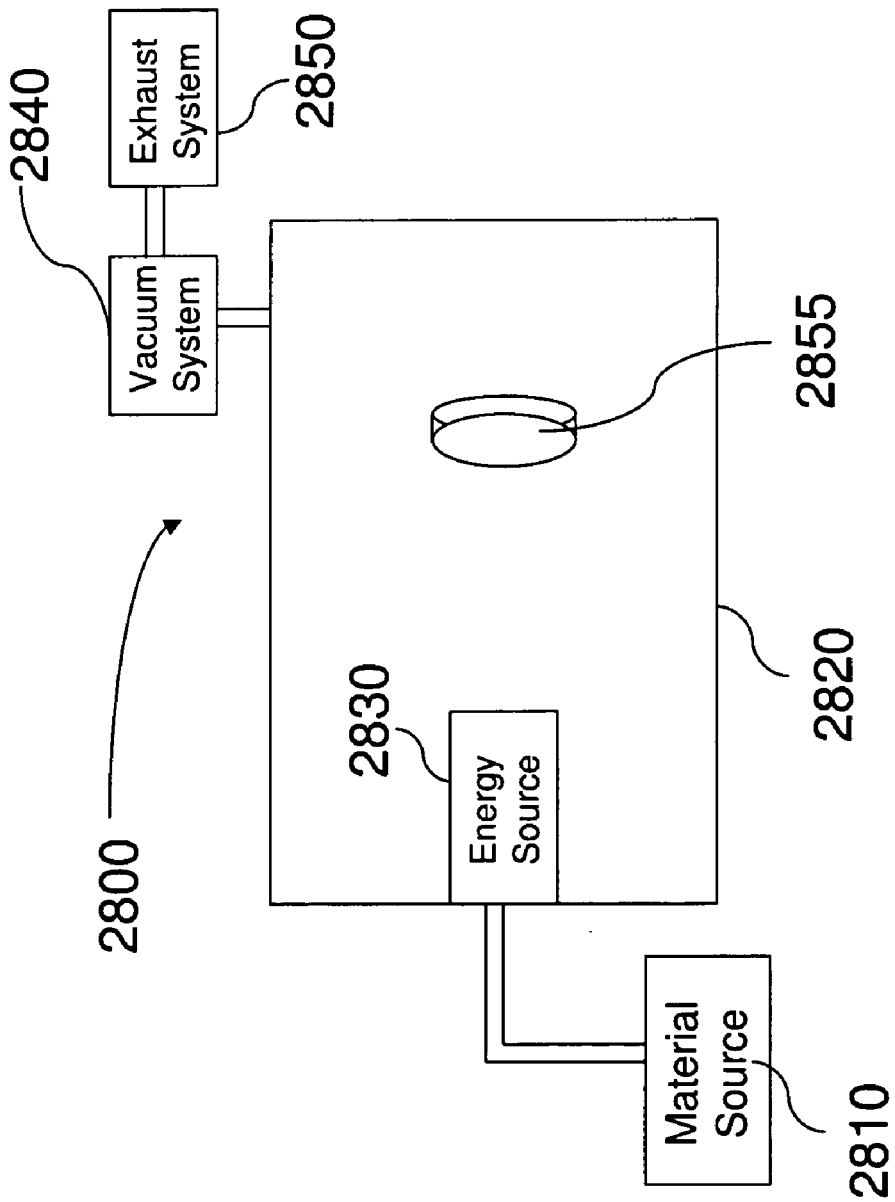
FIG. 28 is an example of vapor deposition device that includes a boost device, in accordance with certain examples.

In accordance with yet an additional aspect, a vapor deposition device that includes a boost device is disclosed. The exact configuration of the vapor deposition device may take numerous forms and illustrative configurations may be found in vapor deposition devices commercially available from, for example, Veeco Instruments (Woodbury, N.Y.) and other vapor deposition device manufacturers. In certain examples, the vapor deposition device may be configured for atomic layer deposition (ALD), diamond like carbon deposition (DLC), ion beam deposition (IBD), physical vapor deposition, etc. In other examples, the vapor deposition device may be configured for chemical vapor deposition (CVD). For illustrative purposes only and without limitation, an exemplary vapor deposition device is shown in FIG. 28. A vapor deposition device 2800 includes a material source 2810, a chamber 2820, an energy source 2830, a vacuum system 2840 and an exhaust system 2850. The material source 2810 may be in fluid communication with the chamber 2820 and may be configured to supply precursors or reactants to the chamber 2820. The chamber 2820 includes the energy source 2830 which may be configured to provide heat or energy to volatize the delivered material or to promote reactions in the reaction chamber. A vacuum system 2840 may be configured to remove by-products and waste from the chamber 2820 and may optionally include scrubbers or other treatment devices to treat the waste prior to release to an exhaust system 2850. A sample or a substrate 2855 that species are to be deposited on may be loaded into the chamber 2820 using suitable assemblies, e.g., belts, conveyers, etc. Material may be introduced into the chamber 2820 and the energy source 2830 may be used to vaporize, atomize and/or ionize material from the material source 2810 to coat or deposit material onto the substrate 2855. The energy source 2830 may include a boost device to assist in vaporization and/or atomization of the gas or species to be deposited. Vapor deposition device 2800 may also include process control equipment including but not limited to, gauges, controls, computers, etc., to monitor process parameters such as, for example, pressure, temperature and time. Alarms and safety devices may also be included. Additional suitable devices will be readily selected by the person of ordinary skill in the art, given the benefit of this disclosure.

Figure 29:
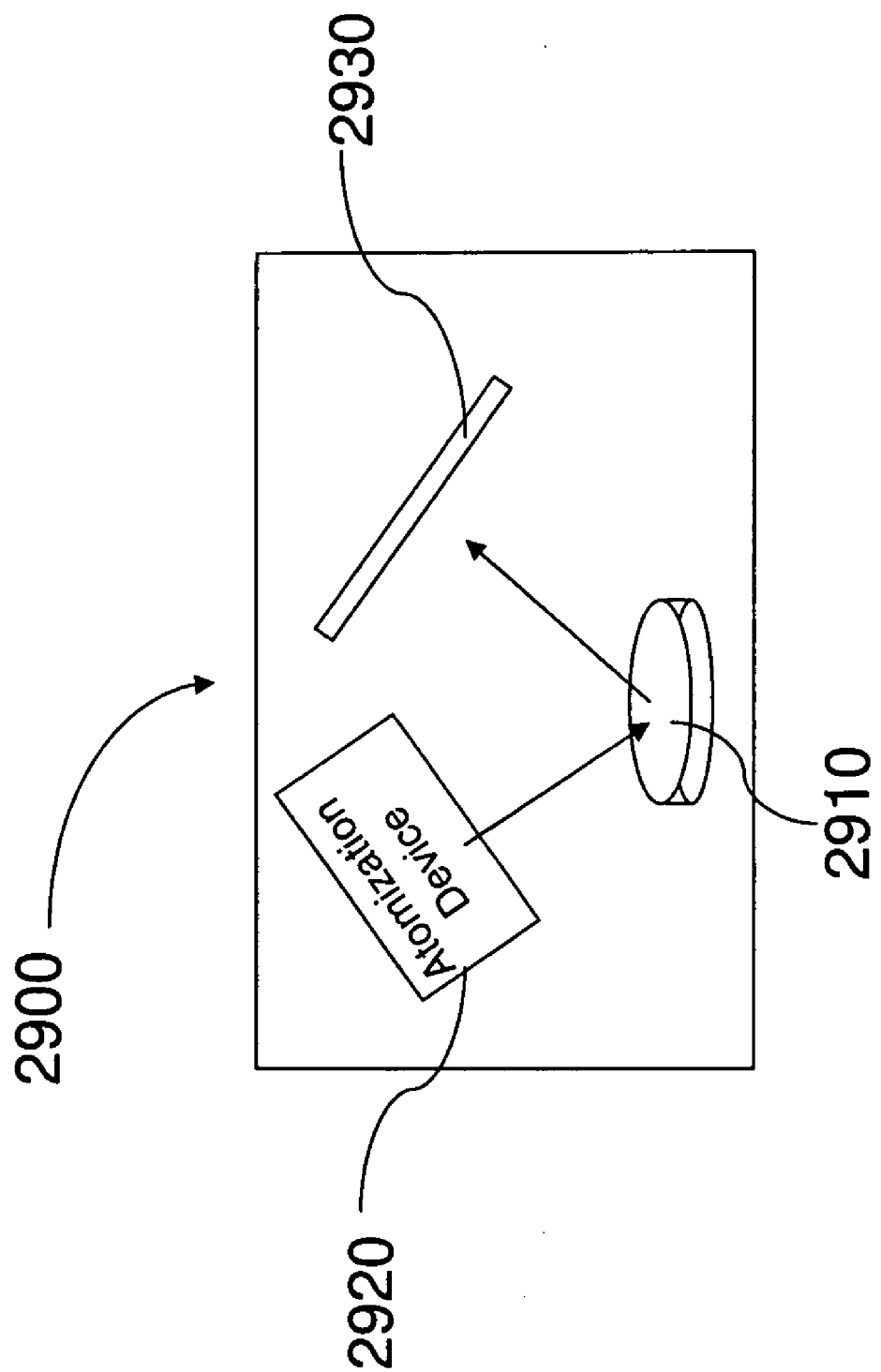
FIG. 29 is an example of a sputtering device that includes a boost device, in accordance with certain examples.

In accordance with certain examples, a sputtering device that includes a boost device is disclosed. For illustrative purposes only and without limitation, an exemplary sputtering device is shown in FIG. 29. A sputtering device 2900 includes a target 2910 and an atomization device 2920 with a boost device. The atomization device 2920 may be any of the atomization devices disclosed herein or other suitable atomization devices that will be selected or designed by the person of ordinary skill in the art, given the benefit of this disclosure. In certain examples, the atomization device 2920 may be a plasma that includes a boost device or a magnetron that includes a boost device. The atomization device 2920 may be operative to strike the target 2910. Ions and atoms may be ejected from the target 2910 and may be deposited on a substrate 2930. One or more assist or carrier gases may be used to flow atoms and ions by the substrate 2930. A boost device may increase the energy of the atoms and/or ions, may increase the number of atoms and/or ions present, etc. The nature of the material to be deposited depends on the selected target. In certain examples, the target may include one or more materials selected from aluminum, gallium, arsenic, and silicon. Other suitable materials for deposition will be readily selected by the person of ordinary skill in the art, given the benefit of this disclosure. Additional devices, such as control devices, vacuum pumps, exhaust systems, etc., may also be used with the sputtering device 2900. The person of ordinary skill in the art, given the benefit of this disclosure, will be able to design suitable sputtering devices that include boost devices.

Figure 30:
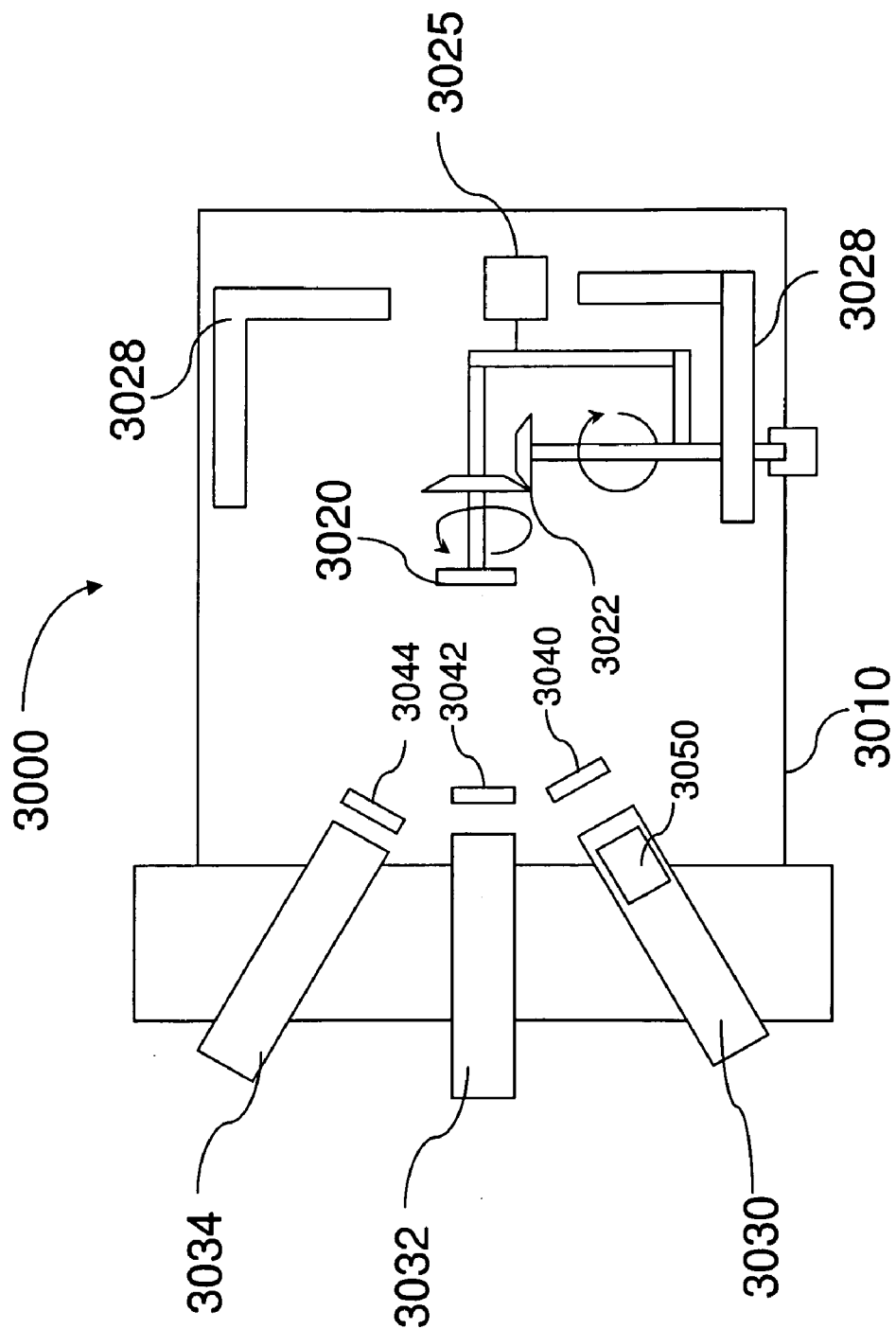
FIG. 30 is an example of device for molecular beam epitaxy that includes a boost device, in accordance with certain examples.

In accordance with certain examples, a device for molecular beam epitaxy (MBE) that includes a boost device is provided. The boost device may be used to increase the vaporization, sublimation, atomization of species such as gallium, aluminum, arsenic, arsenides, beryllium, silicon etc., for deposition onto surfaces, such as a GaAs wafer. For illustrative purposes only, an exemplary MBE device is shown in FIG. 30. An MBE device 3000 includes a growth chamber 3010 for receiving a sample. A sample holder 3020 and all other internal parts that are subjected to high temperatures may be constructed from materials such as tantalum, molybdenum and pyrolytic boron nitride, which do not substantially decompose or outgas impurities even when heated to temperatures around 1400° C. Sample may be loaded into the growth chamber 3010 and placed on the sample holder 3020 which may include a heating device. Suitable methods for placing sample into the growth chamber 3010 will be readily selected by the person of ordinary skill in the art, given the benefit of this disclosure, and exemplary methods include the use of magnetically coupled transfer rods and devices. In certain configurations, the sample holder 3020 rotates on two axes, as shown in FIG. 30. The sample holder 3020 may be configured for continuous azimuthal rotation (CAR) of the sample, and is referred to in some instances as a CAR assembly 3022. In certain examples, the CAR assembly includes an ion gauge 3025 mounted on the side opposite the sample to determine chamber pressure, or, in other examples, the ion gauge 3025 may be positioned facing the sources to measure beam equivalent pressure of material sources 3030, 3032, and 3034. Though the example in FIG. 30 shows three material sources, fewer material sources, e.g., 1 or 2, or more material sources, e.g. 4 or more, may be used. A cooled cryoshroud 3028, e.g., cooled by liquid nitrogen or liquid helium, may be positioned between growth chamber walls and the CAR assembly 3022 and may be operative as an effective pump for many of the residual gasses in the growth chamber 3010. In some examples, one or more cryopumps may be used to remove gasses which are not pumped by the cryopanels. This pumping arrangement may keep the partial pressure of undesired gases, such as $H_2O$, $CO_2$, and CO, to less than about $10^{-9}$ Torr, more particularly less then about $10^{-11}$ Torr. To monitor the residual gases, analyze the source beams, and check for leaks, a detection device (not shown), such as a mass spectrometer (MS), may be mounted in the vicinity of the CAR assembly 3022. The material sources 3030, 3032, and 3034 may be independently heated until the desired material flux is achieved. Computer controlled shutters 3040, 3042, and 3044 may be positioned in front of each of the material sources 3030, 3032, and 3034, respectively, to shutter the flux reaching the sample within a fraction of a second. The exact distance of the material sources 3030, 3032, and 3034 from the sample may vary and typical distances are about 5-50 cm, e.g., 10, 20, 30 or 40 cm. In certain examples, one or more of the material sources 3030, 3032, and 3034 may include a boost device, such as boost device 3050. Boost device 3050 may be configured to increase vaporization, atomization, ionization, sublimation, etc., of material to be delivered by material source 3030. It will be within the ability of the person of ordinary skill in the art, given the benefit of this disclosure, to design MBE devices including boost devices. The MBE devices may further include RHEED guns, fluorescence screens and other suitable devices for monitoring growth in the chamber.

Figure 31:
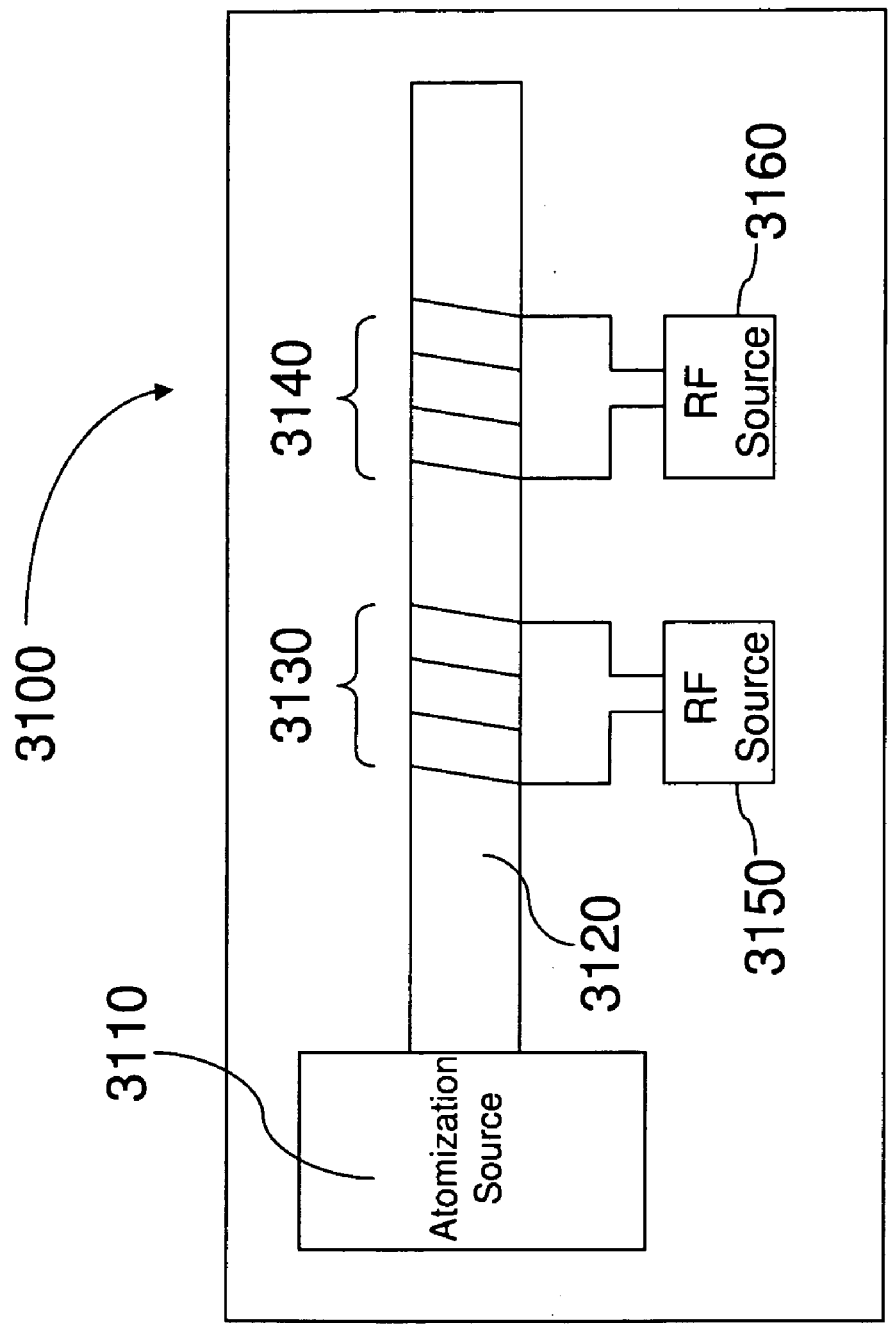
FIG. 31 is an example of a reaction chamber that includes a first boost device and optionally a second boost device, in accordance with certain examples.

In accordance with another aspect, a chemical reaction chamber is disclosed. An exemplary chemical reaction chamber is shown in FIG. 31. A reaction chamber 3100 includes an atomization source 3110 in thermal communication with a tube or a chamber 3120 and a boost device 3130 configured to provide radio frequencies to chamber 3120. In other examples, the reaction chamber 3100 also includes a second boost device 3140. The boost device 3130 may be in electrical communication with an RF source 3150, and the boost device 3140 may be in electrical communication with an RF source 3160. Either of the boost devices 3130 and 3140, or both, may be used to control or assist in chemical reactions within the chamber 3120. For example, the atomization source 3110 may be configured to control the heat or energy within the chamber 3120. The boost device 3130 may provide radio frequencies to increase the energy in certain regions within the chamber 3120. The additional energy supplied by the boost device 3130 may be used to supply additional activation energy to reactants, to favor, or disfavor, thermodynamically or kinetically, one or more specific reaction products, to maintain reactant species in the gas phase, or other suitable applications where it may be necessary to provide additional energy to reactants. In some examples, the chamber 3120 includes one or more catalysts for catalyzing a reaction. In other examples, the atomization source 3110 may be configured to supply gaseous catalyst to chamber 3120 for catalysis of one or more chemical reactions. For example, the atomization source 3110 may be an inductively coupled plasma that may atomize platinum or palladium, which may be supplied to chamber 3120 for catalysis. Additional devices may be included in the reaction chamber including, but not limited to, reflux devices, jacketed coolers, injections ports, withdrawal or sampling ports, etc. It will be within the ability of the person of ordinary skill in the art, given the benefit of this disclosure, to design suitable reaction chambers that include boost devices.

In accordance with certain examples, a device for treatment of radioactive waste is disclosed. In certain examples, the device is configured to dispose of tritiated waste. For example, tritiated waste may be introduced into a chamber, such as chamber 3200 shown in FIG. 32. Chamber 3200 includes an atomization source 3210, a boost device 3220, an inlet 3230 and an outlet 3240. The boost device 3220 may be in electrical communication with an RF source 3250. Radioactive waste may be introduced into the reaction chamber 3200 and subjected to high temperature oxidation to decompose the radioactive waste. For example, the radioactive waste may be introduced into a plasma plume that has been boosted using the boost device 3220. One or more catalysts may also be introduced into the chamber 3200 through the inlet 3230 to promote oxidation of the radioactive waste. In certain examples, the reaction products may be condensed and added to a silica gel, or a clay, to provide stabilized forms that may be properly disposed of, e.g., by burial. It will be within the ability of the person of ordinary skill in the art, given the benefit of this disclosure, to design suitable devices for disposal of radioactive waste that include one or more of the boost devices disclosed here.

In accordance with certain examples, a light source is provided. An illustrative light source is shown in FIG. 33. The light source 3300 includes an atomization device 3310, a boost device 3320 in electrical communication with RF source 3330 and a sample inlet 3340 for introducing a chemical species that may emit light when excited. A sample containing a single chemical species, or in certain examples, multiple chemical species, may be introduced into the atomization device 3310 and excited using the atomization device 3310 and/or the boost device 3320. In examples where a single species is used, e.g., where substantially pure sodium ions dissolved in water are introduced into the atomization device 3310, a single wavelength of light may be emitted as excited sodium atoms decay. This optical emission may be used as a substantially pure light source, e.g., a light source having a narrow width (e.g., less than about 0.1 nm) and approximately a single wavelength. In certain examples, the chemical species may be sodium, antimony, arsenic, bismuth, cadmium, cesium, germanium, lead, mercury, phosphorus, rubidium, selenium, tellurium, tin, zinc, combinations thereof or other suitable metals that may be atomized, ionized and/or excited to provide optical emissions. Suitable optics, choppers, reflective coatings and other devices may be used with the light source to focus or to direct the light or to provide pulsed light sources. The person of ordinary skill in the art, given the benefit of this disclosure, will be able to design suitable light sources using the boost devices disclosed here.

In accordance with certain examples, an atomization device that includes a microwave source or microwave oven is disclosed. For illustrative purposes only and without limitation, an exemplary atomization device including a microwave source is shown in FIG. 34. The atomization device 3400 includes an atomization source 3410 within a microwave oven 3420. A sample inlet 3430 may be configured to introduce sample into the atomization source 3410. Without wishing to be bound by any particular scientific theory, microwave oven 3420 may be operative to provide microwaves to atomization source 3410 which may promote ionization efficiency and/or may be used to excite atoms and ions. Typical microwave ovens use an absorption cell as the oven cavity, and a microwave launcher and magnetron tube as an RF source. The microwave launcher may be a small section of wave guide which mounts the magnetron tube forming the mode of propagation. This launches the RF energy into the oven or absorption cell. This RF energy may reflect off of the walls of the oven until it is absorbed and dissipated as heat. Because the oven is an unstructured cavity, it exhibits voltage maxima and nodes as constructive and destructive reflections collide. When the RF voltage in the standing maxima exceeds the ionization potential of the constituent atoms in the atomization source and the population of free ions and electrons is sufficient to allow for RF circulating currents to form, a plasma may form in the plume of the atomization source, dramatically raising the temperature of the atomization source. The atomization source 3410 may be any of the atomization sources disclosed herein, e.g., flames, plasmas, arcs, sparks and other suitable atomization sources that will be readily selected by the person of ordinary skill in the art, given the benefit of this disclosure. When the atomization source is a flame, the benefits of having both the high heat capacity of a flame needed for efficient desolvation and the extreme plasma temperatures needed for great excitation may be achieved. The flame would tolerate greatly increased sample loading while leaving the RF power available for sample atomization and ionization. For example, when the microwave oven 3420 is turned on, a plasma plume may be formed, or in the case where the atomization source is a plasma, the plasma source may be extended. RF energy, including microwave energy, may be used as a boost source that can be directly coupled with a flame to not only dramatically increase the temperature of flame combustion but to actually change the nature of the resulting combination of both a flame and a plasma discharge. A microwave cavity or resonator may be used in place of the microwave oven to ensure a continuous, well structured, and controlled discharge. The plasma plume may be used for any one or more of the applications discussed herein, e.g., chemical analysis, welding, in a spectrometer, etc. It will be within the ability of the person of ordinary skill in the art, given the benefit of this disclosure, to implement atomization devices including atomization sources with microwave ovens.

In accordance with certain examples, the boost devices disclosed herein may be adapted for use in plasma displays. Without wishing to be bound by any particular scientific theory, plasma displays operate using noble gases and electrodes. Noble gases, such as xenon and neon, are contained within microstructures or cells positioned between at least two glass plates. On both sides of each microstructure or cell are long electrodes. A first set of electrodes, referred to as the address electrodes, are arranged to sit behind the microstructures along the rear or back glass plate and are arranged vertically on the display. Transparent glass electrodes are mounted on top of the microstructures along the front glass plate and are arranged horizontally on the display. The transparent glass electrodes typically are surrounded by a dielectric material and are covered with a protective layer, such as magnesium oxide, for example. The boost devices disclosed here may be adapted for use with plasma displays to enhance or increase ionization of the noble gases. For example, in a typical plasma display, the noble gas in a particular microstructure or cell is ionized by charging the electrodes that intersect at that microstructure. The electrodes are charged thousands or millions of times per second, charging each microstructure in turn. As intersecting electrodes are charged, a voltage differential is created between the electrodes such that an electric current flows through the noble gas in the microstructure. This current creates a rapid flow of charged particles, which stimulates the noble gas atoms and/or ions to release ultraviolet photons. The ultraviolet photons in turn cause phosphors coated on the display to emit visible light. By varying the pulses of current flowing through the different microstructures, the intensity of each sub-pixel color may be increased or decreased to create hundreds of different combinations of red, green and blue. In this way, the entire spectrum of colors may be produced. In certain examples, miniaturized boost devices may be included that surround a portion or all of each microstructure. For example, each microstructure in a plasma display may be surrounded with a boost device to increase the rate of ionization of the noble gases and/or to increase the efficiency at which the noble gases release ultraviolet photons. The boost from the boost device may be provided, e.g., in a continuous or pulsed mode, prior to, during or subsequent to charging of the electrodes. It may be desirable to provide RF shielding to each microstructure so that surrounding microstructures are not affected by RF supplied to any particular microstructure. Such shielding may be accomplished using suitable materials and devices, including, but not limited to, ground-planes and Faraday shields.

In accordance with certain other examples, the atomization devices disclosed here may be miniaturized such that portable devices are provided. In certain examples, a portable device may include an atomization source, e.g., a flame, and a boost device. In other examples, the portable device includes an atomization source, e.g., a flame, and a microwave source. It will be within the ability of the person of ordinary skill in the art, given the benefit of this disclosure, to miniaturize the devices disclosed here. In certain examples, the boost devices may be used with a microplasma in silicon, ceramics, or metal polymer arrays to provide miniaturized devices suitable for detection of chemical species or other applications. Exemplary microplasmas are described, for example, in Eden et al., J. Phys. D: Appl. Phys. 36 (7 Dec. 2003) 2869-2877 and Kikuchi et al., J. Phys. D: Appl. Phys. 37 (7 Jun. 2004) 1537-1534, and other microplasmas, such as those used to join fiber optical cables, are described in U.S. Pat. Nos. 4,118,618 and 5,024,725.

In accordance with certain examples, a single use atomization device is disclosed. The single use device includes an atomization device, a boost device and a detector. The single use device may be configured with enough fuel or power to provide for a single analysis of a sample. For example, a water sample may be introduced into the device for measuring chemical species, such as lead. The device includes a suitable amount of fuel or power to vaporize, atomize and/or ionize the water sample and may include suitable electronics and power sources for detection of the lead in the water sample. For example, the single use device may include a battery or fuel cell to provide sufficient power to a detector to measure the amount of light emitted from excited lead atoms and to provide sufficient power to the boost device. The device may display the reading on an LCD screen or other suitable display to provide an indication of the lead levels. In some examples, it may be desirable to provide sufficient fuel for two or three sample readings so that the levels provided in an initial reading may be confirmed. It will be within the ability of the person of ordinary skill in the art, given the benefit of this disclosure, to design suitable single use atomization devices using the boost devices disclosed here.

Methods Using Boost Devices

In accordance with certain examples, a method of enhancing atomization of species using a boost device is provided. The method includes introducing a sample into an atomization device. The atomization device may include, for example, a device disclosed herein and other suitable atomization devices, e.g., with boost devices that will be designed by the person of ordinary skill in the art, given the benefit of this disclosure. The sample may be introduced, for example, by dissolving a suitable amount of sample in a solvent and injecting, aspirating, nebulizing, etc. the sample into the atomization device. As sample is injected into the atomization device, the sample may be desolvated, atomized and/or excited by the energy from the atomization device. Depending on the nature of the atomization device, a large amount of energy may be used in the desolvation process, leaving less energy for atomization. To enhance atomization, one or more boost devices may provide radio frequencies to provide additional energy for atomization. The boost device may be operated using various powers, e.g., from about 1 Watt to about 10,000 Watts, and various radio frequencies, e.g. from about 10 kHz to about 10 GHz. The boost device may be pulsed or operated in a continuous mode. In certain examples, the boost device may be used to provide additional energy for atomization to increase the number of species available for excitation. It will be within the ability of the person of ordinary skill in the art, given the benefit of this disclosure, to use the boost devices disclosed here to enhance atomization of species.

In accordance with certain examples, a method of enhancing excitation of species using a boost device is provided. The method includes introducing a sample into an atomization device. The atomization device may be, for example, an atomization device with a boost device as disclosed herein, with such examples provided for illustration and not limitation. The sample may be introduced, for example, by dissolving a suitable amount of sample in a solvent and injecting, aspirating, nebulizing, etc. the sample into the atomization device. Without wishing to be bound by any scientific theory, as sample is injected into the atomization device, the sample may be desolvated, atomized and/or excited by the energy from the atomization device. Depending on the nature of the atomization device, a large amount of energy may be used in the desolvation process, leaving less energy for atomization and excitation. To enhance excitation, one or more boost devices may supply radio frequencies to provide additional energy. The boost device may be operated using various powers, e.g. from about 1 Watt to about 10,000 Watts, and various radio frequencies, e.g. from 10 kHz to about 10 GHz. The boost device may be pulsed or operated in a continuous mode. In certain examples, the boost device may be used to provide additional energy for excitation to provide a more intense optical emission signal, which may improve detection limits. The person of ordinary skill in the art, given the benefit of this disclosure, will be able to use the boost devices disclosed here to enhance excitation of species.

In accordance with certain examples, a method of enhancing detection of chemical species is provided. In certain examples, the method includes introducing a sample into an atomization device configured to desolvate and atomize the sample. The atomization device may be, for example, an atomization device with a boost device as disclosed herein, with such examples provided for illustration and not limitation. The sample may be introduced, for example, by dissolving a suitable amount of sample in a solvent and injecting, aspirating, nebulizing, etc. the sample into the atomization device. Radio frequencies may be provided using a boost device to increase signal intensity or to increase path length of a detectable signal. Such an increase in intensity and/or path length may improve detection limits so that lesser amounts of sample may be used or such that lower concentration levels may be detected. Radio frequencies may be provided at various powers, e.g. about 1 Watts to about 10,000 Watts, and various frequencies, for example, about 10 kHz to about 10 GHz. It will be within the ability of the person of ordinary skill in the art, given the benefit of this disclosure, to use the boost devices disclosed here to enhance detection of species.

In accordance with another method aspect, a method of detecting arsenic at levels below about 0.6 μg/L is provided. The method includes introducing a sample comprising arsenic into an atomization device to desolvate, atomize, and/or excite the sample. The atomization device may be, for example, an atomization device with a boost device as disclosed herein, with such examples provided for illustration and not limitation. The boost device may be configured to provide radio frequencies to provide a detectable signal from an introduced sample that includes arsenic at levels less than about 0.6 μg/L. In certain examples, radio frequencies may be provided such that a detectable signal from a sample including arsenic at a level of about 0.3 μg/L or less is observed. It will be within the ability of the person of ordinary skill in the art, given the benefit of this disclosure, to configure and design suitable atomization devices with boost devices for detection of arsenic levels below 0.6 μg/L.

In accordance with another method aspect, a method of detecting cadmium at levels below about 0.014 μg/L is provided. The method includes introducing a sample comprising cadmium into an atomization device to desolvate, atomize, and/or excite the sample. The atomization device may be, for example, an atomization device with a boost device as disclosed herein, with such examples provided for illustration and not limitation. The boost device may be configured to provide radio frequencies to provide a detectable signal from an introduced sample that includes cadmium at levels less than about 0.014 μg/L. In certain examples, radio frequencies may be provided such that a detectable signal from a sample including cadmium at a level of about 0.007 μg/L or less is observed. It will be within the ability of the person of ordinary skill in the art, given the benefit of this disclosure, to configure and design suitable atomization devices with boost devices for detection of cadmium levels below 0.014 μg/L.

In accordance with another method aspect, a method of detecting selenium at levels below about 0.6 μg/L is provided. The method includes introducing a sample comprising selenium into an atomization device to desolvate, atomize, and/or excite the sample. The atomization device may be, for example, an atomization device with a boost device as disclosed herein, with such examples provided for illustration and not limitation. The boost device may be configured to provide radio frequencies to provide a detectable signal from an introduced sample that includes selenium at levels less than about 0.6 μg/L. In certain examples, radio frequencies are provided such that a detectable signal from a sample including selenium at a level of about 0.3 μg/L or less is observed. It will be within the ability of the person of ordinary skill in the art, given the benefit of this disclosure, to configure and design suitable atomization devices with boost devices for detection of selenium levels below about 0.6 μg/L.

In accordance with another method aspect, a method of detecting lead at levels below about 0.28 μg/L is provided. The method includes introducing a sample comprising lead into an atomization device to desolvate, atomize, and/or excite the sample. The atomization device may be, for example, an atomization device with a boost device as disclosed herein, with such examples provided for illustration and not limitation. The boost device may be configured to provide radio frequencies to provide a detectable signal from an introduced sample that includes lead at levels less than about 0.28 μg/L. In certain examples, radio frequencies are provided such that a detectable signal from a sample including lead at a level of about 0.14 μg/L or less is observed. It will be within the ability of the person of ordinary skill in the art, given the benefit of this disclosure, to configure and design suitable atomization devices with boost devices for detection of lead levels below about 0.28 μg/L.

In accordance with another method aspect, a method of separating and analyzing a sample comprising two or more species is provided. The method includes introducing a sample into a separation device. The separation device may be any of the separation devices disclosed herein, e.g., gas chromatographs, liquid chromatographs, etc., and other suitable separation devices and techniques that may provide separation, e.g., baseline separation, of two or more species in a sample. The species may be eluted from the separation device into an atomization device. The atomization device may be, for example, an atomization device with a boost device as disclosed herein, with such examples provided for illustration and not limitation. In certain examples, the atomization device may be configured to desolvate, atomize and/or excite the eluted species. The eluted species may be detected using any one or more of the detection methods and techniques disclosed herein, e.g., optical emission spectroscopy, atomic absorption spectroscopy, mass spectroscopy, etc., and additional detection methods that will be readily selected by the person of ordinary skill in the art, given the benefit of this disclosure.

Certain specific examples are described below to illustrate further a few of the many applications of the boost devices disclosed herein.

Example 1

Hardware Setup

Certain specific examples that were performed with the hardware of this example are discussed below in Examples 3 and 4. Any hardware that was specific to any given example is discussed in more detail in that example.

Referring now to FIG. 35, a computer controlled hardware setup is shown. An atomization device 4000 included a boost device supply control 4010, a boost device excitation source 4020, a plasma sensor 4030, an emergency off switch 4040, a plasma excitation source 4050 and a re-packaged Optima 4000 generator 4060. The boost device supply control 4010 was used as the power supply and control for the boost device. As may be seen in FIG. 35, the plasma excitation source 4050 and boost device excitation source 4020 were located on a plate in the center of the atomization device 4000. The plate used was a 1.5 foot by 2 foot optical bench purchased from the Oriel Corporation (Stratford, Conn.). Each of plasma excitation source 4050 and boost device excitation source 4020 were mounted to a large aluminum angle bracket mounting the source above and at right angles to the plate. Slots were milled into the brackets allowing for lateral adjustment before securing to the plate. The plasma sensor was mounted in an aluminum box that may be positioned for viewing the plasma. The plasma sensor wiring was modified to shutdown both the plasma and boost device excitation sources in the event that the plasma was extinguished. Emergency off switch 4040 was remotely mounted in an aluminum box that could be brought close to the operator. AC and DC power, and the plasma sensor wiring was placed under table 4070. Many safety features found in a conventional ICP-OES device were removed to allow operation of this setup, and there was no protection provided to the operator from hazardous voltages, or RF and UV radiation. This setup was operated remotely inside of a vented shielded screen room with separate torch exhaust. This open frame construction offered ease of setup between experiments. Using the setup shown in FIG. 35, it was possible to evaluate the performance enhancement in each experiment visually by using an yttrium sample and comparing the blue (ion) and red (atom) emission regions and the intensities of these regions or by using a sodium sample.

Figure 36:
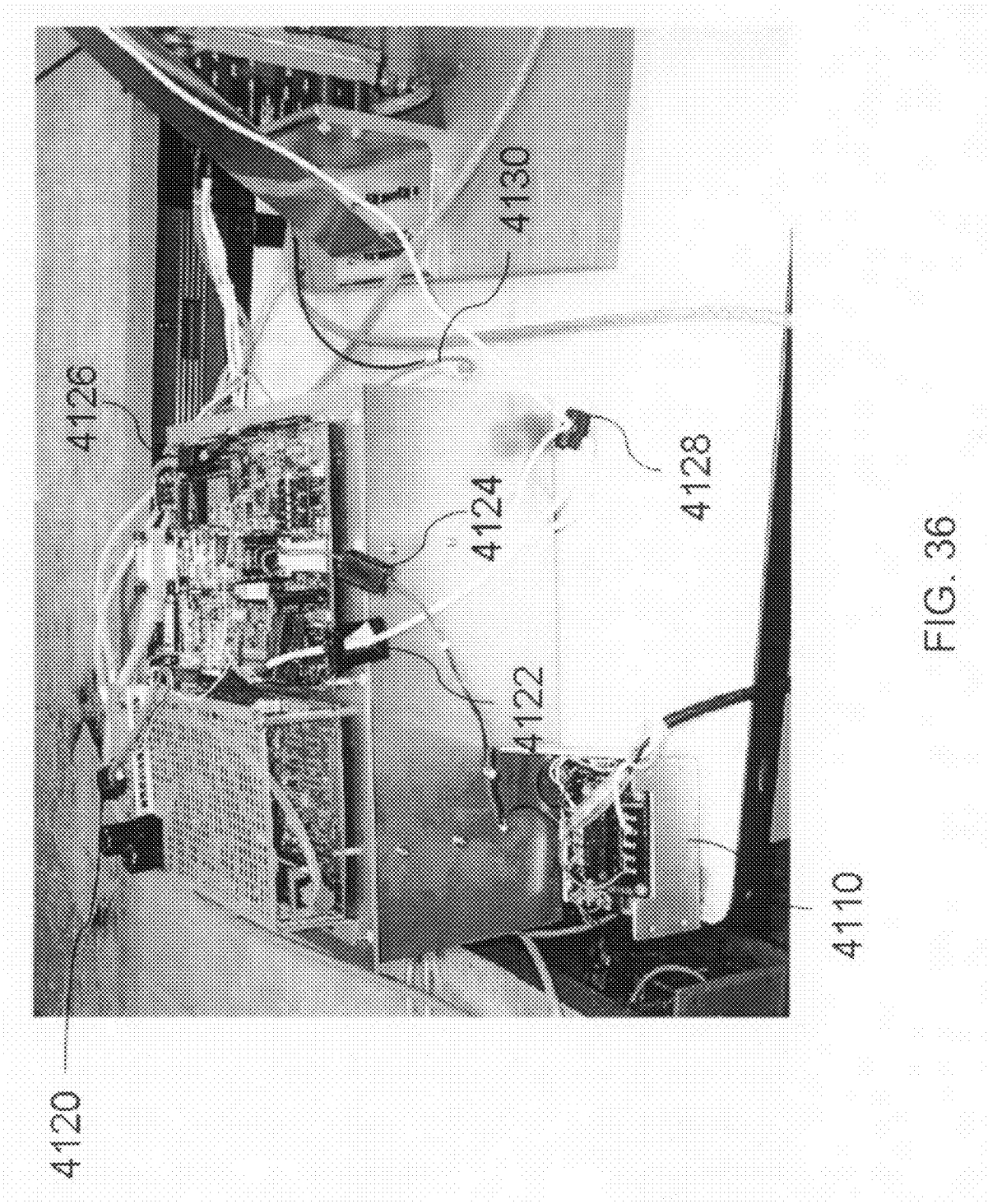
FIG. 36 is an example of an excitation source to generate a plasma, in accordance with certain examples.

Referring now to FIG. 36, primary excitation source was configured with an external 24 V/2.4A DC power supply 4110 made by Power One (Andover, Mass.). Ferrites 4120, 4122, 4124, 4126 and 4128 were added to prevent RF radiation from interfering with the electronics and the computer. An ignition wire 4130 was extended from the original harness with high voltage wire and a plastic insulator to reach the torch and prevent arcing.

Figure 38:
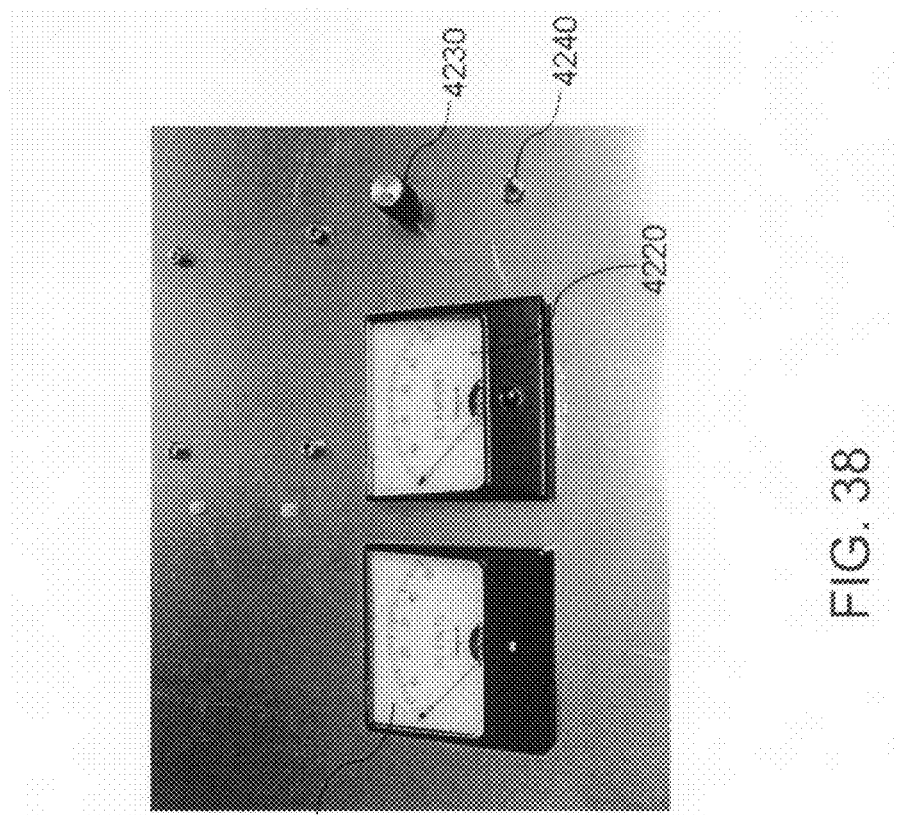
FIGS. 37-39 show a supply and control box used to provide power to a boost device, in accordance with certain examples.
Figure 37:
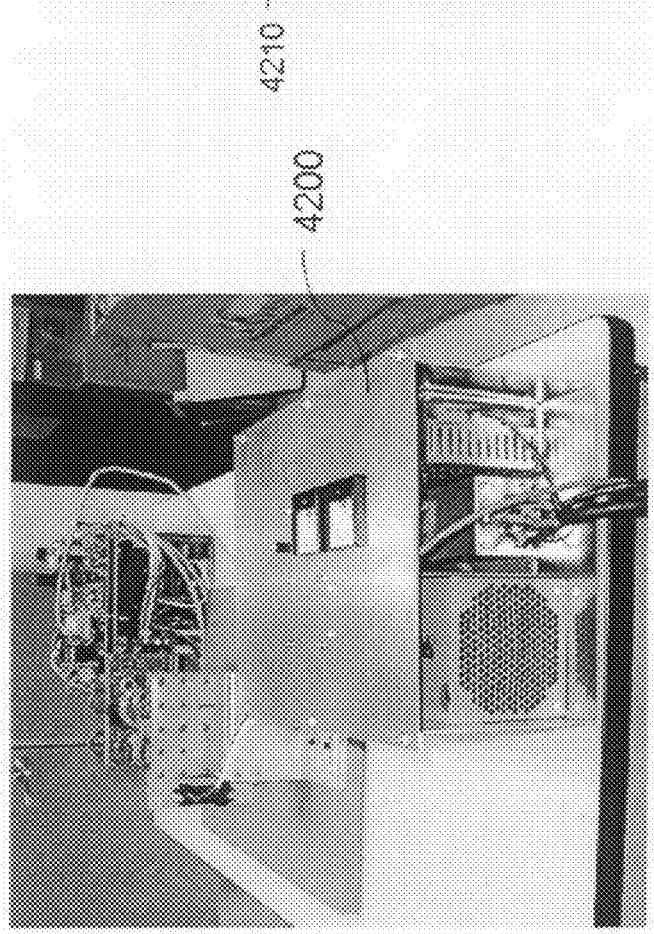
Figure 40:
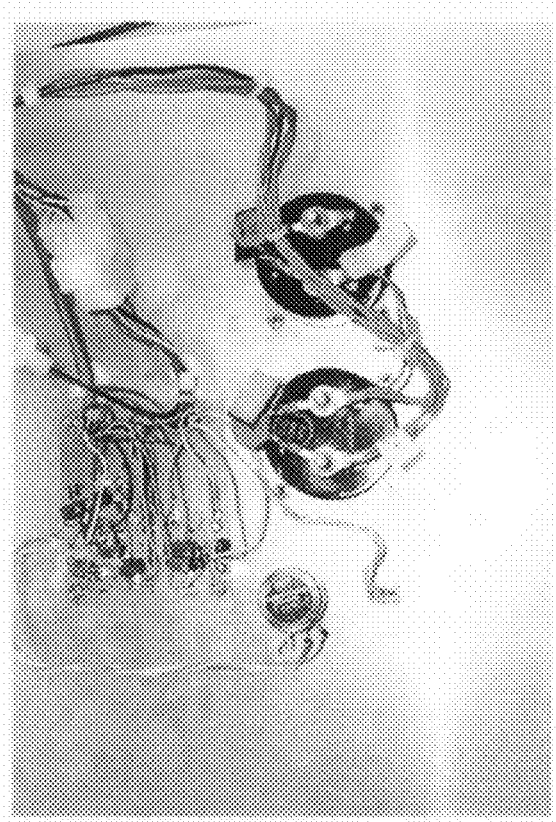
FIG. 40 shows a control board that was used with the supply and control box shown in FIGS. 37-39, in accordance with certain examples.
Figure 39:
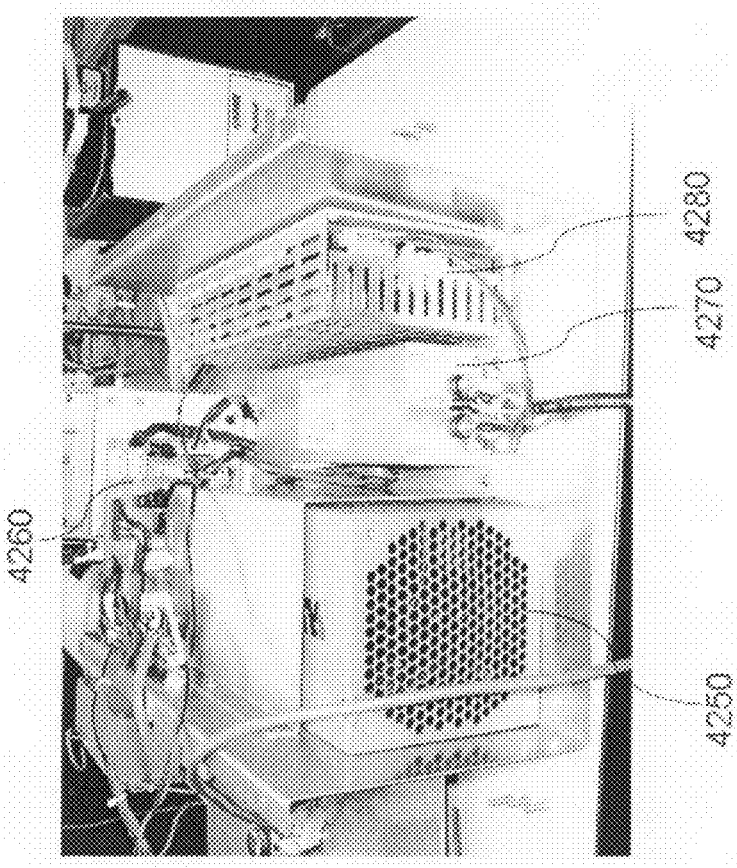

Referring now to FIGS. 37-39, a boost device power supply and control box 4200 was configured with meters 4210 and 4220, a power control knob 4230 and an RF on/off switch 4240. The boost device power supply and control box 4200 was constructed to manually control the power to the boost device excitation source in configurations where the boost device was positioned around a single chamber device (see Example 3 below) or in configurations where the boost device was positioned around a second chamber in fluid communication with the first chamber (see Example 4 below). The control box 4200 contained the same type of 3 kW DC supply 4250, Corcom line filter 4270, solid state relay, and RF Interface board 4260 as found in the shipping version of the Optima 4000 generator, commercially available from PerkinElmer, Inc., as shown in FIG. 39. A 48 V DC supply 4280 was not used. An external 24 V DC supply 4110 was used instead (shown in FIG. 36). Meters 4210 and 4220 were wired to measure the output voltage and current from the 3 kW DC supply 4250. A hand wired control board allowed for rapid fabrication. The layout of the hand wired control board used is shown in FIG. 40 and a schematic of the board is shown in FIG. 41.

Figure 42:
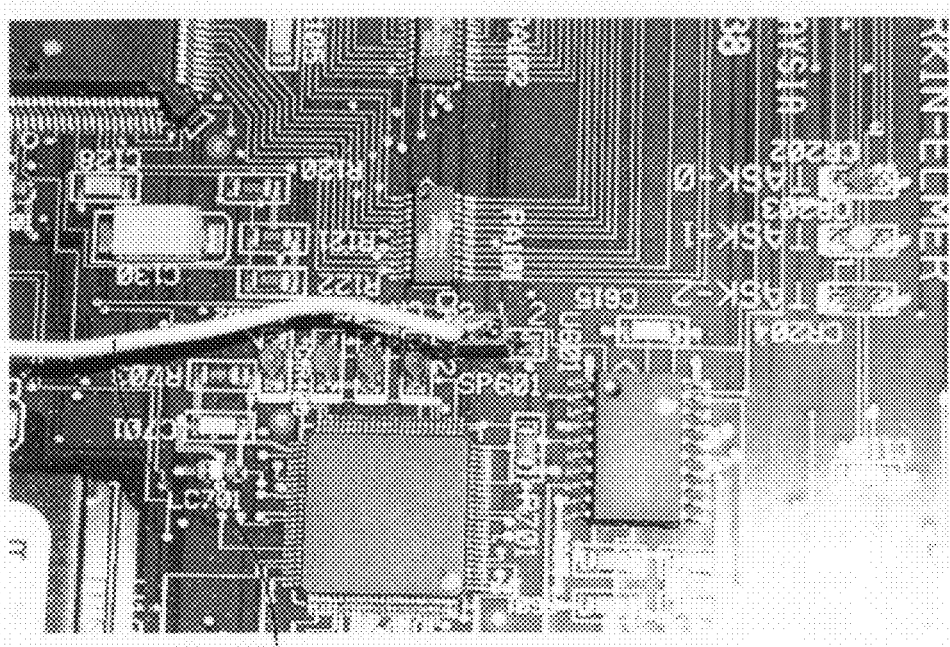
FIG. 42 is a picture of a wire from an interface board from a plasma excitation source to a solid state relay in the supply and control box shown in FIGS. 37-39, in accordance with certain examples.
Figure 43:
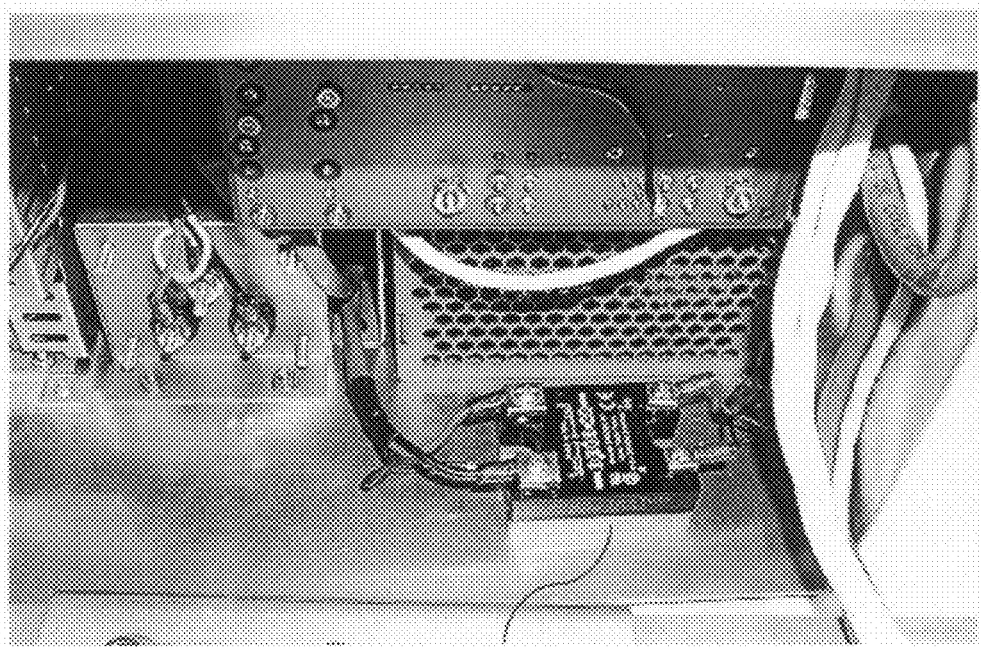
FIG. 43 is a solid state relay in the supply and control box shown in FIGS. 37-39, in accordance with certain examples.
Figure 44:
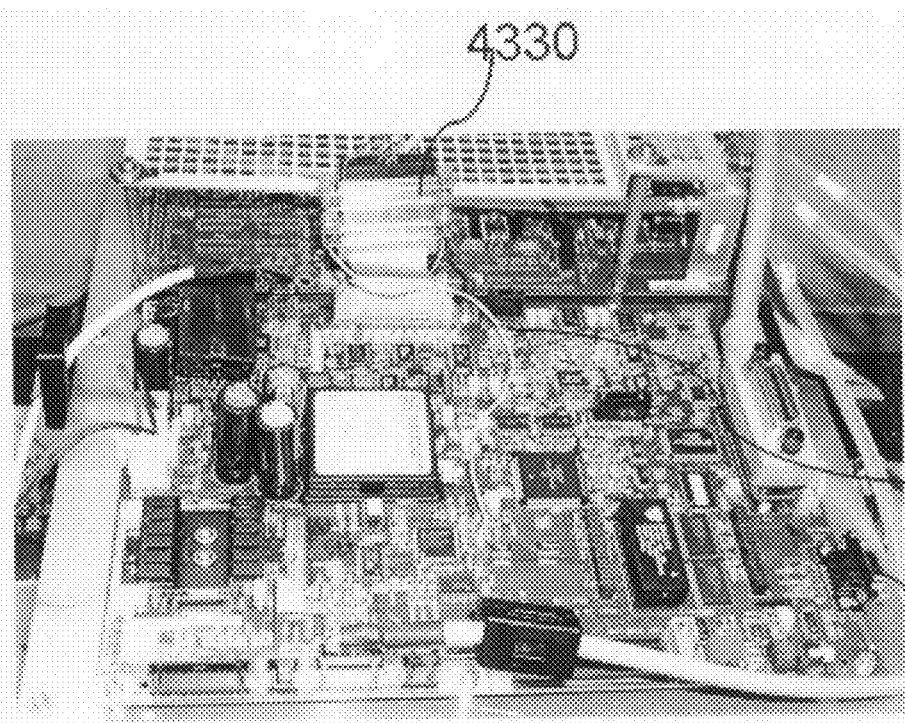
FIG. 44 is a configuration for providing power to the boost device control box shown in FIGS. 37-39, in accordance with certain examples.

FIGS. 42-44 shows wire 4310 from an RF Interface board 4340 on the plasma source control box that drove solid state relay 4320 located in the boost device excitation source box (see FIG. 43). The actual wiring for this plasma sense line is shown schematically in FIG. 41. Power for the boost control box 4200 (FIG. 37) was tapped into from the 220 V AC line cord of the repackaged Optima 4000 generator 4060 (FIG. 35).

Figure 45:
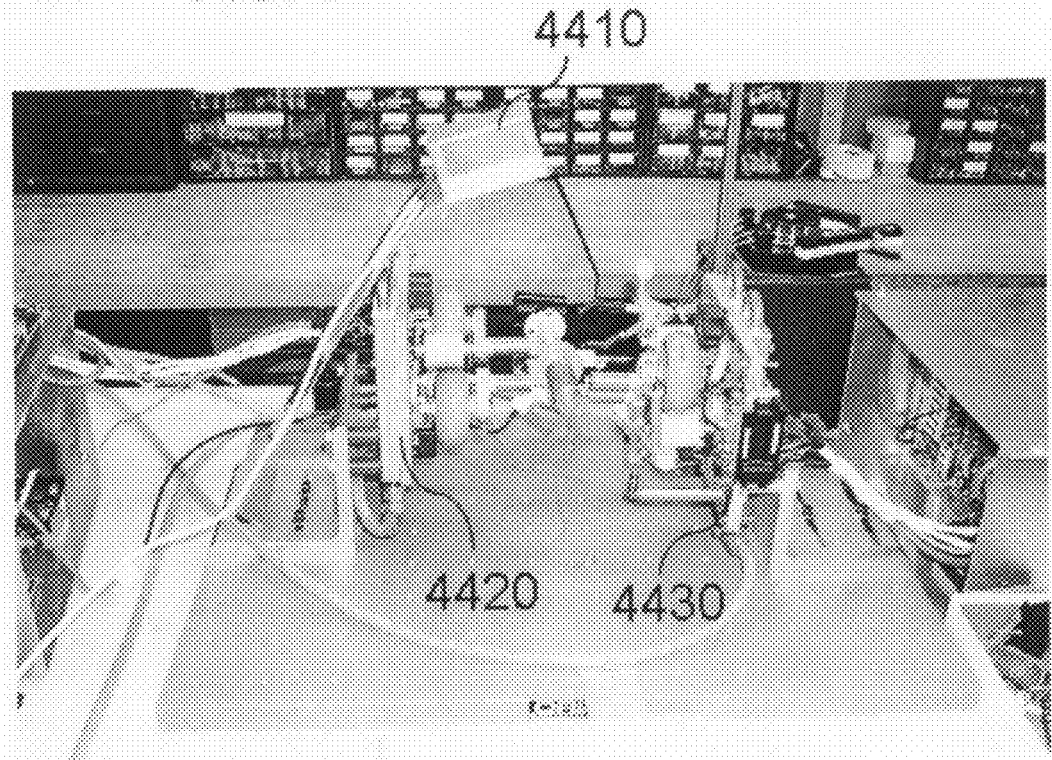
FIG. 45 shows placement of an optical plasma sensor above an atomization device, in accordance with certain examples.

Referring now to FIG. 45, an optical plasma sensor 4410 was located above a plasma source 4420 and a boost device 4430. The optical plasma sensor 4410 had a small hole (about 4.5 mm in diameter) drilled through the aluminum box and mounting bracket to allow the light from the plasma to fall on the optical plasma sensor 4410. Optical plasma sensor 4410 protected the plasma source and the boost source by shutting them down in the event that the plasma was accidentally extinguished. All of the generator functions including primary plasma ignition, gas flow control, power setting and monitoring were performed under manual control. For automated operation, a computer control using standard WinLab™ software, such as that commercially available on the Optima 4000 instruments and purchased from the PerkinElmer, Inc., could be used. After the primary plasma was ignited, the secondary boost power 4240 was switched on and manually controlled with the power control potentiometer 4230 (FIG. 38). Many other safety features were defeated to allow operation of this setup, and there was no protection provided to the operator from hazardous voltages, hazardous fumes, or RF and UV radiation. However, the person of ordinary skill in the art, given the benefit of this disclosure, will be able to implement suitable safety features to provide a safely operating device and operating environment.

Figure 46:
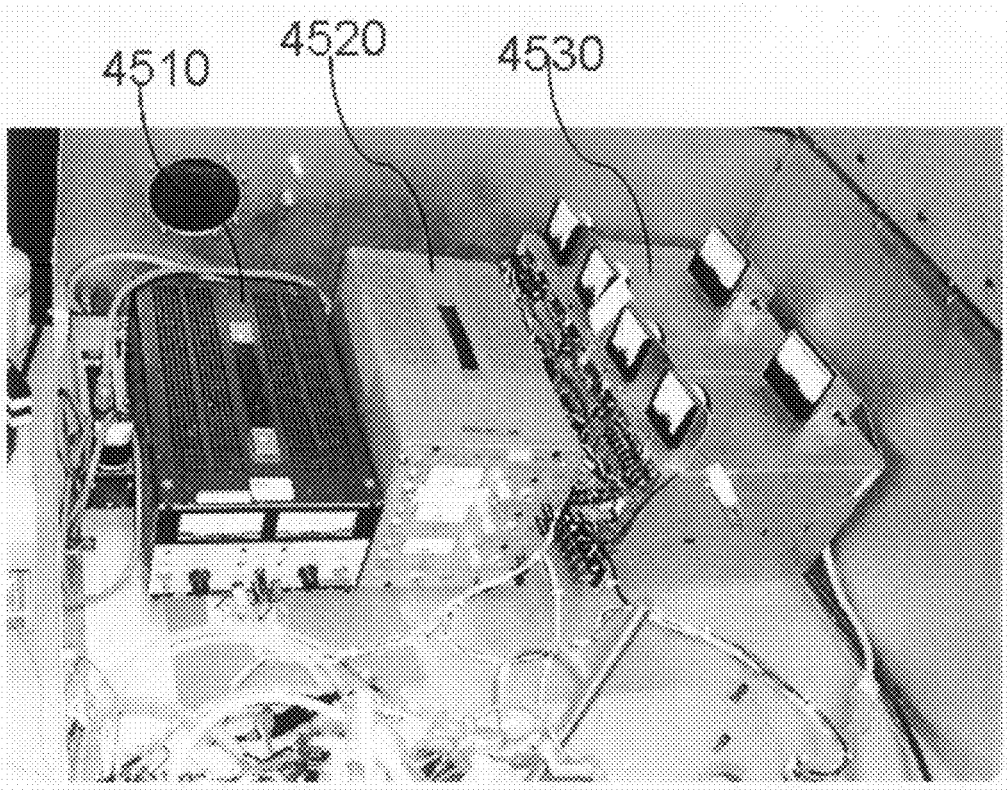
FIGS. 46 and 47 show a manually controlled hardware setup, in accordance with certain examples.
Figure 47:
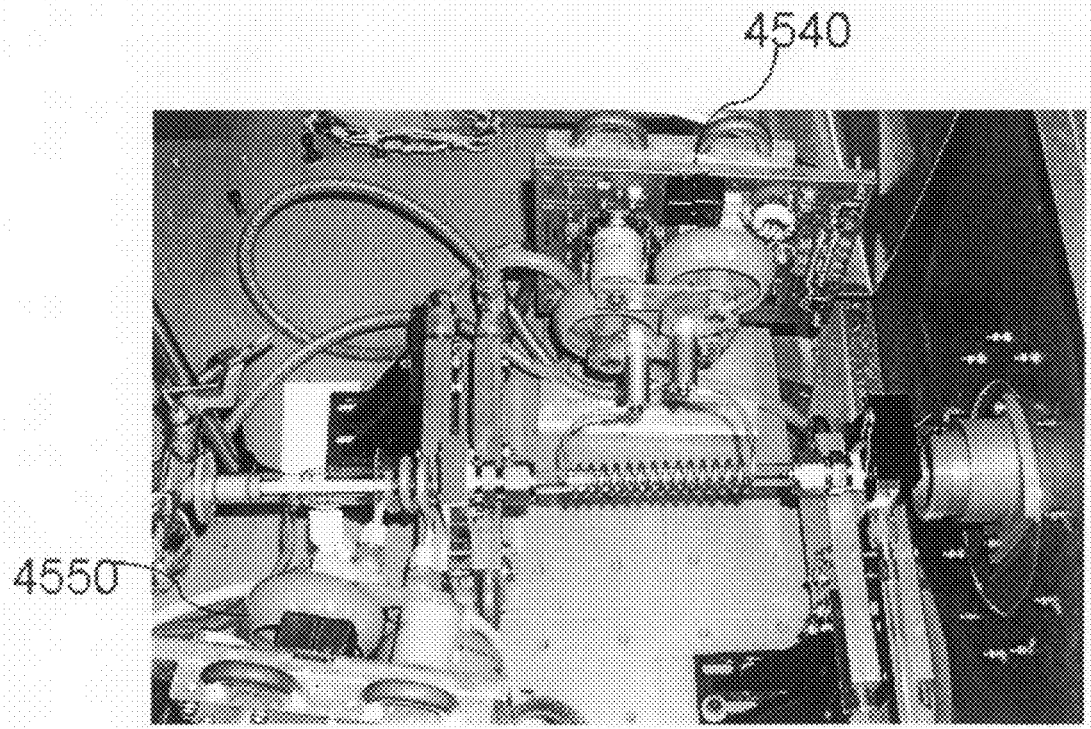

Referring now to FIGS. 46 and 47, a manually controlled hardware setup is shown. The manually controlled hardware performs identically to the computer controlled hardware described above, so the common components in this setup such as the plasma and boost supplies and RF sources will not be described in detail. DC power sources 4510 and 4520 were used to power the protection circuitry for both plasma source 4540 and boost device source 4550. DC power sources 4530 included four 1500 watt switching supplies. Two of the supplies were operated in parallel for a total of 3000 watts for the primary plasma RF source and the boost RF source.

Figure 48:
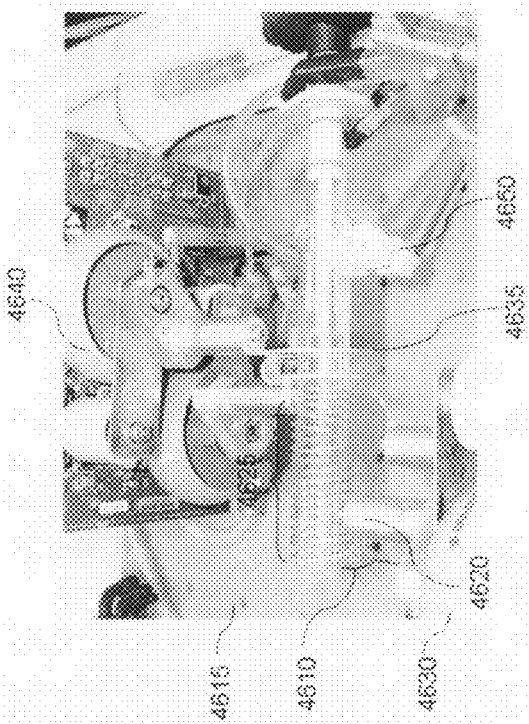
FIG. 48 is a hardware setup used in Example 3 described below, in accordance with certain examples.
Figure 49:
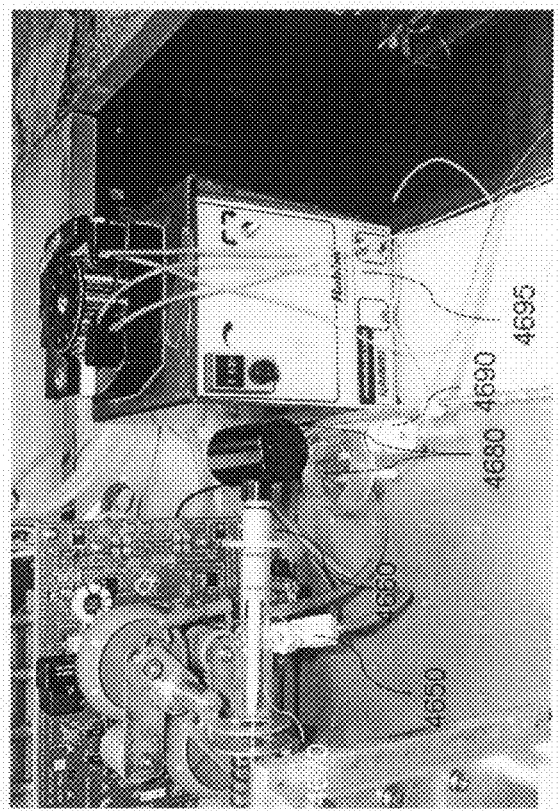
FIG. 49 shows certain components used in Example 3 including a nebulizer and an injector, in accordance with certain examples.

Referring now to FIG. 48, the hardware setup for Example 3, which may be operating using either the manually or the computer controlled system, is shown. Ignition arc ground return wire 4610 was a piece of number 18 gauge solid copper wire located near the end of the plasma torch and connected to grounded plate 4615 that the RF sources were mounted to. Wire 4610 provided a conductive path for the high voltage ignition arc to travel from the igniter assembly, through the center of the torch, traveling through the conductive argon gas and completing this path to ground. The quartz torch was similar to the Optima 3000XL torch (part number N0695379 available from PerkinElmer, Inc.) but the outside body of the torch was lengthened by 2 inches to capture the extended plume region of the boosted plasma. Solid brass coil extensions 4620 were added. These extensions extended the arms 1 3/16 inches and were 5/8 inch in diameter with 1/4 inch NPS (National Pipe Straight) thread on one side and a #4 metric tapped hole at the coil end. FIG. 48 shows a boost device 4625 that used a 17½ turn coil of number 18 gauge solid copper wire, but a 9½ turn coil of number 14 gauge solid copper wire provided better performance. The turns of a secondary source 4630 were evenly spaced and did not touch each other or coil 4635 of plasma source 4640, or extend past the end of the torch. Example 3 described below used the standard parts such as those found in the Optima 3000XL torch mount and sample introduction system. These included an igniter assembly 4650, a torch mount 4660, a 2 mm bore alumina injector 4670, a cyclonic spray chamber 4680, a Type C Concentric Nebulizer 4690, and a peristaltic pump 4695 as shown in FIGS. 48 and 49.

Figure 50:
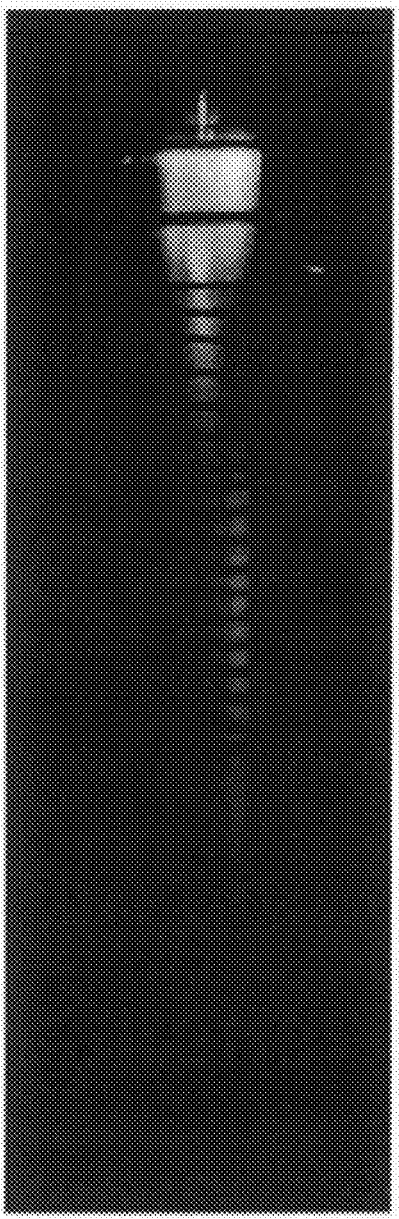
FIG. 50 is a picture of a device including a chamber with a plasma and a boost device turned off, in accordance with certain examples.
Figure 51:
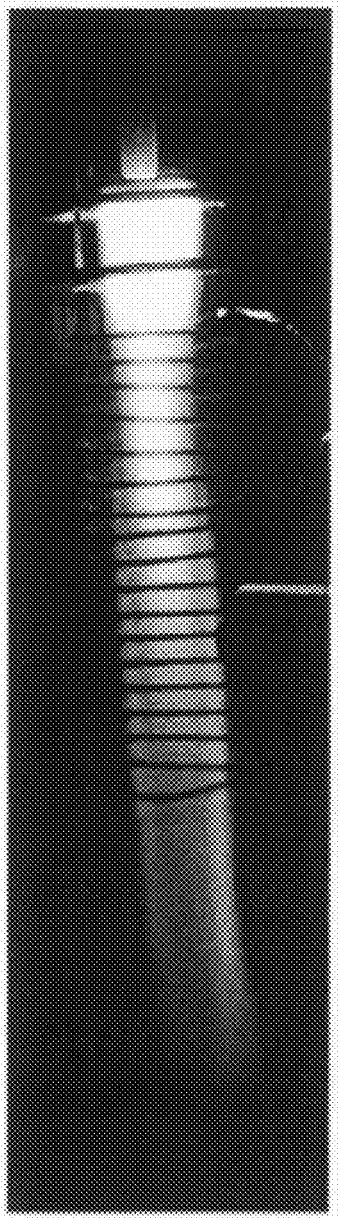
FIG. 51 is a picture of a device including a chamber with a plasma and a boost device turned on, in accordance with certain examples.

Referring now to FIG. 50, a plasma was operated in a typical normal mode of operation using the extended torch described above, with the boost device turned off and with 1300 watts of power to generate the plasma, with 1.2 L/minute of nebulizer gas flow with 500 ppm of yttrium, with 15 L/minute of plasma gas (argon), and with 0.2 L/minute of auxiliary gas flow (also argon). The plasma was operated with all of the same conditions, but with the boost device power on at about 800 watts (FIG. 51). The enhancement of the ionization region of the yttrium sample was clearly observed (blue region in FIG. 51) with the boost device on.

Figure 52:
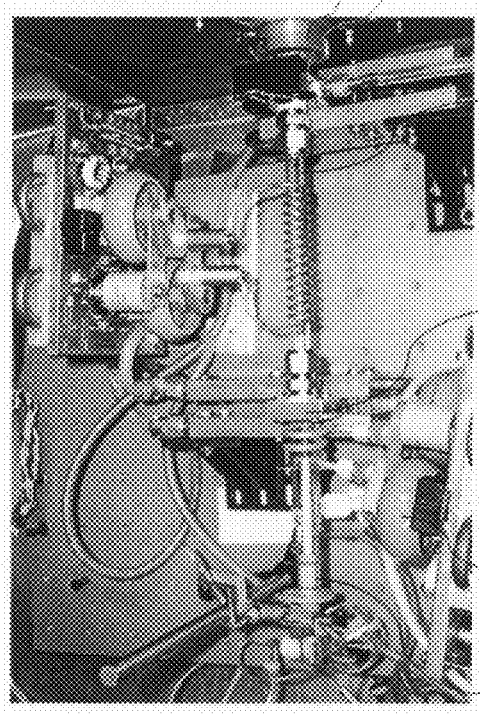
FIG. 52 is a hardware setup that was used in Example 4, in accordance with certain examples.
Figure 53:
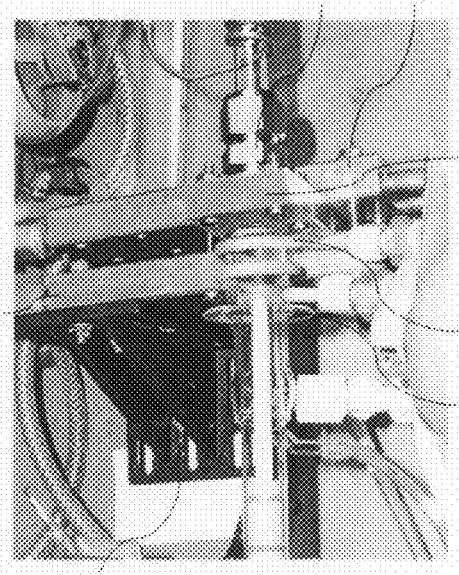
FIG. 53 shows certain components of the hardware setup shown in FIG. 52 including an interface and heat sinks, in accordance with certain examples.
Figure 54:
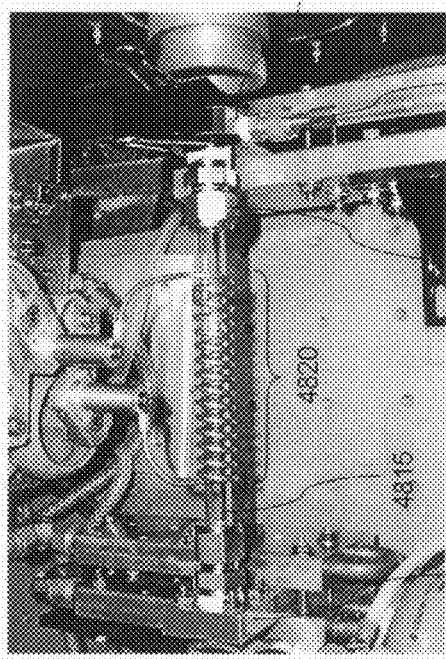
FIG. 54 is an enlarged view of a boost device that includes a 17½ turn coil, in accordance with certain examples.
Figure 56:
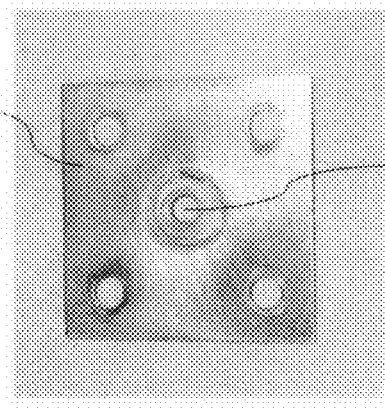
FIG. 56 shows the mounting interface plate of the second chamber used in hardware setup of FIG. 52, in accordance with certain examples.
Figure 55:
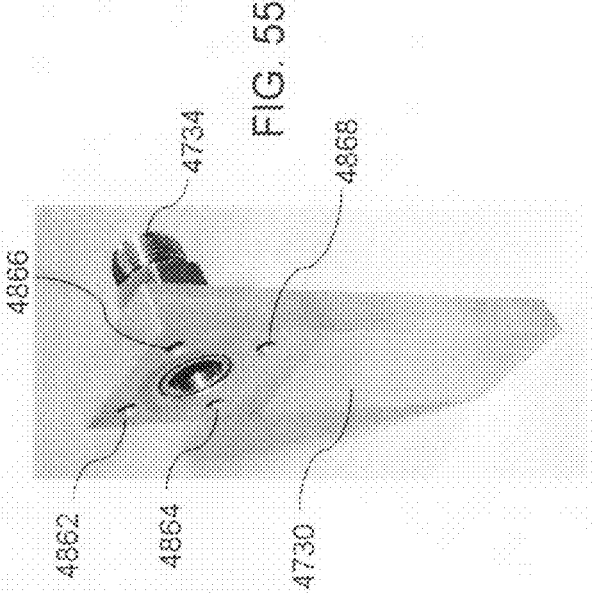
FIG. 55 shows the front mounting block of second chamber used in the hardware setup of FIG. 52, in accordance with certain examples.

Referring now to FIGS. 52-62, the hardware setup used in Example 4, a two chamber device (described below), is shown. FIG. 52 shows an Optima 3000XL sample introduction system 4710 which was similar to the system previously described in detail above. The setup used the standard unmodified Optima 3000XL torch and a torch bonnet 4755, but the torch bonnet 4755 was installed on the back side of a load coil 4760, and aided to center the torch in the load coil 4760 (FIG. 53). A primary RF source 4720 used a standard Optima 4000 load coil and fittings, available from PerkinElmer, Inc., but had the plastic faceplate removed. Water cooled heat sinks 4775 and 4776 were used with a brass front mounting block 4730 and a back mounting block 4732, which were purchased from Wakefield Engineering (Pelham, N.H.) part number 180-20-6C and were 6 inch square heat sinks. These heat sinks were modified by cutting them in half and adding additional mounting holes. The waterlines of each half were rejoined with short pieces of tubing and hose clamps. All of the water cooled heat sinks were placed in a series water path and tied to a NesLab CFT-75 Chiller that was purchased from the former NesLab Instruments Inc. in Newington, N.H., which is now Thermo Electron Corp. in Waltham, Mass. Brass mounting blocks 4730 and 4732 were cooled by sandwiching them between each half of the heat sink and bolted to Newport 360-90 mount 4750. This setup was used for both the front and rear mounting blocks 4730 and 4732, respectively (FIGS. 53 and 54). A perspective view of the brass front mounting 4730 block is shown in FIG. 55. This block was a simple brass rectangular block which was 5.8" high by 1.6" wide and ½" deep, with the center hole tapped for the ½ inch NPT Swaglok fitting 4734. The block was tapped shallow enough that the Swaglok fitting 4734 did not protrude past the front of the mounting block. Four perimeter holes 4862, 4864, 4866 and 4868 were for mounting interface plate 4860 (FIG. 56). The holes were clearance holes in the block and plate for use with #8-32 screws, lock washers, and nuts. The size of center hole orifice 4870 in interface plate 4860 may be varied to control the working pressure for a given flow rate. The size of the orifice hole 4870 shown in FIG. 56 that was used was 0.155" inches (3.94 mm) in diameter. Rear mounting block 4732 may be seen in FIGS. 57 and 58. This block was identical to the front block with the exception of the addition of side vacuum port 4792, and the fact that a ½" NPT tap was shallower so that Swaglok fitting 4794 did not completely block side vacuum fitting 4792. Side vacuum port 4792 was also tapped shallow enough to prevent the ¼" Swaglok vacuum fitting 4792 from protruding and blocking the insertion of the larger Swaglok fitting 4794. A rear quartz viewing window 4796 was held in place with a binder clip 4798 obtained from Office Depot (Delray Beach, Fla.). Any small air leaks at window 4796 did not have any effect on the performance. An axial viewing spectrometer 4740 (see FIG. 52) was setup to capture the emission down the length of a quartz tube 4815. Quartz tubing 4815 (see FIG. 54) was purchased from Technical Glass Products (Painesville Township, Ohio) and was 10¼" long and was sized for ½" compression fittings. It was found that brass fittings would cause less stress fractures of the quartz than stainless steel fittings. Brass ferrules were substituted for stainless steel ferrules in front mounting block 4732 and Teflon ferrules were used in the rear mounting block 4734. Boost device 4820 used a load coil of 14½ turns of ⅛" copper tubing. The tubing oxidized quickly if not cooled, but oxidation did not hamper performance substantially. For ease of use, the coils of boost device 4820 were not cooled and were terminated in bare crimp ring lugs and mounted with #4 metric hardware onto the coil extensions described previously.

A side vacuum port 4792 was connected with 20 feet of ¼" ID BEV-A-LINE tubing to either small 12V DC Sensidyne vacuum pump 4910 (part number C120CNSNF60PC1 and commercially available from Sensidyne in Clearwater, Fla.) and Brooks 0-40SCFH air flow meter 4912 with needle valve as shown in FIG. 59 (used on the computer controlled system), or to a Porter Instrument Company B-1187 0-20 liters/minute flow meter and needle valve assembly (not shown) and Trivac S25B vacuum pump 4920 shown in FIG. 60 (used on the manual controlled system). The vacuum system used on the manual controlled system had a much higher capacity than what was desired.

Figure 62A:
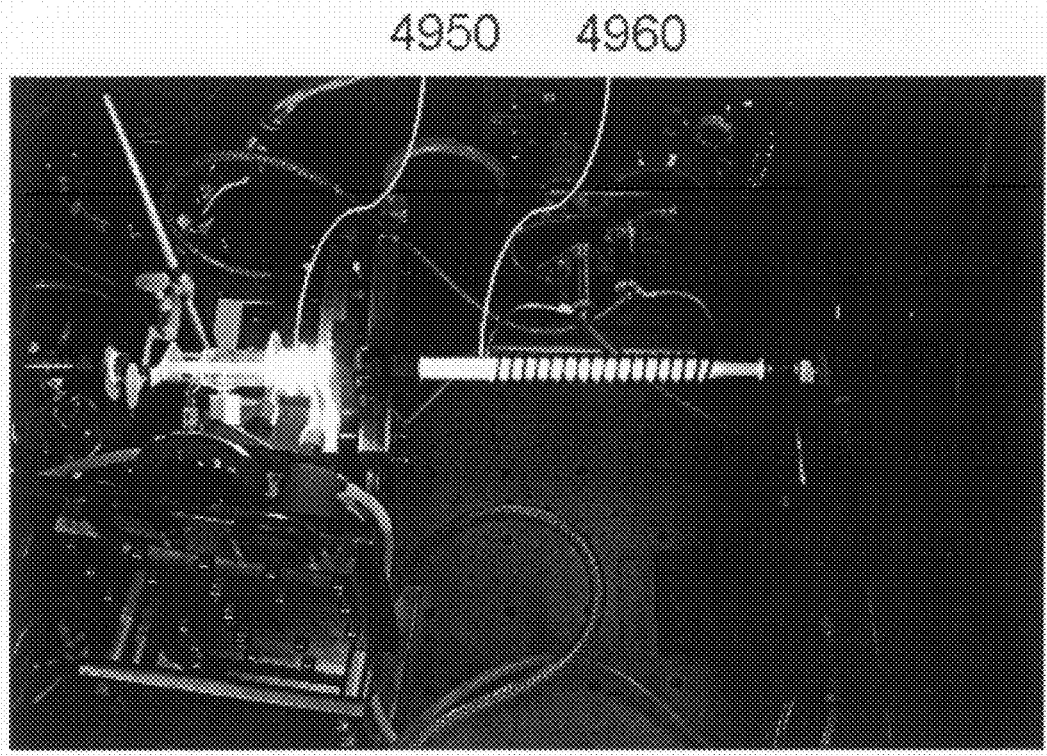
FIGS. 62A-62D are pictures of a device including a first chamber with a plasma and a second chamber with a boost device turned on, in accordance with certain examples.
Figure 62B:
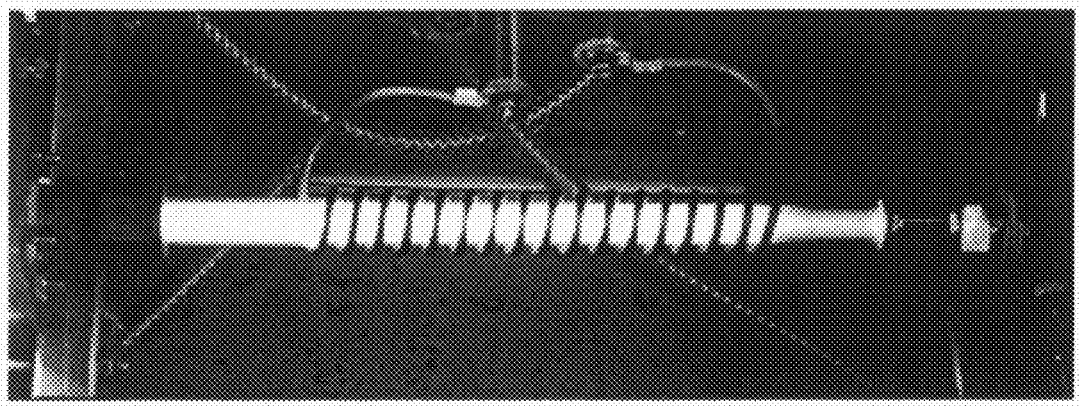
Figure 62C:
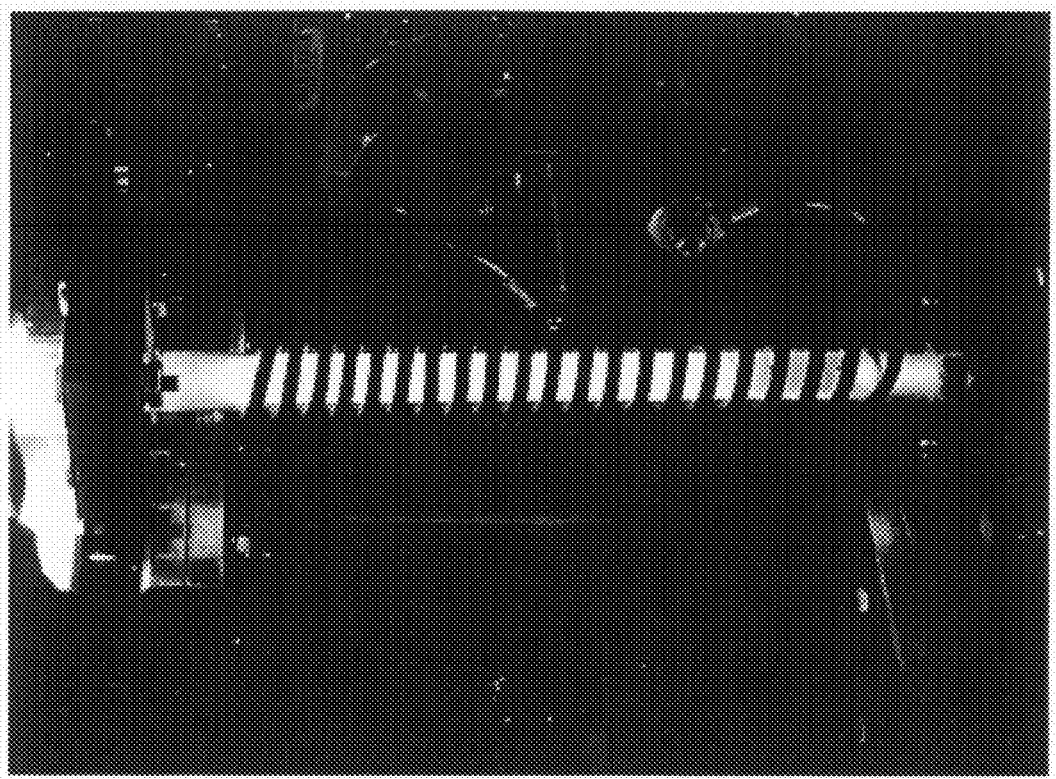
Figure 62D:
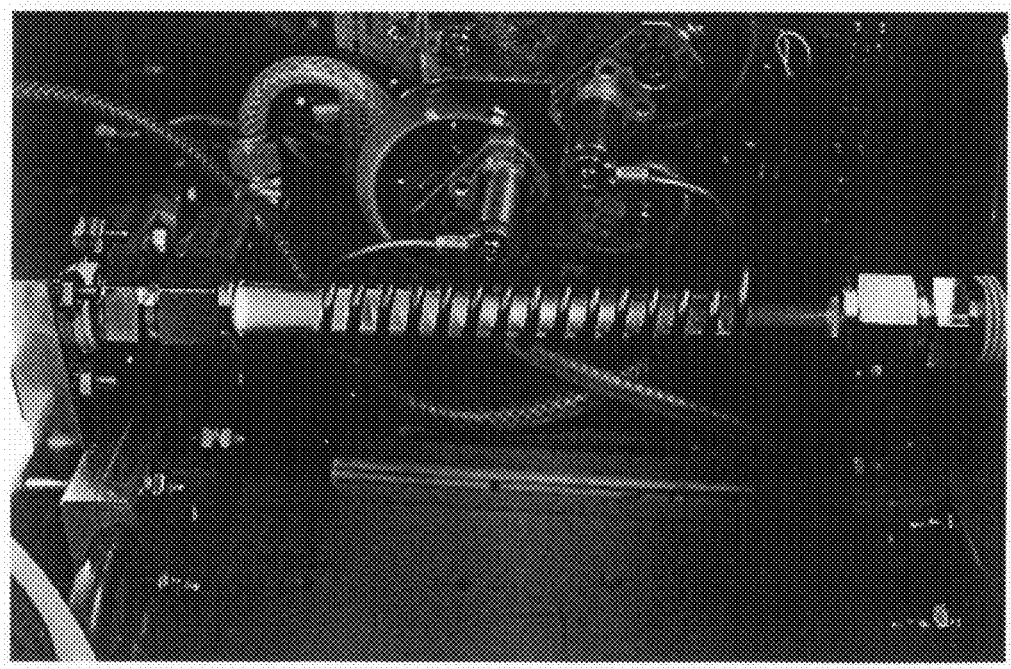

Referring now to FIG. 61, plasma 4950 was operated at 1300 watts with the boost device off using the setup shown in FIGS. 53 and 54. FIG. 62A shows plasma 4950 operating at 1300 watts with 15 L/minute of argon plasma gas, 1.2 L/minute of nebulizer gas flow with 500 ppm of sodium, and 0.2 L/min of auxiliary argon gas flow in the primary discharge. The boost device power was approximately 800 watts at a frequency of 20 MHz, and the flow rate into the second chamber was a low flow of about 1-2 L/min. In operation, the nebulizer gas flow was increased above that which is used in typical ICP operation. By raising the desolvation bullet to extend past the end of the torch to reach the sampling hole in the interface, not only is the available portion of sample increased but it is possible to capture the concentrated sample without it being diluted by mixing with the high flow rate of the plasma gas. The plasma gas may be allowed to escape by the gap between the primary discharge and the interface of the secondary chamber. The gas flow through the interface may be controlled and adjusted for best operation. By keeping the flow of the gas into the secondary chamber close to the same flow rate of the nebulizer, then just the concentrated sample may be carried into the secondary chamber. The interface of the secondary chamber has the added benefit of effectively blocking the background emission of the primary discharge. It is also possible to add an additional photon stop after the sample orifice to block the majority of or all of the primary discharge background light. It would also be possible to view off axis to prevent any of the primary background light from being viewed. FIG. 62B is an enlarged view of the secondary chamber seen in FIG. 62A for a comparative view. FIG. 62C shows a previous version of the secondary chamber (slightly shorter chamber and a few more turns of the boost device) operating at the same gas flow, sample, and primary discharge conditions, but using about 400 watts of boost power. FIG. 62D is also a previous version of the secondary chamber (as shown in FIG. 62C) with the same gas flow, and primary discharge conditions, but with a trace amount of yttrium (about 1-10 ppm) in water and using about 400 watts of boost power.

Example 2

Optical Emission Using an ICP and Boost Device

Figure 63:
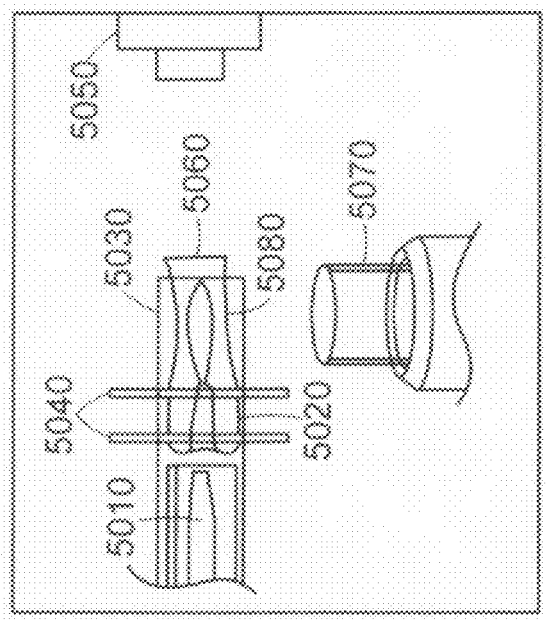
FIG. 63 is a radial view of a schematic of an atomization source suitable for use with the boost devices disclosed here, in accordance with certain examples.

Referring to FIG. 63, a picture of an inductively coupled plasma (ICP) source suitable for use in performing optical emission spectroscopy or mass spectroscopy is shown. An ICP source 5000 includes hollow injector 5010 to introduce aerosolized sample into a plasma 5020, such as an RF induced argon plasma, contained in torch glassware 5030. The ICP source 5000 also includes RF induction coils 5040. In the configuration shown in FIG. 63, an axial viewing window 5050 may be used to monitor axial emission 5060, and radial viewing window 5070 may be used to monitor radial emission 5080. As discussed above, by viewing axially, detection limits may be improved by a factor of 5 to 10 times or more.

Figure 64:
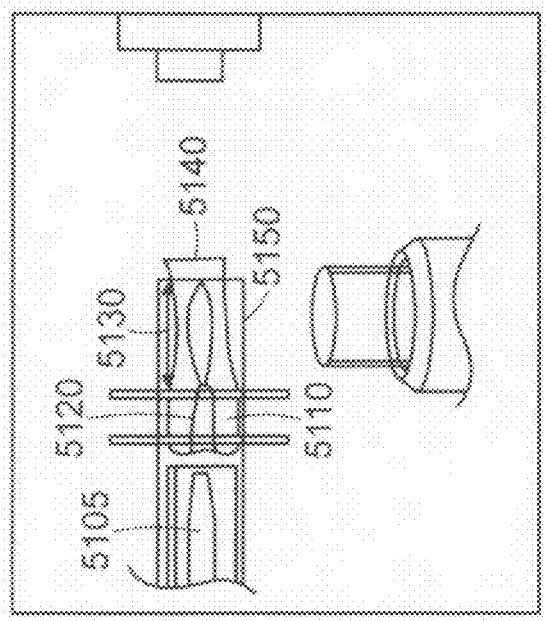
FIG. 64 is a radial view of another schematic of an atomization source suitable for use with the boost devices disclosed here and viewed radially, in accordance with certain examples.

Referring now to FIG. 64, a schematic of an ICP containing a species that emits light is disclosed. ICP 5100 includes those components discussed above in reference to FIG. 63. Sample is atomized into a fine aerosol mist before it passes into injector 5105 and into the plasma. High current torus discharge region 5110 of the plasma is the brightest background region of the plasma. Desolvation region 5120 of the sample is where solvent is removed from the injected sample. Ionization region 5130 is the useful region of the plasma where the atomized and/or ionized sample will emit light. The emitted light may be viewed axially 5140 or may be viewed radially 5150. When yttrium is used as a sample, the blue emission may be about 5 times longer when viewed axially as compared to when viewed radially. Not only is the blue emission longer, but it is also brighter in the lower regions of the plasma; hence a greater than 5× improvement in signal may be realized with axial viewing For radial viewing on the other hand, a region must be selected where there is high signal to background noise. The signal continues to get brighter as the viewing gets closer to the induction plates, but the background emission from the torus discharge increases faster than the signal as the viewing region approaches the induction plates. Hence the optimum radial viewing region is typically about 15 mm from the last induction plate. The torus discharge is "lifesaver" shaped with a hole in the middle. The axial viewing captures the ion emission of the sample but looks through the center of the torus discharge, thereby maximizing the ion emission and minimizing the background emission.

Figure 65:
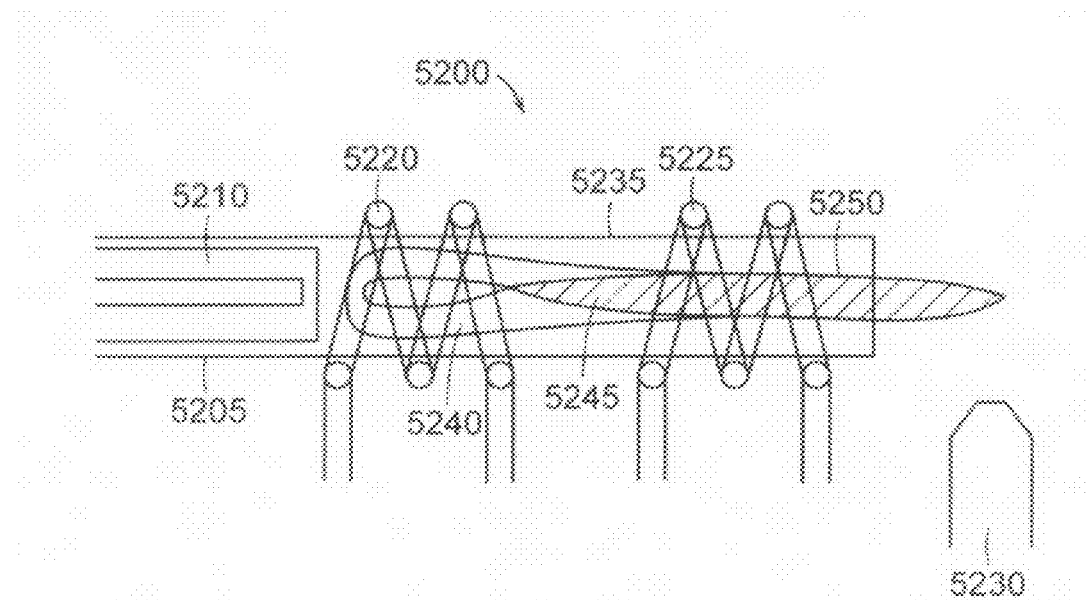
FIG. 65 is a radial view of a schematic of an atomization source with a boost device, in accordance with certain examples.

FIG. 65 shows an ICP including a boost device. An ICP 5200 includes a tube 5205, a torch 5210, an RF induction coil 5220, a boost device 5225 and a shear gas 5230. The shear gas 5230 is operative to terminate the plasma beyond the end of tube 5205. ICP 5200 generates a plasma 5235 which may be used to desolvate an introduced sample. A desolvation region 5240 of the plasma 5235 provides energy to remove liquid from the sample. An ionization region 5250 is the region where excited sample may emit light. By switching on a boost device 5225, the emission region may be extended, or emission may become more intense, or both.

Figure 66:
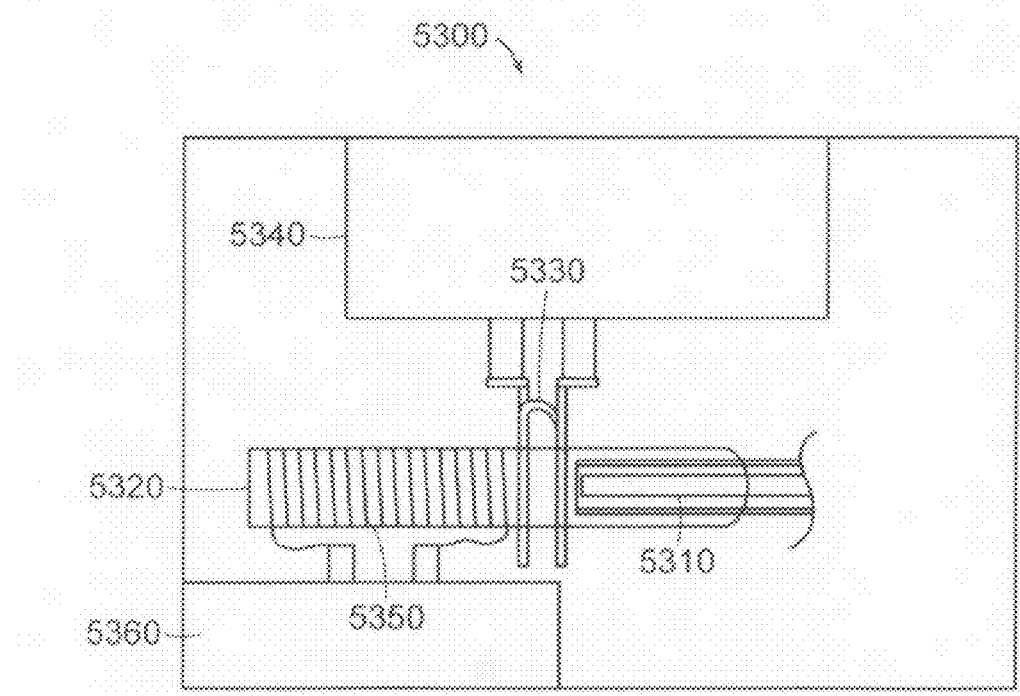
FIG. 66 is radial view of another schematic of an atomization source with a boost device, in accordance with certain examples.
Figure 67:
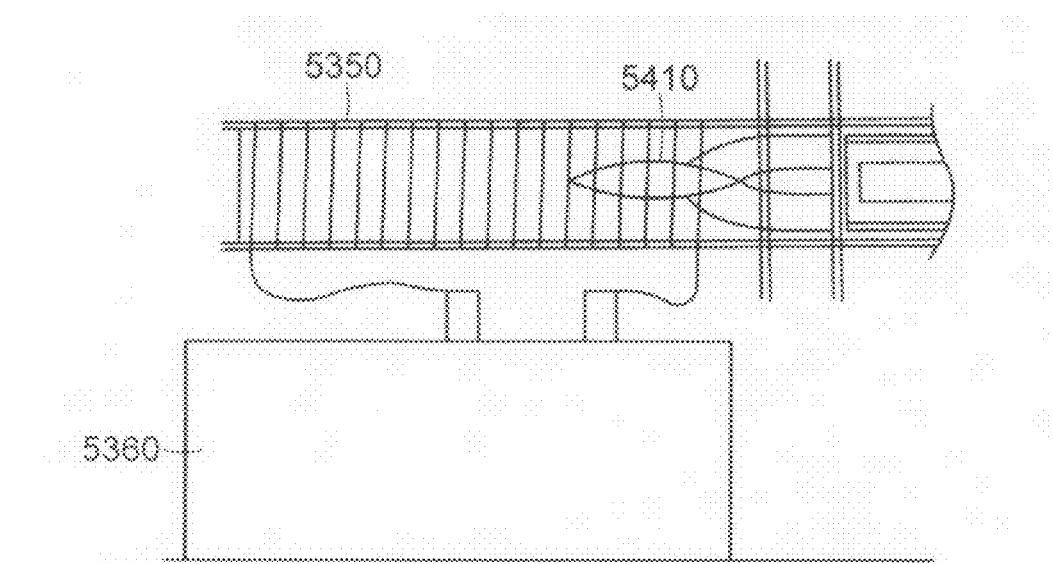
FIG. 67 is a radial view of an enlarged schematic of an atomization device with a boost device turned off, in accordance with certain examples.
Figure 68:
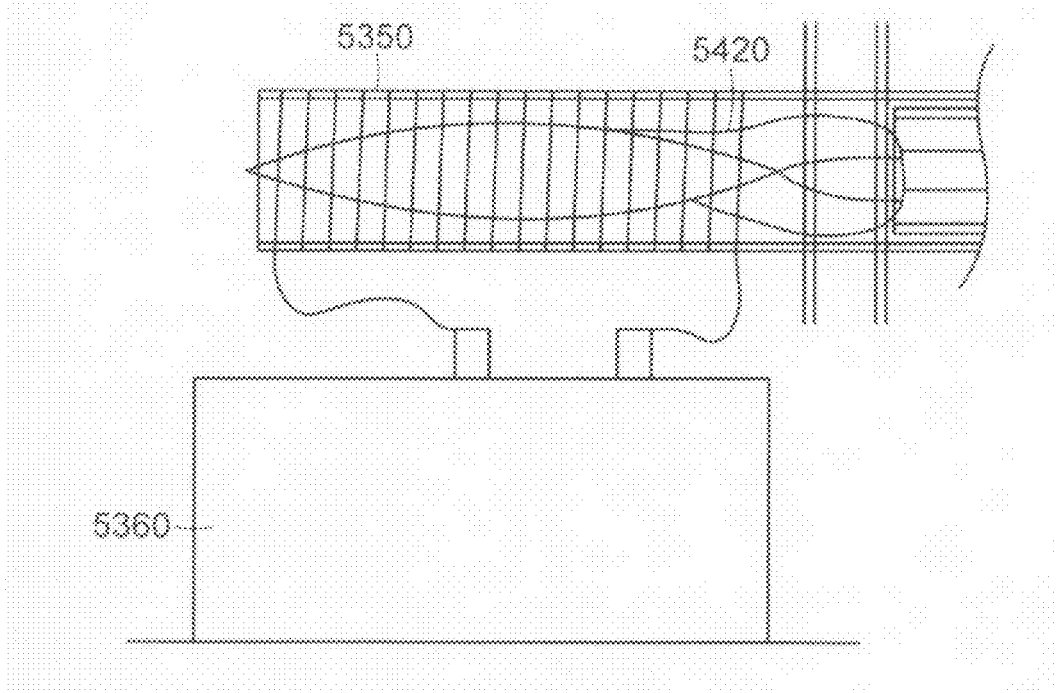
FIG. 68 is radial view of an enlarged schematic of an atomization device with a boost device turned on, in accordance with certain examples.

Referring now to FIG. 66, a second configuration of an ICP including a boost device is shown. An ICP 5300 includes a torch 5310, an extended quartz tube 5320, an RF induction coil 5330 and a primary ICP RF source 5340. The ICP 5300 also includes a boost device 5350 which is in electrical communication with RF source 5360. Referring to FIG. 67, emission 5410 is present when the boost device 5350 is "off" so that no boost is provided. When RF source 5360 is switched "on" to provide radio frequencies to the boost device 5350, emission signal 5420 results. As may be seen in FIG. 68, using the boost device 5350 with the RF source 5360 the emission region from a sample may be extended, which may provide increased levels of signal for detection.

Figure 69:
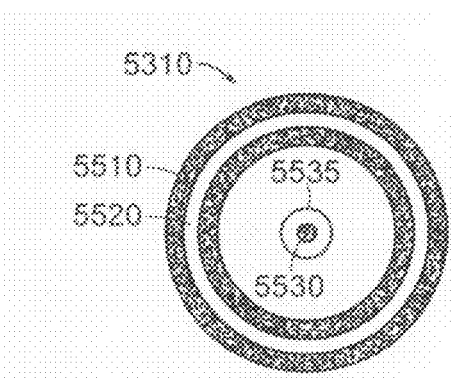
FIG. 69 is an axial view of an atomization device, in accordance with certain examples.
Figure 70:
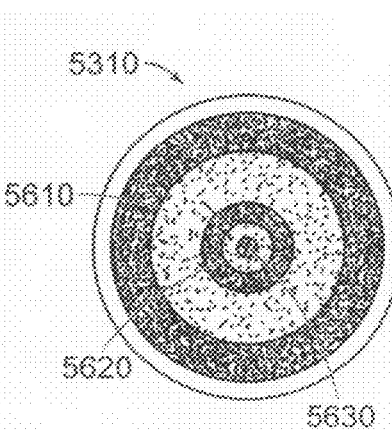
FIG. 70 is an axial view of an atomization device with a boost device turned off, in accordance with certain examples.
Figure 71:
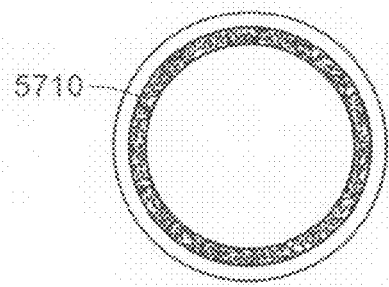
FIG. 71 is an axial view of an atomization device with a boost device turned on, in accordance with certain examples.

Referring now to FIG. 69, a torch 5310 without any plasma is shown from an axial view (looking into the end of torch). Torch 5310 includes exterior tube 5510, auxiliary gas tube 5520 and injector tube 5535 and injector hole 5530. Referring to FIG. 70, as a sample is introduced into a plasma and when the boost device is off, plasma discharge 5610 surrounds sample emission 5620 and the hole in injector tube 5630 is still visible through sample emission 5620. Referring to FIG. 71, as a sample is introduced into a plasma and when boost device is on, emission 5710 from the sample overpowers the plasma discharge and the intensity of emission 5710 increases so that the injector tube may no longer be seen through the sample emission.

Example 3

Optical Emission from an Yttrium Sample Using an ICP Boosted Discharge

Figure 72:
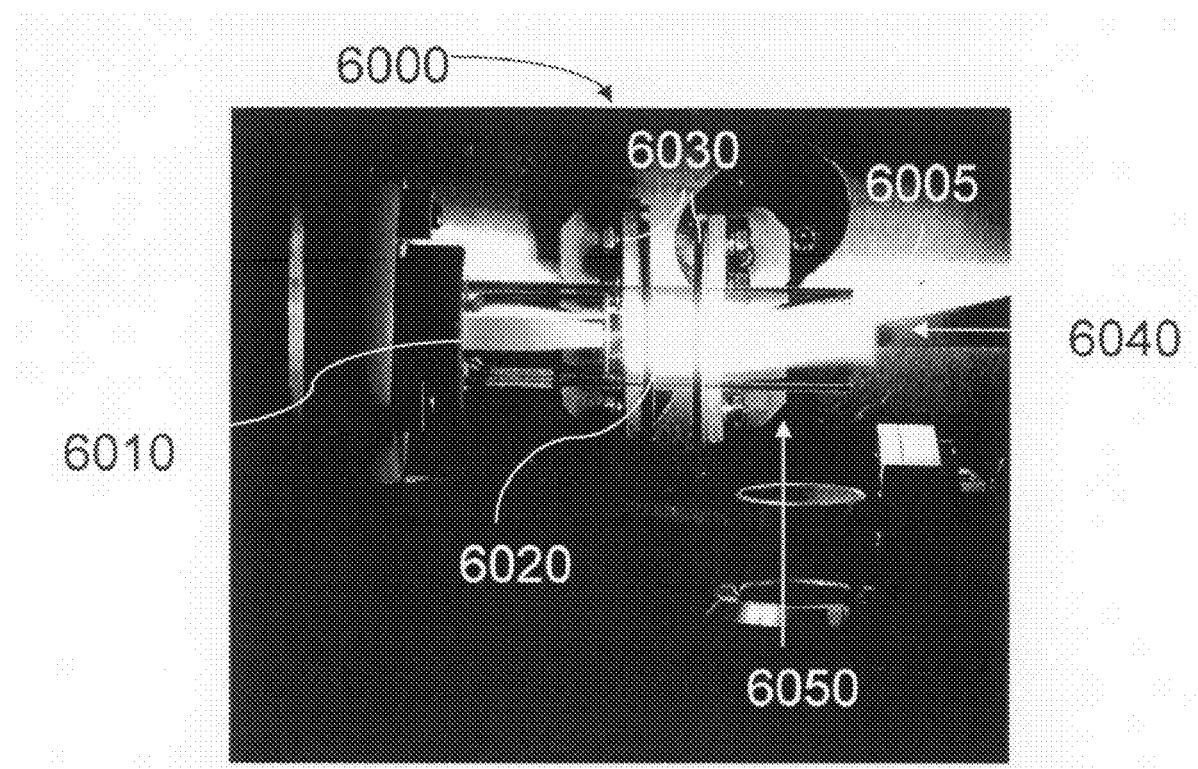
FIG. 72 is a radial view of an inductively coupled plasma suitable for use with the boost devices disclosed here, in accordance with certain examples.
Figure 73:
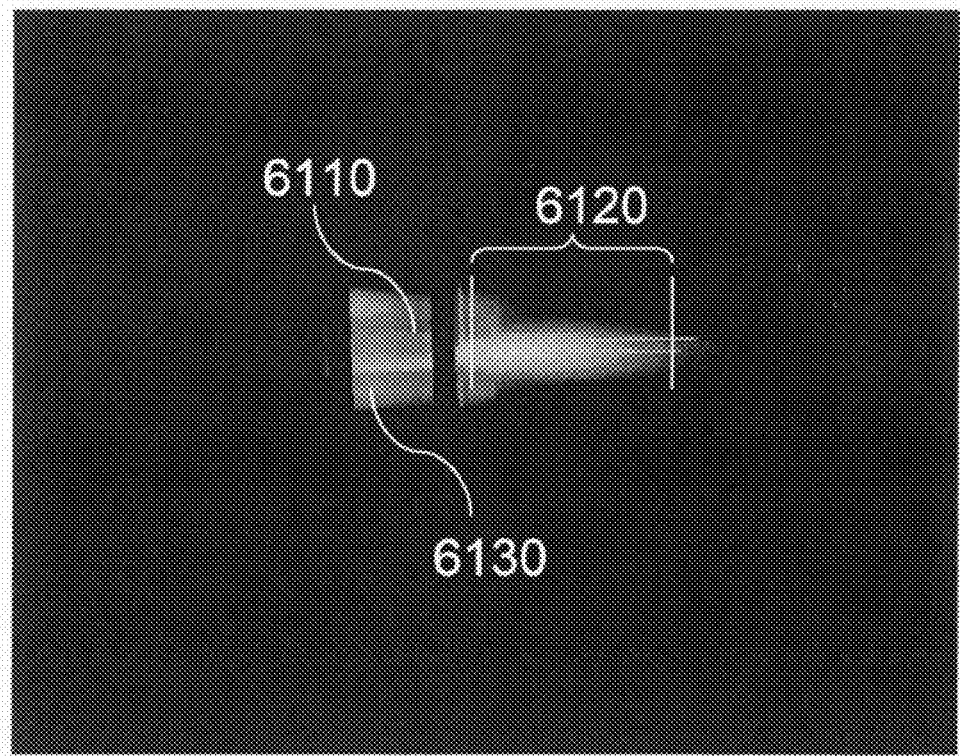
FIG. 73 is a radial view, through a piece of welding glass, of an inductively coupled plasma suitable for use with the boost devices disclosed here, in accordance with certain examples.

Referring to FIG. 72, a picture of an inductively coupled plasma source that was assembled is shown. Inductively coupled plasma source 6000 included torch glassware 6005, a hollow injector 6010 for injection of aerosol sample into a plasma 6020. The plasma 6020 was generated using induction coils 6030. Any emission from the plasma 6020 was viewed either axially 6040 or radially 6050. Axial viewing provided for lower detection limits. 1000 ppm of yttrium in water was injected into the ICP device shown in FIG. 73 using a Meinhard nebulizer and at a flow rate of about 1 mL/min. The plasma source was so bright that the emission could not be viewed without the optical attenuating aide of a piece of welding glass. FIG. 73 shows the optical emission of the yttrium through the piece of welding glass. A desolvation region 6110 (the reddish-pink region) is often referred to as a "bullet" due to its shape. As solvent droplets evaporate, the sample was left as microscopic salt particles. An ionization region 6120 was the region where the sample was ionized and emitted at its characteristic wavelength(s), which in this example where yttrium was used was blue light having a wavelength of about 371.029 nm. A high current discharge region 6130 of the plasma 6020 was the brightest background region of the plasma.

Figure 74:
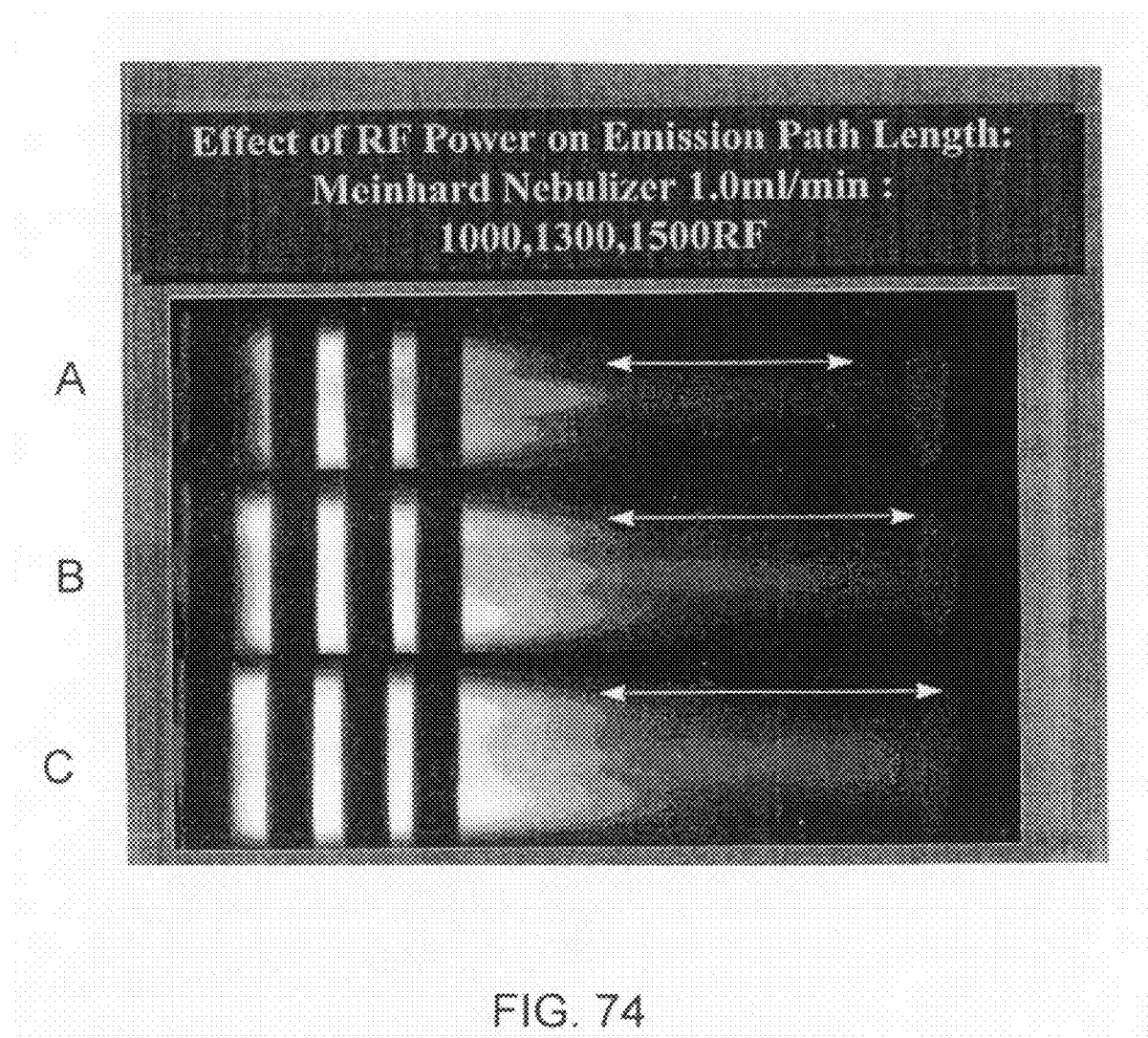
FIG. 74 is a radial view of the effect of RF power on emission path length of 1000 ppm of yttrium introduced into an inductively coupled plasma, in accordance with certain examples.

Referring now to FIG. 74, the effect of boost power on path length was demonstrated. Applying 1300 Watts (panel B) and 1500 Watts (panel C) of RF power through the boost device resulted in an increase in the emission path length when compared with the emission path length observed with 1000 Watts of applied power (Panel A).

Figure 75:
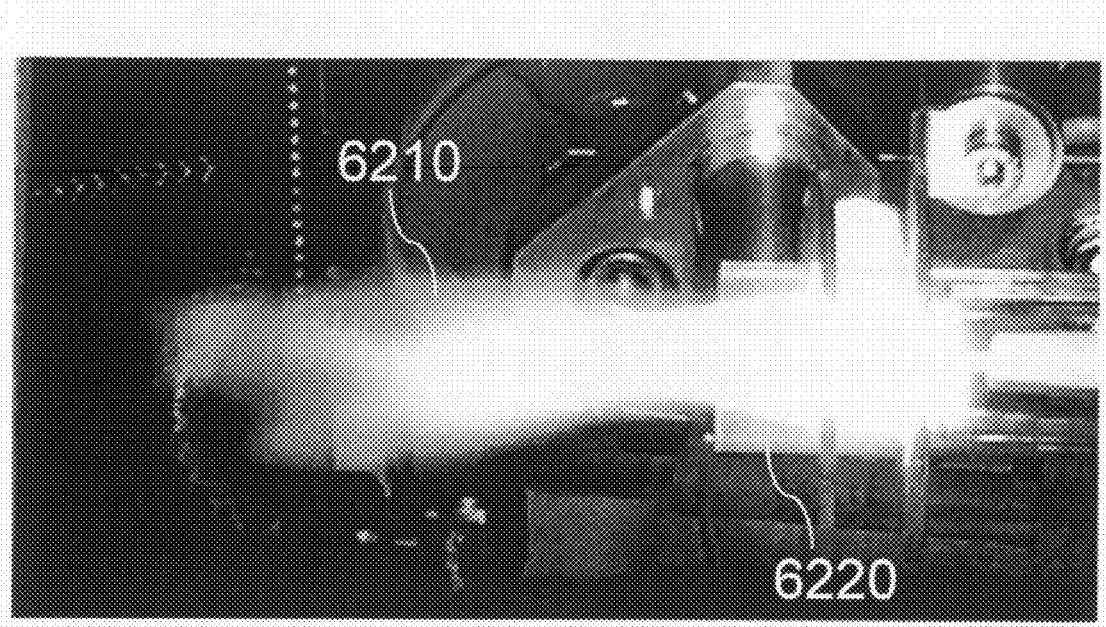
FIG. 75 is a radial view of a plasma discharge and optical emission of 1000 ppm yttrium introduced into an inductively coupled plasma, in accordance with certain examples.
Figure 76:
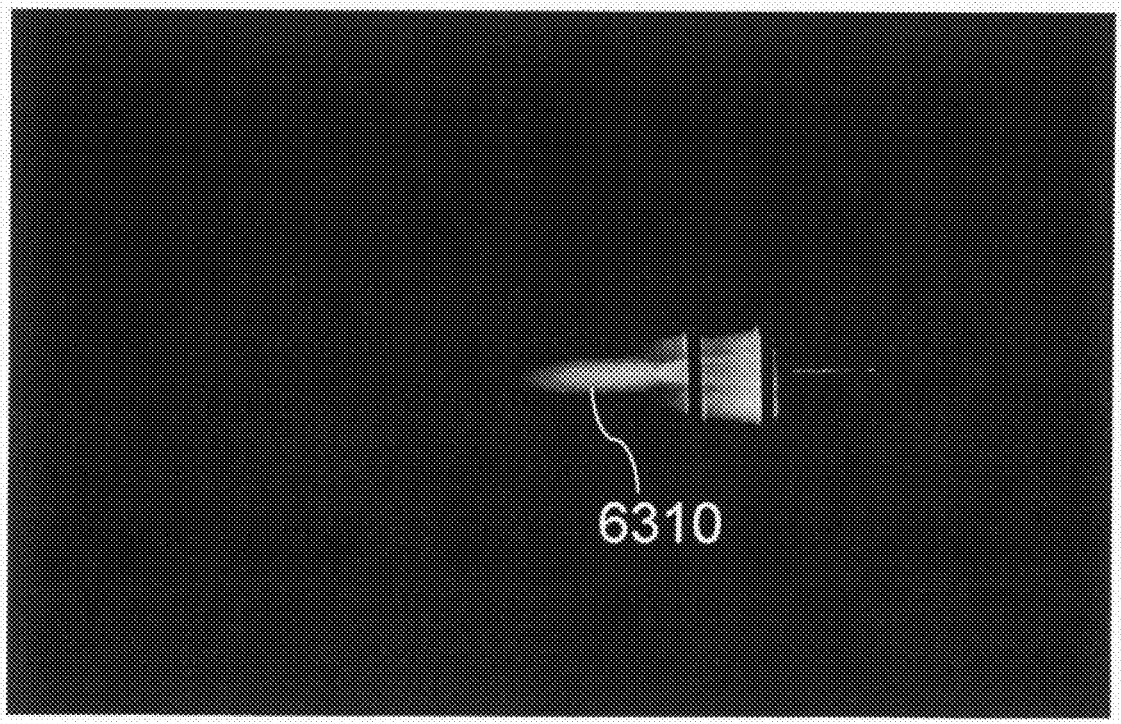
FIG. 76 is a radial view of a plasma discharge and optical emission of 1000 ppm yttrium introduced into an inductively coupled plasma and viewed through a piece of welding glass, in accordance with certain examples.

Yttrium emission from the plasma of FIG. 73 is shown without (FIG. 75) and with the aid of a piece of welding glass (FIG. 76). As may be seen in FIG. 75, plasma plume 6210 extended beyond the end of quartz tube 6220. Referring to FIG. 76, blue ionization region 6310 was the region where the sample emission was viewed either axially or radially. As discussed below, using a boost device, the emission region of the sample was extended.

Figure 77:
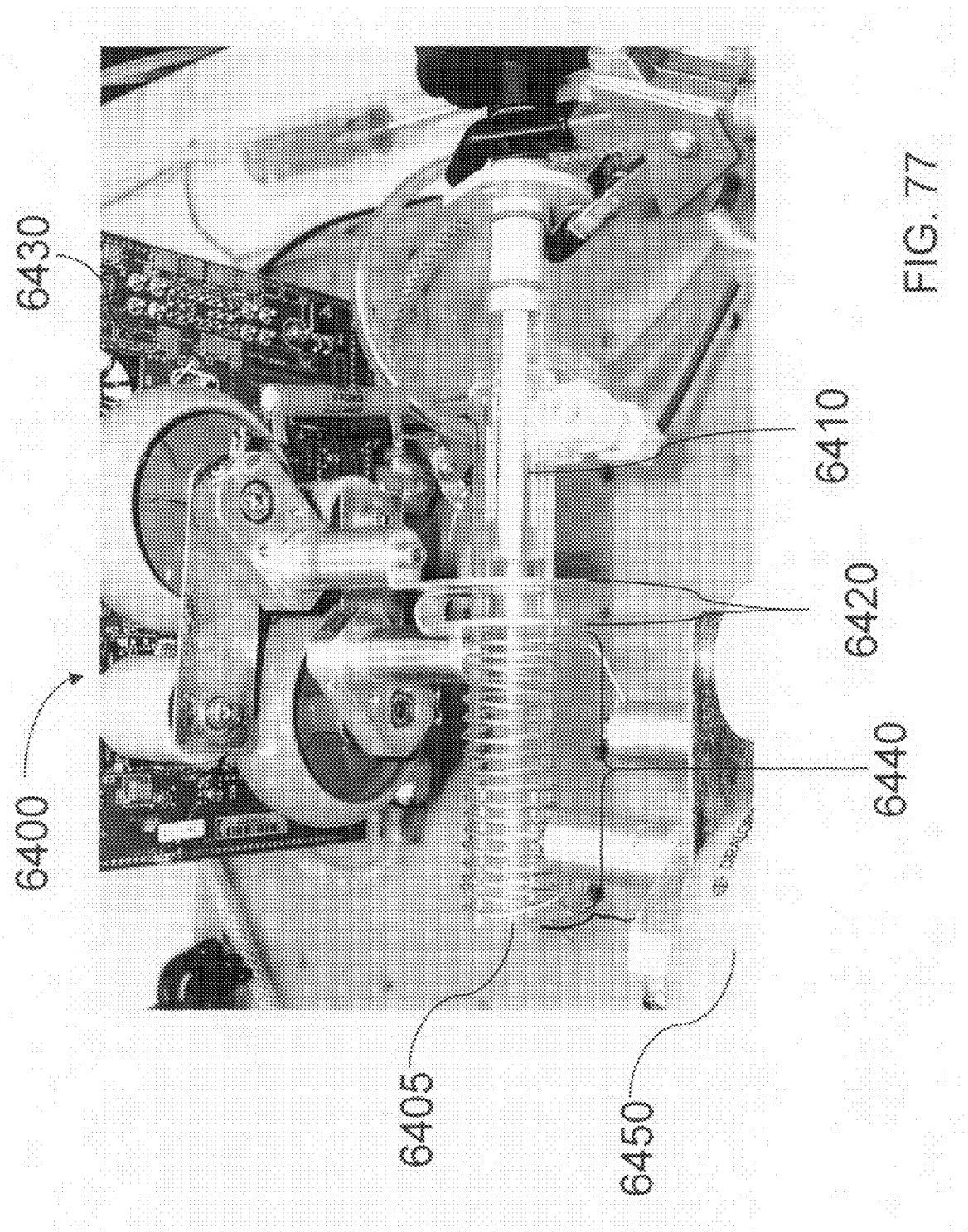
FIG. 77 is a device including an inductively coupled plasma source and a boost device, in accordance with certain examples.
Figure 78:
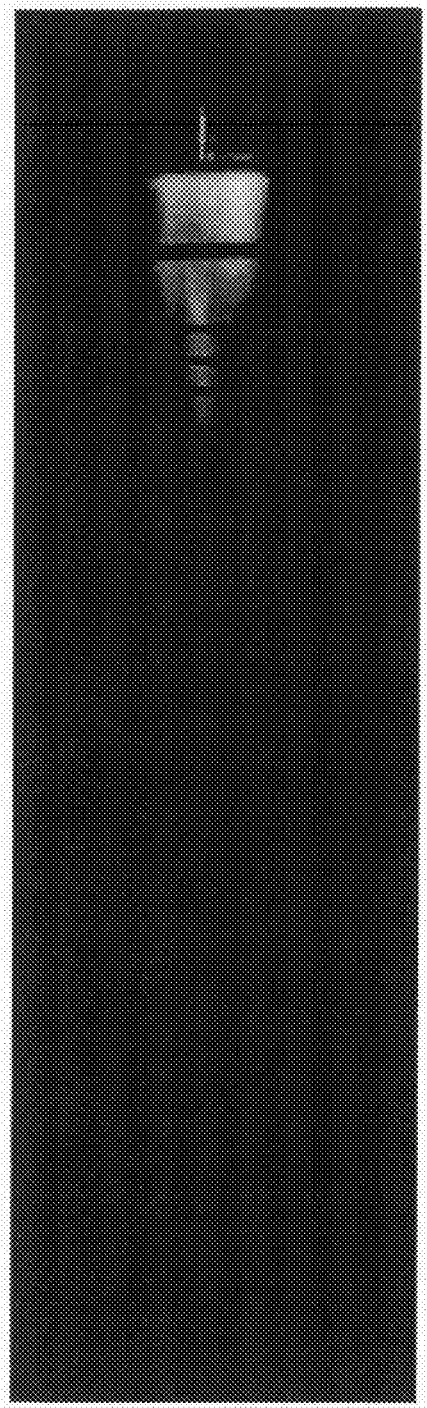
FIG. 78 is a radial view through a piece of welding glass of a plasma discharge and optical emission of 500 ppm yttrium introduced into an inductively coupled plasma with the boost device turned off, in accordance with certain examples.
Figure 79:
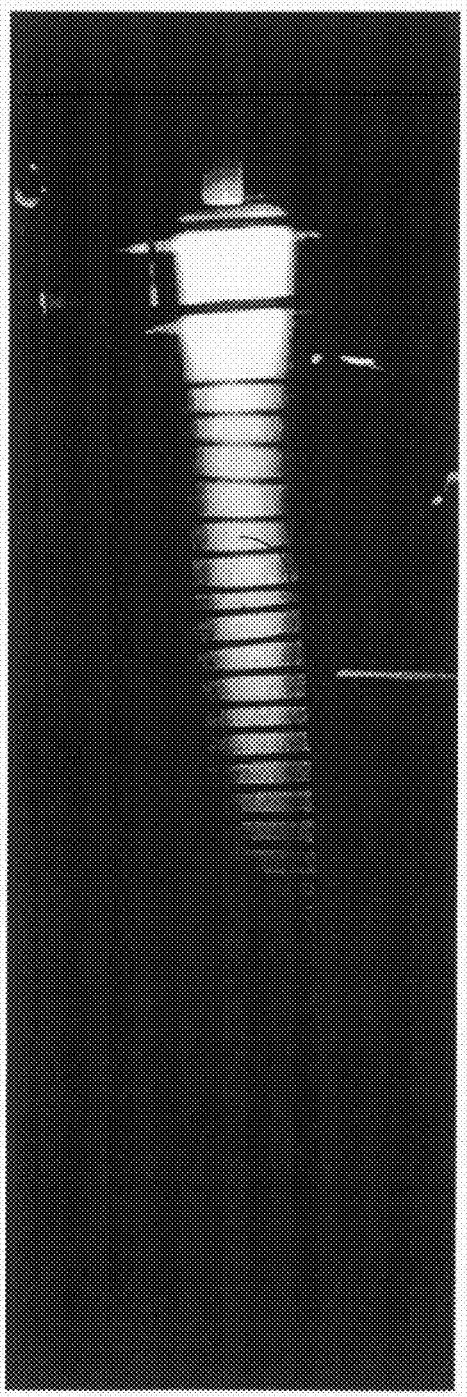
FIG. 79 is a radial view through a piece of welding glass of a plasma discharge and optical emission of 500 ppm yttrium introduced into an inductively coupled plasma with the boost device turned on, in accordance with certain examples.
Figure 80:
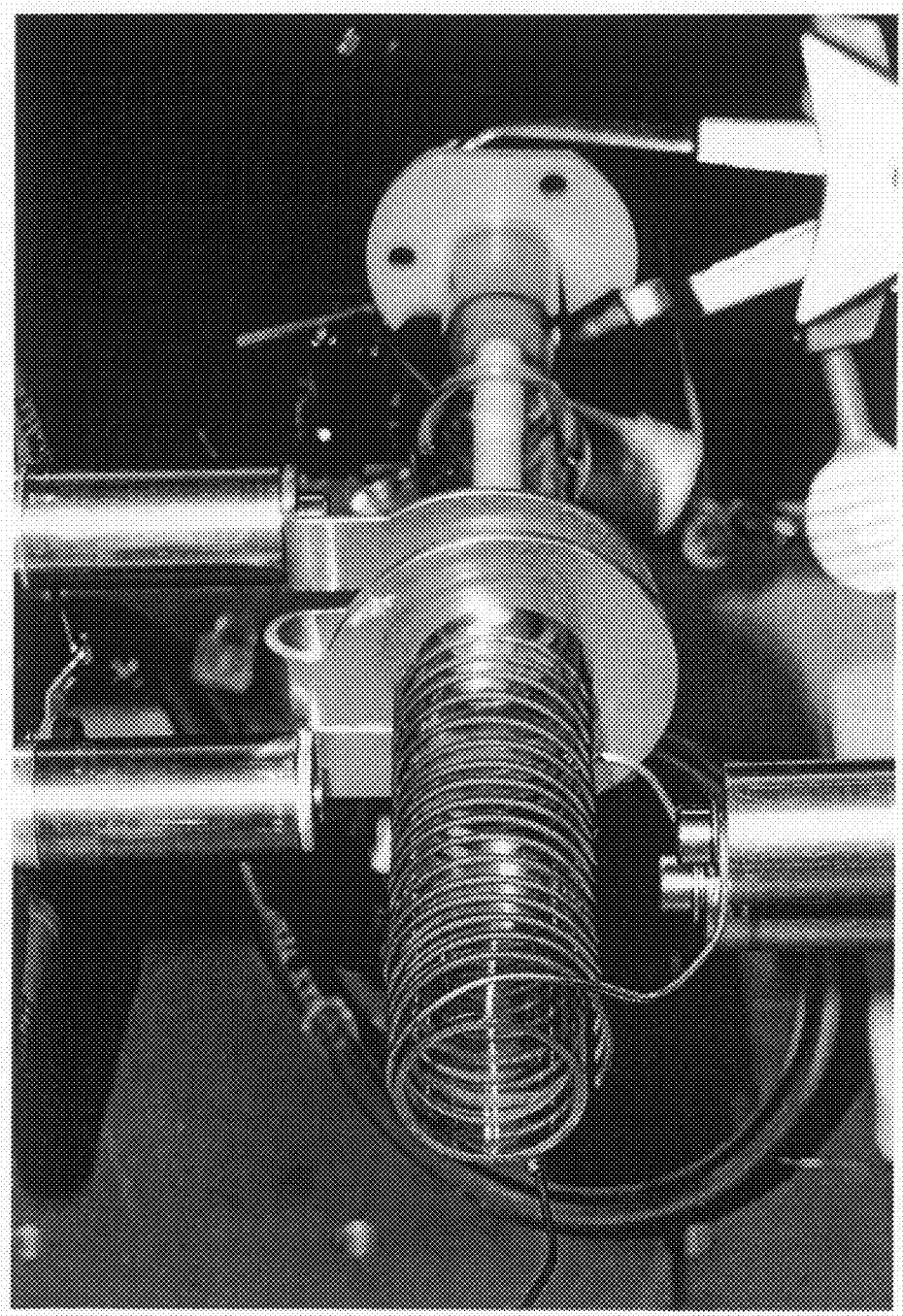
FIG. 80 is a perspective view of a device including an inductively coupled plasma source and a boost device, in accordance with certain examples.
Figure 81:
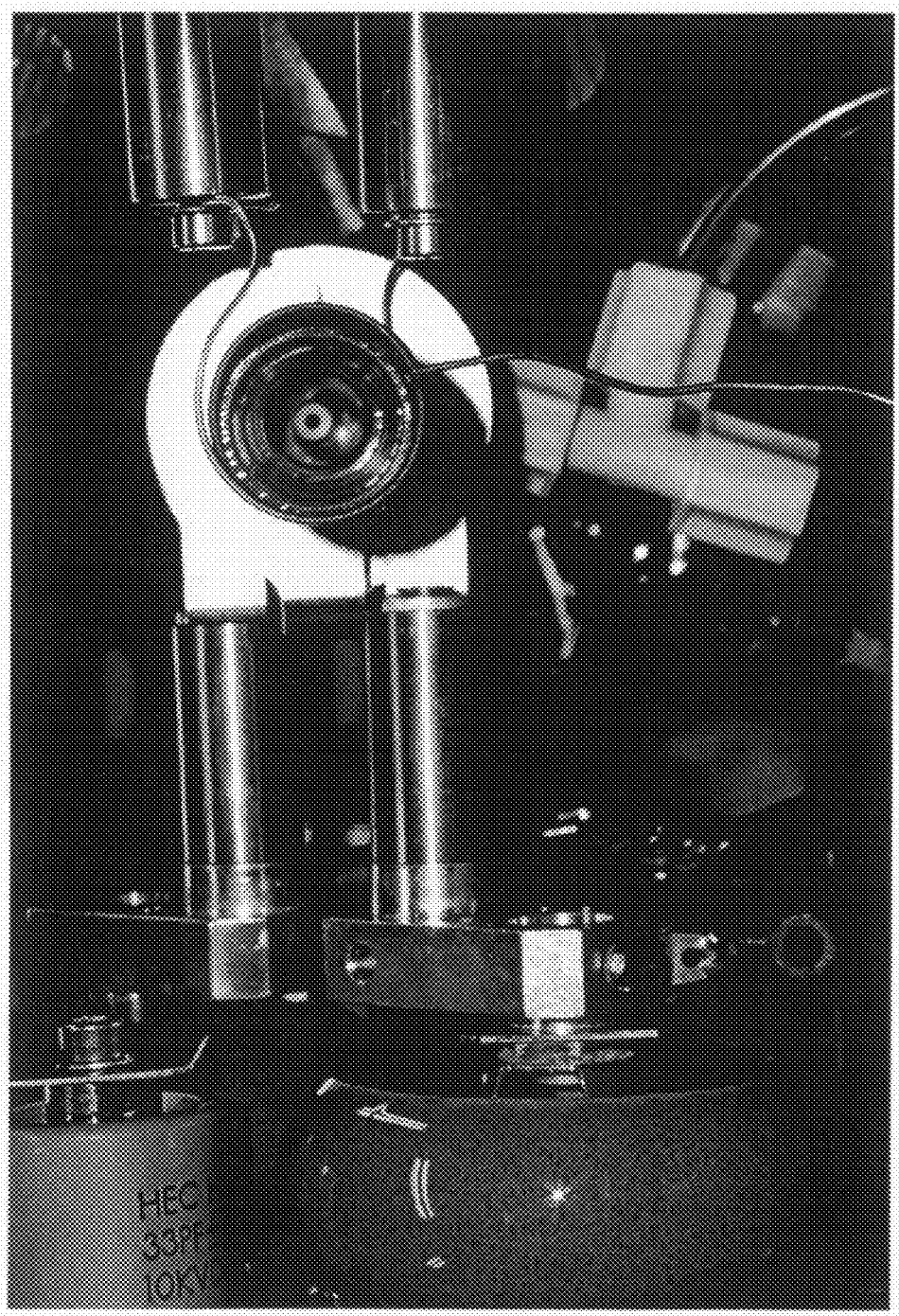
FIG. 81 is an axial view of a device including an inductively coupled plasma source and a boost device with the plasma turned off, in accordance with certain examples.

Referring now to FIG. 77, an ICP including a boost device is shown. ICP 6400 was assembled by replacing a standard quartz tube with an extended quartz tube 6405, as described above in Example 1. The ICP 6400 included an RF injector 6410, induction coils 6420 in electrical communication with a plasma RF source 6430, and a boost device 6440 in electrical communication with an RF source 6450. FIG. 78 shows a picture of the emission signal from a 500 ppm yttrium sample that was introduced into the device shown in FIG. 77 with the boost device turned off. Yttrium emission 6510 was relatively small when compared to the background plasma emission. When boost device 6440 was turned on to provide radio frequencies of about 10.4 MHz and at a power of about 800 Watts, the blue yttrium emission region extended over 5-fold longer than that observed without the boost device and the intensity of the yttrium emission also increased. FIG. 80 shows a perspective view of the device of FIG. 77. FIG. 81 an axial view of the device of FIG. 77.

Figure 83:
FIG. 83 is an axial view of the emission from 500 ppm of yttrium in an inductively coupled plasma with a boost device turned on, in accordance with certain examples.
Figure 82:
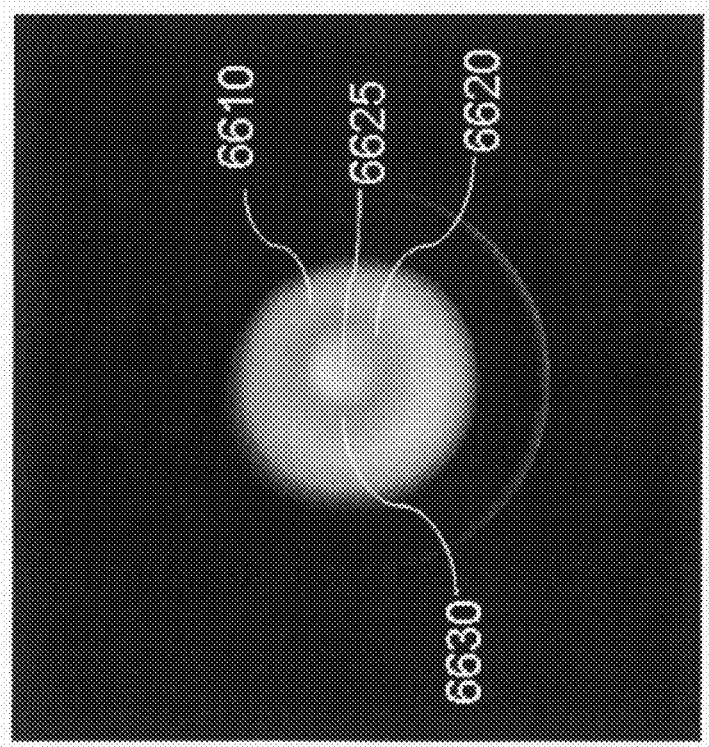
FIG. 82 is an axial view of the emission from 500 ppm of yttrium in an inductively coupled plasma with a boost device turned off, in accordance with certain examples.

Referring now to FIG. 82, when the emission of the device assembled in FIG. 77 was viewed axially through a piece of welding glass and with boost device 6440 off, primary discharge 6610 and an injector 6620, and an injector hole 6625 may still be observed through yttrium emission 6630. When boost device was switched on at a power of about 800 Watts and a frequency of about 10.4 MHz, the blue yttrium emission became so intense that the primary discharge and the injector could not be observed. (FIG. 83). With boost device 6440 turned on, the yttrium emission saturated a camera detector, even when a second piece of welding glass was placed between the camera detector and the yttrium emission.

Figure 85:
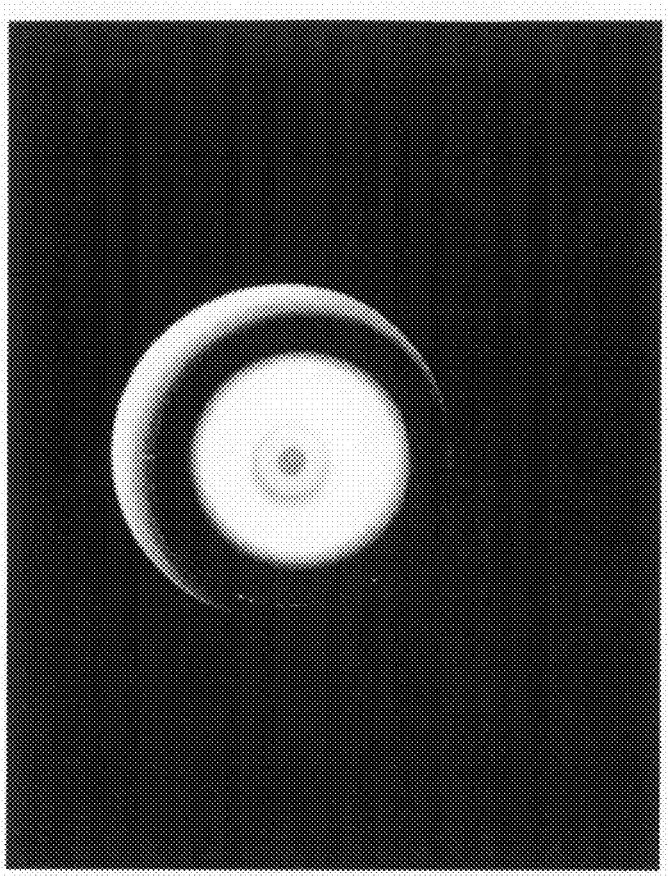
FIG. 85 is an axial view of the emission from water in an inductively coupled plasma with a boost device turned on, in accordance with certain examples.
Figure 84:
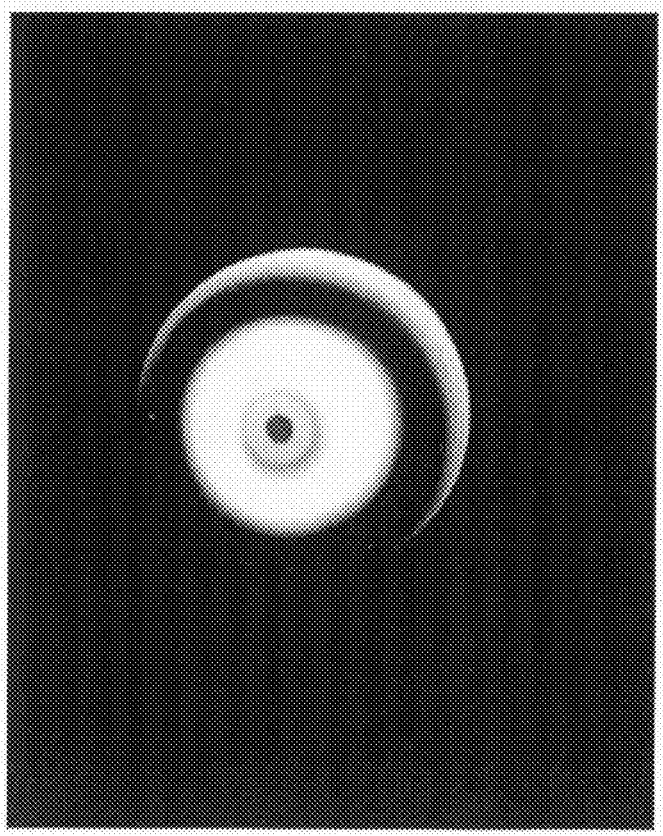
FIG. 84 is an axial view of the emission from water in an inductively coupled plasma with a boost device turned off, in accordance with certain examples.

Referring now to FIG. 84, to determine if the boost device increased the plasma discharge background signal, water was aspirated through the device shown in FIG. 77. FIG. 84 shows the signal from aspirated water when boost device 6440 was turned off, and FIG. 85 shows the signal from the aspirated water when boost device 6440 was turned on at a power of about 800 Watts and at a frequency of about 10.4 MHz. The observed results were consistent with no substantial difference in plasma discharge background emission when a boost device was used.

Example 4

ICP with Secondary Boost Chamber

Figure 86:
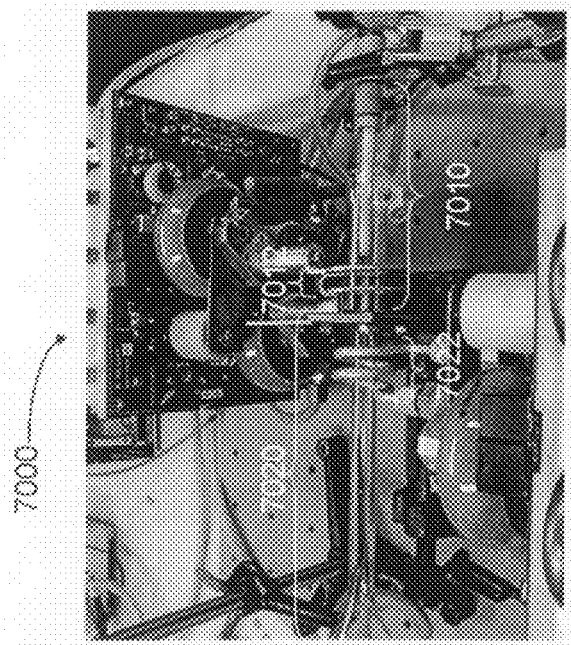
FIG. 86 is a perspective view of a device including a first chamber for generating an inductively coupled plasma and a second chamber with a boost device, in accordance with certain examples.
Figure 87:
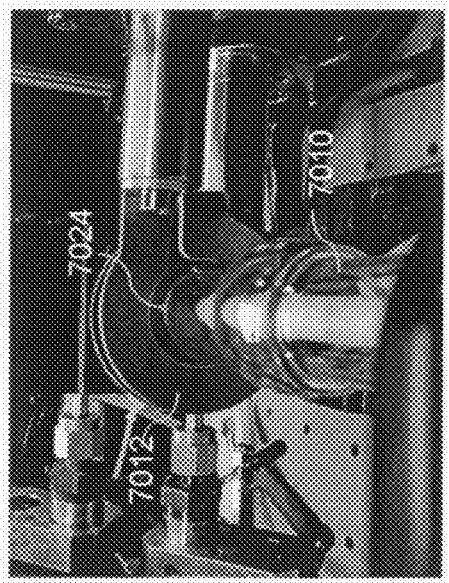
FIG. 87 is a perspective view looking from the first chamber towards the interface of the second chamber with a boost device, in accordance with certain examples.
Figure 88:
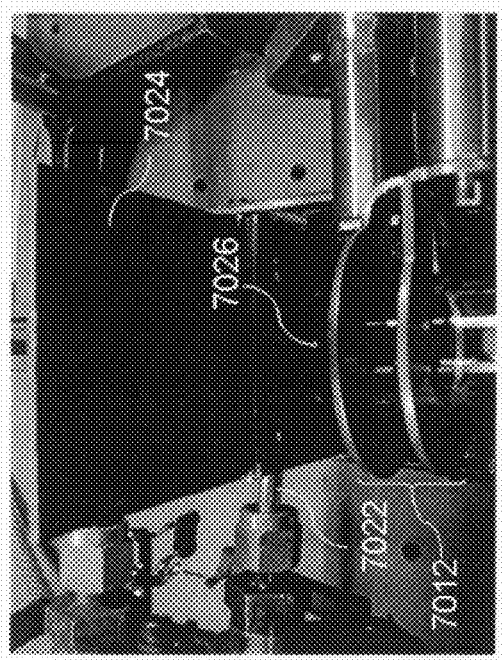
FIG. 88 is a top view between the terminus of the first chamber and the interface of the second chamber with a boost device, in accordance with certain examples.
Figure 89:
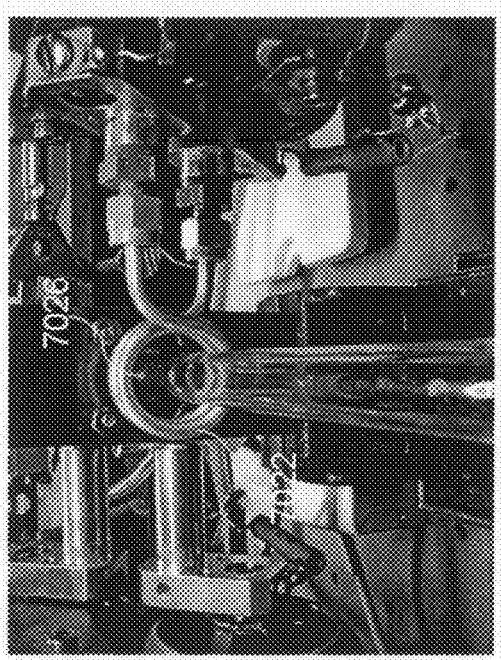
FIG. 89 is a perspective view looking from the second chamber towards the interface and the boost device, in accordance with certain examples.

Referring to FIGS. 86-88, a device 7000 included first chamber 7010 for generation of an inductively coupled plasma, as described above in Example 1. First chamber 7010 included induction coils 7012. A device 7000 also included a second chamber 7020 with a boost device 7022. The second chamber 7020 included an interface 7024 which was configured with an orifice 7026 for introducing atoms and ions from the first chamber 7010 into the second chamber 7020. An interface 7024 was configured to separate the small volume of ionized sample gas from the larger volume of plasma gas which was used to form the plasma discharge and to cool the torch glassware. This configuration preserved the concentration of the sample which otherwise was diluted as it mixed with the plasma gas. The interface 7024 also separated the plasma discharge signal from the emission signal in the second chamber, and the coupling of energy from the induction coils 7012 and energy from the boost device 7022. The interface 7024 also eliminated the high background light from the plasma discharge when viewing of the sample signal in the second chamber. FIG. 87 shows an axial view of the orifice 7026 looking from first chamber 7010 towards the interface 7024. FIG. 88 shows a top view looking down on interface 7024. FIG. 89 shows an axial view of the orifice 7026 looking from second chamber 7020 towards interface 7024. Orifice 7026 had a circular cross-section with a diameter of about 0.155 inches (3.94 mm). The distance between the surface of the manifold and the end of first chamber 7010 was about 3 mm. Unlike certain manifolds used in ICP-MS, the interface used in this example was for a completely different purpose and under completely different operating conditions. The interface used here separated multiple discharges, the orifice hole was much larger than that used in ICP-MS, and the pressure at the back of the interface was much higher, typically close to atmospheric. In contrast, ICP-MS manifolds are used to separate the ICP source from the spectrometer, whereas interface 7024 was part of device 7000 itself.

Figure 90:
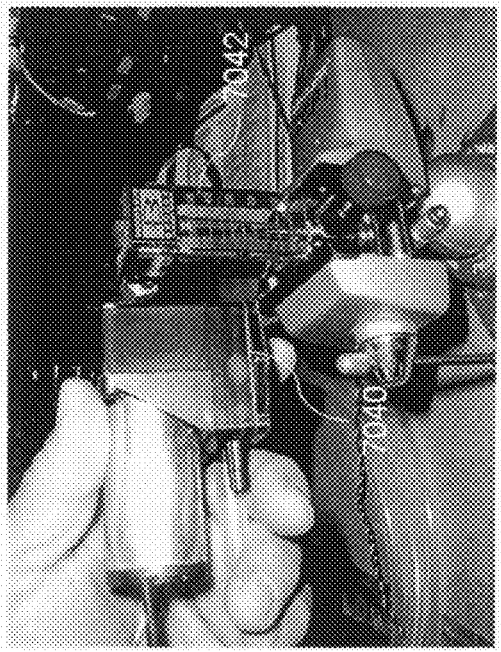
FIG. 90 is a picture of a vacuum pump and flow meter suitable for use with the second chamber shown in FIGS. 58-61, in accordance with certain examples.

Referring now to FIG. 90, vacuum pump 7040 and flow meter 7042 with a needle valve were used to draw atoms and ions from the first chamber 7010 into the second chamber 7020. Vacuum pump was coupled to the second chamber 7020 through an inlet positioned at the opposite end of the second chamber 7020 from the interface 7024, as discussed above in Example 1. The needle valve was used to control the flow rate of sample that was drawn into the second chamber 7020.

Figure 91:
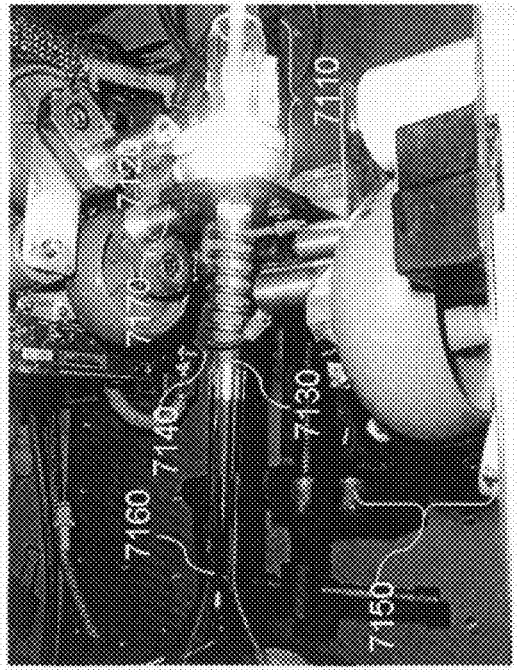
FIG. 91 is an axial view of the emission from 500 ppm of aspirated sodium in the second chamber with a 6½ turn boost device turned on, in accordance with certain examples.

Referring now to FIG. 91, a primary discharge 7110 from an ICP torch 7120 is shown. An emission signal 7130 from 200 ppm of sodium was yellow/orange in color. A boost device 7140 was a coil of ⅛ inch copper tubing (6.5 turns) in electrical communication with RF source 7150 and was placed around a second chamber 7160. A power of about 100 Watts and radio frequencies of about 30 MHz were used to excite the sodium atoms in the second chamber 7160. It was possible to vary the temperature of the regions of the emission signal 7130 in the second chamber 7160 by varying the power supplied to the boost device 7140. An interface 7170 acted as a light shield blocking the bright primary background emission from being viewed when viewing the emission signal 7130 in the second chamber 7160. The interface 7170 also successfully prevented the sample from being diluted with the plasma gas.

Figure 92:
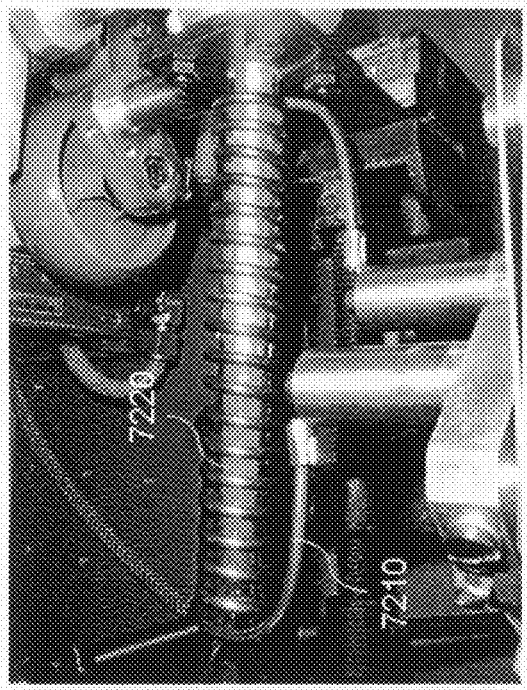
FIG. 92 is an axial view of the emission from 500 ppm of aspirated sodium using a second chamber with a 18½ turn boost device to extend the path length observed in the device of FIG. 91, in accordance with certain examples.

Referring now to FIG. 92, an 18.5 turn boost device 7210 was used to extend the emission path length relative to the emission path length shown in FIG. 91. The remaining components of the device were the same as those described above in reference to FIG. 91. A power of about 300 Watts and radio frequencies of about 20 MHz were supplied to the boost device 7210. The path length was extended along the entire length of the boost device 7210 to provide an emission signal 7220 from 200 ppm of sodium that was aspirated into the device. This result was consistent with extension of path length by using a boost device with additional coils. Air leaks were experienced with the early stage version of hardware depicted in FIGS. 91, 92 and 93. It was found that the silicone O-Ring that was used to seal the glass chamber with the copper interface failed due to the high temperature of the interface. This problem was fixed in later developed versions of the hardware by replacing the silicone O-Ring with metal compression fittings.

Figure 93:
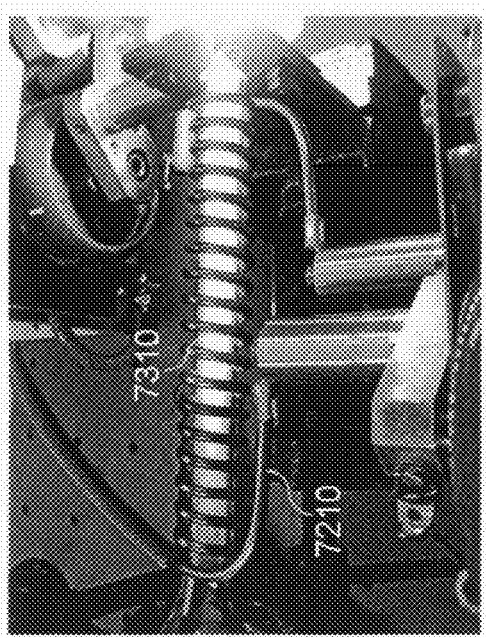
FIG. 93 is an axial view of the emission from 500 ppm of aspirated sodium using a second chamber with a 18½ turn boost device and higher RF power to increase the emission intensity, in accordance with certain examples.

Referring now to FIG. 93, the device of FIG. 92 was used to test the effect of boost device power on emission signal intensity. A power of about 800 Watts and radio frequencies of about 20 MHz were supplied to the 18.5 turn boost device 7210. An emission signal 7310, from 200 ppm of sodium that was aspirated into the device, was more intense than emission signal 7220. This result was consistent with an increase in emission intensity with increasing boost power.

Example 5

Boosted Flame Discharge

Figure 94:
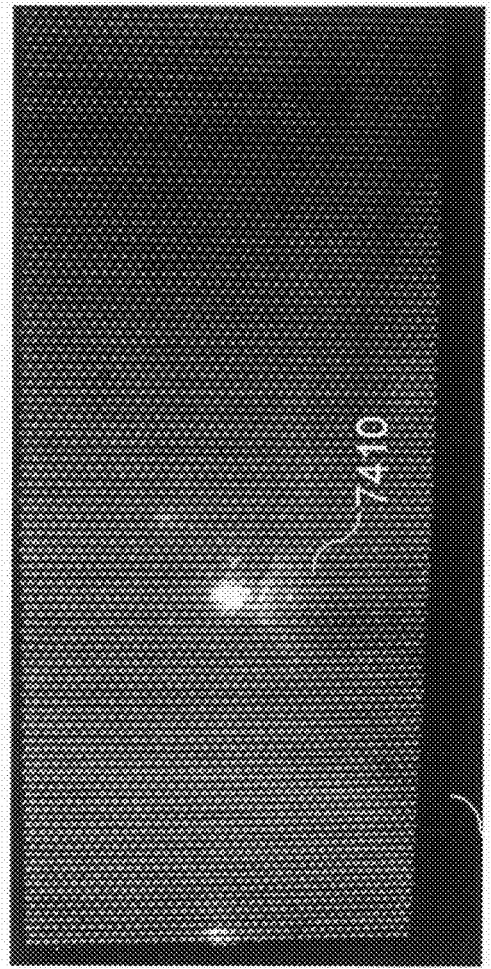
FIG. 94 is a perspective view of a candle in a microwave oven with the microwave oven turned off, in accordance with certain examples.
Figure 95:
FIG. 95 is a perspective view of a flame source in a microwave oven with the microwave over turned on and as the candle flame passes through a standing voltage maxima, in accordance with certain examples.

Referring now to FIG. 94, a flame source 7410 was positioned inside a microwave oven 7420 that was off. The flame source 7410 was a cylindrical paraffin candle having dimensions of about 1.5 inches diameter by about 2 inches high. The microwave oven 7420 was a standard Tappin (1000 Watt) microwave oven which was obtained from Scalzo-White Appliances (New Milford, Conn.). The microwave oven 7420 used an absorption cell as the oven cavity, and a microwave launcher and magnetron tube as an RF source. The flame source 7410 was lit and placed ¼ of the way into the microwave oven 7420. The fan of the microwave oven was blocked by a cardboard sheet covering the vent entering the absorption cell area to prevent any plasma plume from being disturbed and to maintain the maximum amount of ions and electrons present in the flame region. The microwave was turned on high. As the flame source 7410 rotated on the on the turnstile, bright plasma 7510 (see FIG. 95) would form as the candle passed through the standing voltage maxima. The flame source 7410 returned to a regular flame in the voltage nodes where the RF excitation was a minimum. This result was consistent with there being enough free ions and electrons generated in a flame to allow for further ionization from external radio frequencies supplied by the microwave oven. As discussed above, RF energy, including microwave energy, may be used as a source of boost energy to greatly increase the temperature of a flame discharge.

Example 6

Single RF Source

Figure 96A:
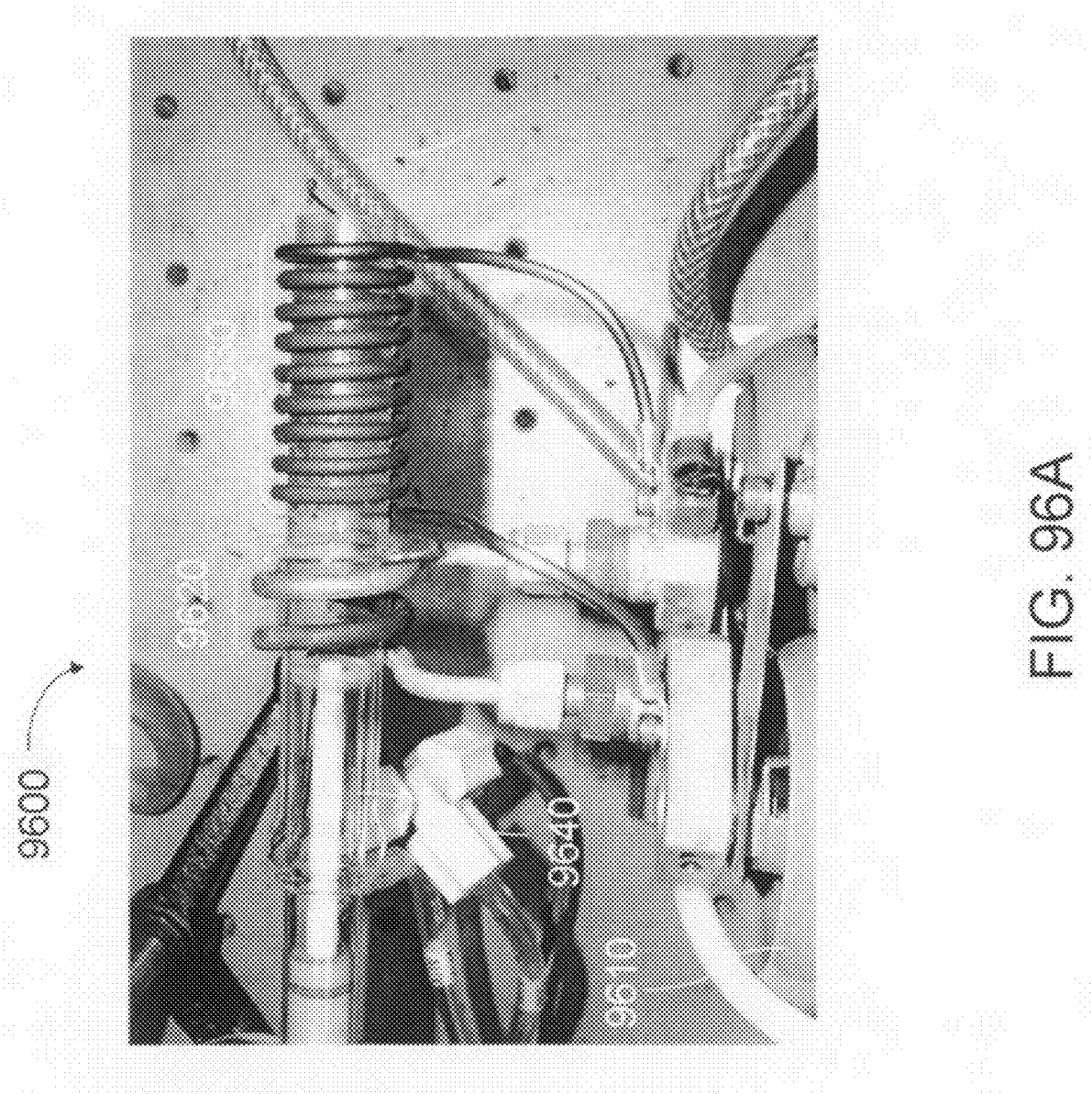
FIG. 96A is a perspective view of a device that includes a single power source for powering a primary induction coil and a boost device, in accordance with certain examples.
Figure 96C:
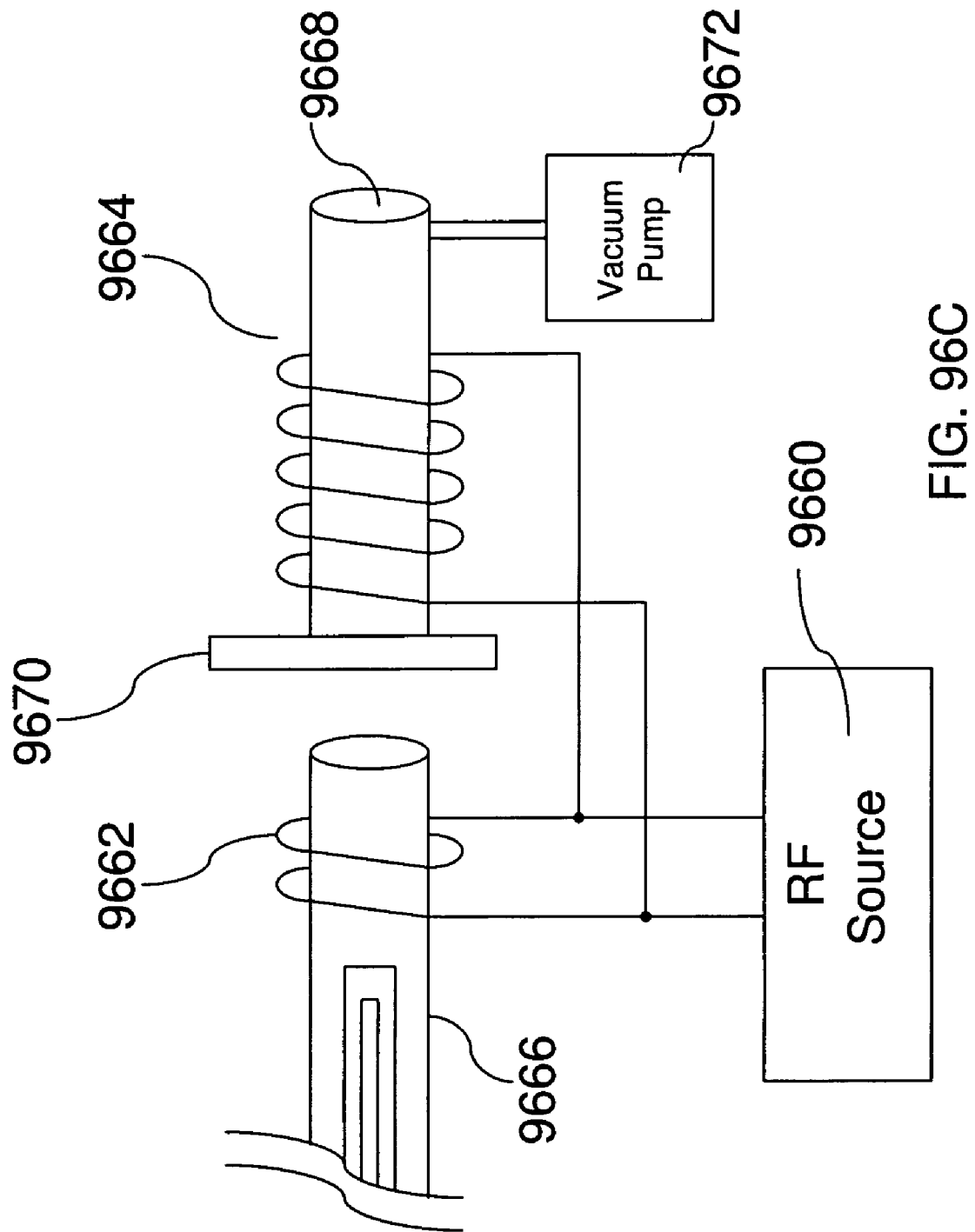
FIG. 96C is an examples of a device with a primary and secondary chamber and comprising a single RF source for powering a primary induction coil and a boost device, in accordance with certain examples.

Referring to FIG. 96A, a device 9600 was assembled using a single RF source 9610 to power a primary induction coil 9620 and a boost device 9630. This example used the same manually controlled hardware setup as described above except that only the primary RF source was used, a continuous ignition arc source (Solid State Spark Tester BD-40B purchased from Electro-Technic Products (Chicago, Ill.)) was used in place of the standard ignition source, and the plastic faceplate was removed from the standard RF source (a single Optima 4000 generator). A boost device 9630 was made by wrapping 9 turns of ⅛" refrigerator grade copper tubing around extended quartz torch 9640. The extended quartz torch was the same torch as described above in the Example 1. The boost device of this example was terminated with un-insulated crimp ring lugs. Since this setup was used for a short term investigation, no cooling of the boost device was used. Due to the lack of cooling, the coil turned black from the heat very quickly. For short term use, this discoloration did not significantly affect the performance.

Figure 97:
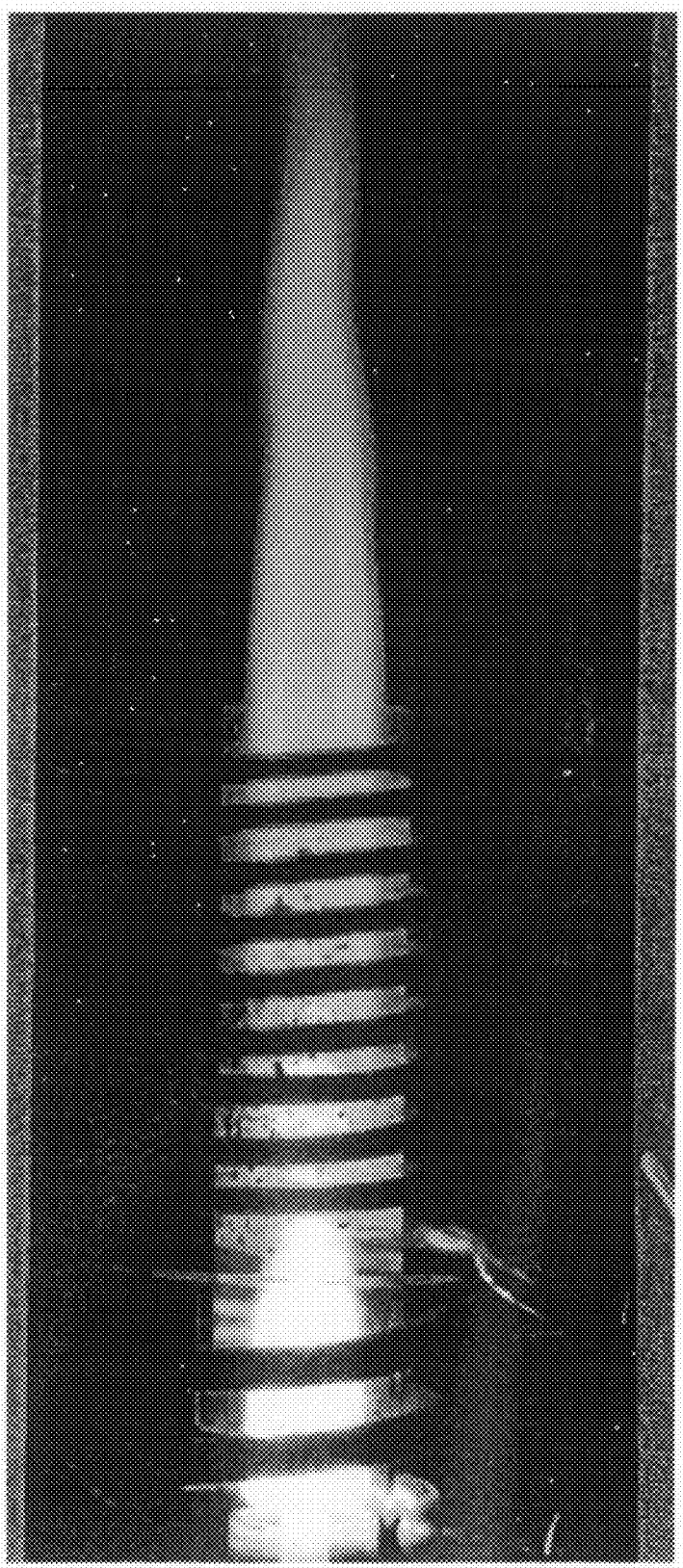
FIG. 97 is close-up radial view of the emission from 1000 ppm of aspirated yttrium using the device of FIG. 96A, in accordance with certain examples.

In operation, the primary plasma formed in the boost region of the torch (high impedance region). By applying a continuous ignition arc, the plasma moved into the region of the primary two-turn induction coil 9620 (low impedance region). Once the plasma transitioned into the low impedance region of the two-turn coil, the continuous ignition arc was removed. After removal of the ignition arc, the plasma remained and operated stably in the two-turn load coil region, and power from the boost coil added additional excitation energy to the sample emission region of the plasma (see FIG. 96B and FIG. 97 showing a close-up view of optical emission of 1000 ppm of Yttrium shown in FIG. 96B).

Referring to FIG. 96C, a single RF source may also be used to power coils in a configuration implementing an interface. Referring to FIG. 96C, an RF source 9660 powers primary induction coil 9662 and boost device 9664. Primary induction coil surrounds first chamber 9666, whereas boost device 9664 surrounds secondary chamber 9668. Interface 9670 is positioned at one end of secondary chamber 9668 and is configured to draw sample from primary chamber 9666 into secondary chamber 9668. A vacuum pump 9672 may be used to control the pressure in the secondary chamber. The interface 9670 may also have a small aperture to help control the flow of sample and the pressure of the chamber. This configuration simplifies construction of atomization devices including boost devices and provides the advantages obtained using an interface.

Example 7

Low UV Optical Emission Spectrometer

Referring to FIGS. 98A-98C, a spectrometer configured with a boost device and configured for optical emission measurements in the low UV is shown. The device shown schematically in FIG. 98B is configured to exclude substantially all air or oxygen from the optical path such that emission lines having wavelengths in the low UV may be detected. In existing ICP-OES configurations a shear gas nozzle extinguishes the end of the plasma. There is about a 0.5 inch space between the end of the plasma and the beginning of the transfer optics where air or oxygen may absorbs light, e.g., low UV light (see arrow in FIG. 98A). The shear gas may be used to prevent melting of the transfer optics and to prevent damage to the aperture or the window located on the spectrometer.

Referring to FIG. 98B, a schematic of a spectrometer configured for use in low UV optical emission measurements is shown. Spectrometer 9700 comprises a primary chamber 9702 with plasma 9704 and induction coils 9707 electrically coupled to RF source 9708. Spectrometer 9700 also includes a secondary chamber 9710 that includes a sampling interface 9706 with a sampling aperture 9712. The secondary chamber 9710 also includes a boost device 9713 electrically coupled to an RF source 9714. The secondary chamber 9710 is fluidically coupled to vacuum pump 9720 and optically coupled to a detector 9740 through a window or aperture 9730. The vacuum pump 9720 may be used to draw sample from the primary chamber 9702 into the secondary chamber 9710 where it may be atomized, ionized and/or excited using the boost device 9713. Purge ports 9742 and 9744 may be used to introduce an inert gas into the detector 9740 to purge the detector 9740 of air or oxygen to prevent unwanted absorption of the emission signal by air or oxygen. Using this configuration, light emitted by excited sample in the secondary chamber 9710 may be detected by detector 9740. In addition, the signal from the plasma in the primary chamber 9702 is minimized using the interface, and the plasma 9704 runs against the sampling interface 9706, which prevents air from entering through the sample aperture 9712 (see FIG. 98C). Because substantially no air or oxygen is in the optical path of the detector 9740, atoms and ions which emit light in the low UV may be detected with precision.

Example 8

Low UV Atomic Absorption Spectrometer

Referring to FIG. 99, a spectrometer configured for optical measurements in the low UV is shown schematically. Spectrometer 9800 includes a light source 9802 (e.g., a UV light source), a primary chamber 9804 with a plasma 9806 and induction coils 9807 electrically coupled to an RF source 9808. Spectrometer 9800 also includes a secondary chamber 9820 that includes a sampling interface 9822 with a sampling aperture 9824. The secondary chamber 9820 also includes a boost device 9825 electrically coupled to an RF source 9826. The secondary chamber 9820 is fluidically coupled to vacuum pump 9845, optically coupled to the light source 9802 through a window or aperture 9830 and optically coupled to a detector 9850 through a window or aperture 9840. The vacuum pump 9845 may be used to draw sample from the primary chamber 9804 into the secondary chamber 9820 where it may be atomized and/or ionized using the boost device 9825. Purge ports 9852 and 9854 may be used to introduce an inert gas into the detector 9850 to purge the detector 9850 of air or oxygen to prevent unwanted absorption of light from the light source 9802 by the air or oxygen. Using this configuration, the amount of light absorbed by sample in the secondary chamber 9820 may be detected by the detector 9850. In addition, the signal from the plasma 9806 in the primary chamber 9804 may be minimized because of the right angle configuration, and the plasma 9806 runs against the sampling interface 9822, which prevents air from entering through the sample aperture 9824. Because substantially no air or oxygen is in the optical path of the detector 9850, atoms and ions which absorb light in the low UV may be detected with precision.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples may be interchanged or substituted with various components in other examples. Should the meaning of the terms of any of the patents or publications incorporated herein by reference conflict with the meaning of the terms used in this disclosure, the meaning of the terms in this disclosure are intended to be controlling.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A device for mass spectroscopy comprising:
   a chamber configured to sustain a primary atomization source;
   an energy delivery mechanism configured to provide radio frequency energy to the chamber to sustain the primary atomization source in the chamber;
   a boost device separate from the primary atomization source and the energy delivery mechanism and configured to provide additional radio frequency energy to the primary atomization source in the chamber; and
   a mass analyzer in fluid communication with the chamber and configured to separate species based on mass-to-charge ratios.

2. The device of claim 1, in which the mass analyzer is selected from the group consisting of a scanning mass analyzer, a magnetic sector analyzer, a quadrupole mass analyzer, and an ion trap analyzer.

3. The device of claim 1, further comprising a detection device in fluid communication with the mass analyzer.

4. The device of claim 3, in which the detection device is selected from the group consisting of an electron multiplier and a Faraday cup.

5. The device of claim 3, further comprising a processing device in electrical communication with the detection device.

6. The device of claim 5, in which the processing device is configured to access a database.

7. The device of claim 1, in which the chamber is configured to provide an atomization source that is selected from the group consisting of a flame, an inductively coupled argon plasma, a spark and an arc.

8. The device of claim 1, in which the boost device is configured to provide the additional radio frequency energy in a pulsed mode or a continuous mode.

9. The device of claim 1, in which the boost device is configured to provide radio frequency energy having a frequency of about 25 MHz to about 50 MHz.

10. The device of claim 1, in which the boost device is configured to provide radio frequency energy at a power of about 100 Watts to about 2,000 Watts.

11. The device of claim 1, further comprising a second chamber in fluid communication with the chamber comprising the atomization source.

12. The device of claim 11, in which the second chamber further comprises a boost device configured to provide radio frequency energy to at least a portion of the second chamber.

13. The device of claim 12, in which the boost device of the second chamber is configured to provide radio frequency energy of about 25 MHz to about 50 MHz and to provide radiofrequencies at a power of about 100 Watts to about 2,000 Watts.

14. The device of claim 12, in which the second chamber is in fluid communication with a vacuum pump configured to draw sample from the first chamber into the second chamber.

15. The device of claim 12, in which the second chamber further comprises an interface comprising an orifice for introducing sample into the second chamber.

16. The device of claim 15, in which the interface is configured to introduce sample from the first chamber into the second chamber so that the sample is diluted by less than about 15:1 with carrier gas.

17. A device for mass spectroscopy comprising:
   a first chamber configured to sustain a primary atomization source;
   an energy delivery mechanism configured to provide radio frequency energy to the first chamber to sustain the atomization source;
   a second chamber in fluid communication with the first chamber;
   a boost device separate from the primary atomization source and the first chamber and configured to provide radio frequency energy to the second chamber; and
   a mass analyzer in fluid communication with the second chamber and configured to separate species based on mass-to-charge ratios.

18. The device of claim 17, in which the mass analyzer is selected from the group consisting of a scanning mass analyzer, a magnetic sector analyzer, a quadrupole mass analyzer, and an ion trap analyzer.

19. The device of claim 17, further comprising a detection device in fluid communication with the mass analyzer.

20. The device of claim 17, in which the first chamber is configured to provide an atomization source that is selected from the group consisting of a flame, an inductively coupled argon plasma, a spark and an arc.

21. The device of claim 17, further comprising an additional boost device configured to provide additional radio frequency energy to the second chamber.

22. The device of claim 17, in which the second chamber further comprises an interface comprising an orifice for introducing sample into the second chamber.

23. The device of claim 17, in which the second chamber is in fluid communication with a vacuum pump configured to draw sample from the first chamber into the second chamber.

24. The device of claim 23, in which the interface is configured to introduce sample from the first chamber into the second chamber so that the sample is diluted by less than about 15:1 with carrier gas.

25. A device for mass spectroscopy comprising:
a first chamber configured to sustain a primary atomization source;
at least one plate electrode configured to sustain the primary atomization source in the chamber, a portion of the first chamber positioned in an aperture of the at least one plate electrode;
a first boost device separate from the primary atomization source and configured to provide additional radio frequency energy to the first chamber, the first boost device comprising a coil of wire surrounding a portion of the first chamber different from the portion surrounded by the at least one plate electrode;
a second chamber in fluid communication with the first chamber;
a second boost device separate from the primary atomization source and the first boost device and configured to provide radio frequency energy to the second chamber, the second boost device comprising a coil of wire surrounding the second chamber; and
a mass analyzer in fluid communication with the second chamber and configured to separate species based on mass-to-charge ratios.

* * * * *